US007811579B2

(12) United States Patent
Lee et al.

(10) Patent No.: US 7,811,579 B2
(45) Date of Patent: Oct. 12, 2010

(54) FULL-LENGTH GENOMIC RNA OF JAPANESE ENCEPHALITIS VIRUS, INFECTIOUS JEV CDNA THEREFROM, AND USE THEREOF

(75) Inventors: Young-Min Lee, #803-1903 Hyundaidaewoo Apt., 1249 Bunpyeong-dong, Heungdeok-gu, Cheongju-si, 361-201 Chungcheongbuk-do (KR); Sang-Im Yun, Chungcheongbuk-do (KR); Seung Han Lee, Gyeonggi-do (KR)

(73) Assignee: Young-Min Lee, Cheongju-si, Chungcheongbuk-do (KR)

( * ) Notice: Subject to any disclaimer, the term of this patent is extended or adjusted under 35 U.S.C. 154(b) by 255 days.

(21) Appl. No.: 10/529,169

(22) PCT Filed: Oct. 9, 2003

(86) PCT No.: PCT/KR03/02081

§ 371 (c)(1),
(2), (4) Date: Mar. 24, 2005

(87) PCT Pub. No.: WO2004/033690

PCT Pub. Date: Apr. 22, 2004

(65) Prior Publication Data

US 2006/0234965 A1 Oct. 19, 2006

(30) Foreign Application Priority Data

Oct. 9, 2002 (KR) ...................... 10-2002-0061589

(51) Int. Cl.
*A61K 39/12* (2006.01)

(52) U.S. Cl. ................................ 424/199.1; 435/320.1

(58) Field of Classification Search ....................... None
See application file for complete search history.

(56) References Cited

FOREIGN PATENT DOCUMENTS

| | | |
|---|---|---|
| WO | 99/63095 | 12/1999 |
| WO | WO 02/072835 | 9/2002 |

OTHER PUBLICATIONS

Mishin et al. A 'minimal' approach in design of flavivirus infectious DNA. Virus Research, Dec. 2001, vol. 81, No. 1-2, pp. 113-123.*

Zhang et al. Amplification and cloning of the full-length genome of Japanese encephalitis virus by a novel long RT-PCR protocol in a cosmid vector. Journal of Virological Methods, Aug. 2001, vol. 96, No. 2, pp. 171-182.*

Sumiyoshi et al. Infectious Japanese Encephalitis Virus RNA Can Be Synthesized from In Vitro-Ligated cDNA Templates. Journal of Virology, Sep. 1992, vol. 66, No. 9, pp. 5425-5431.*

Chang et al. A Single Intramuscular Injection of Recombinant Plasmid DNA Induces Protective Immunity and Prevents Japanese Encephalitis in Mice. Journal of Virology, May 2000, vol. 74, No. 9, pp. 4244-4252.*

Schumacher et al. Reconstitution of Marek's Disease Virus Serotype 1 (MDV-1) from DNA Cloned as a Bacterial Artificial Chromosome and Characterization of a Glycoprotein B-Negative MDV-1 Mutant. Journal of Virology, Dec. 2000, vol. 74, No. 23, pp. 11088-11098.*

Venugopal et al. Vaccine, 1995, vol. 13, No. 11, pp. 1000-1005.*

Almazán et al. PNAS, May 2000, vol. 97, No. 10, pp. 5516-5521.*

NCBI Accession No. U15763, Japanese encephalitis virus, *NIH*, Mar. 30, 1995.

NCBI Accession No. U14163, Japanese encephalitis virus, *NIH*, Mar. 30, 1994.

Shihyun, Y., et al. "A Novel in Vitro Replication System for Dengue Virus" *J. Biological Chemistry*, vol. 274, No. 47, pp. 33714-33722(Nov. 1999).

Schlesinger, S., et al. "Alphavirus vectors for gene expression and vaccines", *Current Opinion in Biotechnology*, vol. 10, pp. 434-439, (1999).

Almazan, Fernando, "Engineering the largest RNA virus genome as an infectious bacterial artificial chromosome," *PNAS*, vol. 97, No. 10, pp. 5516-5521, (May 9, 2000).

Mishin, V.P., et al., "A 'minimal' approach in design of flavivirus infectious DNA", *Virus Research*, vol. 81, pp. 113-123, (2001).

Zhang, F., et al., "Amplification and cloning of the full-length genome of Japanese encephalitis virus by a novel long RT-PCR protocol in a cosmid vector" *Journal of Virological Methods*, vol. 96, pp. 171-182, (2001).

Sumiyoshi, H., et al. "Characterization of a Highly Attenuated Japanese Encephalitis Virus Generated from Molecularly Cloned cDNA", *Journal of Infectious Diseases*, vol. 171, pp. 1144-1151, (May 1995).

Sumiyoshi, H., et al. "Infectious Japanese Encephalitis Virus RNA Can Be Synthesized from In Vitro-Ligated cDNA Templates", *Journal of Virology*, vol. 66, No. 9, pp. 5425-5431, (Sep. 1992).

Agapov, E.V., et al., "Noncytopathic Sindbis virus RNA vectors for heterologous gene expression" *Proc. Natl. Acad. Sci. USA*, vol. 95, pp. 12989-12994, (Oct. 1998).

Frolov, I., et al., "Alphavirus-based expression vectors: Strategies and applications", *Proc. Natl. Acad. Sci. USA*, vol. 93, pp. 11371-11377, (Oct. 1996).

Yamshchikov, Vladmir, et al., A New Strategy in Design of {+)RNA Virus Infectious Clones Enabling Their Stable Propagation in *E. coli*, Virology 281(2): 272-280, 2001.

Yamshchikov, Vladmir, et al., An Infectious Clone of the West Nile Flavivirus, Virology 281(2): 294-304, 2001.

(Continued)

*Primary Examiner*—Ali R. Salimi
(74) *Attorney, Agent, or Firm*—The Nath Law Group

(57) ABSTRACT

The present invention relates to a novel genomic RNA of Japanese encephalitis virus (JEV) and an infectious JEV cDNA therefrom. Particularly, the present invention relates to a full-length genomic RNA of JEV represented by SEQ. ID. No 15 and an infectious JEV cDNA therefrom. JEV genomic RNA and infectious JEV cDNA of the present invention can be used not only for the identification of the JEV genes, but also for the molecular biological studies including JEV replication, transcription, and translation. Moreover, they can also be applied to the development of the therapeutic agents, vaccines, diagnostic reagents, and diagnostic devices for Japanese encephalitis, and can be used as an expression vector for the various foreign genes.

16 Claims, 16 Drawing Sheets

OTHER PUBLICATIONS

Communication pursuant to Article 94(3) EPC [Official Action] in Applicaiton No. EP 03748780.8, mailing date: Dec. 5, 2008, and claims pending.

Mendez et al., "Infectious Bovine Viral Diarrhea Virus (Strain NADL) RNA from Stable cDNA Clones: a Cellular Insert Determines NS3 Production and Viral Cytopathogenicity", J. Virol., 1998, 72(6): 4737-4745.

Yun et al., "Development and Application of a Reverse Genetics System for Japanese Encephalitis Virus", J. Virol., 2003, 77(11): 6450-6465.

Rice et al., "Production of Infectious RNA Transcripts from Sindbis Virus cDNA Clones: Mapping of Lethal Mutations, Rescue of a Temperature-Sensitive Marker, and In Vitro Mutagenesis To Generate Defined Mutants", J. Virol., 1987, 61(12): 3809-3819.

Lai et al., "Infectious RNA transcribed from stably cloned full-length cDNA of dengue type 4 virus", Proc. Nati. Acad. Sci. USA , 1991, 88: 5139-5143.

Shizuya et al., Proc. Natl. Acad. Soc. U.S.A., 89: 8794-8797, 1992.

* cited by examiner

FIGURES (A) 10968 nucleotides

C prM E NS1 NS2A NS2B NS3 NS4A NS4B NS5

JVF (3865 bp) 1—3865
JVR (3329 bp) 7565—10893
JVM (4905 bp) 3266—8170

(B) JEV genomic RNA — OH + (P) Oligo T — H
↓ *RNA-oligo ligation*
↓ *cDNA synthesis & amplification*
↓ *Cloning & sequence analysis*

(C) RT + −
900
700
600
500
400
M 1 2

(D) JEV genomic RNA — OH
↓ *Decapping*
(P) — OH
↓ *Self-ligation*
↓ *cDNA synthesis & amplification*
↓ *Cloning & sequence analysis*

(E) RT + −
1100
900
800
700
600
M 1 2

FULL-LENGTH GENOMIC RNA OF JAPANESE ENCEPHALITIS VIRUS, INFECTIOUS JEV CDNA THEREFROM, AND USE THEREOF

FIELD OF THE INVENTION

The present invention relates to the determination of an authentic Japanese encephalitis virus (JEV) genome RNA sequences, to construction of infectious JEV cDNA clones, and to utility of the clones or their derivatives for the purpose of therapeutic, vaccine, and diagnostic applications. In addition, the invention is also related to JEV vectors, e.g., for heterologous gene expression systems, genetic immunization, and transient gene therapy.

BACKGROUND

JEV is a member of the Flaviviridae family and is transmitted by mosquitoes. It is an important human pathogen that causes permanent neuropsychiatric sequelae and even fatal disease, especially in children (Tsai, *Vaccine,* 2000, 18(Suppl 2), 1-25; Solomon, *Neurological Infections and Epidemiology,* 1997, 2, 191-199; Umenai et al., *Bull. W.H.O.,* 1985, 63, 625-631). Up to 50,000 cases with a mortality rate of about 25% are reported annually, and about half of the survivors exhibit permanent neuropsychiatric sequelae (Vaughn and Hoke, *Epidemiol. Rev.,* 1992, 14, 197-221; Burke and Leake, *Japanese encephalitis,* 1988, 63-92, CRC Press Publisher). JEV is distributed mostly in Asia from the former Soviet Union to India. In recent years, however, transmission of the virus has recently been observed in the southern hemisphere, indicating that this virus could become a worldwide public health threat (Hanna, et al., *Med. J. Aust.,* 1999, 170, 533-536; Hanna, et al., *Med. J. Aust.,* 1996, 165, 256-260; Mackenzie et al., *Arch. Virol.,* 1994, 136, 447-467).

JEV is a small-enveloped virus with a single-stranded, positive-sense RNA genome approximately 11 kb in length. The genome contains a single long open reading frame (ORF) flanked by 5' and 3' nontranslated regions (NTRs) that are important cis-acting elements for viral replication. The RNA genome of JEV has a type I cap structure at its 5'-terminus but lacks a poly(A) tail at its 3' terminus. The ORF is translated into a large polyprotein that is co- or posttranslationally processed into three structural and seven nonstructural proteins whose genes are arranged in the genome as follows: C-prM-E-NS1-NS2A-NS2B-NS3-NS4A-NS4B-NS5 (Lindenbach and Rice, *Flaviviridae: The viruses and their replication,* 2001, 991-1041, Lippincott Williams&Wilkins Publishers; Venugopal and Gould, *Vaccine,* 1994, 12, 966-975; Chamber et al., *Ann. Rev. Microbiol.,* 1990, 44, 649-688). Further information, for example, on the function of the majority of the JEV gene products and the molecular mechanisms involved in JEV replication, neurovirulence, and pathogenesis, is limited largely because of the lack of a reliable reverse genetics system.

Research investigating positive-sense RNA viruses has been considerably advanced by the development of the reverse genetics system. Here, infectious cDNA clones of the viral genome in question are constructed and become the templates for infectious RNA synthesis that generates synthetic viruses. There are two approaches, RNA-launched approach and DNA-launched approach, for the reverse genetics system. In the classical "RNA-launched" approach, cells are transfected with RNA transcripts made from the infectious cDNA clones, and the synthetic viruses are then recovered from these cells (Satyanarayana et al., *Proc. Natl. Acad.*

*Sci. USA,* 1999, 96, 7433-7438; van Dinten et al., *Proc. Natl. Acad. Sci. USA,* 1997, 94, 991-996; Liljestrom and Garoff, *Biotechnology,* 1991, 9, 1356-1361; Rice et al., *New Biol.,* 1989, 1, 285-296, Rice et al., *J. Virol.,* 1987, 61, 3809-3819). In an alternative "DNA-launched" approach, synthetic viruses are generated by directly transfecting infectious cDNA clones into susceptible cells. This approach was first reported for poliovirus (Racaniello and Baltimore, *Science,* 1981, 214, 916-919), and has been adapted for alphaviruses (Schlesinger and Dubensky, *Curr. Opin. Biotechnol.,* 1999, 10, 434-439).

Both of these approaches have been used to construct infectious cDNA clones for many positive-sense RNA virus families, including coronaviruses, which have the largest RNA genomes (Almazan et al., *Proc. Natl. Acad. Sci. USA,* 2000, 97, 5516-5521). These clones have been invaluable in addressing many questions regarding the positive-sense RNA viruses. However, the construction of a full-length infectious cDNA clone for JEV has been hampered, largely because of the genetic instability of the cloned cDNA. Despite extensive efforts, a genetically stable full-length infectious cDNA molecular clone for JEV does not exist (Mishin et al., *Virus Res.,* 2001, 81, 113-123; Zhang et al., *J. Virol. Methods,* 2001, 96, 171-182; Sumiyoshi et al., *J. Infect. Dis.,* 1995, 171, 1144-1151; Sumiyoshi et al., *J. Virol.,* 1992, 66, 5425-5431).

Thus, the present inventors have disclosed the complete full-length nucleotide sequence of the JEV strain CNU/LP2, isolated from a pool of circulating mosquitoes in Korea. Based on this sequence, the present inventors also have developed a convenient and reliable reverse genetics system for JEV by synthesizing full-length infectious JEV cDNA molecular clones. The reverse genetics system based on the novel infectious JEV cDNA of the present invention can be effectively used for investigating the functions of JEV gene products and other molecular biological mechanisms related to replication, neurovirulence, and pathogenesis of JEV. Further, the present inventors have completed the present invention by confirming that the infectious JEV cDNA can be effectively used as a vector for the heterologous gene expression in a variety of ways.

DETAILED DESCRIPTION OF PREFERRED EMBODIMENTS

It is an object of the present invention to provide an authentic JEV genome RNA sequences, infectious JEV cDNA clones therefrom, and utility of the clones or their derivatives for novel gene expression vectors.

To accomplish the above object,

1) The present invention provides an authentic JEV genome RNA sequences.

2) The present invention provides infectious JEV cDNA clones that are able to produce self-replicable JEV RNA transcripts.

3) The present invention provides a JEV-based vector.

4) The present invention provides a self-replicable RNA transcript synthesized from the above JEV-based vector.

5) The present invention provides a recombinant JEV virus obtained from cells transfected with a synthetic RNA transcript synthesized from the JEV-based vector.

6) The present invention provides a JEV-based expression vector.

7) The present invention provides a variety of strategies for expressing heterologous genes using the JEV-based expression vector.

Further features of the present invention will appear hereinafter.

I. The present invention provides an authentic JEV genome RNA sequences.

Korean isolate JEV genomic RNA of the present invention is composed of a 5'nontranslated region (NTR), a polypeptide coding region and a 3'NTR. Particularly, the full-length RNA genome is 10,968 bp in length and consists of a 95 bp 5'NTR followed by a 10,299 bp single open reading frame and terminated by a 574 bp 3'NTR.

According to the preferred embodiment of the present invention, the novel genomic RNA of JEV has a sequence represented by SEQ. ID. No 15. And the novel genomic RNA of the present invention also includes any sequence having 98% homology with JEV genomic RNA represented by SEQ. ID. No 15.

Korean isolate JEV of the present invention was isolated and purified from Korean JEV strain K87P39 by taking advantage of plaque-purification technique, and was named "JEV CNU/LP2" (see FIG. 1).

In order to determine the complete nucleotide sequence of CNU/LP2, a Korean isolate JEV, the present inventors amplified the entire viral RNA genome apart from the 5' and 3' termini using long reverse transcription-polymerase chain reaction (RT-PCR) and yielded three overlapping cDNA products denoted JVF (nucleotide (nt) 1-3865), JVM (nt 3266-8170), and JVR (nt 7565-10893) (about 3.9, 4.9, and 3.3 kb in length, respectively) (see FIG. 2A).

The 3'-terminal sequence of CNU/LP2 viral RNA was analyzed after synthetic oligonucleotide T was ligated to it. Oligonucleotide T serves as a specific priming site for cDNA synthesis and PCR amplification (see FIG. 2B). Agarose gel electrophoresis revealed that the amplified products migrated as two bands, a larger band of approximately 700 bp and a smaller band of about 450 bp (see FIG. 2C). Both bands were purified and cloned, and 20 and 10 randomly picked clones containing the larger and the smaller bands, respectively, were sequenced. As has been documented for most of the fully sequenced JEV isolates, the present inventors found that all the clones with the larger insert (about 700 bp) terminated the viral genome with -GATCT$^{10968}$. In contrast, all the clones with the smaller insert (about 450 bp) showed the viral genome truncated at nt 10,684, resulting in a band 284 bp shorter. During assembly of the full-length JEV cDNA, the present inventors used the nucleotide sequences of the larger insert because the smaller insert did not contain 284 nucleotides at the 3' end of the viral genome.

The 5'-terminal sequence of CNU/LP2 viral RNA was examined after the cap structure at its 5' end had been removed by incubation with tobacco acid pyrophosphatase. The resulting viral RNA was then self-ligated, and the 3'-5' junction was subjected to cDNA synthesis and PCR amplification with a positive-sense primer for RT-PCR complementary to a sequence near the viral 3' end (nt 10259-nt 10276) and a negative-sense primer corresponding to a sequence near the viral 5' end (nt 164-nt 181) (see FIG. 2D). Agarose gel electrophoresis revealed the amplified products as a single band of about 850 bp (see FIG. 2E). The amplicons were cloned, and 12 randomly picked clones were sequenced. In all 12 clones, the -GATCT$^{10968}$ of the viral 3'-terminal sequence was followed by the 5'-terminal sequence $^{1}$AGAAGT- (see FIGS. 2B and 2C).

Thus, the present inventors have determined the complete nucleotide sequence of the JEV CNU/LP2 isolate represented by SEQ. ID. No 15. The full-length RNA genome of JEV CNU/LP2 is 10,968 bp in length and consists of a 95 bp 5'NTR followed by a 10,299 bp single open reading frame and terminated by a 574 bp 3'NTR. The present inventors compared the complete nucleotide sequence of the CNU/LP2 isolate with sequences of all 26 JEV strains (Ishikawa, K94P05, FU, CH2195LA, CH2195SA, RP-2 ms, RP-9, CH1392, T1P1, YL, JaGAr01, HVI, TC, TL, Beijing-1, Ling, Vellore P20778, p3, SA14-14-2, SA(A), SA14-12-1-7, SA14-2-8, SA14, SA(V), GP78, and JaOArS982) available in GenBank database. Such informations concerning viral strains used for the comparison as isolation regions, isolation years, sources and GenBank accession numbers are briefly stated hereinafter (see Table 1).

TABLE 1

| Geographic location | Year | Strain | Source | GenBank accession number |
|---|---|---|---|---|
| Australia | 1995 | FU | Human serum | AF217620 |
| China | 1954 | SA14 | Mosquito | U14163 |
| | | SA14-14-2 | SA14 derivative | AF315119 |
| | | SA14-12-1-7 | SA14 derivative | AF416457 |
| | | SA14-2-8 | SA14 derivative | U15763 |
| | | SA(V) | SA14 derivative | D90194 |
| | | SA(A) | SA14-14-2 derivative | D90195 |
| | 1949 | Beijing-1 | Human brain | L48961 |
| | 1949 | p3 | Mosquito | U47032 |
| India | 1978 | GP78 | Human brain | AF075723 |
| | 1958 | Vellore P20778 | Human brain | AF080251 |
| Japan | 1982 | JaOArS982 | Mosquito | M18370 |
| | IU | Ishikawa | IU | AB051292 |
| | 1959 | JaGAr01 | Mosquito | AF069076 |
| Korea | 1994 | K94P05 | Mosquito | AF045551 |
| | 1987 | CNU/LP2 | Mosquito | This invention |
| Taiwan | 1997 | T1P1 | Mosquito | AF254453 |
| | 1994 | CH2195LA | CH2195 derivative | AF221499 |
| | 1994 | CH2195SA | CH2195 derivative | AF221500 |
| | 1990 | CH1392 | Mosquito | AF254452 |
| | 1985 | RP-2ms | Mosquito | AF014160 |
| | 1985 | RP-9 | Mosquito | AF014161 |
| | 1965 | Ling | Human brain | L78128 |
| | IU | YL | IU | AF486638 |
| | IU | TC | Mosquito | AF098736 |
| | IU | TL | Mosquito | AF098737 |
| | IU | HVI | Mosquito | AF098735 |

IU: Information unavailable

From the comparison of the nucleotide sequence of the CNU/LP2 isolate with nucleotide sequences of other JEV strain, it was shown that the JEV isolate CNU/LP2 genome shared various degrees of sequence similarity with these other genomes [89.0% (Ishikawa), 89.1% (K94P05), 89.3% (FU), 95.8% (CH2195LA), 95.9% (RP-2 ms), 97.2% (RP-9), 97.3% (CH1392), 97.3% (T1P1), 97.0% (YL), 97.4% (JaGAr01), 97.1% (HVI), 96.9% (TC), 96.7% (TL), 96.4% (Beijing-1), 96.3% (Ling), 96.0% (Vellore P20778), 97.1% (p3), 97.4% (SA14-14-2), 97.5% (SA(A)), 97.5% (SA14-12-1-7), 97.7% (SA14-2-8), 97.9% (SA14), 97.9% (SA(V)), 96.3% (GP78), and 97.1% (JaOArS982)] (see Table 2). Therefore, the nucleotide sequences of JEV viral genomic RNA having over 98% sequence similarity with the nucleotide sequence of the present invention represented by SEQ. ID. NO 15 can be included in the category of the claim of the present invention.

TABLE 2

| | % sequence identity[a] | | | | | | | | | | | | | |
|---|---|---|---|---|---|---|---|---|---|---|---|---|---|---|
| Isolate | Ishkawa | K94P05 | FU | CH2195LA | CH2195SA | RP-2m s | RP-9 | CH1392 | T1P1 | YL | JaGAr01 | HVI | TC | TL |
| Ishkawa | | 97.0 | 90.1 | 88.3 | 88.3 | 88.9 | 89.0 | 89.1 | 89.1 | 88.9 | 89.2 | 89.0 | 88.9 | 88.6 |
| K94P05 | 97.7 | | 89.6 | 88.6 | 88.6 | 89.2 | 89.3 | 89.4 | 89.4 | 89.1 | 89.5 | 89.2 | 89.1 | 88.0 |
| FU | 97.7 | 97.0 | | 88.9 | 88.9 | 89.3 | 89.4 | 89.4 | 89.4 | 89.2 | 89.5 | 89.4 | 89.2 | 89.1 |
| CH2195LA | 97.7 | 97.0 | 89.9 | | 89.9 | 96.2 | 96.3 | 96.3 | 96.3 | 86.1 | 96.5 | 86.2 | 95.9 | 95.8 |
| CH2195SA | 97.1 | 96.5 | 99.0 | 99.0 | | 96.3 | 96.3 | 96.3 | 96.3 | 96.1 | 96.5 | 96.2 | 95.9 | 95.8 |
| RP-2m s | 97.5 | 96.8 | 99.4 | 99.4 | 98.8 | | 99.9 | 99.5 | 99.5 | 99.3 | 89.4 | 98.8 | 88.2 | 96.1 |
| RP-9 | 97.6 | 96.9 | 89.5 | 99.5 | 88.9 | 99.7 | | 99.6 | 99.5 | 89.3 | 98.5 | 88.8 | 98.2 | 96.2 |
| CH1392 | 97.8 | 97.2 | 99.7 | 99.7 | 99.1 | 99.6 | 99.7 | | 98.9 | 99.5 | 89.7 | 89.0 | 98.3 | 98.3 |
| T1P1 | 97.5 | 96.8 | 89.3 | 99.3 | 98.7 | 99.1 | 99.2 | 99.4 | | 89.5 | 99.7 | 89.0 | 98.3 | 98.3 |
| YL | 97.4 | 96.7 | 99.2 | 99.2 | 98.7 | 89.1 | 99.2 | 99.4 | 89.0 | | 89.4 | 98.8 | 88.1 | 98.0 |
| JaGAr01 | 97.1 | 96.4 | 98.9 | 88.9 | 98.2 | 98.7 | 98.8 | 99.1 | 96.6 | 98.7 | | 99.1 | 88.4 | 88.4 |
| HVI | 97.2 | 96.5 | 98.9 | 98.9 | 98.3 | 98.8 | 98.9 | 99.1 | 98.7 | 98.8 | 98.7 | | 98.6 | 98.4 |
| TC | 97.0 | 96.4 | 98.8 | 98.6 | 98.2 | 88.7 | 98.8 | 99.0 | 98.6 | 98.5 | 88.2 | 98.4 | | 89.0 |
| TL | 87.2 | 96.6 | 89.0 | 99.0 | 88.4 | 96.8 | 88.9 | 99.2 | 98.8 | 98.7 | 96.4 | 88.5 | 99.7 | |
| Beijing-1 | 97.3 | 96.6 | 99.0 | 99.0 | 98.5 | 98.9 | 99.0 | 89.2 | 98.8 | 88.7 | 96.4 | 98.6 | 99.2 | 99.3 |
| Ling | 97.4 | 96.7 | 89.1 | 99.1 | 98.5 | 99.0 | 99.1 | 99.3 | 96.9 | 88.9 | 98.6 | 98.7 | 99.0 | 99.2 |
| Vellore P20778 | 97.7 | 97.1 | 99.5 | 99.5 | 98.9 | 99.4 | 99.5 | 99.7 | 99.3 | 99.2 | 98.9 | 99.1 | 99.1 | 99.2 |
| p3 | 97.8 | 97.1 | 99.5 | 99.5 | 98.8 | 99.4 | 99.5 | 99.7 | 99.4 | 99.3 | 99.0 | 99.2 | 99.0 | 99.2 |
| SA14-14-2 | 97.9 | 97.1 | 99.5 | 99.5 | 98.9 | 99.3 | 99.4 | 89.7 | 89.2 | 99.2 | 98.9 | 89.0 | 98.8 | 89.0 |
| SA(A) | 97.1 | 96.6 | 98.8 | 98.8 | 98.2 | 98.7 | 98.6 | 99.0 | 96.6 | 98.5 | 86.2 | 98.3 | 98.1 | 98.3 |
| SA14-12-1-7 | 97.2 | 96.6 | 88.9 | 98.8 | 88.3 | 96.7 | 98.9 | 99.1 | 98.7 | 88.6 | 98.3 | 98.4 | 96.2 | 98.4 |
| SA14-2-8 | 97.7 | 97.3 | 99.4 | 99.4 | 98.8 | 99.3 | 99.4 | 99.6 | 99.2 | 99.2 | 98.8 | 98.9 | 98.8 | 98.9 |
| SA14 | 97.5 | 96.7 | 89.0 | 99.0 | 98.4 | 96.9 | 89.0 | 99.2 | 98.9 | 96.6 | 98.6 | 98.7 | 98.4 | 98.5 |
| SA(V) | 97.3 | 96.6 | 98.9 | 98.9 | 98.3 | 98.7 | 98.8 | 99.1 | 98.7 | 96.6 | 98.4 | 98.5 | 98.2 | 98.4 |
| CNU/LP2 | **97.4** | **96.7** | **96.9** | **89.9** | **96.2** | **98.7** | **98.8** | **99.1** | **88.6** | **83.6** | **88.2** | **88.4** | **88.2** | **88.4** |
| GP78 | 97.0 | 96.4 | 98.6 | 88.6 | 98.0 | 96.5 | 98.6 | 98.8 | 98.5 | 98.4 | 88.0 | 98.1 | 98.0 | 88.2 |
| JaOArS982 | 97.6 | 96.6 | 97.8 | 97.6 | 97.2 | 97.7 | 97.8 | 98.0 | 97.6 | 97.6 | 97.2 | 97.3 | 97.1 | 97.3 |
| WNV | 76.2 | 75.8 | 76.6 | 76.6 | 76.1 | 76.4 | 76.5 | 76.7 | 76.5 | 76.5 | 76.3 | 76.4 | 76.1 | 76.2 |

| | % sequence identity[a] | | | | | | | | | | | | | |
|---|---|---|---|---|---|---|---|---|---|---|---|---|---|---|
| Isolate | Beijing-1 | Ling | Vellore P20778 | p3 | SA14-14-2 | SA(A) | SA14-12-1-7 | SA14-2-8 | SA14 | SA(V) | **CNU/LP2** | GP78 | JaOArS982 | WNV |
| Ishkawa | 88.9 | 88.8 | 88.8 | 89.1 | 88.8 | 88.9 | 88.9 | 89.1 | 89.2 | 89.2 | **89.0** | 68.8 | 68.9 | 69.0 |
| K94P05 | 89.0 | 89.0 | 68.9 | 89.4 | 89.1 | 89.2 | 69.2 | 89.3 | 89.5 | 89.5 | **89.1** | 69.0 | 68.5 | 68.7 |
| FU | 69.3 | 89.0 | 89.1 | 89.4 | 89.1 | 89.2 | 89.2 | 89.3 | 69.6 | 89.6 | **89.3** | 68.7 | 69.4 | 69.5 |
| CH2195LA | 95.6 | 95.7 | 95.1 | 96.3 | 96.6 | 96.7 | 96.7 | 96.8 | 97.1 | 97.1 | **85.8** | 95.7 | 97.3 | 69.4 |
| CH2195SA | 95.6 | 95.7 | 95.1 | 96.3 | 96.6 | 96.7 | 96.7 | 96.9 | 97.1 | 97.1 | **95.9** | 95.7 | 97.3 | 69.5 |
| RP-2m s | 97.2 | 97.1 | 96.6 | 97.9 | 98.0 | 98.1 | 98.1 | 98.3 | 98.5 | 98.5 | **97.1** | 98.9 | 97.7 | 69.4 |
| RP-9 | 97.2 | 97.2 | 96.7 | 98.0 | 98.1 | 98.1 | 98.1 | 98.3 | 98.5 | 98.5 | **97.2** | 96.9 | 97.6 | 69.4 |
| CH1392 | 97.3 | 97.3 | 96.8 | 98.2 | 98.2 | 98.3 | 98.3 | 98.4 | 86.6 | 98.7 | **97.3** | 97.0 | 97.8 | 69.4 |
| T1P1 | 97.3 | 97.3 | 96.8 | 98.1 | 88.2 | 98.2 | 88.3 | 98.4 | 98.6 | 98.6 | **97.3** | 97.0 | 97.8 | 69.4 |
| YL | 97.1 | 97.1 | 96.5 | 97.9 | 98.0 | 98.0 | 98.3 | 98.2 | 98.4 | 98.4 | **97.0** | 96.8 | 97.6 | 69.2 |
| JaGAr01 | 97.4 | 97.4 | 96.9 | 98.3 | 96.3 | 98.4 | 98.4 | 98.5 | 98.8 | 98.8 | **97.4** | 97.1 | 98.0 | 69.5 |
| HVI | 97.2 | 97.2 | 96.7 | 98.1 | 96.1 | 99.1 | 98.1 | 98.3 | 98.6 | 98.5 | **97.1** | 96.9 | 97.7 | 69.4 |
| TC | 97.2 | 97.1 | 96.4 | 97.7 | 97.8 | 97.9 | 97.8 | 98.1 | 98.3 | 93.3 | **86.9** | 96.7 | 97.4 | 69.5 |
| TL | 97.0 | 96.8 | 86.1 | 97.5 | 97.8 | 97.7 | 97.7 | 97.9 | 98.1 | 98.1 | **96.7** | 96.5 | 97.2 | 69.3 |
| Beijing-1 | | 99.1 | 96.7 | 97.4 | 97.2 | 97.2 | 97.3 | 97.5 | 97.6 | 97.6 | **86.4** | 98.1 | 97.0 | 69.5 |
| Ling | 99.2 | | 96.7 | 97.3 | 97.1 | 97.2 | 97.2 | 97.4 | 97.6 | 97.6 | **86.3** | 95.2 | 97.2 | 69.5 |
| Vellore P20778 | 99.3 | 99.4 | | 96.8 | 96.8 | 96.7 | 96.7 | 96.9 | 97.1 | 97.1 | **88.0** | 95.6 | 96.4 | 69.5 |
| p3 | 99.2 | 99.5 | 99.6 | | 96.2 | 98.3 | 98.3 | 98.5 | 98.7 | 98.7 | **97.1** | 97.1 | 97.8 | 69.5 |
| SA14-14-2 | 89.1 | 99.2 | 99.6 | 89.6 | | 89.8 | 99.6 | 99.4 | 89.4 | 99.4 | **97.4** | 97.3 | 88.1 | 69.4 |
| SA(A) | 88.4 | 96.5 | 98.8 | 88.9 | 96.9 | | 99.6 | 99.4 | 99.4 | 99.4 | **97.5** | 97.4 | 88.2 | 69.4 |
| SA14-12-1-7 | 98.5 | 93.6 | 99.0 | 99.0 | 96.9 | 99.7 | | 99.4 | 99.5 | 89.5 | **97.5** | 87.4 | 96.2 | 69.4 |
| SA14-2-8 | 99.0 | 99.2 | 99.5 | 99.6 | 99.5 | 89.1 | 99.2 | | 99.6 | 89.6 | **97.7** | 97.6 | 96.3 | 69.5 |
| SA14 | 98.6 | 98.7 | 89.1 | 99.2 | 99.2 | 99.5 | 98.5 | 99.2 | | 89.9 | **97.9** | 97.6 | 98.6 | 69.6 |
| SA(V) | 98.5 | 98.6 | 98.9 | 89.0 | 99.0 | 98.3 | 93.4 | 99.0 | 99.5 | | **97.9** | 97.8 | 98.6 | 69.6 |
| **CNU/LP2** | **88.5** | **88.6** | **98.9** | **89.0** | **89.0** | **98.4** | **98.4** | **89.0** | **98.6** | **88.5** | | **98.3** | **97.1** | **59.5** |
| GP78 | 98.3 | 98.3 | 98.7 | 88.7 | 98.7 | 98.1 | 88.2 | 98.7 | 88.2 | 98.2 | **88.2** | | 87.2 | 69.6 |
| JaOArS982 | 97.4 | 97.5 | 97.9 | 97.9 | 98.0 | 97.3 | 97.4 | 97.9 | 97.6 | 97.4 | **97.5** | 97.1 | | 69.6 |
| WNV | 76.3 | 76.4 | 76.6 | 76.6 | 76.8 | 76.2 | 76.3 | 76.7 | 76.6 | 76.5 | **76.4** | 76.5 | 76.7 | |

[a]The percent nucleotide sequence identities of the complete genomes are presented at the upper right. The percent amino acid sequence identities of the complete genomes are shown in the lower left. The percentages of CNU/LP2 sequence identities are indicated in boldface type.

In addition to determine the nucleotide sequence of polypeptide coding region of JEV, the nucleotide sequences of 5' and 3'NTRs including cis-acting elements involved in the regulation of viral replication, transcription, and translation of the virus were also determined by taking advantage of molecular biological approaches. The importance of both regions have been supported by some of earlier studies reporting that both the 5'- and 3'-terminal regions are required for the initiation of flavivirus RNA replication in vitro (You and Padmanabhan, *J. Biol. Chem.*, 1999, 274, 33714-33722) and in vivo (Khromykh et al., *J. Virol.*, 2001, 75, 6719-6728). Especially, $^{1}$AGAAGT- and -GATCT$^{10968}$, which were proved to be the nucleotide sequence of 5'- and 3'-terminal regions of JEV CNU/LP2 in the present invention, are highly expected to play an important role in self-replication of the virus.

The present inventors proved through the experiments illustrated hereinafter that infectious synthetic JEV could be produced when cells were transfected with a synthetic RNA transcript having a full-length nucleotide sequence of JEV, and further, the inventors are the first to prove the function of the complete full-length nucleotide sequence which is necessary for JEV self-replication.

II. The present invention provides infectious JEV cDNA clones that are able to produce a self-replicable JEV RNA transcripts.

The infectious JEV cDNA clones of the present invention was synthesized with a nucleotide sequence represented by SEQ. ID. No 15 or nucleotide sequences of full-length JEV genomic RNA having over 98% sequence similarity therewith, and was used as a template for the synthesis of self-replicable JEV RNA transcript through in vitro transcription. In order to construct the full-length JEV cDNA clones, a viral genomic RNA including 5'- and 3'-terminal regions should be amplified by RT-PCR and then the obtained overlapping cDNAs were sequentially assembled.

In order to produce a full-length synthetic JEV RNA transcript through in vitro runoff transcription reaction, SP6 or T7 promoter transcription start site was located at the front of 5'-end of JEV genomic RNA and a unique restriction endonuclease recognition site was located at the end of the viral genome (see FIG. 3A). In the preferred embodiment of the present invention, three SP6-driven full-length JEV cDNAs and three T7-driven full-length JEV cDNAs were constructed by using three overlapping JEV cDNAs (JVF, JVM and JVR) and two additional cDNAs; one is corresponding to 5'-terminal region including SP6 or T7 promoter sequence and the other is corresponding to 3'-terminal region including Xho I and Xba I recognition sequence as a runoff site (see FIGS. 3B and 3C). However, it is a common knowledge for the people in this field that other promoters but the above two promoters can be used as well. The full-length JEV cDNA developed in the present invention uses Xho I and Xba I as a runoff site but other restriction enzymes can be used as commonly known.

The JEV cDNA clones of the present invention are constructed by producing subclones containing many overlapping cDNAs using the bacterial artificial chromosome (BAC) plasmid pBeloBAC11 as a vector and sequentially linking those subclones into the full-length JEV cDNAs.

In the preferred embodiment of the present invention, the present inventors provide one set of three JEV cDNA clones having SP6 promoter and represented by SEQ. ID. No 43, No 44, and No 45, respectively. In addition, the present inventors also provide the other set of three JEV cDNA clones having T7 promoter and represented by SEQ. ID. No 46, No 47, and No 48, respectively (see FIGS. 3B and 3C). To ensure that the 3' end of the viral genome after runoff transcription would be close to authentic, in all cases, the present inventors placed a unique restriction endonuclease recognition site, either Xho I or Xba I, at the end of the viral genome (see FIGS. 3B and 3C).

III. The present invention provides a JEV-based vector.

The vector of the present invention is characterized by including a full-length infectious JEV cDNA. In the preferred embodiment of the present invention, the inventors provide vectors ‘pBAC.sup.SP6/JVFL/XhoI’, ‘pDBAC.sup.SP6/JVFLx/XhoI’, and ‘pBAC.sup.SP6/JVFLx/XbaI’ which all have SP6 promoter and each is represented by SEQ. ID. No 43, No 44, and No 45, and also vectors ‘pBAC.sup.T7/JVFL/XhoI’, ‘pBAC.sup.T7/JVFLx/XhoI’, and ‘pBAC.sup.T7/JVFLx/XbaI’ which all have T7 promoter and each is represented by SEQ. ID. No 46, No 47, and No 48.

The present inventors deposited two most efficient vectors of the above, $pBAC^{T7}$/JVFLx/XbaI and $pBAC^{SP6}$/JVFLx/XbaI, at Gene Bank of Korea Research Institute of Bioscience and Biotechnology (KRIBB) on Oct. 2, 2002 (Accession No: KCTC 10346BP, KCTC 10347BP). All restrictions imposed by the depositor on the availability to the public of the deposited material will be irrevocably removed upon the granting of a patent.

IV. The present invention provides a self-replicable RNA transcript synthesized from the above JEV-based vector.

For in vitro runoff transcription, JEV cDNA templates were linearized by digestion with Xho I or Xba I which is engineered for run-off site right behind 3'-terminal region of the viral genome (see FIG. 3). SP6 polymerase runoff transcription of the two Xho I-linearized plasmids ($pBAC^{SP6}$/JVFL/XhoI and $pBAC^{SP6}$/JVFLx/XhoI) in the presence of the $m^7G(5')ppp(5')A$ cap structure analog yielded capped synthetic RNAs containing three nucleotides (CGA) of virus-unrelated sequence at their 3' ends (see FIG. 3B). This is the result of copying the 5' overhang left by the Xho I digestion. Similarly, SP6 polymerase runoff transcription of the Xba I-linearized $pBAC^{SP6}$/JVFLx/XbaI plasmid in the presence of the $m^7G(5')ppp(5')A$ cap structure analog produced capped synthetic RNAs with four nucleotides (CTAG) of virus-unrelated sequence at their 3' ends (see FIG. 3B).

The present inventors have performed infectious center assay to measure the specific infectivity of the synthetic JEV RNA transcripts. As a result, when susceptible BHK-21 cells were transfected with the synthetic RNA transcripts, all were highly infectious ($3.4\text{-}4.3\times10^5$ PFU/μg) (see Table 3). Similar results ($2.9\text{-}3.8\times10^5$ PFU/μg) were also obtained with synthetic RNAs transcribed from the T7-driven cDNA constructs by T7 polymerase runoff transcription (see Table 3).

It has been reported that for some flaviviruses, the presence of virus-unrelated sequences at the 3' end of synthetic RNAs transcribed from infectious cDNA diminishes or abrogates their specific infectivity (Yamshchikov et al., *Virology,* 2001, 281, 294-304). Based on this report, the present inventors generated synthetic RNAs lacking virus-unrelated sequences at their 3'ends and compared their specific infectivities. Particularly, the present inventors generated synthetic RNAs lacking the unrelated sequences by treating the Xba I-linearized $pBAC^{SP6}$/JVFLx/XbaI plasmid with mung bean nuclease (MBN) prior to the transcription reaction, which removed the four excess nucleotides of CTAG. To verify MBN activity, Xba I-linearized and MBN-treated $pBAC^{SP6}$/JVFLx/XbaI plasmid was self-ligated, and its viral 3' end was sequenced, demonstrating removal of the four excess nucleotides of CTAG. RNA transcripts from Xba I-linearized and MBN-treated $pBAC^{SP6}$/JVFLx/XbaI and $pBAC^{T7}$/JVFLx/XbaI ($pBAC^{SP6}$/JVFLx/$XbaI^{MBN}$, see FIG. 3B and $pBAC^{T7}$/JVFLx/$XbaI^{MBN}$, see FIG. 3C) both had increased specific infectivities compared to the untreated transcripts. Precisely, the specific infectivity of RNAs transcribed from $pBAC^{SP6}$/JVFLx/$XbaI^{MBN}$ was estimated to be $3.1\times10^6$ PFU/μg, approximately 10-fold higher than the specific infectivity ($3.4\times10^5$ PFU/μg) of the unmodified template (see Table 3, infectivity). The RNAs derived from $pBAC^{T7}$/JVFLx/XbaI also had increased specific infectivity after MBN modification ($2.7\times10^6$ PFU/μg) (see Table 3, infectivity). Therefore, the present inventors confirmed that the authentic 3' end of the JEV genome should be present to ensure highly infectious synthetic JEV RNA transcripts are generated. Thus, the infectious JEV cDNA clones of the present invention could be used as templates for runoff transcription that generated highly infectious synthetic RNAs with a specific infectivity of $10^5$ to $10^6$ PFU/μg.

Previous attempts (Mishin et al., *Virus Res.,* 2001, 81, 113-123; Zhang et al., *J. Virol. Methods,* 2001, 96, 171-182; Sumiyoshi et al., *J. Infect. Dis.,* 1995, 171, 1144-1151; Sumiyoshi et al., *J. Virol.,* 1992, 66, 5425-5431) to assemble a full-length infectious JEV cDNA were all failed because of the genetic instability of cloned JEV cDNA. One study attempted to overcome this problem by designing a system in which the template would be generated by in vitro ligation of two overlapping JEV cDNAs (Sumiyoshi et al., *J. Virol.,* 1992, 66, 5425-5431). This template was then used to synthesize infectious RNA transcripts in vitro. However, the specific infectivity of these transcripts was about 100 PFU/μg, which was too low to make this system useful for molecular and genetic analyses of virus biology (Sumiyoshi et al., *J. Virol.,* 1992, 66, 5425-5431).

In the present invention, the present inventors were able to overcome the genetic instability of JEV cDNA by cloning it into a BAC plasmid that is maintained at one or two copies in *E. coli*. The genetic structure and functional integrity of the infectious cDNA plasmid remained stable for at least 180 generations during its propagation in *E. coli* (see FIG. 7). So, the present inventors settled the problem of genetic instability of making full-length infectious JEV cDNA by introducing BAC, and further had skills to treat the synthetic infectious JEV cDNA stably.

It is important to produce full-length infectious JEV cDNA that, in in vitro transcription, would generate RNA transcripts with authentic 5' and 3' ends because several studies have shown that both the 5'- and 3'-terminal regions are needed for the initiation of flavivirus RNA replication in vitro (You and Padmanabhan, *J. Biol. Chem.,* 1999, 274, 33714-33722) and in vivo (Khromykh et al., *J. Virol.,* 2001, 75, 6719-6728). To achieve this objective, the present inventors adapted approaches used previously for other flaviviruses (van der Werf et al., *Proc. Natl. Acad. Sci. USA,* 1986, 83, 2330-2334; Rice et al., *New Biol.,* 1989, 1, 285-296). The cap structure in JEV genomic RNA is followed by the dinucleotide AG, an absolutely conserved feature of the flaviviruses (Rice, *Flaviviridae*: The viruses and their replication, 1996, 931-960, Lippincott-Raven Publisher). The authenticity of the 5' end was ensured by placing either the SP6 or the T7 promoter transcription start at the beginning of the viral genome. Incorporating the $m^7G(5')ppp(5')A$ cap structure analog in the SP6 or T7 polymerase-driven transcription reactions (Contreras et al., *Nucleic Acids Res.,* 1982, 10, 6353-6362), the present inventors synthesized capped RNA transcripts with authentic 5' ends that were highly infectious upon transfection into susceptible cells. In addition, incorporating the $m^7G(5')ppp(5')G$ cap structure analog in the SP6 or T7 polymerase-driven transcription reactions (Contreras et al., *Nucleic Acids Res.,* 1982, 10, 6353-6362) places an unrelated extra G nucleotide upstream of the dinucleotide AG. As reported earlier (Rice et al., *New Biol.,* 1989, 1, 285-296), the present inventors did find that the extra nucleotide was lost from the genomic RNA of the recovered JEV progeny. Furthermore, the present inventors did not observe that the infectivity or the replication of synthetic RNAs transcribed from infectious cDNA templates was altered if the inventors added the extra nucleotide.

The dinucleotide CT located at the 3' end of JEV RNA is absolutely conserved among the flaviviruses (Rice, *Flaviviridae*: The viruses and their replication, 1996, 931-960, Lippincott-Raven Publisher). This suggests that these nucleotides are important in viral replication and that transcripts from infectious cDNAs must have authentic 3' ends. Thus, the present inventors designed our reverse genetics system for JEV so that the synthetic RNA would be terminated with the authentic 3' ends. Indeed, the present inventors showed that RNA transcripts with authentic 3' ends were 10-fold more infectious than transcripts with three or four virus-unrelated nucleotides hanging on their 3' ends.

V. The present invention provides a recombinant JEV virus obtained from cells transfected with a synthetic RNA transcript synthesized from the JEV-based vector.

In the present invention, synthetic JEV viruses produced from the cells transfected with JEV RNA transcripts synthesized from full-length infectious JEV cDNAs were produced. Transfected cells showed strong cytopathic effect induced by JEV virus infection and all the synthetic viruses were indistinguishable from the CNU/LP2 parental virus in terms of plaque morphology, cytopathogenicity, growth kinetics, protein expression and RNA accumulation (see FIG. 5). Furthermore, recombinant JEV virus mutants could be produced by inducing site-directed mutation on a specific region of JEV cDNA, indicating that the infectious JEV cDNA can be manipulated in *E. coli*. Thus, the reverse genetics system using the infectious JEV cDNAs of the present invention can be effectively used for the genetic studies on the replication mechanism of JEV genome.

VI. The present invention provides a JEV-based expression vector.

The present invention provides the use of JEV cDNA as a novel expression vector in a variety of cell types. Alphaviruses, which are also RNA viruses, can replicate in a variety of commonly used animal cells and thus have been successfully exploited as eukaryotic expression vectors in cell culture and in vivo (Agapov et al., *Proc. Natl. Acad. Sci. USA,* 1998, 95, 12989-12944; Frolov et al., *Proc. Natl. Acad. Sci. USA,* 1996, 93, 11371-11377; Schlesinger, *Trends Biotechnol.,* 1993, 11, 18-22). It was reported that JEV, like the alphaviruses, is also able to replicate in a wide variety of primary and continuous cell cultures from humans, mice, monkeys, pigs, and hamsters (Burke and Monath, *Flaviviruses,* 2001, 1043-1125, Lippincott Williams&Wilkins Publishers). This suggests that JEV could be useful as a vector for the expression of heterologous genes in a variety of different cells. When a full-length infectious JEV cDNA is used as an expression vector, in which heterologous genes are inserted, RNA transcripts having heterologous genes are produced by in vitro transcription reaction. Those transcripts can self-replicate as they are transfected into cells, so that lots of foreign proteins can be produced.

An expression cassette is preferably inserted at the beginning of JEV 3'NTR for the expression of a heterologous gene. A deletion of 9-25 bp exists at the beginning of the viral 3'NTR in CNP/LP2 and three other fully sequenced JEV strains (Williams et al., *J. Gen. Virol.,* 2000, 81, 2471-2480; Nam et al., *Am. J. Trop. Med. Hyg.,* 2001, 65, 388-392; Jan et al., *Am. J. Troop. Med. Hyg.,* 1996, 55, 603-609), suggesting that this may be a good site to insert the foreign genes. Thus, the infectious JEV cDNA developed by the present invention can act as a vector for rapid expression of heterologous genes in a variety of cells including mammalian cells.

VII. The present invention provides a variety of strategies for expressing heterologous genes using the JEV-based expression vector.

It is a function of the expression vector to deliver heterologous genes of interest into cells for the expression of those genes. In the present invention, the full-length infectious JEV cDNA has been demonstrated to act as a heterologous gene expression vector in a variety of cell types including mammalian cells.

Here, the present inventors also describe a heterologous gene expression system based on the full-length infectious JEV cDNA, which serves as a BAC (Yun et al., *J. Virol.,* 2003, 77, 6450-6465). As a transient expression system, JEV offers several advantages: (i) high titers of the virus are rapidly produced, (ii) the virus infects a wide range of host cells, including insect and mammalian cell types, (iii) the genetically stable infectious cDNA is available and readily manipulable, and (iv) the cytoplasmic replication of the RNA genome minimizes the possibility of its integration into the host's genome and the consequent undesirable mutagenic consequences.

The present inventors demonstrated here that the JEV-based system can be used to express foreign genes in three different ways. One involves infectious recombinant vector RNAs/viruses encoding the foreign gene, the second involves the production of a viral replication-competent but propagation-deficient JEV viral replicon vector RNA. The third involves the use of packaging systems for viral replicon particle (VRP) formation. Thus, the present inventors have shown here that the JEV system can be used to produce a JEV virus/infectious RNA/replicon RNA/VRP vector that will rapidly express foreign genes of interest in a wide variety of mammalian cell types.

The basic method for the expression of heterologous genes using the infectious or replicon JEV cDNA vectors of the present invention is composed of the following steps:

1) Preparing a recombinant JEV cDNA expression vector by inserting heterologous genes into the infectious or relicon JEV cDNA vector;

2) Producing a JEV RNA transcript from the above recombinant JEV cDNA expression vector;

3) Preparing a transformant by transfecting host cells with the above JEV RNA transcript; and 4) Expressing foreign proteins by culturing the above transformant.

The present inventors produced full-length infectious recombinant JEV cDNAs expressing green fluorescent protein (GFP), an enhanced version of GFP (EGFP), luciferase (LUC), and LacZ genes and the dominant selective marker puromycin N-acetyltransferase (PAC), which confers resistance to the drug puromycin, according to the method explained hereinbefore (see FIGS. 8 and 9). BHK-21 cells were transfected with JEV RNA transcripts transcribed from the recombinant JEV cDNAs. GFP, EGFP, LUC, LacZ and PAC expression is shown in FIGS. 8 and 10. In addition, recombinant infectious JEV viral particles containing those heterologous genes were prepared from culture supernatants. The expression of those heterologous genes was further investigated after infecting various animal cell lines (BHK-21, Vero, NIH/3T3, ST, HeLa, MDCK, CRFK, B103 and SHSY-5Y), which have been generally used in the field of biology and medicine, with the recombinant viruses. As a result, GFP or LUC gene inserted in virus genome was expressed in all cells tested (see Table 4). Thus, it was confirmed that recombinant JEV cDNAs, JEV RNA transcripts, and recombinant JEV viral paticles could be effectively used as a vector for expression of foreign heterologous genes in a variety of cell types.

To independently express foreign genes using the JEV RNA replication machinery, the present inventors generated a panel of self-replicating self-limiting viral replicons by deleting one, two, or all of the viral structural genes, which meet stringent safety concerns (FIG. 11A). These viral replicons were capable of initiating replication and gene expression upon RNA transfection (see FIGS. 11B and 11C).

The utility of the JEV replicon-based expression vectors was further elaborated by developing a panel of stable replicon packaging cell lines (PCLs) that would constitutively express all JEV viral structural proteins (C, prM, and E) in trans (see FIG. 12). These PCLs allowed the trans-complementation of the efficient packaging of JEV viral replicons. Thus, these PCLs were shown to be useful for efficiently producing high titer viral VRPs upon introducing JEV viral replicons (see FIG. 12).

The present inventors also showed that infectious JEV recombinant viral RNAs encoding heterologous genes up to 3 kb can be packaged into the viral particles. By the choice of JEV viral replicon vectors such as JEV/Rep/ΔC+ΔprM+ΔE and JEV/Rep/NS1, it was estimated that a foreign gene of at least 5 kb could be packaged into the JEV VRPs. It will be of interest to examine the upper size limit of the foreign sequences that can be packaged in the JEV virion. This may be an important issue if one wishes to express lengthy genes such as cystic fibrosis transmembrane conductance regulator, whose coding sequence is approximately 4.5 kb (Flotte et al., *J. Biol. Chem.,* 1993, 268, 3781-3790). In addition, a large packaging capacity of JEV viral replicons would be useful if one wishes to add two or more expression units (Thiel et al., *J. Virol.,* 2003, 77, 9790-9798; Agapov et al., *Proc. Natl. Acad. Sci. USA,* 1998, 95, 12989-12994). In the case of the adeno-associated virus-based vector, its packaging capacity has been elegantly expanded to bypass its natural size limitation (Duan et al., *Nat. Med.,* 2000, 6, 595-598; Yan et al., *Proc. Natl. Acad. Sci. USA,* 2000, 97, 6716-6721), which shows that it may be possible to expand the packaging capabilities of JEV viral replicons in a similar manner.

As with other RNA virus-derived vectors (Agapov et al., *Proc. Natl. Acad. Sci. USA,* 1998, 95, 12989-12994; Pushko et al., *Virology,* 1997, 239, 389-401; Berglund et al., *Nat. Biotechnol.,* 1998, 16, 562-565; Basak et al., *J. Interferon Cytokine Res.,* 1998, 18, 305-313; Barclay et al., *J. Gen. Virol.,* 1998, 79, 1725-1734; Khromykh and Westaway, *J. Virol.,* 1997, 71, 1497-1505; Molenkamp et al., *J. Virol.,* 2003, 77, 1644-1648; Shi et al., *Virology,* 2002, 296, 219-233; Varnavski and Khromykh, *Virology,* 1999, 255, 366-375; Perri et al., *J. Virol.,* 2000, 74, 9802-9807; Curtis et al., *J. Virol.,* 2002, 76, 1422-1434), the present inventors could also engineer a variety of JEV viral replicon vector RNAs that can be packaged when the structural proteins are supplied in trans by using the alphavirus-based expression system (Agapov et al., *Proc. Natl. Acad. Sci. USA,* 1998, 95, 12989-12994). Thus, the ability of packaging systems to efficiently generate biosafe JEV vectors has clearly been demonstrated. Unlike alphaviruses (Frolova et al., *J. Virol.,* 1997, 71, 248-258; White et al., *J. Virol.,* 1998, 72, 4320-4326) and retroviruses (Rein, *Arch. Virol. Suppl.,* 1994, 9, 513-522), little is known about the packaging signals employed by flaviviruses, including JEV. Our trans-complementation system for JEV provides evidence that suggests the whole JEV structural region is unlikely to play a role in packaging. Thus, this system will be useful in defining the packaging signals in JEV RNA and the regions in the structural proteins that are involved in RNA encapsidation and morphogenesis. This information will further enhance the utility of our JEV-based expression systems.

In summary, the full-length JEV genomic RNA and the infectious JEV cDNA therefrom of the present invention are not only able to identify neurovirulence- and pathogenesis-related JEV genes but also available for the study of molecular mechanisms of JEV replication, transcription and translation. In addition, the full-length JEV genomic RNA and the infectious JEV cDNA can be effectively used for the development of treatment agents, vaccines, diagnostic reagents and diagnostic kits for JEV, and an expression vector for heterologous genes of interest in eukaryotic cells as well. Furthermore, the JEV-based vector system described in the present invention is a promising system by which foreign genes can be delivered into cells in vitro and possibly in vivo for DNA immunization and transient gene therapy.

BRIEF DESCRIPTION OF THE DRAWINGS

The application of the preferred embodiments of the present invention is best understood with reference to the accompanying drawings, wherein.

(A) Representative plaque assays of synthetic JEVs and parent CNU/LP2. BHK-21 cells were infected with parent or synthetic viruses, overlaid with agarose, and stained 3 days later with crystal violet. (B) Growth kinetics in BHK-21 cells of synthetic JEVs and parent CNU/LP2 infected at multiplicities of infection (MOI) of 0.01, 1, and 10. Viruses were harvested at the hour postinfection (h.p.i) indicated, and titers were determined by plaque assays. (C-D) Viral protein and RNA levels were analyzed by immunoblotting (C) and Northern blotting (D), respectively. BHK-21 cells were infected at an MOI of 1 with synthetic JEVs (lanes 1-4) or CNU/LP2 (lane 5) or mock-infected (lane 6) and cultured for 18 hrs. (C) Protein extracts were prepared from approximately $3\times10^4$ cells and separated on 10% SDS-polyacrylamide gels. Viral proteins were visualized by immunoblotting with JEV-specific mouse hyperimmune ascites (top panel). In parallel, actin protein was detected as a loading and transfer control (bottom panel). The positions of viral protein-related cleavage intermediates and actin are indicated with arrowheads on the left. Molecular mass markers in kDa are indicated on the right. (D) Total RNA from approximately $1\times10^5$ cells was extracted and analyzed by Northern blotting using a $^{32}$P-labeled antisense riboprobe hybridizing to the sequence in the NS5 gene encompassing nt 9143-9351 (top panel). Etbr-stained 18S rRNA bands are shown as a loading control (bottom panel). Full-length genomic viral RNA (11 kb) and 18S rRNA are indicated on the left.

Figure 6:
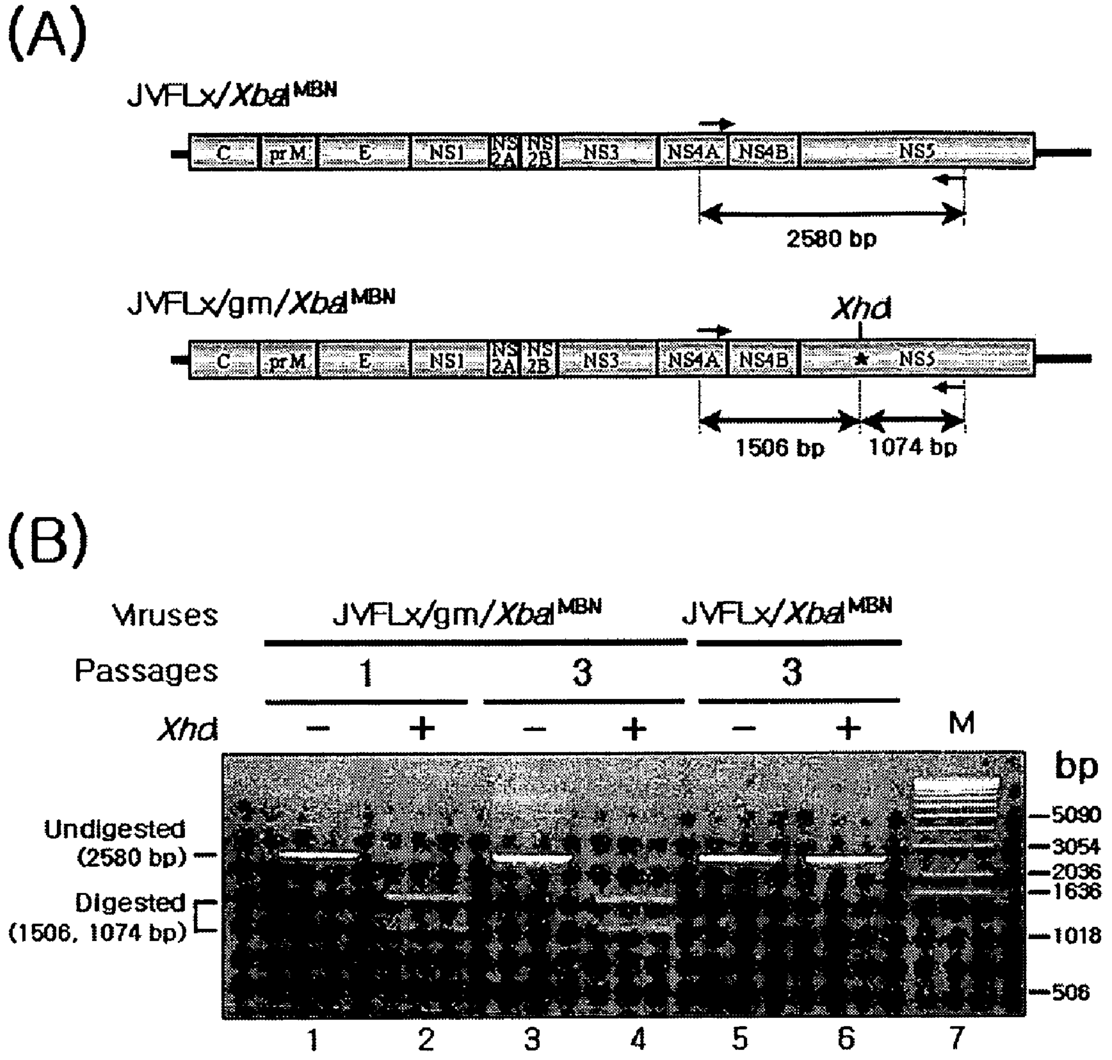

FIG. 6 is a set of diagrams and an electrophoresis photograph showing the presence of Xho I genetic marker in recombinant JEVs derived from pBAC$^{SP6}$/JVFLx/gm/XbaI. (A) Schematic diagram of the RT-PCR fragments of JVFLx/XbaI$^{MBN}$ and JVFLx/gm/XbaI$^{MBN}$ expected after Xho I digestion. Indicated are the primers used for RT-PCR (arrows), the introduced Xho I site (asterisk), and the sizes of the RT-PCR products (2,580 bp) and the two Xho I digestion products (1,506 bp and 1,074 bp) expected after digestion of JVFLx/gm/XbaI$^{MBN}$ with Xho I. (B) BHK-21 cells were transfected with synthetic RNAs transcribed from either pBAC$^{SP6}$/JVFLx/XbaI$^{MBN}$ or pBAC$^{SP6}$/JVFLx/gm/XbaI$^{MBN}$. Viruses were recovered 24 hr later and serially passaged in BHK-21 cells at a multiplicity of infection of 0.1. At each passage prior to the next round of infection, viruses were incubated with DNase I and RNase A. At passage 1 and 3, viral RNA was extracted from the culture supernatant containing the released viruses and used for RT-PCR. The PCR products were incubated in the presence (+) or absence (−) of Xho I, separated on a 1% agarose gel, and stained with EtBr. The expected sizes of the undigested and digested PCR products are shown on the left. Lane M indicates a 1-kb DNA ladder marker (in base pairs).

Figure 7:
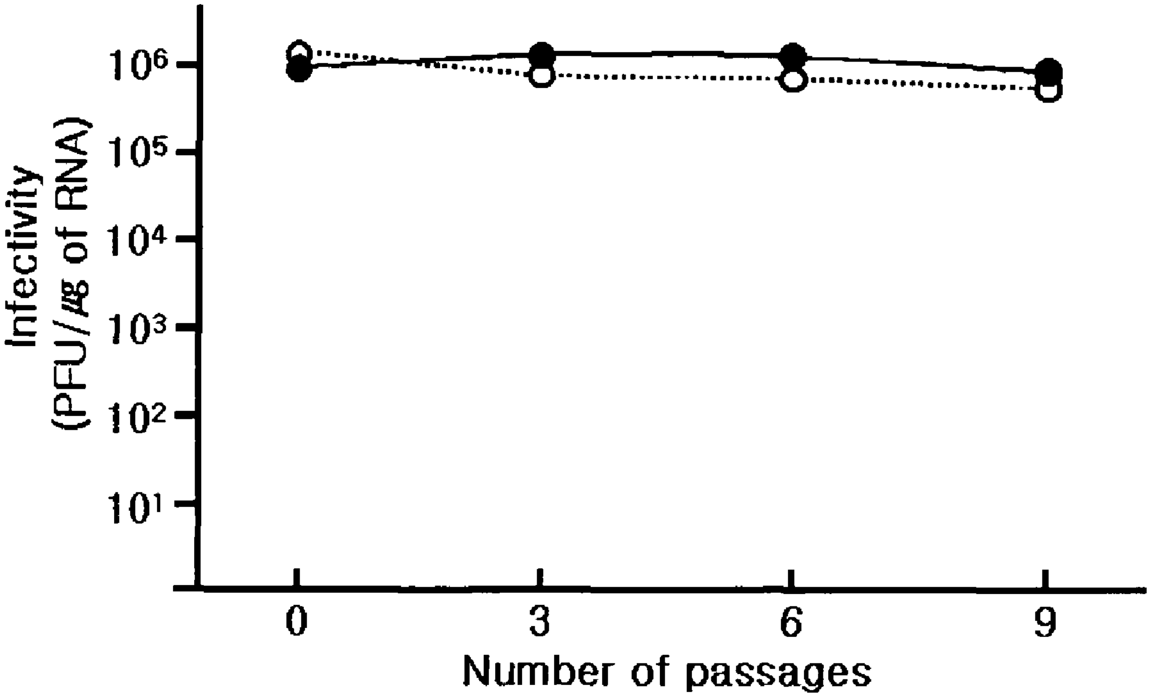

FIG. 7 is a graph showing the specific infectivity of synthetic RNAs transcribed from infectious JEV cDNA clones (pBAC$^{SP6}$/JVFLx/XbaI) propagated for 180 generations. Two independent clones carrying pBAC$^{SP6}$/JVFLx/XbaI (solid and open circles) were cultivated at 37° C. overnight in 2×YT with chloramphenicol. The primary cultures were propagated every day for nine days by $10^6$-fold dilution and adding fresh broth for overnight growth. Each passage was estimated to be about 20 generations. At the indicated passages, the DNA plasmids were purified, linearized by Xba I digestion and treated with MBN, and used as templates for runoff transcription using SP6 RNA polymerase. The transcripts were then used to transfect BHK-21 cells to determine specific infectivity.

Figure 8:
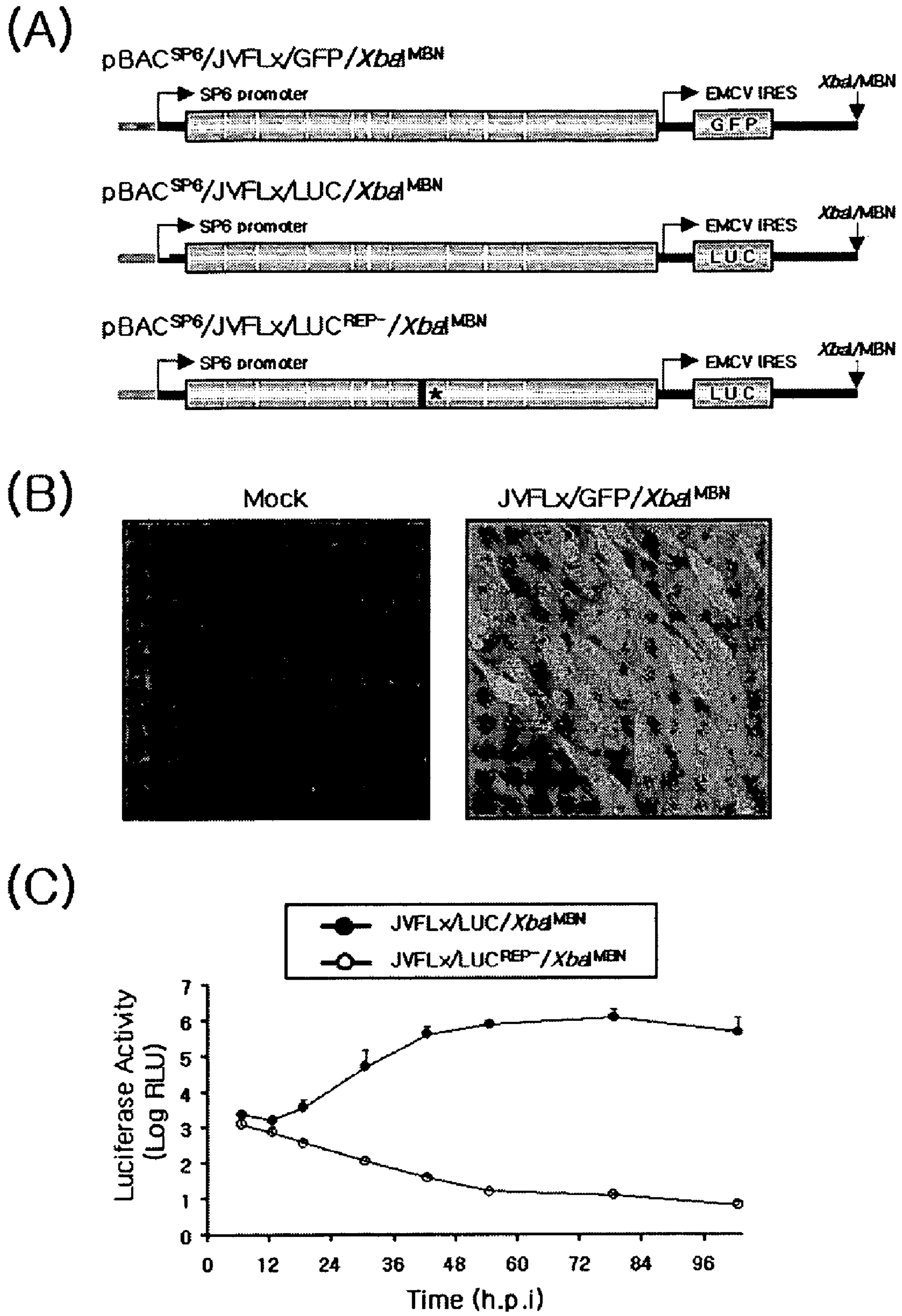

FIG. 8 is a set of diagrams, photographs, and a graph showing the expression of foreign genes with JEV cDNA as a vector. (A) Schematic diagram of the cDNA templates used for runoff transcription with SP6 RNA polymerase. Indicated are the encephalomyocarditis virus (EMCV) internal ribosome entry site (IRES)-driven GFP or LUC genes that were inserted at the beginning of the 3'NTR of the viral genome, the SP6 promoter transcription start, and the runoff site generated by Xba I digestion and MBN treatment (XbaI/MBN). In pBAC$^{SP6}$/JVFLx/LUC$^{REP-}$/XbaI$^{MBN}$, a solid vertical bar indicates an 83-nucleotide deletion (nt 5580-5663) in the middle of the NS3 gene that preterminates viral translation at nt 5596 (asterisk). (B) Expression of GFP protein. BHK-21 cells were mock-transfected (Mock) or transfected with 2 μg of synthetic RNAs transcribed from the pBAC$^{SP6}$/JVFLx/GFP/XbaI$^{MBN}$ template (JVFLx/GFP/XbaI$^{MBN}$), incubated for 30 hr, and then fixed and examined by confocal microscopy. (C) Induction of LUC protein. BHK-21 cells ($8\times10^6$) were mock-transfected or transfected with 2 μg of synthetic RNAs transcribed from the pBAC$^{SP6}$/JVFLx/LUC/XbaI$^{MBN}$ (●) or pBAC$^{SP6}$/JVFLx/LUC$^{REP-}$/XbaI$^{MBN}$ (○) templates, and seeded in a 6-well plate at a density of $6\times10^5$ cells per well. Cells were lysed at the indicated time points and LUC activity was determined. The standard deviations obtained from three independent experiments are indicated by error bars.

Figure 9:
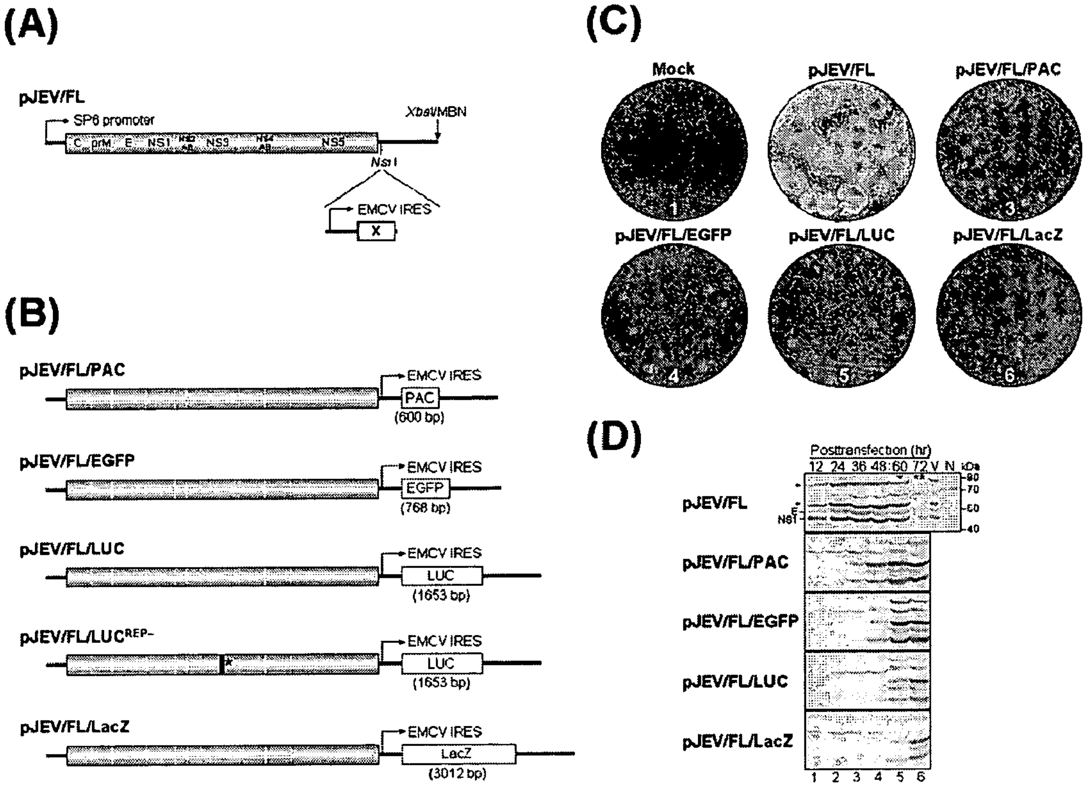

FIG. 9 shows the construction and characterization of heterologous gene-encoding infectious recombinant JEVs that are based on the bicistronic full-length infectious JEV cDNA that serves as a BAC. (A) Strategy to construct the infectious recombinant JEV cDNAs. The structure of the parental infectious JEV cDNA (pJEV/FL) is shown (Yun et al., *J. Virol.,* 2003, 77, 6450-6465). The viral ORFs are illustrated by thick solid lines at both termini that indicate the 5' and 3' NTRs of the viral genome. The additional expression unit driven by the EMCV IRES was inserted at the beginning of the 3'NTR using the unique natural Nsi I site. Indicated are the SP6 promoter transcription start site (SP6 promoter) and the runoff site generated by Xba I digestion and MBN treatment (XbaI/MBN). X indicates a foreign gene of interest. (B) The structures of the infectious recombinant JEV cDNAs constructed in the present invention are shown. Three commonly used reporters (EGFP, 768 bp; LUC, 1653 bp; and LacZ, 3012 bp) or a dominant selective marker PAC (600 bp) were engineered to be at the beginning of the 3'NTR. In case of the replication-competent pJEV/FL/LUC cDNA, the replication-incompetent pJEV/FL/LUC$^{REP-}$ cDNA was also used as a negative control by introducing an 83-nucleotide deletion (■) in the middle of the NS3 gene, which results in the premature termination of viral translation at nt 5596 (*) as previously described (Yun et al., *J. Virol.,* 2003, 77, 6450-6465). (C-D) Comparison of the infectiousness of the recombinant JEVs with that of the parent. BHK-21 cells ($8\times10^6$) were mock-transfected or transfected with 2 μg of the parent or recombinant JEV RNAs that had been transcribed from the relevant JEV cDNA, as indicated. (C) Representative plaques. The transfected cells were overlaid with agarose and stained 5 days later with crystal violet. (D) Viral protein accumulation. The transfected cells ($4\times10^5$) were lysed with 1× sample loading buffer at the indicated time points and the protein extracts were resolved on 10% SDS-polyacrylamide gels. The viral proteins were visualized by immunoblotting with JEV-specific mouse hyperimmune sera (Yun et al., *J. Virol.,* 2003, 77, 6450-6465). The positions of the viral proteins (E and NS1) and the cleavage-related intermediates are indicated by arrowheads on the left. Molecular mass markers in kDa are indicated on the right. V indicates JEV CNU/LP2-infected BHK-21 cells and N indicates naïve BHK-21 cells.

Figure 10:
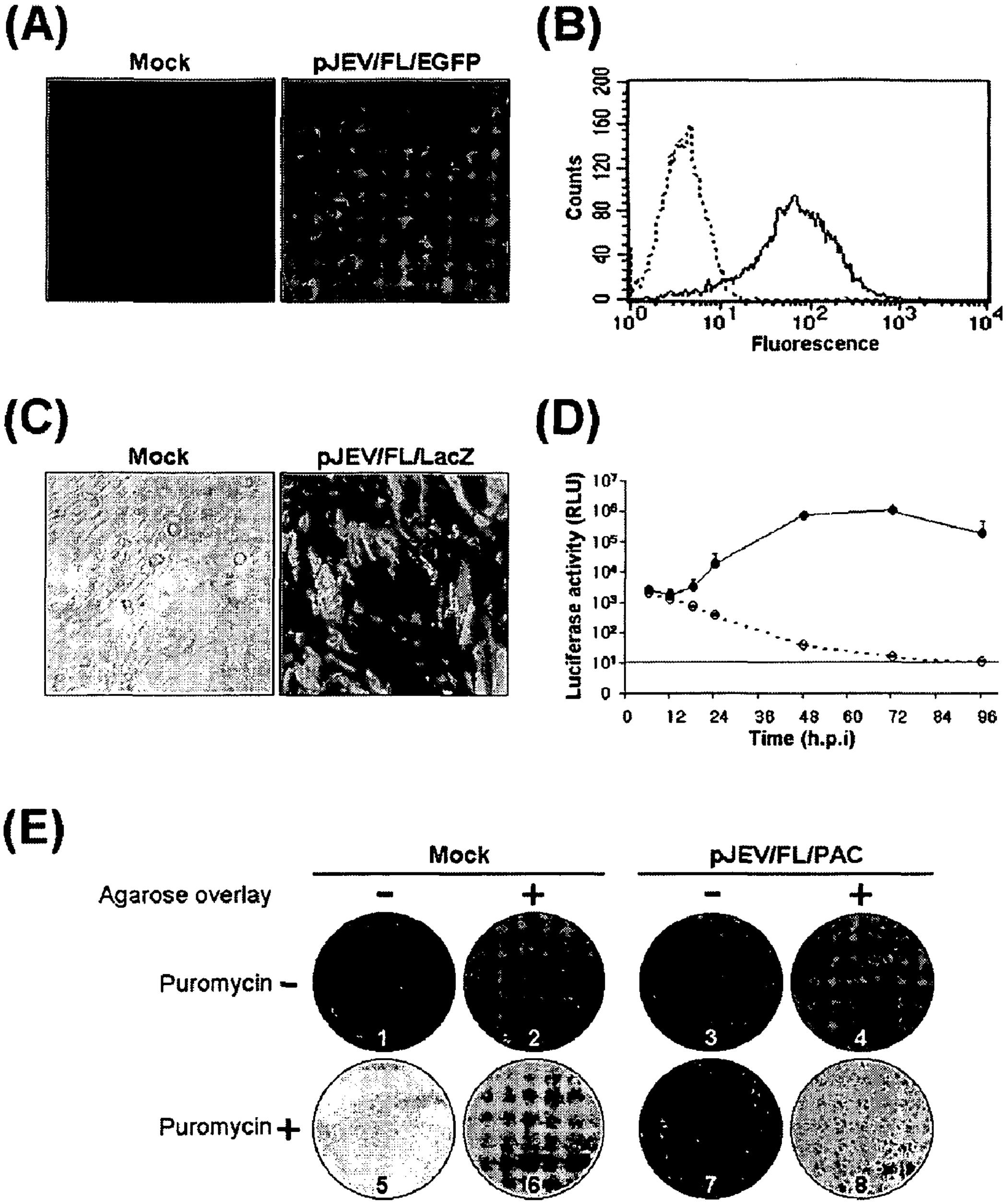

FIG. 10 shows the expression of the commonly used reporter genes and a dominant selective marker using infectious JEV cDNA as the vector. BHK-21 cells ($8\times10^5$) were mock-transfected or transfected with 2 μg of the parent or recombinant JEV RNAs that had been transcribed from each plasmid. (A-B) pJEV/FL/EGFP, (C) pJEV/FL/LacZ, (D) pJEV/FL/LUC or pJEV/FL/LUC$^{REP-}$, (E) pJEV/FL/PAC. (A-B) Expression of EGFP. The transfected cells were prepared 36 hr posttransfection for confocal microscopy (A) and flow cytometric analysis (B). — indicates JEV/FL/EGFP RNA-transfected cells and . . . indicates mock-transfected cells. (C) Expression of LacZ. The transfected cells were processed for X-gal staining 36 hr posttransfection. (D) Induction of LUC. The transfected cells were seeded on six-well plates at a density of $4\times10^5$ cells per well. At the indicated time points, the cell lysates were subjected to LUC assays. The experiments were done in triplicate and the mean values are shown by error bars. ● indicates JEV/FL/LUC RNA-transfected cells, ○ indicates JEV/FL/LUC$^{REP-}$ RNA-transfected cells, and — indicates the level of background luminescence of naïve cells. (E) Expression of PAC. The transfected cells were plated on a 6-well plate and incubated in complete media (dishes 1, 3, 5, and 7) or under a 0.5% agarose-containing overlay (dishes 2, 4, 6, and 8). After 2 days incubation, the plates were incubated for an additional 3 days in the presence of 10 μg/ml puromycin (dishes 5-8) or in its absence (dishes 1-4). The cells were then fixed and stained with crystal violet.

Figure 11A:
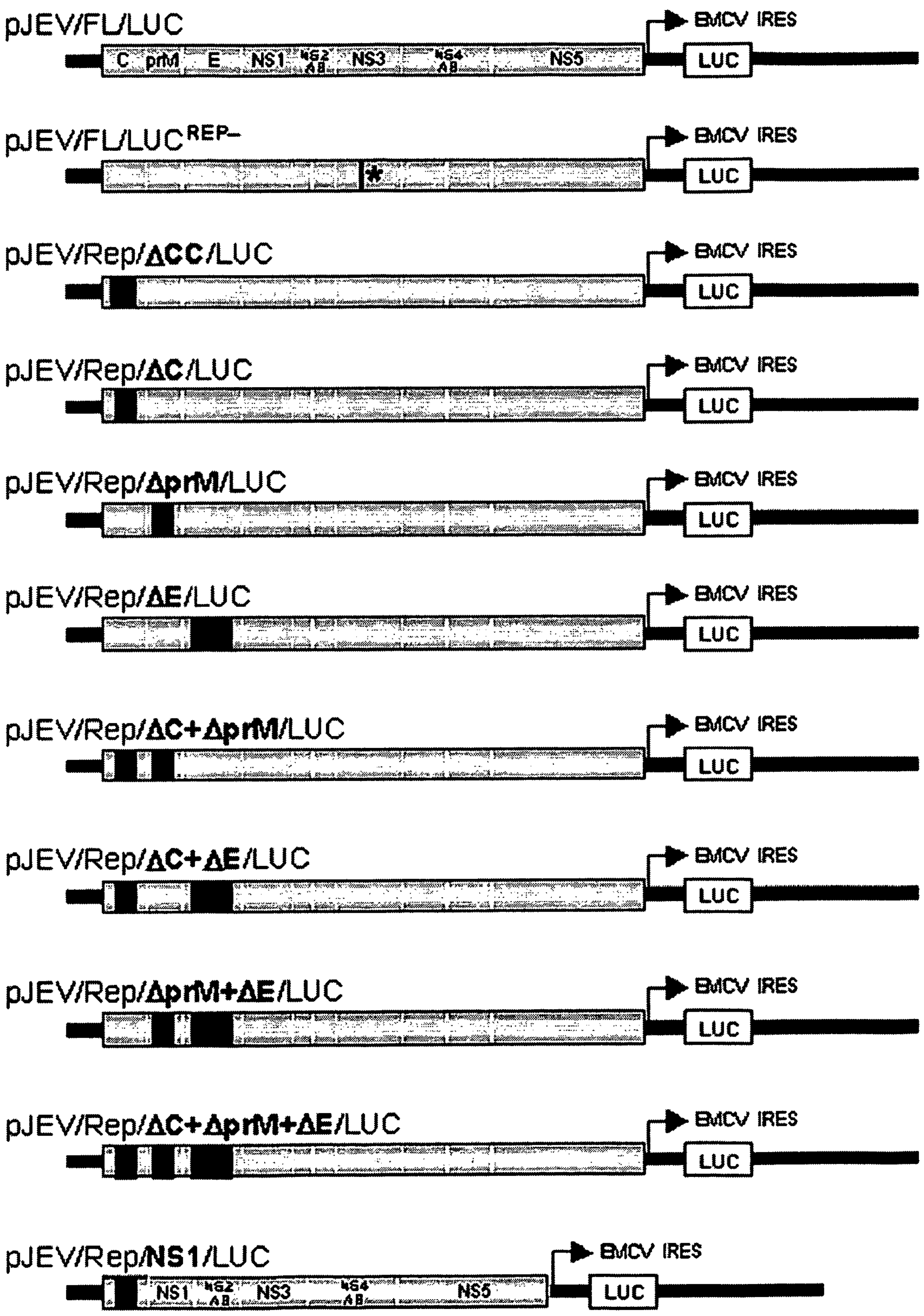
Figure 11B:
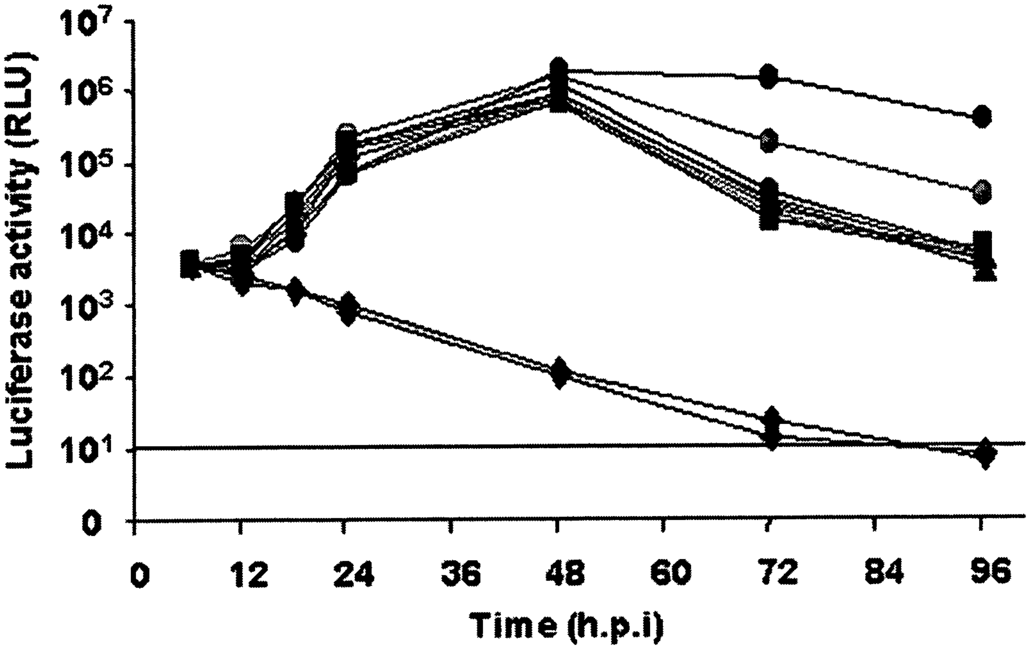
Figure 11C:
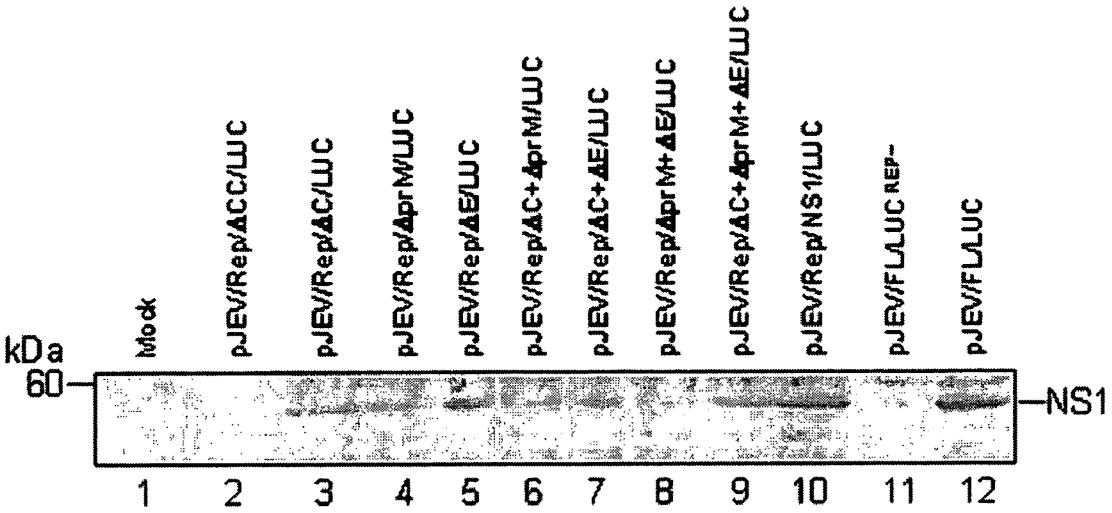

FIG. 11 shows the construction and vector characteristics of JEV viral replicons. (A) The structures of the JEV viral replicons are shown. Solid boxes (█) indicate in-frame deletions that had been introduced into the genome of the infectious pJEV/FL/LUC construct. Four constructs, namely, pJEV/Rep/ΔCC/LUC, pJEV/Rep/ΔC/LUC, pJEV/Rep/ΔprM/LUC, and pJEV/Rep/ΔE/LUC, contain a single in-frame deletion in each structural gene of JEV. pJEV/Rep/ΔCC/LUC has a deletion that extends to the proposed cyclization sequence motif in the 5' region of the C gene, unlike pJEV/Rep/ΔC/LUC. Three constructs, namely, pJEV/Rep/ΔC+ΔprM/LUC, pJEV/Rep/ΔC+ΔE/LUC, and pJEV/Rep/ΔprM+ΔE/LUC, contain double in-frame deletions, while pJEV/Rep/ΔC+ΔprM+ΔE/LUC bears triple in-frame deletions in all of the structural proteins. Also engineered was pJEV/Rep/NS1/LUC, which encodes the 35 N-terminal and 24 C-terminal amino acids of the C protein followed immediately by the N-terminus of the NS1 protein and the rest of the viral genome. (B) Induction of LUC. Naïve BHK-21 cells ($8\times10^6$) were transfected with 2 μg of the parent or JEV viral replicon RNAs that had been transcribed from each plasmid and then seeded on 6-well plates at a density of $4\times10^5$ cells per well. At the indicated time points, the cell lysates were subjected to LUC assays. The experiments were performed in triplicate and the mean values are shown. ● black, pJEV/FL/LUC; ♦ black, pJEV/FL/LUC$^{REP-}$; ♦ blue, pJEV/Rep/ΔCC/LUC; ■ blue, pJEV/Rep/ΔC/LUC; ▲ blue, pJEV/Rep/ΔprM/LUC; ● blue, pJEV/Rep/ΔE/LUC; ■ red, pJEV/Rep/ΔC+ΔprM/LUC; ▲ red, pJEV/Rep/ΔC+ΔE/LUC; ● red, pJEV/Rep/ΔprM+ΔE/LUC; ■ green, pJEV/Rep/ΔC+ΔprM+ΔE/LUC; ● green, pJEV/Rep/NS1/LUC. — indicates the level of background luminescence of naïve cells. (C) Viral protein accumulation. The transfected cells ($4\times10^5$) were lysed with 1× sample loading buffer 48 hr posttransfection and the protein extracts were resolved on 10% SDS-polyacrylamide gels. The proteins were transferred onto the nitrocellulose membrane and immunoblotted with JEV-specific mouse hyperimmune sera.

FIG. 12 shows the construction of the packaging system for JEV viral replicons. (A) Structures of the JEV structural protein expression cassettes based on the Sindbis virus-based expression vector. pSinRep19 is the double subgenomic non-cytopathic RNA vector. A foreign gene and the PAC gene are expressed by using separate subgenomic promoters, as indicated by arrows. The pSinRep19/JEV C-E cassette encodes the JEV C, prM, and E genes. The pSinRep19/JEV C-E-BglII cassette encodes the JEV C, prM, and E genes, followed by the N terminal 58 residues of NS1, whereas the pSinRep19/JEV C-NS1 bears a remnant of the NS1 gene. MCS indicates multiple cloning sites. (B) Western blot analysis of the JEV structural proteins expressed from three JEV structural protein expression cassettes. The BHK-21 cells were mock-transfected or transfected with each JEV structural protein expression vector RNA and lysates were obtained 48 hr later. Equivalent amounts of cell lysates were resolved by SDS-PAGE and probed with the JEV-specific hyperimmune sera. Indicated are the positions of viral proteins E and NS1 on the right and the molecular mass markers in kDa on the left. (C) Schematic representation showing how JEV VRPs can be generated by (i) co-transfection of the JEV structural protein expression vector RNAs with JEV viral replicon RNAs or (ii) transfection of the JEV structural protein-expressing PCLs with JEV viral replicon RNAs. (D-E) The production of JEV VRPs. Two approaches were taken. One approach is involved the cotransfection of naïve BHK-21 cells with two vector RNAs, namely, JEV structural protein expression vector RNA and the JEV viral replicon vector RNA indicated (D). The other approach involved JEV PCLs, which were transfected with the JEV viral replicon vector RNA indicated (E). The JEV viral replicon RNAs used were as follows: □ green, JEV/Rep/ΔC+ΔprM+ΔE/EGFP; ■ green, JEV/Rep/NS1/EGFP; □ blue, JEV/Rep/ΔC+ΔprM+ΔE/LacZ; ■ blue, JEV/Rep/NS1/LacZ; □ black, JEV/Rep/ΔC+ΔprM+ΔE/LUC; ■ black, JEV/Rep/NS1/LUC. The supernatants were collected 48 hr posttransfection and used to infect naïve BHK-21 cells for the titration of VRPs and the examination of the respective reporter gene expression. — indicates the level of background luminescence of naïve cells.

EXAMPLES

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1

Isolation of JEV Viruses

<1-1> Cell Lines and Viruses

BHK-21 cell line was provided from Dr. Charles M. Rice of the Rockefeller University, and maintained in alpha minimal essential medium (MEM) supplemented with 10% fetal bovine serum (FBS), 2 mM L-glutamine, vitamins, and antibiotics. All reagents used in cell culture were purchased from Gibco/BRL Life Technologies, Inc., Gaithersburg, Md. The Korean JEV strain K87P39 (Chung et al., *Am. J. Trop. Med. Hyg.,* 1996, 55, 91-97) was obtained from the Korean National Institute of Health. This JEV K87P39 was isolated from wild mosquitoes in Korea in 1987 and underwent five passages in suckling mouse brains. The YF17D yellow fever virus strain was generated from the infectious cDNA pACNR/YF17D (provided from Dr. Charles M. Rice) by SP6 polymerase runoff transcription as described bellow.

<1-2> Plaque Purification

Figure 1:
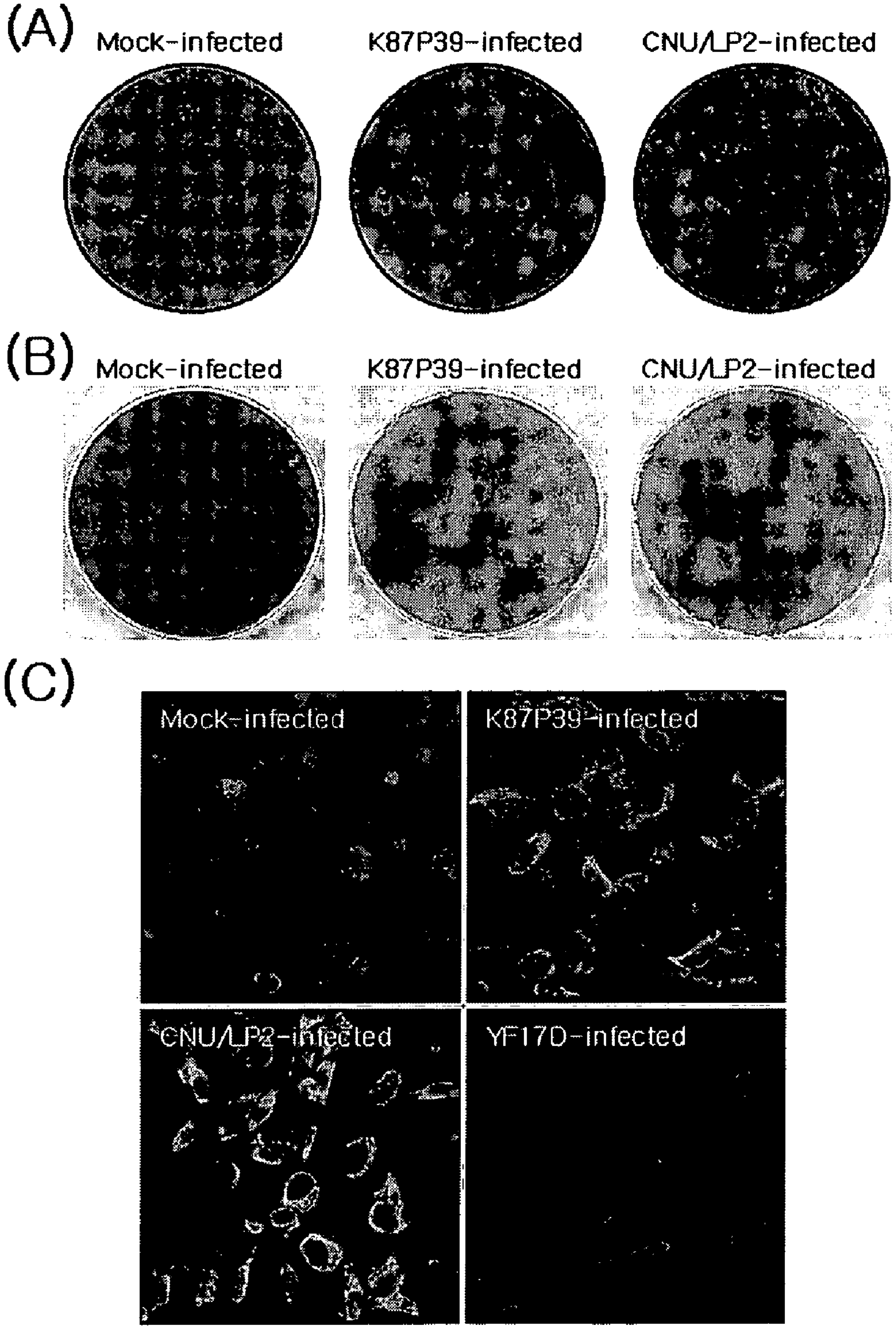
FIG. 1 is a set of photographs showing the comparison of large-plaque-forming JEV isolate CNU/LP2 and original K87P39 strain. (A-B) A set of photographs showing plaque morphology using BHK-21 cells (A) or Vero cells (B). BHK-21 (A) or Vero (B) cells were mock infected (Mock-infected) or infected with the original JEV K87P39 strain (K87P39-infected), which formed a heterogeneous mixture of viral plaque sizes. The CNU/LP2 isolate purified in the present invention formed a homogeneous population of large plaques (CNU/LP2-infected). (C) Levels and patterns of JEV protein expression. BHK-21 cells were mock infected or infected with K87P39, CNU/LP2 or the yellow fever virus strain YF17D. Eighteen hours later, they were fixed and stained with JEV-specific mouse hyperimmune ascites followed by fluorescein isothiocyanate-conjugated goat anti-mouse immunoglobulin G (green fluorescence) and confocal microscopy. Nuclei were visualized by staining with propidium iodide (red fluorescence) in the presence of RNase A.

Cells infected with the JEV K87P39 strain were overlaid with MEM containing 10% fetal bovine serum and 0.5% SeaKem LE agarose (FMC BioProducts, Rockland, Me.) and incubated in a 5% $CO_2$, 37° C. incubator for 3 to 4 days. After being cultured for 3 to 4 days, the infected cells were fixed with 3.7% formaldehyde at room temperature for 4 hr. Then, agarose covering the cells was removed. Plaques were visualized by crystal violet staining. As a result, K87P39 strain formed a heterogeneous mixture of viral plaque sizes (FIG. 1A, K87P39-infected).

Consequently, the present inventors performed the plaque purification assay with BHK-21 cells to isolate a homogeneous population of a large-plaque-forming variant that the present inventors named CNU/LP2. BHK-21 cells infected with the JEV K87P39 strain were overlaid with MEM containing 10% fetal bovine serum and 0.5% SeaKem LE agarose and incubated in a 5% $CO_2$, 37° C. incubator for 3 to 4 days. Individual plaques were picked with sterile Pasteur pipettes and resuspended in 1 Ml of MEM. Viruses were eluted from the agarose at 4° C. for 2 hr. The eluate was amplified only once in BHK-21 cells and stored at −80° C.

Plaque assay was performed to compare the viral plaque sizes of susceptible BHK-21 cells infected with JEV K87P39 and JEV CNU/LP2 strains. As a result, the viral plaque sizes of susceptible BHK-21 cells infected with K87P39 varied (FIG. 1A, K87P39-infected). On the other hand, the CNU/LP2 purified in the present invention formed a homogeneous population of large plaques (FIG. 1A, CNU/LP2-infected). In addition, similar plaque morphologies were also observed when Vero cells were infected with JEV K87P39 and JEV CNU/LP2 strains (FIG. 1B).

<1-3> Immunofluorescence

In order to examine JEV expression in infected BHK-21 cells by confocal microscopy, cells ($2\times10^5$) were seeded in a four-well chamber slide, incubated for 12 hr, and then mock-infected or infected at an MOI of 1 for 18 hr with either the original JEV K87P39 strain, the JEV CNU/LP2 isolate, or the YF17D strain. Immunostaining for JEV viral proteins was accomplished by first fixing the cells by incubation in phosphate-buffered saline (PBS) containing 0.37% (v/v) formaldehyde for 30 min at 25° C. The cells were then washed three times with PBS and permeabilized for 10 min at 37° C. with PBS containing 0.2% (v/v) Triton X-100. Thereafter, the cells were washed four times with PBS, rehydrated in PBS for 15 min, and blocked for 1 hr at 37° C. with PBS containing 5% (w/v) bovine serum albumin (BSA). The cells were then incubated for 2 hr at 25° C. with 1:500-diluted mouse hyperimmune ascites fluid specific for JEV, washed three times with PBS, incubated for 2 hr at 25° C. with 1:500-diluted FITC-conjugated goat anti-mouse IgG (Jackson ImmunoResearch Labs Inc.), and washed again three times with PBS. Thereafter, the cells were incubated for 30 min at 37° C. in PBS containing 5 μg/Ml of propidium iodide and 5 μg/Ml of RNase A to localize the nuclei and mounted with 0.2 ml of 80% glycerol. Images were acquired on a Zeiss Axioskop confocal microscope equipped with a 63× objective with a Bio-Rad MRC 1024 and LaserSharp software.

Confocal microscopy with anti-JEV hyperimmune ascites revealed that CNU/LP2-infected BHK-21 cells expressed JEV viral proteins around the perinuclear membranes (FIG. 1C, CNU/LP2-infected), similar to K87P39-infected cells (FIG. 1C, K87P39-infected). This fluorescence staining was not observed in mock-infected BHK-21 cells (FIG. 1C, Mock-infected). As a negative control, BHK-21 cells infected with yellow fever virus 17D, a flavivirus closely related to JEV, did not stain with anti-JEV hyperimmune ascites (FIG. 1C, YF17D-infected). CNU/LP2 infection of a variety of animal cell lines, including the neuronal SHSY-5Y(human) and B103 (mouse) cell lines and the normeuronal Vero(monkey) and MDCK (dog) cell lines, resulted in high virus titers ($10^6$-$10^7$ PFU/Ml) in the culture supernatants. Thus, the present inventors decided to use CNU/LP2 as the parental strain for developing a reverse genetics system for JEV.

Example 2

Complete Nucleotide Sequence Analysis of JEV CNU/LP2 Genomic RNA

Figure 2:
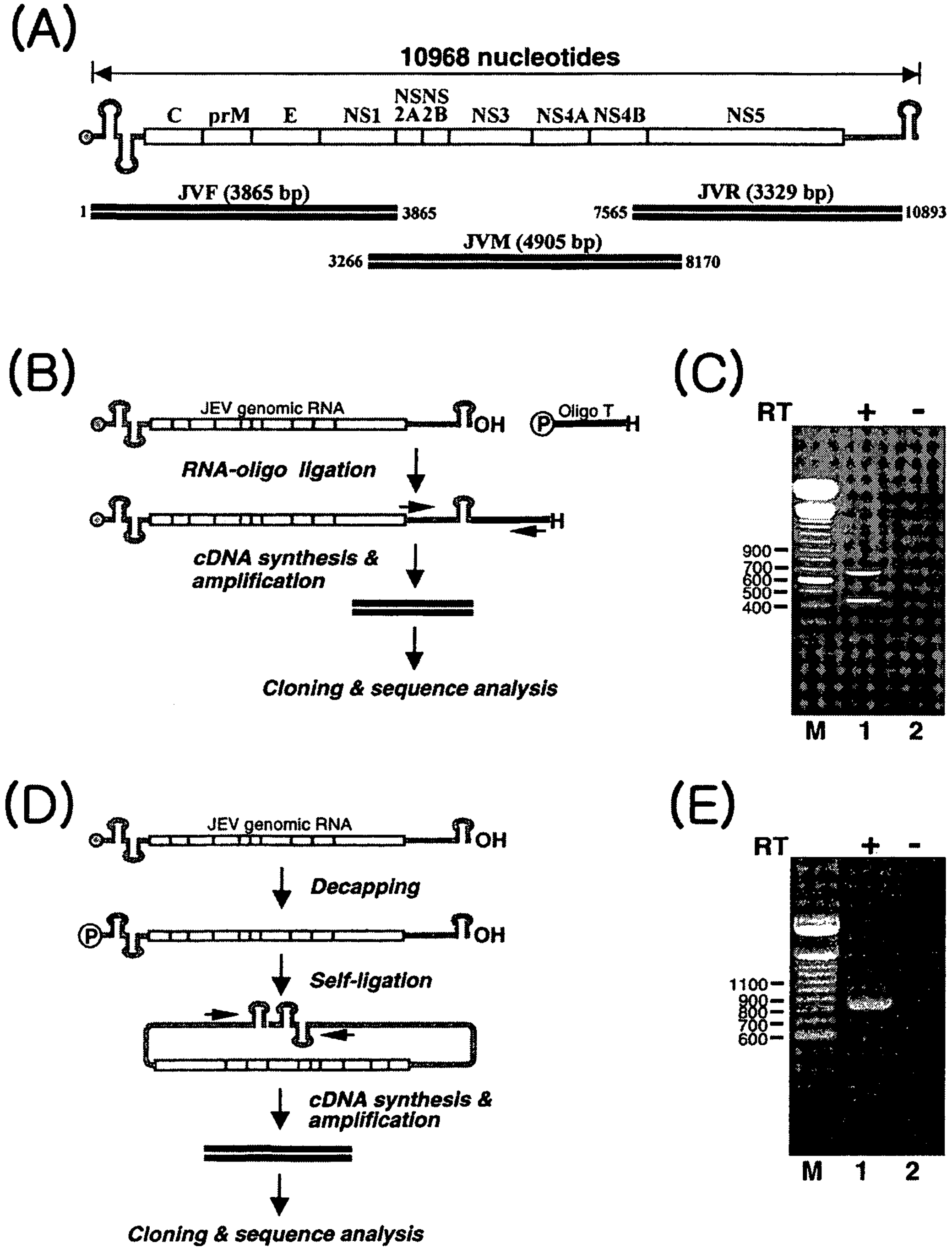
FIG. 2 is a set of diagrams and a pair of electrophoresis photographs showing strategies used to sequence genomic RNA of CNU/LP2. (A) A schematic diagram showing the RT-PCR amplification of three overlapping cDNA amplicons representing the entire JEV genomic RNA apart from the 5' and 3' termini. RNA is indicated in gray, and cDNA is indicated by solid parallel lines. The top panel schematically depicts the CNU/LP2 JEV genomic RNA (10,968 base pairs in length). The bottom panels portray the three overlapping cDNAs, JVF (nt 1 to 3865), JVM (nt 3266 to 8170), and JVR (nt 7565 to 10893). (B) A schematic diagram showing the procedure to sequence the 3' end of CNU/LP2 genomic RNA. The 5'-phosphorylated and 3'-blocked oligonucleotide T (Oligo T) was ligated to the 3' end of JEV genomic RNA by T4 RNA ligase, and the resulting RNA was then used for cDNA synthesis and amplification with the primers indicated by arrows. The resulting products were cloned and sequenced. (C) An electrophoresis photograph showing the JEV-specific amplicons synthesized from the oligonucleotide T-ligated JEV genomic RNA described in (B). First-strand cDNA was synthesized with oligonucleotide TR, complementary to oligonucleotide T, and the RT reaction was carried out in the presence (lane 1) or absence (lane 2) of Superscript II reverse transcriptase. The cDNA was amplified with oligonucleotide TR and primer J35, which is complementary to nt 10259 to 10276. The expected size of the PCR product is 727 base pairs. The products were separated on a 1.2% agarose gel and visualized by staining with ethidium bromide (EtBr). (D) A schematic diagram showing the procedure to sequence the 5' end of CNU/LP2 genomic RNA. The cap structure of viral genomic RNA was removed with tobacco acid pyrophosphatase, and the decapped viral RNA was then self-ligated with T4 RNA ligase and used for cDNA synthesis and amplification. The resulting amplified products were cloned and sequenced. (E) An electrophoresis photograph showing the JEV-specific amplicons synthesized from the self-ligated JEV genomic RNA described in (D). First strand cDNA synthesis was carried out with primer J40, which is complementary to nt 215 to 232. The RT reaction was performed in the presence (lane 1) or absence (lane 2) of Superscript II reverse transcriptase. The cDNA was amplified with primer J35 and primer J39, which is complementary to nt 164 to 181. The expected size of the PCR product is 890 base pairs. The amplified products were separated on a 1.2% agarose gel and visualized by staining with EtBr. Lane M indicates a 100-bp DNA size ladder marker (in base pairs).

Viral genomic RNA was extracted from 100 μl of virus-containing culture fluid with 300 μl of TRIzol LS reagent as recommended by the manufacturer (Gibco/BRL) and then resuspended in 20 μl of RNase-free water. To analyze the complete nucleotide sequence of the viral genomic RNA, five overlapping cDNAs (JVF, JVM, JVR, JV3NTR, and JV35NTR) representing the entire viral RNA genome were amplified by long RT-PCR (FIG. 2). Oligonucleotides used for cDNA synthesis and amplification were designed according to the consensus sequence of all 16 fully sequenced JEV RNA genomes available from the GenBank database (CH2195LA, CH2195SA, FU, GP78, HVI, JaGArOl, JaOArS982, K94P05, Vellore P20778, p3, SA(A), SA(V), SA14, SA14-14-2, TC, and TL strains).

<2-1> Nucleotide Sequence Analysis of JEV CNU/LP2 Genomic RNA

For JVF amplicons (nt 1-3865), primer J7, represented by SEQ. ID. No 1 and complementary to nt 3986-4003 of the JEV genome, was used for cDNA synthesis (FIG. 2A). The primers for PCR amplification were primer J8 represented by SEQ. ID. No 2 and complementary to nt 1-18, and primer J6 represented by SEQ. ID. No 3 and complementary to nt 3845-3865. For JVM amplicons (nt 3266-8170), primer J4, represented by SEQ. ID. No 4 and complementary to nt 8150-8170 of the JEV genome, was used for cDNA synthesis. The primers for PCR amplification were primer J20 represented by SEQ. ID. No 5 and complementary to nt 3266-3283, and primer J4. For JVR amplicons (nt 7565-10893), primer J1, represented by SEQ. ID. No 6 and complementary to nt 10947-10967 of the JEV genome, was used for cDNA synthesis. The primers for PCR amplification were primer J12 represented by SEQ. ID. No 7 and complementary to nt 7565-7582, and primer J2 represented by SEQ. ID. No 8 and complementary to nt 10870-10893. The standard RT reaction was conducted in a 20-μl reaction mixture containing 10 μl of extracted viral RNA, 5 p mol of the appropriate primer, 100 U of Superscript II reverse transcriptase (Gibco/BRL), 40 U of RNaseOUT (Gibco/BRL), 0.1 mM dithiothreitol (DTT), 10 mM deoxynucleotide triphosphate (dNTP) mix, and the RT buffer supplied by the manufacturer (Gibco/BRL) The reaction mixture was incubated at 37° C. for 1 hr and then heated at 70° C. for 15 min. A 5-μl aliquot of the RT mixture was subsequently used for PCR amplification with Pyrobest DNA polymerase (Takara Bio Inc., Shiga, Japan) and the appropriate primer pair. The PCRs were performed with 30 cycles of denaturation at 94° C. for 30 sec, annealing at 60° C. for 30 sec, and extension at 72° C. for 5 min, followed by a final extension at 72° C. for 10 min. To avoid the selection bias that can occur due to cloning, the uncloned materials of the amplified products were directly sequenced in both directions with an automatic 3700 DNA sequencer. Sequencing analysis with two independently isolated preparations of viral RNA resulted in identical sequences.

As a result, the complete nucleotide sequence of the entire viral genome of JEV CNU/LP2 except for 3'- and 5'-terminal regions was determined and represented by SEQ. ID. No 9.

<2-2> Determination of 3'-Terminal Sequence of JEV CNU/LP2 Genomic RNA

In order to sequence the 3'-terminal sequences of the JEV CNU/LP2 genomic RNA, a synthetic oligonucleotide T represented by SEQ. ID. No 10 was ligated to the 3' end of the viral genomic RNA to provide a primer-binding site for cDNA synthesis and PCR amplification (Kolykhalov et al., *J. Virol.,* 1996, 70, 3363-3371). The 3' end of oligonucleotide T was first modified by incorporating ddATP with terminal deoxynucleotidyltransferase (Takara), which blocks the intramolecular and intermolecular ligation of oligonucleotide T. The 5' end of oligonucleotide T was also phosphorylated with T4 polynucleotide kinase (Takara). Thereafter, the modified oligonucleotide T was ligated to the 3' end of the viral genomic RNA by T4 RNA ligase (New England Biolabs, Inc., Beverly, Mass.). The 20 μl of ligation reaction mixture contained 10 U of T4 RNA ligase, 40 U of RNaseOUT, 10 p mol of oligonucleotide T, viral genomic RNA, and the buffer supplied by the manufacturer (NEB). After incubation at 16° C. for 12 hr, the ligated viral RNA was phenol extracted, precipitated with ethanol, and resuspended with 20 μl of RNase-free water. Subsequently, 10 μl of the oligonucleotide-ligated viral RNA was used for cDNA synthesis with oligonucleotide TR represented by SEQ. ID. No 11, which is complementary to oligonucleotide T, as previously described. First-strand cDNA was amplified with primer J35 represented by SEQ. ID. No 12 and complementary to nt 10259 to 10276, and primer TR. For PCR, 5 μl aliquot of the RT reaction mixture was amplified with Pyrobest DNA polymerase and 30 cycles of 30 sec at 94° C., 30 sec at 60° C., and 1 min at 72° C., followed by a final extension of 10 min at 72° C. The PCR mixtures were as described above. The cDNA amplicons designated as JV3NTR were cloned into the pRS2 vector (provided by Dr. Charles M. Rice) with Hind III and EcoR I sites incorporated in the positive-sense and negative-sense primers, respectively (FIG. 2B).

As a result of agarose gel electrophoresis, it was revealed that the amplified products migrated as two bands, a larger band of approximately 700 bp and a smaller band of about 450 bp (FIG. 2C). Both bands were purified and cloned, and 20 and 10 randomly picked clones containing the larger and the smaller bands, respectively, were sequenced. As has been documented for most of the fully sequenced JEV isolates, the present inventors found that all the clones with the larger insert (about 700 bp) terminated the viral genome with -GATCT$^{10968}$. In contrast, all the clones with the smaller insert (about 450 bp) showed the viral genome truncated at nt 10684, resulting in a band 284 bp shorter. During assembly of the full-length JEV cDNA, the present inventors used the nucleotide sequences of the larger insert because the smaller insert did not contain 284 nucleotides at the 3' end of the viral genome.

<2-3> Determination of 5'-Terminal Sequence of JEV CNU/LP2 Genomic RNA

The 5'-terminal sequence of JEV CNU/LP2 genomic RNA was determined by self-ligation of viral RNA (Campbell and Pletnev, *Virology,* 2000, 269, 225-237). The cap structure of viral genomic RNA was first cleaved off with tobacco acid pyrophosphatase (TAP). The cleavage reaction mixture (20 μl) contained 10 U of TAP (Epicentre Technology Co., Madison, Wis.), 10 μl of viral RNA, and the buffer supplied by the manufacturer (Epicentre Technology Co.). After incubation at 37° C. for 1 hr, the TAP-treated viral RNA was subjected to phenol extraction and ethanol precipitation, and resuspended with 20 μl of RNase-free water. Half (10 μl) of the decapped viral RNA was self-ligated in a 20-μl reaction mixture with T4 RNA ligase as described above. A quarter (5 μl) of the self-ligated viral RNA was used for cDNA synthesis with primer J40, represented by SEQ. ID. No 13 and complementary to nt 215 to 232. First-strand cDNA was PCR amplified with primer J39 represented by SEQ. ID. No 14 and complementary to nt 164 to 181, and primer J35 (FIG. 2D). Agarose gel electrophoresis revealed the amplified products as a single band of about 850 bp (FIG. 2E). The amplified cDNA amplicons (JV35NTR) were digested with Apo I and Spe I, and ligated into the pRS2 vector which had been digested with Apo I and Xba I, leading to construct pRS2/JV3'5'.

To sequence the 5'-terminal sequences of the JEV CNU/LP2 genomic RNA, 12 randomly picked clones were sequenced. In all 12 clones, the present inventors found that the -GATCT$^{10968}$ of the viral 3'-terminal sequence was followed by the 5'-terminal sequence $^{1}$AGAAGT- (FIGS. 2B and 2C). Identical results were also obtained by direct cycle sequencing of uncloned material. Thus, the present inventors have determined the complete nucleotide sequence of the CNU/LP2 isolate and confirmed that the sequence is represented by SEQ. ID. No 15.

Example 3

Construction of Full-length Infectious cDNAs for JEV

During our initial attempts to clone the cDNA of the CNU/LP2 RNA genome, it became apparent that a particular region of the viral genome was not compatible with cloning in high-copy-number plasmids in *E. coli* because the cloned DNA underwent genetic rearrangements. These difficulties have also been reported for other flaviviruses (Campbell and Pletnev, *Virology,* 2000, 269, 225-237; Polo et al., *J. Virol.,* 1997, 71, 5366-5374; Gritsun and Gould, *Virology,* 1995, 214, 611-618; Sumiyoshi et al., *J. Infect. Dis.,* 1995, 171, 1144-1151; Sumiyoshi et al., *J. Virol.,* 1992, 66, 5425-5431; Rice et al., *New Biol.,* 1989, 1, 285-296). Attempts to clone this region into a low-copy-number bacterial plasmid were also unsuccessful due to genetic instability together with a low DNA yield. Thus, the present inventors used the bacterial artificial chromosome (BAC) plasmid pBeloBAC11 as a vector to house full-length infectious cDNAs for JEV.

<3-1> Subcloning of Three Long Overlapping JEV cDNA Amplicons

The present inventors used recombinant DNA techniques according to standard procedures (Sambrook et al., *Molecular cloning,* 1989, Cold Spring Harbor Laboratory). First, three overlapping cDNA amplicons (JVF, JVM and JVR) originally used for complete nucleotide sequence analysis were subcloned into pBAC/SV represented by SEQ. ID. No 42, a derivative of the pBeloBAC11 plasmid. The pBAC/SV plasmid contains the 491-bp Not I-Aat II (T4 DNA polymerase-treated) fragment of pACNR/NADL (Mendez et al., *J. Virol.,* 1998, 72, 4737-4745), the 9,215-bp Sac I (T4 DNA polymeras-treated)-Ssp I (T4 DNA polymerase-treated) fragment of pSINrep19 (Frolov et al., *Proc. Natl. Acad. Sci., USA.,* 1996, 93, 11371-11377), and the 6,875-bp Sfi I (T4 DNA polymerase-treated)-Not I fragment of pBeloBAC11. Thus, the 3,863-bp Rsr II-Avr II fragment of the JVF amplicons, the 4,717-bp BspE I-Mlu I fragment of the JVM amplicons, and the 3,326-bp Rsr II-Bgl II fragment of the JVR amplicons were inserted into the pBAC/SV plasmid, which had been digested with the same enzymes. This led to the pBAC/JVF, pBAC/JVM, and pBAC/JVR subclone constructs, respectively. These BAC plasmids were grown in *E. coli* DH10B cells and sequenced. The nucleotide sequences of the cloned cDNAs were identical to that of CNU/LP2 with the exception of a point mutation, $T^{8906}$→C (silent), within the NS5 gene in pBAC/JVR. The $T^{8906}$→C substitution was translationally silent and must have arisen during the cloning because sequencing of eight randomly picked individual clones revealed a T residue at nt 8906. Although the $T^{8906}$→C substitution does not alter the corresponding amino acid, it is possible that this change could affect viral replication (van Dinten et al., *Proc. Natl. Acad. Sci. USA,* 1997, 94, 991-996), and thus the present inventors corrected this substitution back to a T residue. The $T^{8906}$→C substitution was corrected by recloning a 315-bp Apa I-Hind III fragment corresponding to nt 8827 to 9142, leading to the construct pBAC/JVRR. During their manipulation and propagation in the *E. coli* strain DH10B, all three subcloned JEV cDNAs remained genetically stable.

<3-2> Insertion of SP6 Promoter into the 5' End of the Full-Length JEV cDNA

In order to facilitate the precise adjoining of the bacteriophage SP6 promoter transcription start to the 5' end of the full-length JEV cDNA, the present inventors modified the pBAC/JVF. First, two fragments were isolated by PCR of pBAC/SV with primer J41 represented by SEQ. ID. No 16 and primer J43 represented by SEQ. ID. No 17, which incorporates the negative-sense sequence of the SP6 promoter and PCR of pBAC/JVF with primer J42 represented by SEQ. ID. No 18 and primer J40 represented by SEQ. ID. No 19. These two fragments were fused by a second round of PCR with primers J41 and J40. The resulting amplicons were digested with Pac I and Pme I, and ligated with pBAC/JVF which had been digested with the same two enzymes. This produced $pBAC^{SP6}$/JVF.

<3-3> Construction of Full-Length JEV cDNAs Containing SP6 Promoter

In order to generate an authentic or nearly authentic 3' terminus during runoff transcription of plasmid linearized at the 3' end of the viral genome, the present inventors modified pBAC/JVRR so that the nucleotide sequence of the authentic 3' terminus was followed by a unique restriction endonuclease recognition site, either Xho I or Xba I. To create the pBAC/JVRR/XhoI subclone containing a unique Xho I site at the end of the viral genome, fragment I was synthesized by PCR amplification of pRS2/JV3'5' with primer J90 represented by SEQ. ID. No 20 and primer J45 represented by SEQ. ID. No 21, which incorporates an Xho I site. The 298-bp Sfi I-Spe I portion of fragment I amplicons was ligated with pBAC/JVRR which had been digested with Sfi I and Nhe I. To create pBAC/JVRRx/XbaI, which has an Xba I site at the end of the viral genome, the existing Xba I site at nt 9,131 to 9,136 within the NS5 gene was first inactivated by introducing a silent point mutation ($A^{9134}$→T) by PCR. In this construct, the “x” denotes the presence of the silent point mutation ($A^{9134}$→T) that destroyed the original Xba I site. Particularly, PBAC/JVRR was amplified with primer J31 represented by SEQ. ID. No 22 and primer J47 represented by SEQ. ID. No 23, which incorporated the $A^{9134}$ →T substitution. The 315-bp Apa I-Hind III portion of the cDNA amplicons, corresponding to nt 8,828 to 9,143, was cloned into pBAC/JVRR, leading to the construct pBAC/JVRRx. Subsequently, pBAC/JVRRx/XbaI was constructed in the same manner as described for pBAC/JVRR/XhoI. Thus, fragment II was obtained by PCR amplification of pRS2/JV3'5' with primer J90 and primer J46 represented by SEQ. ID. No 24, which incorporated an Xba I site. The 298-bp Sfi I-Spe I portion of the fragment II amplicons was then ligated into pBAC/JVRRx which had been digested with Sfi I and Nhe I. To create pBAC/JVRRx/XhoI containing a unique Xho I site and the $A^{9134}$→T substitution, the 298-bp Sfi I-Spe I portion of fragment I amplicons was ligated into pBAC/JVRRx which had been digested with Sfi I and Nhe I.

Figure 3:
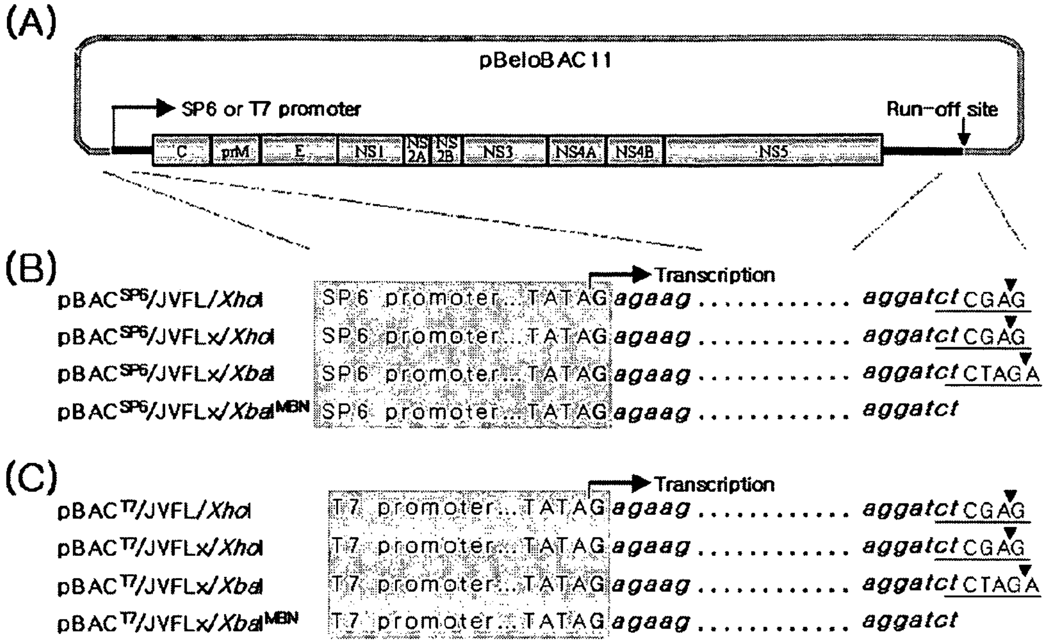
FIG. 3 is a set of diagrams showing the construction of full-length JEV cDNA clones in bacterial artificial chromosome (BAC) pBeloBAC11. (A) A schematic diagram of the full-length JEV cDNAs constructed in pBeloBAC11. Viral proteins are shown with thick solid lines at both termini representing the 5' and 3' NTRs of the viral genome. The SP6 and T7 promoter transcription start sites and the unique restriction endonuclease recognition site ensuring runoff transcription are shown at the 5' and 3' ends, respectively. (B-C) A set of schematic diagrams showing the 5' and 3' termini of full-length JEV cDNA clones. Nucleotide sequences of JEV genomic RNA are shown as bold italic lowercase letters. Illustrated are the 5' termini of four SP6-driven (B) and four T7-driven (C) full-length JEV cDNA templates (SEQ. ID. No: 68). To produce SP6 and T7 RNA polymerase runoff products, the 3' termini of two SP6-driven (B, pBAC$^{SP6}$/JVFL/XhoI and pBAC$^{SP6}$/JVFLx/XhoI) and two T7-driven (C, pBAC$^{T7}$/JVFL/XhoI and pBAC$^{T7}$/JVFLx/XhoI) JEV cDNA templates were linearized by Xho I digestion (SEQ. ID. No: 69), resulting in three nucleotides (CGA) of virus-unrelated sequence at the 3' ends. Similarly, the cutting of the 3' termini of an SP6-driven (B, pBAC$^{/SP6}$/JVFLx/XbaI) and a T7-driven (C, pBAC$^{T7}$/JVFLx/XbaI) JEV cDNA template with Xba I resulted in four nucleotides (CTAG) of virus-unrelated sequence at the 3' ends (SEQ. ID. NO: 70). In contrast, the authentic 3' end of JEV genomic RNA was present when SP6-driven (B, pBAC$^{SP6}$/JVFLx/XbaI$^{MBN}$) and T7-driven (C, pBAC$^{T7}$/JVFLx/XbaI$^{MBN}$) JEV cDNA templates were linearized by Xba I digestion and then treated with mung bean nuclease (MBN) to remove the unrelated single-stranded sequences (SEQ. ID. No: 71). Underlined is the restriction endonuclease recognition site introduced at the 3' end of the viral genome. An arrowhead indicates a cleavage site.

Thus, the present inventors constructed five plasmids, $pBAC^{SP6}$/JVF, pBAC/JVM, pBAC/JVRR/XhoI, pBAC/JVRRx/XbaI, and pBAC/JVRRx/XhoI. These plasmids contained contiguous regions of the JEV genome and could now be used to assemble three different full-length JEV cDNAs (FIG. 3). First, the $pBAC^{SP6}$/JVFM subclone was constructed by ligating together the 4,717-bp BspE I-Mlu I fragment of pBAC/JVM, the 8,970-bp BspE I-Xba I fragment of $pBAC^{SP6}$/JVF, and the 3,670-bp Xba I-Mlu I fragment of pBAC/SV. Subsequently, two fragments of $pBAC^{SP6}$/JVFM (the 8,142-bp Pac I-Sap I fragment and the 4,801-bp Pac I-BsrG I fragment) were ligated with either i) the 5,620-bp Sap I-BsrG I fragment of pBAC/JVRR/XhoI to generate $pBAC^{SP6}$/JVFL/XhoI, ii) the 5,622-bp Sap I-BsrG I fragment of pBAC/JVRRx/XbaI to generate $pBAC^{SP6}$/JVFLx/XbaI, or iii) the 5,620-bp Sap I-BsrG I fragment of pBAC/JVRRx/XhoI to generate $pBAC^{SP6}$/JVFLx/XhoI. Finally, three assembled full-length JEV cDNAs were designated $pBAC^{SP6}$/JVFL/XhoI, $pBAC^{SP6}$/JVFLx/XhoI, and $pBAC^{SP6}$/JVFLx/XbaI and represented by SEQ. ID. No 43, No 44, and No 45, respectively (FIG. 3B). These cDNA clones all had the SP6 promoter transcription start at the beginning of the viral genome so that synthetic RNA transcripts with an authentic 5' end would be generated through in vitro transcription using SP6 RNA polymerase (FIG. 3B, gray box). To ensure that the 3' end of the viral genome after runoff transcription would be close to authentic, the present inventors placed a unique restriction endonuclease recognition site, either Xho I or Xba I, at the end of the viral genome (FIG. 3B, underlined). Thus, $pBAC^{SP6}$/JVFL/XhoI bears an Xho I site at the end of the viral genome. For the construct with an Xba I site immediately at the end of viral genome, as the viral genome already contains an Xba I site in the NS5 gene, this site had to be destroyed by introducing a silent point mutation ($A^{9134}$→T). This construct was designated $pBAC^{SP6}$/JVFLx/XbaI, where the “x” denotes the presence of the silent point mutation that destroyed the original Xba I site. The third clone, $pBAC^{SP6}$/JVFLx/XhoI, contains both the Xho I site at the end of viral genome and the $A^{9134}$→T substitution.

The present inventors deposited the $pBAC^{SP6}$/JVFLx/XbaI at Gene Bank of Korea Research Institute of Bioscience and Biotechnology (KRIBB) on Oct. 2, 2002 (Accession No: KCTC 10347 BP).

<3-4> Construction of Full-Length JEV cDNAs Containing T7 promoter

In addition to the SP6-driven JEV cDNAs, the present inventors also constructed a set of three T7-driven full-length JEV cDNAs in a similar manner of the Example <3-3>. First, a fragment from pBAC/NADLcIn-/PAC (provided by Dr. Charles M. Rice) was synthesized by PCR with the primer J81 represented by SEQ. ID. No 25 and the primer J80 represented by SEQ. ID. No 26. A fragment from $pBAC^{SP6}$/JVFLx/XbaI was also synthesized with the primer J42 represented by SEQ. ID. No 27 and the primer J82 represented by SEQ. ID. No 28. These two fragments were fused by the second round of PCR with the primers J81 and J82. The 793-bp EcoR I-Spe I fragment of the resulting amplicons was inserted into the pRS2 vector digested with EcoR I and Xba I, leading to the construct pRS2$^{T7}$/5'JV. The 675-bp Pvu I-Pme I fragment of pRS2$^{T7}$/5'JV was ligated with either i) the 18,364-bp Pac I-Pme I fragment of pBAC$^{SP6}$/JVFL/XhoI to create pBAC$^{T7}$/JVFL/XhoI, ii) the 18,364-bp Pac I-Pme I fragment of pBAC$^{SP6}$/JVFLx/XhoI to create pBAC$^{T7}$/JVFLx/XhoI, or iii) 18,366-bp Pac I-Pme I of pBAC$^{SP6}$/JVFLx/XbaI to create pBAC$^{T7}$/JVFLx/XbaI. Finally, three assembled full-length JEV cDNAs were designated pBAC$^{T7}$/JVFL/XhoI, pBAC$^{T7}$/JVFLx/XhoI, and pBAC$^{T7}$/JVFLx/XbaI and represented by SEQ. ID. No 46, No 47, and No 48, respectively (FIG. 3C). At every cloning step during the assembly process, the structural integrity of the cloned cDNAs was assessed by extensive restriction and nucleotide sequence analyses. Structural instability of the inserts leading to deletions or rearrangements was not observed.

The present inventors deposited the pBAC$^{T7}$/JVFLx/XbaI at Gene Bank of Korea Research Institute of Bioscience and Biotechnology (KRIBB) on Oct. 2, 2002 (Accession No: KCTC 10346BP).

Example 4

Transcriptions and Transfections

The present inventors synthesized RNA transcripts by in vitro transcription. Particularly, 100 to 200 ng of the template DNA linearized with Xho I or Xba I digestion and in some cases modified with MBN was added to a 25-μl reaction mixture consisting of the buffer supplied by the manufacturer (Gibco/BRL) plus 0.6 mM cap analog [m$^7$G(5')ppp(5')A or m$^7$G(5')ppp(5')G, NEB Inc.], 0.5 μM [$^3$H]UTP (1.0 mCi/Ml, 50 Ci/m mol, New England Nuclear Corp., Boston, Mass.), 10 mM DTT, 1 mM each UTP, GTP, CTP and ATP, 40 U of RNaseOUT, and 15 U of SP6 RNA polymerase (Gibco/BRL). The reaction mixtures were incubated at 37° C. for 1 hr. RNAs were quantified on the basis of [$^3$H]UTP incorporation as measured by RNA adsorption to DE-81 (Whatman, Maidstone, UK) filter paper (Sambrook et al., *Molecular cloning,* 1989, Cold Spring Harbor Laboratory). A 1- to 1.5-μl aliquot of reaction mixture was examined by agarose gel electrophoresis, and aliquots were stored at −80° C. until use.

For RNA transfection, cells were electroporated with synthetic RNAs with a model ECM 830 electroporator (BTX Inc., San Diego, Calif.), as recommended by the manufacturer. Briefly, subconfluent cells were trypsinized, washed three times with ice-cold RNase-free PBS, and resuspended at a density of 2×10$^7$ cells/Ml in PBS. A 400-μl aliquot of the suspension was mixed with 2 μg of synthetic RNA, and the cells were immediately electroporated under the conditions determined previously to be optimal (980 V, 99-μs pulse length, and five pulses). The electroporated mixture was then transferred to 10 Ml of fresh medium.

An infectious center assay was used to quantify the specific infectivity of the synthetic RNA. Particularly, for runoff transcription, JEV cDNA templates were linearized by digestion with Xho I or Xba I. SP6 polymerase runoff transcription of the two Xho I-linearized plasmids (pBAC$^{SP6}$/JVFL/XhoI and pBAC$^{SP6}$/JVFLx/XhoI) in the presence of the m$^7$G(5')ppp(5')A cap structure analog yielded capped synthetic RNAs containing three nucleotides (CGA) of virus-unrelated sequence at their 3' ends (FIG. 3B). This is the result of copying the 5' overhang left by the Xho I digestion (FIG. 3B). Similarly, SP6 polymerase runoff transcription of the Xba I-linearized pBAC$^{SP6}$/JVFLx/XbaI plasmid in the presence of the m$^7$G(5')ppp(5')A cap structure analog produced capped synthetic RNAs with four nucleotides (CTAG) of virus-unrelated sequence at their 3' ends (FIG. 3B). The electroporated cells were serially diluted 10-fold and plated on monolayers of untransfected cells (5×10$^5$) in a six-well plate. Cells were allowed to attach to the plate for 6 hr, after which they were overlaid with 0.5% SeaKem LE agarose-containing MEM as described above. The plates were incubated for 3 to 4 days at 37° C. with 5% $CO_2$, and infectious plaque centers were visualized by crystal violet staining.

When susceptible BHK-21 cells were transfected with the synthetic RNAs from these constructs, all were highly infectious (Table 3). That is, the synthetic RNAs obtained from pBAC$^{SP6}$/JVFL/XhoI, pBAC$^{SP6}$/JVFLx/XhoI, and pBAC$^{SP6}$/JVFLx/XbaI transfected under optimal electroporation conditions had specific infectivities of 3.5×10$^5$, 4.3×10$^5$, and 3.4×10$^5$ PFU/μg, respectively (Table 3, infectivity). Similar results were also obtained with synthetic RNAs transcribed from the T7-driven cDNA constructs by T7 polymerase runoff transcription (Table 3, infectivity).

TABLE 3

Specific infectivity of in vitro RNA transcripts generated from full-length JEV cDNAs and virus titer

| Templates used for transcription[a] | Infectivity[b] (PFU/μg of RNA) | Virus titer[c](PFU/Ml) 24 hr | 48 hr |
|---|---|---|---|
| pBAC$^{SP6}$/JVFL/XhoI | 3.5 × 10$^5$ | 4.4 × 10$^5$ | 3.6 × 10$^6$ |
| pBAC$^{T7}$/JVFL/XhoI | 2.9 × 10$^5$ | 2.0 × 10$^5$ | 2.3 × 10$^6$ |
| pBAC$^{SP6}$/JVFLx/XhoI | 4.3 × 10$^5$ | 2.1 × 10$^5$ | 5.2 × 10$^6$ |
| pBAC$^{T7}$/JVFLx/XhoI | 3.8 × 10$^5$ | 3.3 × 10$^5$ | 4.1 × 10$^6$ |
| pBAC$^{SP6}$/JVFLx/XbaI | 3.4 × 10$^5$ | 3.5 × 10$^5$ | 3.2 × 10$^6$ |
| pBAC$^{T7}$/JVFLx/XbaI | 3.0 × 10$^5$ | 2.4 × 10$^5$ | 2.7 × 10$^6$ |
| pBAC$^{SP6}$/JVFLx/XbaI$^{MBN}$ | 3.1 × 10$^6$ | 6.2 × 10$^6$ | 1.4 × 10$^6$ |
| pBAC$^{T7}$/JVFLx/XbaI$^{MBN}$ | 2.7 × 10$^6$ | 5.6 × 10$^6$ | 2.4 × 10$^6$ |

[a]All full-length JEV cDNAs were linearized with an appropriate restriction endonuclease for runoff transcription as indicated in the names of the cDNAs. For pBAC$^{SP6}$/JVFLx/XbaI$^{MBN}$ and pBAC$^{T7}$/JVFLx/XbaI$^{MBN}$, these cDNA templates were prepared by linearization with XbaI digestion, which was followed by treatment with MBN.
[b]After in vitro transcription with SP6 or T7 RNA polymerase, as indicated, samples were used to electroporate BHK-21 cells, and infectious plaque centers were determined.
[c]Virus titers at 24 and 48 hr postelectroporation.

<4-1> Construction of JEV RNA Transcripts Lacking the Virus-unrelated Sequences at their 3' Ends It has been reported that for some flaviviruses, the presence of unrelated sequences at the 3' end of synthetic RNAs transcribed from infectious cDNA diminishes or abrogates their specific infectivity (Yamshchikov et al., *Virology,* 2001, 281, 294-304). Based on this report, the present inventors generated synthetic RNAs lacking the virus-unrelated sequences at their 3'ends and compared their specific infectivities. Particularly, the present inventors generated synthetic JEV RNAs lacking the virus-unrelated sequences by treating the Xba I-linearized pBAC$^{SP6}$/JVFLx/XbaI plasmid with MBN prior to the transcription reaction, which removed the four excess nucleotides of CTAG. RNA transcripts from Xba I-linearized and MBN-treated pBAC$^{SP6}$/JVFLx/XbaI and pBAC$^{T7}$/JVFLx/XbaI (pBAC$^{SP6}$/JVFLx/XbaI$^{MBN}$, FIG. 3B and pBAC$^{T7}$/JVFLx/XbaI$^{MBN}$, FIG. 3C) both had increased specific infectivities compared to the untreated transcripts. Precisely, the specific infectivity of RNAs transcribed from pBAC$^{SP6}$/JVFLx/XbaI$^{MBN}$ was estimated to be 3.1×10$^6$ PFU/μg, approximately 10-fold higher than the specific infectivity (3.4×10$^5$ PFU/μg) of the unmodified template (Table 3, infectivity). The RNAs derived from pBAC$^{T7}$/JVFLx/XbaI also had increased specific infectivity after MBN modification (2.7×10$^6$ PFU/μg) (Table 3, infectivity). Therefore, the present inventors demonstrated that the authentic 3' end of the JEV genome should be present to ensure highly infectious synthetic JEV RNA transcripts are generated.

In addition, the altered specific infectivity of the RNA transcripts due to the presence of three or four virus-unrelated nucleotides at the 3' end also influences the virus titers harvested from culture supernatants of the transfected BHK-21 cells. Virus titers released from BHK-21 cells transfected with RNA transcripts from MBN-untreated $pBAC^{SP6}$/JVFL/XhoI, $pBAC^{SP6}$/JVFLx/XhoI, and $pBAC^{SP6}$/JVFLx/XbaI ranged from $2.1\times10^5$ to $4.4\times10^5$ PFU/Ml at 24 hr posttransfection (Table 3, virus titer 24 hr), at which time half of the transfected cells were still attached to culture dishes showing virus-induced strong cytopathic effect. These titers increased about 10-fold to the range of $3.2\times10^6$ to $5.2\times10^6$ PFU/Ml at 48 hr posttransfection (Table 3, virus titer 48 hr), at which point most of the cells had died and detached from the bottom of the culture dishes. In contrast, the virus titer released from BHK-21 cells transfected with RNA transcripts from MBN-treated $pBAC^{SP6}$/JVFLx/$XbaI^{MBN}$ had already reached $6.2\times10^6$ PFU/Ml at 24 hr posttransfection, at which time the majority of the transfected cells had died (Table 3, virus titer 24 hr). This titer decreased slightly to $1.4\times10^6$ PFU/Me at 48 hr posttransfection (Table 3, virus titer 48 hr). Similar patterns of virus production were seen with the T7 polymerase-driven RNA transcripts (Table 3).

Example 5

Confirmation of Specific Infectivity of Synthetic RNA Transcripts

Figure 4:
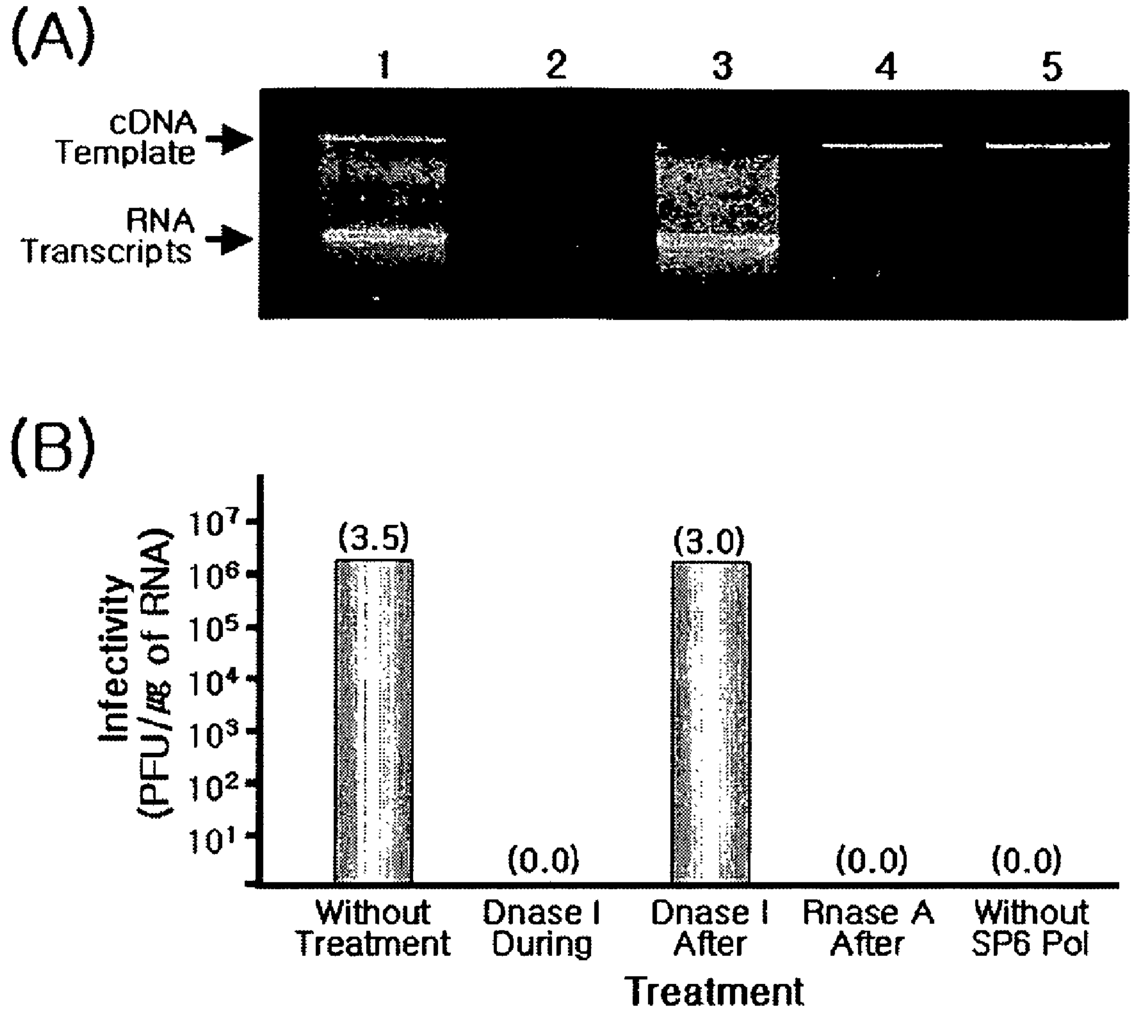
FIG. 4 is a set of a photograph and a graph showing the fact that full-length JEV cDNA template alone is not infectious but is required for the generation of infectious synthetic RNAs during in vitro transcription. (A) An electrophoresis photograph showing the cDNA template and synthetic RNA transcripts. (B) A graph showing infectivity obtained by transfecting BHK-21 cells with an in vitro transcription reaction mixture, which contains full-length JEV cDNA template and synthetic RNA transcripts. pBAC$^{SP6}$/JVFLx/XbaI (100-200 ng) linearized with Xba I and treated with MBN was used for SP6 polymerase transcription in the absence (A, lane 1; B, Without Treatment) or presence (A, lane 2; B, Dnase I During) of DNase I. After synthesis, the transcription reaction mixture was treated for 30 min at 37° C. with DNase I (A, lane 3; B, Dnase I After) or RNase A (A, lane 4; B, Rnase A After). As a control, the reaction was carried out in the absence of SP6 RNA polymerase (A, lane 5; B, Without SP6 Pol). (A) Following treatment, 5% of the reaction mixture was separated on a 0.6% agarose gel and the cDNA template and RNA transcripts were visualized by staining with EtBr. (B) The reaction mixtures were used to transfect BHK-21 cells, and infectious centers of plaques were estimated.

The present inventors confirmed that specific infectivity requires the transcription of RNA from the full-length JEV cDNA template by using the full-length cDNA clone $pBAC^{SP6}$/JVFLx/$XbaI^{MBN}$ (FIG. 4). The cDNA template alone was not infectious (FIG. 4A, lane 5 and B, without SP6 Pol), but the intact cDNA template was needed during the transcription reaction because DNase I treatment abolished infectivity (FIG. 4A, lane 2 and B, DNase I During). Addition of DNase I after the transcription reaction had no effect (FIG. 4A, lane 3 and B, DNase I after) relative to the intact reaction mixture (FIG. 4A, lane 1 and B, without treatment), but RNase A treatment abolished the infectivity of the transcribed synthetic RNAs (FIG. 4A, lane 4 and B, RNase A after).

Example 6

Comparison of Synthetic JEVs Recovered from Full-length Infectious cDNAs with the CNU/LP2 Parental Virus The present inventors compared the synthetic JEVs recovered from full-length infectious cDNAs ($pBAC^{SP6}$/JVFL/XhoI, $pBAC^{SP6}$/JVFLx/XhoI, $pBAC^{SP6}$/JVFLx/XbaI, and $pBAC^{SP6}$/JVFLx/$XbaI^{MBN}$) with the parental virus CNU/LP2 originally used for cDNA construction (plaque morphology, growth kinetics, protein expression, RNA production, etc).

<6-1> Comparison of Plaque Morphology by Plaque Assay

Figure 5:
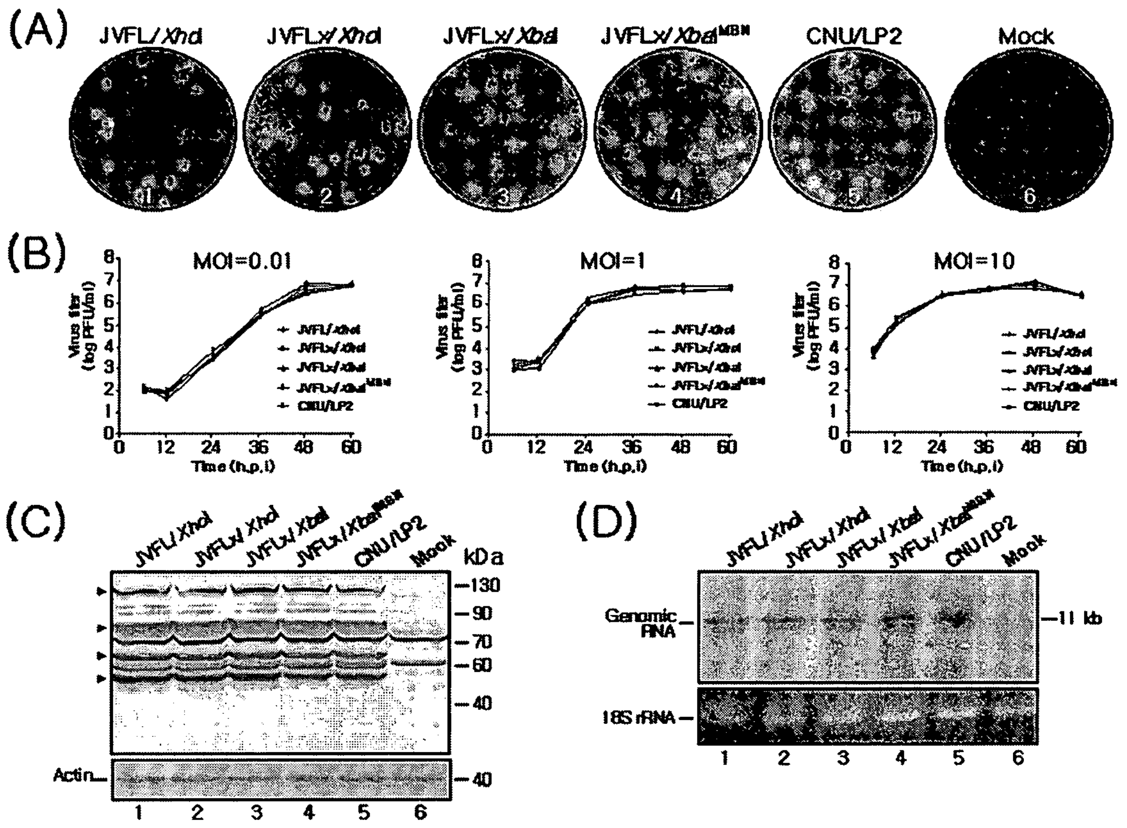
FIG. 5 is a set of photographs and graphs showing the comparison of synthetic JEVs with parental virus CNU/LP2.

BHK-21 cells were infected with the synthetic JEVs recovered from full-length infectious cDNAs ($pBAC^{SP6}$/JVFL/XhoI, $pBAC^{SP6}$/JVFLx/XhoI, $pBAC^{SP6}$/JVFLx/XbaI, and $pBAC^{SP6}$/JVFLx/$XbaI^{MBN}$) and the parental virus CNU/LP2. The cells were overlaid with MEM containing 10% fetal bovine serum and 0.5% SeaKem LE agarose (FMC BioProducts, Rockland, Me.) and incubated in a 5% $CO_2$, 37° C. incubator for 3 to 4 days. After being cultured for 3 to 4 days, the infected cells were fixed with 3.7% formaldehyde at room temperature for 4 hr. Then, agarose covering the cells was removed. Plaques were visualized by crystal violet staining. As shown in FIG. 5A, BHK-21 cells infected with synthetic JEVs recovered from $pBAC^{SP6}$/JVFL/XhoI (dish 1), $pBAC^{SP6}$/JVFLx/XhoI (dish 2), $pBAC^{SP6}$/JVFLx/XbaI (dish 3), and $pBAC^{SP6}$/JVFLx/$XbaI^{MBN}$ (dish 4) formed homogeneous large plaques, similar to the cells infected with CNU/LP2 (dish 5).

<6-2> Comparison of Growth Kinetics

The present inventors infected BHK-21 cells with the synthetic JEVs recovered from full-length infectious cDNAs ($pBAC^{SP6}$/JVFL/XhoI, $pBAC^{SP6}$/JVFLx/XhoI, $pBAC^{SP6}$/JVFLx/XbaI, and $pBAC^{SP6}$/JVFLx/$XbaI^{MBN}$) and the parental virus CNU/LP2. BHK-21 cells were infected with low (0.01 PFU/cell), medium (1.0 PFU/cell), and high (10 PFU/cell) MOI, after which the cell culture fluids were harvested periodically and used to determine the kinetics of infectious virus release over time. Particularly, viruses were harvested at the indicated time points, and titers were determined by plaque assay. As shown in FIG. 5B, the MOI-dependent virus titers accumulating over time were similar for the four recovered viruses ($pBAC^{SP6}$/JVFL/XhoI, $pBAC^{SP6}$/JVFLx/XhoI, $pBAC^{SP6}$/JVFLx/XbaI, and $pBAC^{SP6}$/JVFLx/$XbaI^{MBN}$) and the parental virus CNU/LP2.

<6-3> Comparison of Viral Protein Level by Western Blot Analysis

The present inventors compared viral protein expressed in BHK-21 cells infected with the synthetic JEVs recovered from full-length infectious cDNAs ($pBAC^{SP6}$/JVFL/XhoI, $pBAC^{SP6}$/JVFLx/XhoI, $pBAC^{SP6}$/JVFLx/XbaI, and $pBAC^{SP6}$/JVFLx/$XbaI^{MBN}$) with that in BHK-21 cells infected with the parental virus CNU/LP2. Particularly, BHK-21 cells ($3\times10^5$) were lysed with 200 µl of sample loading buffer [80 mM Tri-HCl (pH 6.8), 2.0% SDS, 10% glycerol, 0.1 M DTT, 0.2% bromophenol blue], and one-tenth of the lysate was boiled for 5 min and fractionated on an SDS-polyacrylamide gel. Proteins were transferred electrophoretically onto a methanol-activated polyvinylidene difluoride membrane with a Trans-Blot SD electrophoretic transfer cell machine (Bio-Rad Laboratories Inc., Hercules, Calif.), and the membrane was blocked at room temperature for 1 hr with 5% nonfat dried milk in washing solution (0.2% Tween 20 in PBS). After three washes with washing solution, membranes were incubated at room temperature for 2 hr with either a monoclonal anti-actin antibody (A4700, Sigma, St. Louis, Mo.) that recognizes the epitope conserved in the C terminus of all actin isoforms or mouse hyperimmune ascites fluid specific for JEV (ATCC VR-1259AF, American Type Culture Collection). The membranes were then washed three times with washing solution and incubated at room temperature for 2 hr with alkaline phosphatase (AP)-conjugated goat anti-mouse immunoglobulin G (Jackson ImmunoResearch Labs Inc., West Grove, Pa.). The membranes were washed three times with washing solution and once with PBS. Actin and JEV protein bands were visualized by incubation with the substrates 5-bromo-4-chloro-3-indolylphosphate and nitroblue tetrazolium. As a result, it was demonstrated that the synthetic JEVs and the parental virus produced similar amounts and identical patterns of virus-specific proteins (FIG. 5C, top panel). Actin protein was measured as an internal sample loading control and revealed equivalent levels of actin protein in mock-infected and infected cells (FIG. 5C, bottom panel).

<6-4> Comparison of Viral RNA Level by Northern Blot Analysis

The present inventors compared viral RNA expressed in BHK-21 cells infected with the synthetic JEVs recovered from full-length infectious cDNAs (pBAC$^{SP6}$/JVFL/XhoI, pBAC$^{SP6}$/JVFLx/XhoI, pBAC$^{SP6}$/JVFLx/XbaI, and pBAC$^{SP6}$/JVFLx/XbaI$^{MBN}$) with that in BHK-21 cells infected with the parental virus CNU/LP2. Particularly, total RNA was extracted from infected BHK-21 cells ($3\times10^5$) with 1 Ml of TRIzol reagent (Gibco/BRL). One-third of the RNA was analyzed for JEV-specific RNA by Northern blot analysis (Sambrook et al., *Molecular cloning,* 1989, Cold Spring Harbor Laboratory). The RNA was electrophoresed in denaturing 2.2 M formaldehyde-1% agarose gels and transferred onto nylon membranes (Amersham Biosciences Inc., Piscataway, N.J.). The RNA on the membranes was cross-linked by irradiation with a 254-nm light source (Stratalinker UV crosslinker, Stratagene, La Jolla, Calif.), and the JEV-specific RNAs were detected by hybridization with a [$^{32}$P]CTP-labeled antisense riboprobe that binds to nt 9,143 to 9,351 of the JEV genome. This probe had been synthesized by in vitro transcription from the BamH I-linearized cDNA clone pGEM3Zf(+)/JV9143, which was constructed by ligating the 209-bp Hind III-Sac I fragment of pBAC$^{SP6}$/JVFLx/XbaI with pGEM3Zf(+) digested with the same enzymes. This clone was transcribed with the T7-MEGAscript kit (Ambion, Austin, Tex.) as recommended by the manufacturer with a 20-μl reaction mixture containing 3.12 μM [α-$^{32}$P]CTP(800 Ci/m mol, Amersham). After being treated with DNase I, the reaction mixture was spun in a Quick Spin G-50 Sephadex column (Boehringer Mannheim) to remove unincorporated ribonucleoside triphosphates. The membrane was prehybridized at 55° C. for 6 hr in hybridization solution [5×SSPE(0.9 M NaCl, 50 mM $NaH_2PO_4$, and 5 mM EDTA pH 7.7), 5× Denhardt's reagent, 0.5% SDS, 100 μg/Ml of denatured salmon sperm DNA, 50% formamide] and then incubated at 55° C. overnight in the hybridization solution containing $10^7$ cpm of the labeled riboprobe. The membrane was washed three times at 55° C. for 10 min with 1×SSPE-0.5% SDS and once for 10 min with 0.1×SSPE-0.5% SDS. Viral RNA bands were visualized by autoradiography and quantified with a Molecular Imager (Bio-Rad Lab). As a result, viral RNA levels were all similar (FIG. 5D). Quantification of these blots by image analysis revealed that the ratios of viral genomic RNA (FIG. 5D, top panel) to 18S rRNA (FIG. 5D, bottom panel) did not differ significantly, demonstrating that all viral genomic RNAs were produced at similar levels.

Thus, all the synthetic viruses recovered from full-length infectious cDNAs (pBAC$^{SP6}$/JVFL/XhoI, pBAC$^{SP6}$/JVFLx/XhoI, pBAC$^{SP6}$/JVFLx/XbaI, and pBAC$^{SP6}$/JVFLx/XbaI$^{MBN}$) were indistinguishable from the parental virus CNU/LP2 in terms of plaque morphology, cytopathogenicity, growth kinetics, protein expression, and RNA production. Furthermore, analyses of the 3' end sequence did not reveal an extra three (CGA) or four (CTAG) nucleotides of virus-unrelated sequence at the 3' end of the viral RNA genomes derived from any of the synthetic viruses. These results validate the use of infectious JEV cDNA clones developed in the present invention for future molecular genetics.

Example 7

Check the Possibility that the Transfected Cultures were Contaminated with the Parental Virus While the above results strongly suggest that the JEV cDNA clones can produce highly infectious RNA transcripts after SP6 or T7 polymerase transcription, the possibility that the transfected cultures were contaminated with the parental virus CNU/LP2 was not formally excluded. To assess this remote possibility, the present inventors used PCR-based site-directed mutagenesis to introduce a genetic marker (gm) into the pBAC$^{SP6}$/JVFLx/XbaI construct. Particularly, the point mutation A$^{8171}$→C (silent) was placed inside the NS5 gene in PBAC SP6/JVFLx/XbaI by PCR-based site-directed mutagenesis to generate pBAC$^{SP6}$/JVFLx/gm/XbaI (FIG. 6A). The point mutation resulted in the acquisition of a unique Xho I restriction endonuclease recognition site. A fragment from pBAC$^{SP6}$/JVFLx/XbaI was first generated by PCR with primer J48 represented by SEQ. ID. No 29, in which the Xho I was created by the A$^{8171}$→C substitution, and primer J3 represented by SEQ. ID. No 30. The 665-bp Mlu I-Apa I fragment of the resulting amplicons was then ligated with the 4,802-bp Apa I-BsrG I and the 5,874-bp BsrG I-Mlu I fragments of pBAC$^{SP6}$/JVFLx/XbaI, resulting in the pBAC$^{SP6}$/JVFLx/gm/XbaI construct. BHK-21 cells transfected with RNA transcripts from Xba I-linearized MBN-treated pBAC$^{SP6}$/JVFLx/gm/XbaI$^{MBN}$ produced infectious virus containing the genetic marker (denoted JVFLx/gm/XbaI$^{MBN}$) (FIG. 6A). The phenotypic characteristics of JVFLx/gm/XbaI$^{MBN}$ did not differ from those of the original virus JVFLx/XbaI$^{MBN}$, indicating that the A$^{8171}$→C substitution did not affect viral replication.

To verify that the JVFLx/gm/XbaI$^{MBN}$ virus had been recovered from the cDNA template of pBAC$^{SP6}$/JVFLx/gm/XbaI$^{MBN}$, the present inventors serially passaged the recovered virus in BHK-21 cells at an MOI of 0.1. The viruses resulted from each passage were incubated with RNase A and DNase I to avoid the carryover of the input transcript RNA and template plasmid cDNA (Mendez et al., *J. Virol.,* 1998, 72, 4737-4745). Viral RNAs extracted from the JVFLx/gm/XbaI$^{MBN}$ and JVFLx/XbaI$^{MBN}$ viruses released at passages 1 and 3 were used in RT-PCR to amplify a 2,580-bp product that encompassed the A$^{8171}$→C substitution (FIG. 6B, lanes 1, 3, and 5). Digestion of the amplified product from JVFLx/gm/XbaI$^{MBN}$ with Xho I resulted in two fragments of 1,506 and 1,074 bp (FIG. 6B, lanes 2 and 4). On the other hand, the JVFLx/XbaI$^{MBN}$-derived RT-PCR product did not digest with Xho I (FIG. 6B, compared lane 5 with lane 6), demonstrating that the A$^{8171}$→C substitution was indeed present in the JVFLx/gm/XbaI$^{MBN}$ virus. Thus, it was confirmed that the recovered virus JVFLx/gm/XbaI$^{MBN}$ originated from the full-length infectious cDNA pBAC$^{SP6}$/JVFLx/gm/XbaI$^{MBN}$.

Example 8

Genetic Stability of Full-length Infectious JEV cDNA

A previous study has shown that constructs containing full-length JEV cDNA frequently acquired stabilizing nonsense mutations in the regions encoding the structural proteins prM and E (Sumiyoshi et al., *J. Virol.,* 1992, 66, 5425-5431). Since studies into the molecular genetics of JEV will indispensably require a reliable infectious JEV molecular clone for manipulation, the present inventors manipulated pBAC$^{SP6}$/pJVFLx/XbaI in several ways and extensively investigated its genetic structure and functional integrity.

Particularly, the genetic structure and functional integrity of the infectious JEV cDNAs were analyzed as follows. *E. coli* strain DH10B was transformed with pBAC$^{SP6}$/JVFLx/XbaI, and two independently derived clones were grown at 37° C. overnight in 10 Ml of 2×YT containing 12.5 μg/Ml of chloramphenicol. Cells from these primary cultures were maintained for 9 days by diluting them $10^6$-fold every day (Almazan et al., *Proc. Natl. Acad. Sci. USA,* 2000, 97, 5516-5521). In the experimental conditions of the present invention, each passage represented approximately 20 generations, which was consistent with observations made previously (Alamzan et al., *Proc. Natl. Acad. Sci. USA,* 2000, 97, 5516-5521). After the third, sixth, and ninth passages, large-scale preparation of the infectious cDNA plasmid was made by the SDS-alkaline method and purified further by cesium chloride density gradient centrifugation (Sambrook et al., *Molecular cloning,* 1989, Cold Spring Harbor Laboratory). The genetic structure of the plasmid DNA was monitored by its restriction endonuclease pattern. The plasmids extracted from the two cultures at passage 0, 3, 6 and 9 were examined by restriction enzyme analysis. The restriction enzyme patterns at passages 3, 6 and 9 did not differ visibly from those at passage 0. Thus, within the resolution of agarose gel electrophoresis analysis, the two infectious cDNA clones appeared to be structurally stable.

The functional integrity of the JEV cDNA plasmid was also investigated by measuring the specific infectivities of the synthetic RNAs transcribed from the cDNA template, which was linearized by Xba I digestion and MBN treatment. As a result, the infectivity of the RNA transcripts made from the two cDNA clones did not differ between passage 0 and passage 9 (FIG. 7). From the above result, it was confirmed that the infectious JEV cDNA remained functionally stable during serial growth in *E. coli.*

Example 9

Infectious JEV cDNA as a Vector for Foreign Gene Expression

As previously described (Burke and Monath, *Flaviviruses,* 2001, 1043-1125, Lippincott Williams & Wilkins Publishers), the present inventors found that JEV was able to replicate in a wide variety of eukaryotic cells originating from a number of species, including humans, mice, monkeys, swine, dogs, cats, and hamsters. This suggests that JEV could be useful as a vector for the expression of heterologous genes in a variety of different cells. To test this, two commonly used reporter genes, the *Aequeorea victoria* GFP and the *Photinus pyralis* LUC, were inserted at the beginning of the viral 3'NTR of $pBAC^{SP6}$/JVFLx/XbaI as expression cassettes driven by the IRES element of EMCV (FIG. 8A).

To create the $pBAC^{SP6}$/JVFLx/GFP/XbaI construct (FIG. 8A), a fragment from $pBAC^{SP6}$/JVFLx/XbaI was amplified by PCR with the primer J72 represented by SEQ. ID. No 31 and the primer J73 represented by SEQ. ID. No 32. A fragment was also amplified from pRSGFP-C1 with the primer J74 represented by SEQ. ID. No 33 and the primer J75 represented by SEQ. ID. No 34. These two fragments were fused by the second round of PCR with the primers J72 and J75. The 913-bp Kpn I-Nsi I fragment of the resulting amplicons was then ligated with the 8,011-bp Nsi I-Pac 1 and 11,021-bp Pac I-Kpn I fragments of $pBAC^{SP6}$/JVFLx/XbaI, resulting in the $pBAC^{SP6}$/JVFLx/GFP/XbaI construct.

To generate the $pBAC^{SP6}$/JVFLx/LUC/XbaI construct (FIG. 8A), a fragment of $pBAC^{SP6}$/JVFLx/XbaI was amplified with the primer J72 and the primer J76 represented by SEQ. ID. No 35. A fragment was also amplified from pACNR/NADLcIn-/LUC (provided by Dr. Charles M. Rice) with the primer J77 represented by SEQ. ID. No 36 and the primer J78 represented by SEQ. ID. No 37. These two fragments were then fused by the second round of PCR with the primers J72 and J78. The 1,801-bp Kpn I-Nsi I fragment of the resulting amplicons was then ligated with the 8,011-bp Nsi I-Pac 1 and 11,021-bp Pac I-Kpn I fragments of $pBAC^{SP6}$/JVFLx/XbaI, leading to $pBAC^{SP6}$/JVFLx/LUC/XbaI.

To generate $pBAC^{SP6}$/JVFLx/$LUC^{REP-}$/XbaI (FIG. 8A), which contains an 83-nucleotide deletion (nt 5,581 to 5,663) in the middle of the NS3 gene that results in premature termination of viral translation at nt 5,596, a fragment of $pBAC^{SP6}$/JVFLx/LUC/XbaI was amplified with the primer J89 represented by SEQ. ID. No 38 and the primer J91 represented by SEQ. ID. No 39. A fragment was also amplified from pBAC SP6/JVFLx/LUC/XbaI with the primer J92 represented by SEQ. ID. No 40 and the primer J93 represented by SEQ. ID. No 41. These two fragments were then fused by the second round of PCR with the primers J89 and J93. The 3,960-bp Sfi I-Eag I fragment of the resulting amplicons was then ligated with the 6,493-bp Eag I-Sfi I and 10,297-bp Sfi I-Sfi I fragments of $pBAC^{SP6}$/JVFLx/LUC/XbaI, leading to $pBAC^{SP6}$/JVFLx/$LUC^{REP-}$/XbaI.

A deletion of 9 to 25 nucleotides exists at the beginning of the viral 3'NTR in CNP/LP2 and three other fully sequenced JEV strains (Williams et al., *J. Gen. Virol.,* 2000, 81, 2471-2480; Nam et al., *Am. J. Trop. Med. Hyg.,* 2001, 65, 388-392; Jan et al., *Am. J. Troop. Med. Hyg.,* 1996, 55, 603-609), suggesting that this may be a good site to insert the foreign genes. Therefore, when BHK-21 cells were transfected with the synthetic RNAs transcribed from $pBAC^{SP6}$/JVFLx/GFP/XbaI and $pBAC^{SP6}$/JVFLx/LUC/XbaI cDNAs, the insertion did not alter the specific infectivity of the synthetic RNA transcripts.

To examine GFP expression, naïve BHK-21 cells were transfected with infectious synthetic RNA transcribed from the $pBAC^{SP6}$/JVFLx/GFP/$XbaI^{MBN}$ template and examined by confocal microscopy. Particularly, BHK-21 cells were mock-transfected or transfected with 2 μg of JVFLx/GFP/$XbaI^{MBN}$ RNA. Transfected cells ($1\times10^5$) were incubated for 30 hr in a four-well chamber slide. Cells were washed twice with PBS, fixed by incubation for 30 min at 25° C. in PBS containing 0.37% (v/v) formaldehyde, and mounted with 0.2 Ml of 80% glycerol. Cells were viewed by confocal microscopy and analyzed. As a result, BHK-21 cells expressing GFP displayed green fluorescence in both the nucleus and the cytoplasm (FIG. 8B, JVFLx/GFP/$XbaI^{MBN}$) because GFP is small enough to permit diffusion between the nucleus and the cytoplasm. As expected, this fluorescence was not observed in mock-transfected cells (FIG. 8B, mock) or in cells transfected with RNA transcripts from $pBAC^{SP6}$/JVFLx/$XbaI^{MBN}$.

To monitor the induction of LUC over time in a quantitative manner, the present inventors produced not only replication-competent RNA transcripts from $pBAC^{SP6}$/JVFLx/LUC/$XbaI^{MBN}$ but also replication-incompetent RNA transcripts from $pBAC^{SP6}$/JVFLx/$LUC^{REP-}$/$XbaI^{MBN}$ (FIG. 8A). The $pBAC^{SP6}$/JVFLx/$LUC^{REP-}$/$XbaI^{MBN}$ template contains an 83-nucleotide deletion (nt 5,581 to nt 5,663) in the middle of the NS3 gene that prematurely terminates viral translation at nt 5,596 (see * in FIG. 8A, $pBAC^{SP6}$/JVFLx/$LUC^{REP-}$/$XbaI^{MBN}$).

For the LUC assay, BHK-21 cells ($8\times10^6$) were mock-transfected or transfected with 2 μg of JVFLx/LUC/$XbaI^{MBN}$ RNA or JVFLx/$LUC^{REP-}$/$XbaI^{MBN}$ RNA. Cells were seeded at a concentration of $6\times10^5$ cells/well in a six-well plate and cultivated. At the given time points, the cells were washed with $Ca^{2+}$- and $Mg^{2+}$-free PBS solution and then lysed by adding 0.2 W of lysis buffer [25 mM Tris-phosphate (pH 7.8), 2 mM DTT, 2 mM 1,2-diaminocyclohexane-N,N,N',N'-tetraacetic acid, 10% glycerol, 1% Triton X-100(v/v)] to each well. Cell lysates were incubated for 10 min at room temperature, and cellular debris was then removed by centrifugation. The supernatants were quickly placed at −80° C. for storage until use. To determine the LUC activity, 20 μl of the cell lysates was placed in a luminometer tube containing 100 μl of LUC assay reagent [20 mM Tricine, 1.07 mM $(MgCO_3)_4Mg(OH)_2.5H_2O$, 2.67 mM $MgSO_4$, 0.1 mM EDTA, 33.3 mM DTT, 270 μM coenzyme A, 470 μM luciferin (Promega), 530 μM ATP]. The activity was usually measured for 10 sec. Each data point represents the results of three independent experiments.

As a result, in BHK-21 cells transfected with the replication-competent JVFLx/LUC/XbaI$^{MBN}$ RNA (FIG. 8C, ●), the initial LUC activity 6 hr posttransfection was $2.4\times10^3$+$0.2\times10^3$ relative light units (RLU). This activity was dramatically increased to $5.3\times10^4\pm0.1\times10^4$ RLU 30 hr posttransfection and reached $7.8\times10^5\pm0.6\times10^5$ RLU 54 hr posttransfection, at which point >50% of the cells were dying. In contrast, in BHK-21 cells transfected with the replication-incompetent JVFLx/LUC$^{REP-}$/XbaI$^{MBN}$ RNA, the initial LUC activity 6 hr posttransfection was $1.9\times10^3$+$0.4\times10^3$ RLU (FIG. 8C, ○), like the JVFLx/LUC/XbaI$^{MBN}$-transfected cells (FIG. 8C, ●), but this activity gradually decreased over time to 16±1.2 RLU at 54 posttransfection, which is at the level of background luminescence of naïve cells (FIG. 8C, ○) Thus, the level of LUC activity expressed over time varied depending on the presence or absence of viral replication.

The present inventors produced full-length infectious recombinant JEV cDNAs having GFP and LUC genes according to the method explained hereinbefore. BHK-21 cells were transfected with JEV RNA transcripts transcribed from the recombinant JEV cDNAs, and then, recombinant JEV JVFLx/GFP/XbaI$^{MBN}$ and JVFLx/LUC/XbaI$^{MBN}$ containing GFP and LUC genes were recovered from culture supernatants. The expression of GFP and LUC genes in the recombinant JEV was investigated after infecting a variety of animal cell lines (BHK-21, Vero, NIH/3T3, ST, HeLa, MDCK, CRFK, B103, and SHSY-5Y), which have been generally used in the field of biology and medicine, with the virus. As a result, GFP or LUC gene inserted in virus genome was expressed in all cells tested (Table 4). Thus, it was confirmed that recombinant JEV cDNAs, JEV RNA transcripts, and recombinant JEV viral particles could be effectively used as a vector for expression of foreign heterologous genes in a variety of cell types.

TABLE 4

Expression of GFP and LUC genes engineered in the infectious JEV cDNAs

| Cell line | GFP expression[a] | LUC induction[b] |
|---|---|---|
| BHK-21 | Expressed | Expressed |
| Vero | Expressed | Expressed |
| HeLa | Expressed | Expressed |
| MDCK | Expressed | Expressed |
| CRFK | Expressed | Expressed |
| NIH/3T3 | Expressed | Expressed |
| ST | Expressed | Expressed |
| B103 | Expressed | Expressed |
| SHSY-5Y | Expressed | Expressed |

[a]Expression of GFP protein was analyzed after infecting cells with recombinant JEV JVFLx/GFP/XbaI$^{MBN}$.
[b]Expression of LUC protein was analyzed after infecting cells with recombinant JEV JVFLx/LUC/XbaI$^{MBN}$.

Example 10

Utility of the Infectious JEV cDNA for a Novel Heterologous Gene Expression System The present inventors further investigated the utility of JEV-based expression system in expressing foreign genes of interest. First, the present inventors engineered the full-length viral genome to express three commonly used and variously sized heterologous reporter genes, namely, an improved version of the *Aequorea victoria* GFP gene (EGFP, 768 bp), the LUC gene from *Photinus pyralis* (1653 bp), and the LacZ (3012 bp) gene (FIG. 9B). The present inventors also introduced the dominant selective marker PAC (600 bp), which facilitates resistance to the drug puromycin (FIG. 9B).

<10-1> Construction and Characterization of Heterologous Gene-encoding Infectious Recombinant JEVs That are Based on the Bicistronic Full-Length Infectious JEV cDNA that Serves as a BAC.

<10-1-1> Plasmid Construction of Infectious Recombinant JEV Vectors

All plasmids were constructed by standard molecular biology protocols (Sambrook et al., *Molecular cloning: a laboratory manual,* 2$^{nd}$ ed. Cold Spring Harbor Laboratory, Cold Spring Harbor, N.Y., 1989) and all regions amplified by PCR were verified by sequencing. All of the recombinant JEV vectors used in the present invention were constructed based on pBAC$^{SP6}$/JVFLx/XbaI (Yun et al., *J. Virol.,* 2003, 77, 6450-6465), which is designated as pJEV/FL hereinafter (FIG. 9A).

The present inventors constructed a set of four infectious recombinant JEV vectors expressing the LUC, EGFP, LacZ, and PAC genes. pJEV/FL/LUC is identical to the construction designated as pBAC$^{SP6}$/JVFLx/LUC/XbaI hereinbefore in the Example 9 (FIG. 9B). To construct pJEV/FL/LacZ, the 2,409-bp Kpn I-Avr II fragment of pJEV/FL/LUC was first subcloned into pGEM3Zf(+) which was digested with Kpn I and Xba I, resulting in pGEM/LUC. The 3,177-bp Nco I-Stu I fragment of pSinRep3/LacZ (a generous gift from Dr. Charles Rice) was ligated to the 3,935-bp Nco I-Nsi I (T4 DNA polymerase-treated) fragment of pGEM/LUC, leading to pGEM/LacZ. The 3,873-bp Kpn I-Not I fragment of pGEM/LacZ was ligated to the 7,456-bp Not I-Pac 1 and 11,021-bp Pac I-Kpn I fragments of pJEV/FL/LUC, creating pJEV/FL/LacZ (FIG. 9B). To facilitate the construction of pJEV/FL/EGFP, the 5,792-bp Sac II-Not I fragment of pJEV/FL/LacZ was inserted into pRS2, which was digested with the same enzymes, resulting in pRS/LacZ. A fragment of the sequence coding for EGFP was produced by PCR amplification of pEGFP-C1 with the primers EGFPF (represented by SEQ. ID. No 49) and EGFPR (represented by SEQ. ID. No 50). The 773-bp Nco I-Stu I portion of the EGFP fragment amplicons was ligated to the 3,241-bp EcoR V-Sac II and 2,062-bp Sac II-Nco I fragments of pRS/LacZ, resulting in pRS/EGFP. The 3,406-bp Sac II-Not I fragment of pRS/EGFP was ligated to the 7,456-bp Not I-Pac 1 and 9,102-bp Pac I-Sac II fragments of pJEV/FL/LUC, leading to pJEV/FL/EGFP (FIG. 9B). To generate pJEV/FL/PAC, a fragment of pACNR/NADLcIns$^-$/PAC (a generous gift from Dr. Charles Rice) was PCR-amplified with primers PACF (represented by SEQ. ID. No 51) and PACR (represented by SEQ. ID. No 52). The 881-bp Dra III-Nsi I portion of the resulting amplicons was ligated to the 8,011-bp Nsi I-Pac I, 10,096-bp Pac I-Nde I, and 842-bp Nde I-Dra III fragments of pJEV/FL/LUC, resulting in pJEV/FL/PAC (FIG. 9B). An expression cassette driven by the EMCV IRES was inserted at the beginning of the viral 3' NTR of pJEV/FL (FIGS. 9A and 9B).

<10-1-2> Assay for EGFP Expression

Cells were seeded in a four-well chamber slide for 36-48 hr posttransfection. After incubation, cells were fixed by being incubated in PBS containing 0.37% (v/v) formaldehyde and then mounted with 0.2 ml 80% glycerol. Cells were observed under a confocal microscope outfitted with an appropriate filter. The expression of EGFP was also examined by flow cytometric analysis. Particularly, the cells were trypsinized, washed once with PBS, and resuspended in 0.37% (v/v) formaldehyde in PBS, followed by analysis with a FACScan flow cytometer FACSCalibur (Becton Dickinson). Dead cells were excluded by appropriate forward and side light-scattering gates. Ten thousand viable cells were counted.

<10-1-3> β-Galactosidase Assay

Cells were washed once with PBS, fixed with 0.05% (v/v) glutaraldehyde in PBS for 15 min at room temperature, and carefully washed three times with PBS. The cells were assessed for β-gal activity by being incubated in staining solution [5 mM potassium ferricyanide, 5 mM potassium ferrocyanide, 2 mM $MgCl_2$ in PBS] with 5-bromo-4-chloro-3-indolyl-β-galactopyranoside (Sigma) at 37° C.

<10-1-4> Luciferase Assay

Cells were analyzed for LUC activity by using the substrate luciferin (Promega) as described hereinbefore (Yun et al., *J. Virol.,* 2003, 77, 6450-6465). Each experiment was performed in triplicate and the mean values are presented.

<10-1-5> Puromycin Selection

Cells were seeded in 6-well plates at 37° C. for 6 hr. To measure $Pur^R$ foci formation, the cells were overlaid with 0.5% SeaKem LE agarose (FMC BioProducts, Rockland, Me.) in MEM containing 10% heat-inactivated FBS and penicillin/streptomycin and incubated at 37° C. for 2 days. Thereafter, the plates were incubated for an additional 3 days in the absence or presence of puromycin (10 μg/ml). After the selection, the $Pur^R$ foci were visualized by crystal violet staining of the formaldehyde-fixed cells (Yun et al., *J. Virol.,* 2003, 77, 6450-6465). For $Pur^R$ cell culture, the cells were left unplugged with the agarose and incubated in complete medium at 37° C. for 2 days. Subsequently, the cells were cultivated in complete media containing 10 μg/ml puromycin and 24-48 hr after selection, the surviving cells were visualized by staining with crystal violet.

<10-1-6> Heterologous Proteins are Expressed in BHK-21 Cells Transfected/Infected with Recombinant Synthetic JEV RNAs/Viruses Containing an Additional Expression Unit To examine whether the insertion of the expression cassette altered its specific infectivity/replication, the present inventors examined the specific in vitro infectivity of the synthetic RNAs that had been transcribed from the four SP6-driven foreign gene-bearing infectious JEV cDNA constructs (Table 5). Purified pJEV/FL and its derivative plasmids were linearized by digestion with Xba I followed by treatment with MBN. The linearized plasmids were used in vitro transcription reactions (25 μl) employing SP6 RNA polymerase, as described hereinbefore. After transcription, the reaction mixtures were further incubated with 10 U DNase I for 30 min and extracted with phenol-chloroform-isoamylalcohol. RNA yields were quantified on the basis of [$^3$H]UTP incorporation as measured by RNA absorption to DE-81 filter paper (Whatman, Maidstone, UK). RNA (2 μg) was transfected into cells by electroporation as described hereinbefore (Yun et al., *J. Virol.,* 2003, 77, 6450-6465).

The synthetic RNAs derived from pJEV/FL/PAC, pJEV/FL/EGFP, pJEV/FL/LUC, and pJEV/FL/LacZ introduced into susceptible BHK-21 cells had specific infectivities of $3.5\times10^6$, $2.5\times10^6$, $3.4\times10^6$, and $1.1\times10^6$ PFU/μg, respectively, which are similar to the infectivity of the parental pJEV/FL ($3.2\times10^6$ PFU/μg). However, the BHK-21 cells transfected with the recombinant synthetic RNAs did form homogeneous smaller plaques than the pJEV/FL-transfected cells (FIG. 9C). This accords with the delayed production of infectious virus (Table 5, Virus titer) and reduced cytopathogenicity (Table 5, CPE) that was observed in the recombinant RNA-transfected cells. The present inventors also showed that the delayed accumulation of the viral proteins (FIG. 9D) in the recombinant RNA-transfected BHK-21 cells correlated with the length of foreign gene that had been inserted (FIG. 9B).

TABLE 5

Specific infectivity of in vitro RNA transcripts generated from full-length JEV cDNA derivatives containing various reporter genes and recombinant virus titer

| Template used for transcription[a] | Infectivity[b] (PFU/μg of RNA) | Virus titer[c] (PFU/ml) 48 hr | 72 hr | CPE[d] |
|---|---|---|---|---|
| pJEV/FL | $3.2\times10^6$ | $3.0\times10^6$ | $5.1\times10^5$ | ++++ |
| pJEV/FL/PAC | $3.5\times10^6$ | $6.2\times10^4$ | $4.0\times10^5$ | ++ |
| pJEV/FL/EGFP | $2.5\times10^6$ | $9.0\times10^4$ | $2.1\times10^5$ | ++ |
| pJEV/FL/LUC | $3.4\times10^6$ | $2.0\times10^4$ | $3.2\times10^5$ | + |
| pJEV/FL/$LUC^{REP-}$ | 0 | 0 | 0 | − |
| pJEV/FL/LacZ | $1.1\times10^6$ | $1.1\times10^4$ | $1.3\times10^5$ | + |

[a]All JEV cDNA templates used for in vitro transcription reaction were prepared by linearization with Xba I digestion, which was followed by treatment with MBN.

[b]After in vitro transcription with SP6 RNA polymerase, samples were used to electroporate BHK-21 cells, and infectious plaque centers were determined (Yun et al., J. Virol., 2003, 77, 6450-6465).

[c]Virus titers at 48 hr and 72 hr postelectroporation.

[d]Virus-induced CPE was observed after electroporation with RNA transcripts generated from full-length JEV cDNA derivatives. At 24 hr postelectroporation, strong CPE was observed for the parental pJEV/FL as indicated by ++++. For pJEV/FL/PAC and pJEV/FL/EGFP, CPE was observed at 60 hr postelectroporation as indicated by ++. For pJEV/FL/LacZ, clear CPE began to be displayed at 72 hr postelectroporation as indicated by +. − indicates no CPE.

EGFP, LUC, LacZ and PAC expression using infectious JEV cDNA is shown in FIG. 10. The JEV/FL/EGFP RNA-transfected BHK-21 cells showed bright green fluorescence under a fluorescence microscope (FIG. 10A). The green fluorescent cells (–), as determined by flow cytometry analysis, comprised 99.7% of the cells compared to mock-transfected cells (. . .) (FIG. 10B). FIG. 10C demonstrates the X-gal staining pattern of the JEV/FL/LacZ RNA-expressing BHK-21 cells. The present inventors also monitored the LUC activity over time of BHK-21 cells that had been transfected with either the replication-competent JEV/FL/LUC RNA (●) or the replication-incompetent JEV/FL/$LUC^{REP-}$ RNA (○), which lacks a section that prematurely terminates viral translation at nt 5596 (*). This demonstrated that the increased viral replication correlated with increased LUC activity (FIG. 10D), as previously described (Yun et al., *J. Virol.,* 2003, 77, 6450-6465). Furthermore, selection of the JEV/FL/PAC RNA-transfected BHK-21 cells with puromycin (FIG. 10E) revealed the JEV/FL/PAC RNA-transfected cells survived and become confluent in the puromycin-containing media (dish 7) or formed $Pur^R$ foci under semisolid agar overlaid with puromycin-containing media (dish 8), whereas the mock-transfected cells died within 24 hr of selection (dishes 5-6). As expected, both cell types became confluent in the absence of puromycin (dishes 1-4).

<10-2> Construction and Vector Characteristics of JEV Viral Replicons

<10-2-1> Plasmid Construction of JEV Viral Replicon Vectors

Plasmids for all JEV viral replicons were constructed based on pJEV/FL/LUC by engineering in-frame deletions in the coding sequences of the structural proteins. All deletions were distinguished by a novel Xho I site that resulted in the insertion of two residues, namely, Leu and Glu. First, the present inventors generated a set of four JEV viral replicon vectors containing a single in-frame deletion in each structural protein. To construct pJEV/Rep/ΔCC/LUC, which contains a 273-nucleotide deletion (nt 132-404) in the C gene, two fragments were synthesized by PCR amplification of pJEV/FL, namely, fragment C1 with primers DelF (represented by SEQ. ID. No 53) and C1R (represented by SEQ. ID. No 54), and fragment C2 with primers C2F (represented by SEQ. ID. No 55) and DelR (represented by SEQ. ID. No 56). Two fragments (the 267-bp Pac I-Xho I portion of the C1 fragment amplicons and the 226-bp Xho I-BsiW I portion of the C2 fragment amplicons) were ligated to the 20,073-bp BsiW I-Pac I fragment of pJEV/FL/LUC, resulting in the pJEV/Rep/ΔCC/LUC construct. To generate pJEV/Rep/ΔC/LUC, which contains a 204-nucleotide deletion (nt 201-404) in the C gene, fragment C3 from pJEV/FL was amplified by PCR with the primers DelF and C3R (represented by SEQ. ID. No 57). The 336-bp Pac I-Xho I fragment of the resulting amplicons was ligated to the 12,850-bp Xho I-Rsr II and 7,449-bp Rsr II-Pac I fragments of pJEV/Rep/ΔCC/LUC, resulting in the pJEV/Rep/ΔC/LUC construct. To create pJEV/Rep/ΔprM/LUC, which contains a 282-nucleotide deletion (nt 531-812) in the prM gene, two fragments were obtained by the PCR amplification of pJEV/FL, namely, fragment prM1 with the primers DelF and prM1R (represented by SEQ. ID. No 58), and fragment prM2 with primers prM2F (represented by SEQ. ID. No 59) and DelR. Two fragments (the 666-bp Pac I-Xho I portion of the prM1 fragment amplicons and the 1,616-bp Xho I-Sfi I portion of the prM2 fragment amplicons) were ligated to the 10,264-bp Sfi I-Nsi 1 and 8,011-bp Nsi I-Pac I fragments of pJEV/FL/LUC, resulting in the pJEV/Rep/ΔprM/LUC construct. To engineer pJEV/Rep/ΔE/LUC, which contains a 1,170-nucleotide deletion (nt 1,032-2,201) in the E gene, two fragments were produced by PCR amplification of pJEV/FL, namely, fragment E1 with primers DelF and E1R (represented by SEQ. ID. No 60), and fragment E2 with primers E2F (represented by SEQ. ID. No 61) and DelR. Two fragments (the 1,167-bp Pac I-Xho I portion of the prM1 fragment amplicons and the 227-bp Xho I-Sfi I portion of the prM2 fragment amplicons) were ligated to the 10,264-bp Sfi I-Nsi 1 and 8,011-bp Nsi I-Pac I fragments of pJEV/FL/LUC, resulting in the pJEV/Rep/ΔE/LUC construct (FIG. 11A).

Second, the present inventors constructed a panel of three JEV viral replicon vectors that contain a double in-frame deletion in the JEV structural genes. Two fragments of pJEV/FL/LUC (the 10,264-bp Sfi I-Nsi 1 and 8,011-bp Nsi I-Pac I fragments) were ligated to either (i) the 438-bp Pac I-Hind III fragment of pJEV/Rep/ΔC/LUC and the 1,646-bp Hind III-Sfi I fragment of pJEV/Rep/ΔprM/LUC to generate pJEV/Rep/ΔC+ΔprM/LUC, (ii) the 866-bp Pac I-Mlu I fragment of pJEV/Rep/ΔC/LUC and the 330-bp Mlu I-Sfi I fragment of pJEV/Rep/ΔE/LUC to generate pJEV/Rep/ΔC+ΔE/LUC, or (iii) the 788-bp Pac I-Mlu I fragment of pJEV/Rep/ΔprM/LUC and the 330-bp Mlu I-Sfi I fragment of pJEV/Rep/ΔE/LUC to generate pJEV/Rep/ΔprM+ΔE/LUC (FIG. 11A).

Third, the present inventors created a set of two JEV viral replicon vectors in which all JEV structural proteins were lacking. To generate pJEV/Rep/ΔC+ΔprM+ΔE/LUC, two fragments of pJEV/FL/LUC (the 10,264-bp Sfi I-Nsi 1 and 8,011-bp Nsi I-Pac I fragments) were ligated to the 590-bp Pac I-Mlu I fragment of pJEV/Rep/ΔC+ΔprM/LUC and the 330-bp Mlu I-Sfi I fragment of pJEV/Rep/ΔE/LUC. The present inventors also constructed pJEV/Rep/NS1/LUC, which contains the 35 N-terminal and 24 C-terminal amino acids of the C protein followed immediately by the N-terminus of the NS1 protein and the rest of the viral genome. A fragment from pJEV/Rep/ΔC/LUC was first synthesized by PCR with the primers DelF and NS1R (represented by SEQ. ID. No 62). A fragment from pJEV/FL was then synthesized with the primers NS1F (represented by SEQ. ID. No 63) and RR (represented by SEQ. ID. No 64). These two fragments were fused by a second round of PCR with the primers DelF and RR. The 474-bp Pac I-ApaL I fragment of the resulting amplicons was ligated to the 3,038-bp ApaL I-BamH 1 and 15,122-bp BamH I-Pac I fragments of pJEV/FL/LUC, leading to pJEV/Rep/NS1/LUC (FIG. 11A).

In addition to pJEV/Rep/ΔC+ΔprM+ΔE/LUC and pJEV/Rep/NS1/LUC, the present inventors also constructed eight other JEV viral replicon vectors. The 6,797-bp BamH I-Not I fragment of pJEV/FL/EGFP was ligated to either (i) the 11,529-bp BamH I-Not I fragment of pJEV/Rep/ΔC+ΔprM+ΔE/LUC to create pJEV/Rep/ΔC+ΔprM+ΔE/EGFP, or (ii) the 10,968-bp BamH I-Not I fragment of pJEV/Rep/NS1/LUC to create pJEV/Rep/NS1/EGFP. The 5,792-bp Sac II-Not I fragment of pJEV/FL/LacZ was ligated to either (i) the 7,456-bp Not I-Pac I and the 7,464-bp Pac I-Sac II fragments of pJEV/Rep/ΔC+ΔprM+ΔE/LUC to create pJEV/Rep/ΔC+ΔprM+ΔE/LacZ, or (ii) the 7,456-bp Not I-Pac I and the 6,903-bp Pac I-Sac II fragments of pJEV/Rep/NS1/LUC to create pJEV/Rep/NS1/LacZ. The 6,663-bp BamH I-Not I fragment of pJEV/FL/PAC was ligated to either (i) the 11,529-bp BamH I-Not I fragment of pJEV/Rep/ΔC+ΔprM+ΔE/LUC to create pJEV/Rep/ΔC+ΔprM+ΔE/PAC, or (ii) the 10,968-bp BamH I-Not I fragment of pJEV/Rep/NS1/LUC to create pJEV/Rep/NS1/PAC.

<10-2-2> Heterologous Proteins are Expressed From a Variety of Self-replicating Self-limiting JEV Viral Replicons To independently express foreign genes using the JEV RNA replication machinery, the present inventors generated a panel of self-replicating self-limiting viral replicons that meet stringent safety concerns (FIG. 11A). Initially, the present inventors used the LUC reporter as the heterologous gene as it facilitates the monitoring of viral replication in a sensitive and quantitative manner. Thus, a variety of replicon vectors were carefully engineered in the context of pJEV/FL/LUC by the in-frame deletion of one, two, or all of the viral structural genes (C, prM, and E), in consideration with the membrane orientation of each protein (FIG. 11A).

The LUC activities of the BHK-21 cells that had been transfected with the various viral replicons were plotted over time (FIG. 11B). In BHK-21 cells transfected with the replication-competent JEV/FL/LUC RNA (●, black) as a positive control, the initial LUC activity at 6 hr posttransfection was $5.5\pm0.3\times10^3$ RLU. This activity dramatically increased to $2.7\pm0.5\times10^6$ RLU at 48 hr posttransfection and was maintained through to 96 hr posttransfection. In BHK-21 cells transfected with the replication-incompetent JEV/FL/LUC$^{REP-}$ RNA (♦, black), the initial LUC activity expressed from the input viral RNA at 6 hr posttransfection was similar, namely, $5.2\pm0.6\times10^3$ RLU. However, this activity gradually decreased over time to $8.8\pm1.0$ RLU at 96 hr posttransfection, which is equivalent to the background luminescence of naïve cells. Apart from pJEV/Rep/ΔCC/LUC (♦, blue), which lacks a sequence that is complementary to a proposed cyclization sequence in the 3'NTR that is conserved in all flaviviruses (Bredenbeek et al., *J. Gen. Virol.,* 2003, 84, 1261-1268; Lo et al., *J. Virol.,* 2003, 77, 10004-10014; Khromykh et al., *J. Virol.,* 2001, 75, 6719-6728), the LUC activities of the BHK-21 cells transfected with the viral replicons lacking part of one or more structural protein genes were almost identical in the 6-48 hrs posttransfection to those of the replication-competent JEV/FL/LUC RNA-transfected BHK-21 cells (●, black). Thereafter, however, these activities decreased dramatically over time due to a lack of viral spread, similar to JEV/FL/$LUC^{REP-}$. Interestingly, the LUC activities due to JEV/Rep/NS1/LUC RNA (●, green), but not to JEV/Rep/ΔC+ΔprM+ΔE/LUC RNA (■, green), were approximately 5-fold higher at all time points compared to the activities of the other replication-competent viral replicons.

The LUC expression profiles agreed with the viral protein accumulation (FIG. 1C), as quantified by immunoblotting with JEV-specific hyperimmune sera. The present inventors also confirmed that other reporter genes could be efficiently expressed in various commonly used animal cells by using JEV-based replicon vectors such as pJEV/Rep/NS1 and pJEV/Rep/ΔC+ΔprM+ΔE.

<10-3> Construction of the Packaging System for JEV Viral Replicons

Figure 12A:
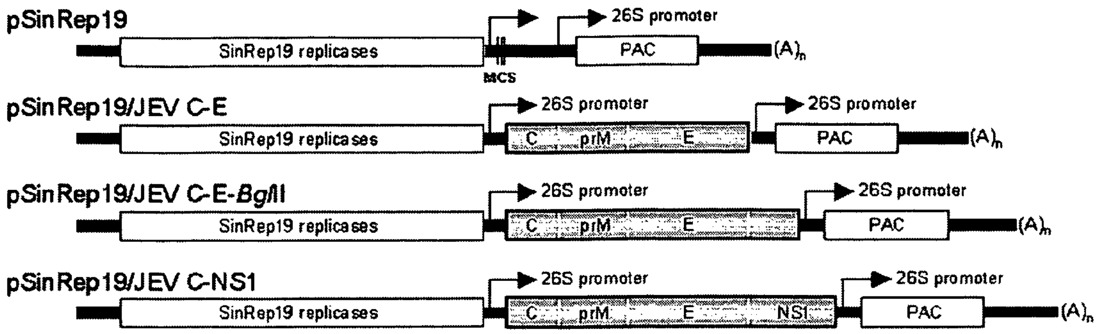

<10-3-1> Plasmid Construction of JEV Structural Protein Expression Vectors Based on the pSinRep19 Vector The present inventors constructed three JEV structural protein expression vectors based on pSinRep19 (Agapov et al., *Proc. Natl. Acad. Sci. USA,* 1998, 95, 12989-12994). For pSinRep19/JEV C-E, a fragment of pJEV/FL was amplified with primer JEVCF (5'-GATTCTAGAATGACTAAAAAACCA, represented by SEQ. ID. No 65), which incorporates an Xba I site (underlined) and primer JEVER (5'-GATGTTTAAACTATTAAGCATGCACATTGGT, represented by SEQ. ID. No 66), which incorporates a Pme I site (underlined). The 2,393-bp Xba I-Pme I fragment of the resulting amplicons was ligated to the 10,864-bp Xba I-Mlu I (T4 DNA polymerase-treated) fragment of pSinRep19 to construct pSinRep19/JEV C-E (FIG. 12A). For pSinRep19/JEV C-NS1, a fragment was obtained by PCR amplification of pJEV/FL with primer JEVCF and primer JEVNS1R (5'-GATGTTTAAACTATTAAGCATCAACCTGTGA, represented by SEQ. ID. No 67), which incorporates a Pme I site (underlined). The 3,449-bp Xba I-Pme I fragment of the resulting amplicons was then ligated to the 10,864-bp Xba I-Mlu I (T4 DNA polymerase-treated) fragment of pSinRep19 to construct pSinRep19/JEV C-NS1 (FIG. 12A). For pSinRep19/JEV C-E-BglII, the 2,559-bp Xba I-Bgl II (T4 DNA polymerase-treated) fragment of pSinRep19/JEV C-NS1 was ligated to the 10,864-bp Xba I-Mlu I (T4 DNA polymerase-treated) fragment of pSinRep19 (FIG. 12A).

<10-3-2> Generation of Packaging Cell Lines for JEV-derived Replicon Vector RNAs.

The utility of the JEV replicon-based expression vectors was elaborated by developing packaging cell lines (PCLs) that constitutively express all the structural proteins of JEV (C, prM, and E) and allow the trans-complementation of the efficient packaging of JEV viral replicons. Based on the pSinRep19 expression vector that contains the PAC gene driven by the subgenomic promoter, which facilitates selection (FIG. 12A), the present inventors constructed three different JEV structural protein expression cassette constructs that encode the sequences for C-E (pSinRep19/JEV C-E), C-E plus the 58 N-terminal residues of NS1 (pSinRep19/JEV C-E-BglII), and C-NS1 (pSinRep19/JEV C-NS1).

Figure 12B:
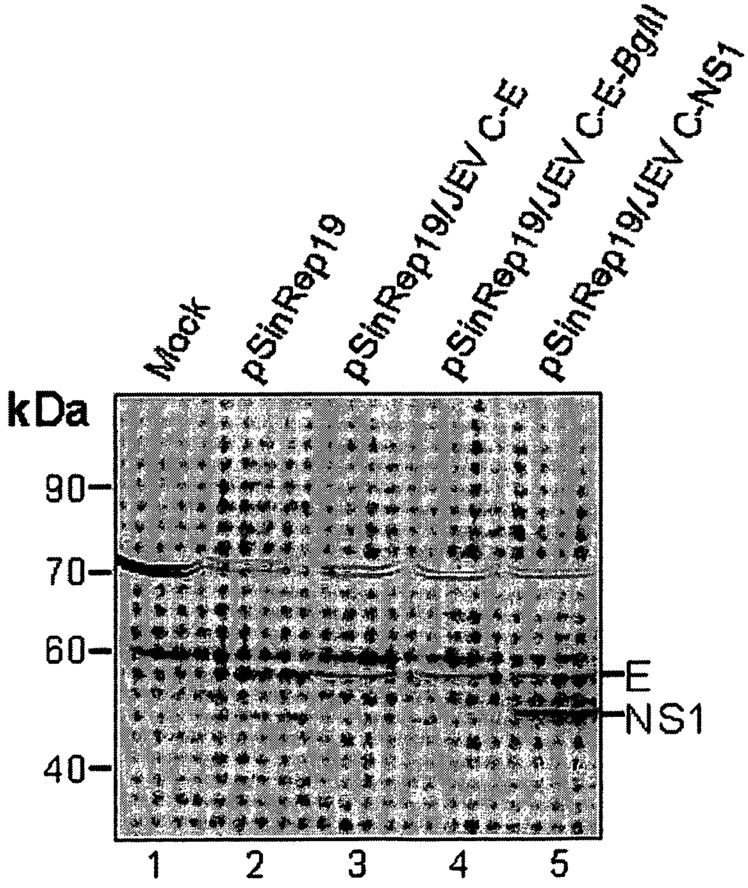

The protein expression yielded by these vectors was evaluated in BHK-21 cells transfected with the synthetic RNAs that had been transcribed in vitro from the corresponding vector. pSinRep19 and its derivatives were linearized by digestion with Xho I. The linearized plasmids were used in vitro transcription reactions (25 μl) employing SP6 RNA polymerase, as described hereinbefore. After transcription, the reaction mixtures were further incubated with 10 U DNase I for 30 min and extracted with phenol-chloroform-isoamylalcohol. RNA yields were quantified on the basis of [$^3$H]UTP incorporation as measured by RNA absorption to DE-81 filter paper (Whatman, Maidstone, UK). RNA (2 μg) was transfected into cells by electroporation as described hereinbefore (Yun et al., *J. Virol.,* 2003, 77, 6450-6465). When the cell lysates from the transfected cells were analyzed by immunoblotting with JEV-specific hyperimmune sera, equal amounts of viral glycoprotein E were detected in the BHK-21 cells transfected with each of the three vectors (FIG. 12B). As designed, the NS1 protein was detected only in the SinRep19/JEV C-NS1 RNA-transfected cells (FIG. 12B).

Figure 12C:
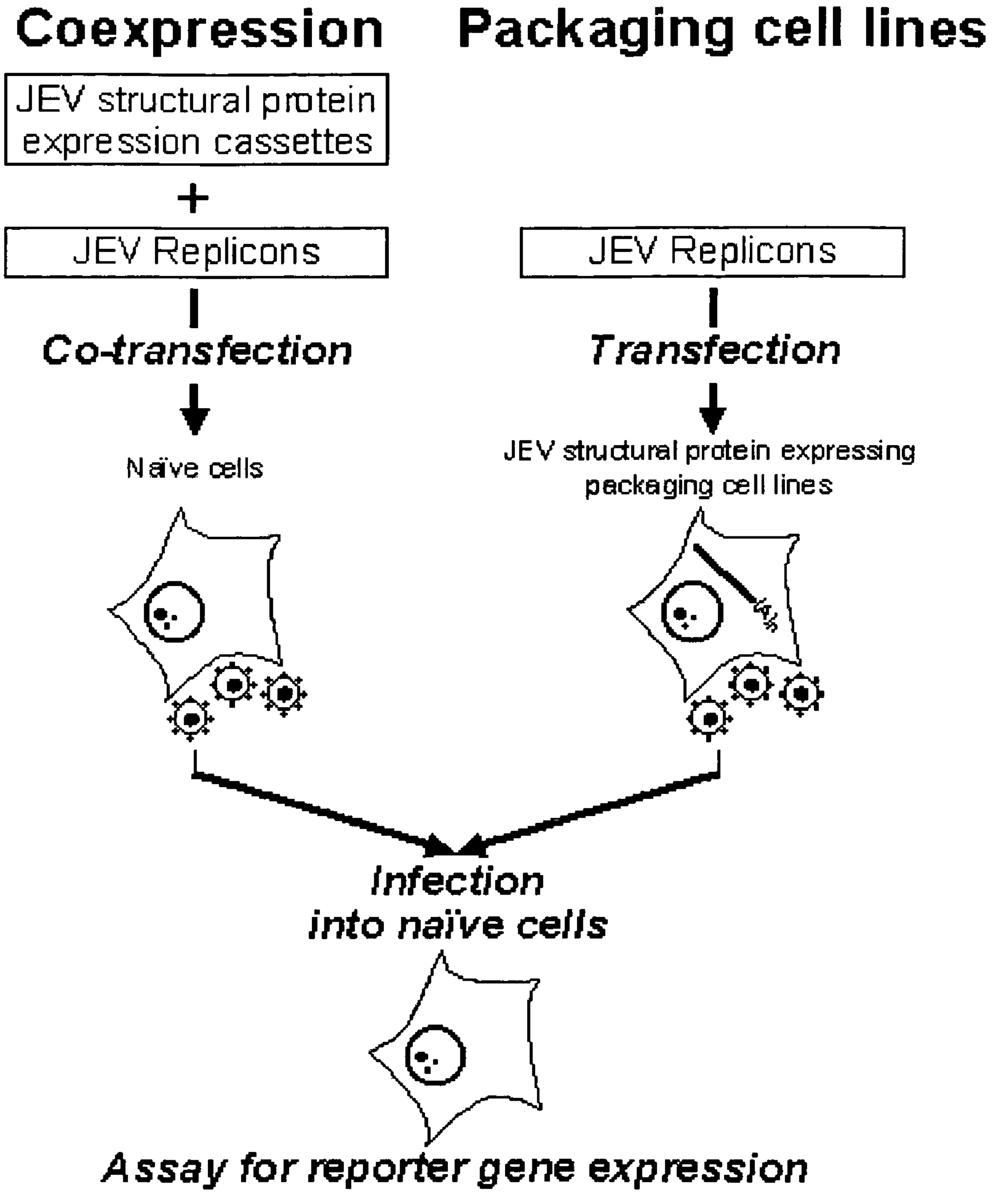
Figure 12D:
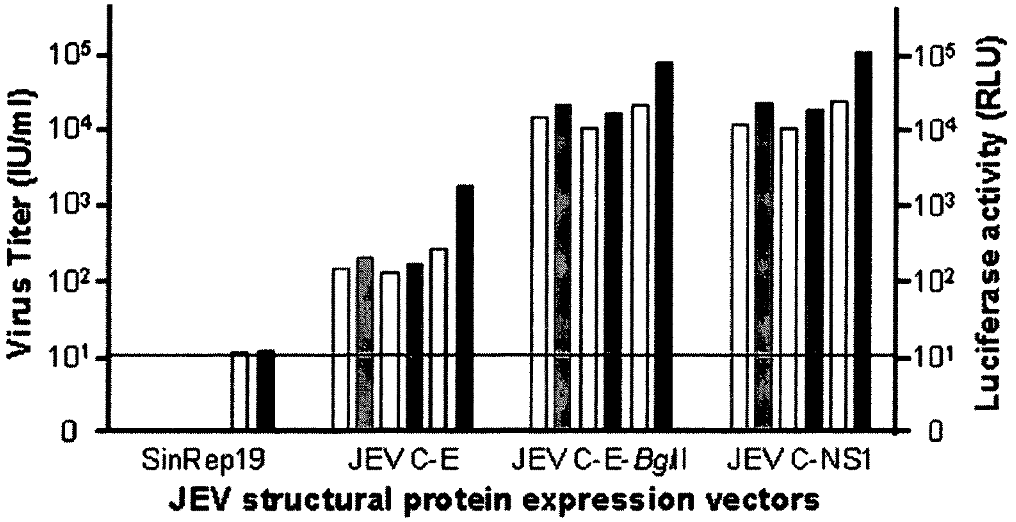

Two approaches to produce JEV viral replicon particles (VRPs) are illustrated in FIG. 12C. One involves the transient cotransfection of in vitro-transcribed JEV replicon vector RNA with the SinRep19 vector RNA that expresses the JEV structural proteins. Titering and monitoring of the packaged VRPs was made possible by infecting naïve BHK-21 cells with the VRPs and then assaying for reporter gene expression. Cotransfection of SinRep19/JEV C-NS1 RNA with EGFP-expressing JEV viral replicon RNAs [either JEV/Rep/ΔC+ΔprM+ΔE/EGFP (□, green) or JEV/Rep/NS1/EGFP (■, green)] in several experiments produced 1.1-4.3×$10^4$ infectious units/ml (IU/ml) of VRPs (FIG. 12D). Similar results were obtained using LacZ-expressing JEV viral replicons, namely, either JEV/Rep/ΔC+ΔprM+ΔE/LacZ (□, blue) or JEV/Rep/NS1/LacZ (■, blue). No difference was observed when the SinRep19/JEV C-NS1 or the SinRep19/JEV C-E-BglII JEV structural protein expression cassettes were used. However, cotransfection of the SinRep19/JEV C-E vector RNA with the viral replicons expressing either EGFP or LacZ produced≈100-fold fewer VRPs (FIG. 12D). These observations were confirmed by cotransfecting all JEV structural protein expression vector RNAs with the LUC-expressing JEV replicon RNAs, namely, JEV/Rep/ΔC+ΔprM+ΔE/LUC (□, black) or JEV/Rep/NS1/LUC (●, black) (FIG. 12D)

The other approach to producing JEV VRPs is based on using a continuous PCL, which is established by transfecting cells with the JEV structural protein expression vector RNA and selecting with puromycin. The BHK-21 cells were transfected with JEV structural protein expression vector RNAs as mentioned hereinbefore. After transfection, the cells were seeded for ≈24 hr and the media were replaced with fresh complete media containing 10 μg/ml puromycin (Sigma). Thereafter, the cells were maintained in the presence of puromycin and passaged or frozen as the parental BHK-21 cells.

Figure 12E:
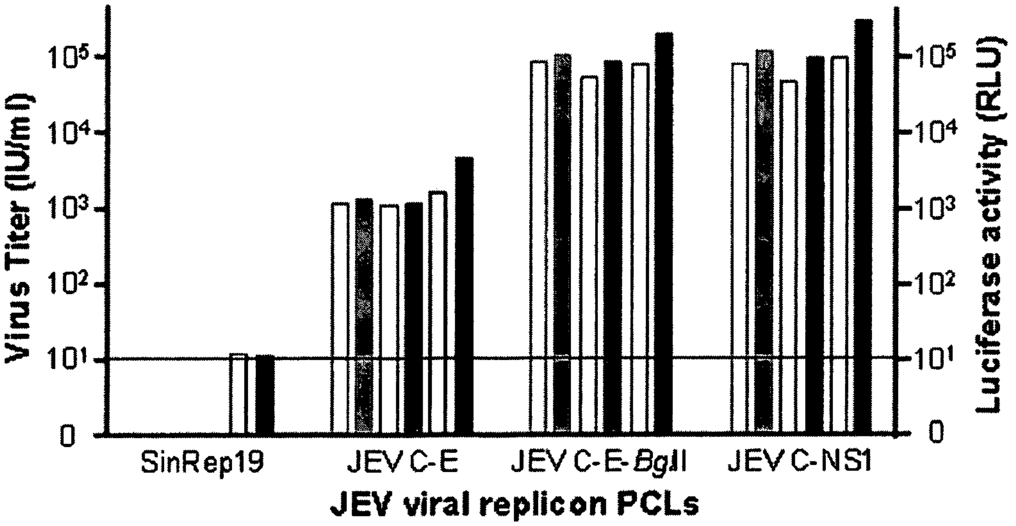

The selected cells were shown to stably express the JEV structural proteins without any deleterious effects to the host cell and were slightly more efficient in producing JEV-based VRPs than the parental BHK-21 cells. In all cases, higher VRP titers (1.0×$10^3$-1.2×$10^5$ IU/ml) were obtained upon transfection of these PCLs with the JEV viral replicon vector RNAs, as compared to the protocol involving the cotransfection of the parental BHK-21 cells with two vector RNAs (FIG. 12E).

To test for the presence of replication-competent viral particles in the packaging system developed in the present invention, naïve BHK-21 cells were infected with $3\times10^5$ IU of the VRPs at an MOI of 1 for 72 hr. The undiluted supernatant obtained from the infected cells was further passaged three times to amplify the possible existence of very low amounts of replication-competent viral particles. At the end of these passages, the infected cells were tested for the expression of the reporter gene or viral protein by IFA using JEV-specific hyperimmune sera. No replication-competent viral particles were ever detected. Furthermore, Sindbis replicon RNAs that express JEV structural proteins were not encapsidated in the released VRPs.

INDUSTRIAL APPLICABILITY

As explained hereinbefore, the authentic nucleotide sequence of JEV genomic RNA and the full-length infectious JEV cDNA of the present invention synthesized therefrom can be used not only for the identification of the JEV genes, but also for the molecular biological studies including JEV replication, transcription, and translation. Moreover, they can also be applied to the development of the therapeutic agents, vaccines, diagnostic reagents, and diagnostic devices for Japanese encephalitis, and can be used as an expression vector for the various foreign genes.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

What is claimed is:

1. A full-length infectious and genetically stable cDNA clone of Japanese encephalitis virus (JEV), wherein a full-length cDNA of JEV is cloned into a bacterial artificial chromosome (BAC) and an infectious RNA transcript of JEV is transcribed directly from the cDNA clone; wherein the cDNA clone contains a promoter at the beginning of 5' end of a DNA sequence corresponding to a JEV genomic RNA and a restriction endonuclease recognition sequence at the end of 3' end of the DNA sequence as a runoff site; and wherein the restriction endonuclease recognition sequence is XHo I or Xba I.

2. The cDNA clone as set forth in claim 1, wherein the promoter is SP6 or T7.

3. The cDNA clone as set forth in claim 1, wherein the restriction endonuclease recognition sequence does not exist in the JEV genomic RNA.

4. The cDNA clone as set forth in claim 1, wherein the cDNA clone has a sequence represented by SEQ. ID. No 45, having SP6 promoter or SEQ. ID. No 48 having T7 promoter.

5. The cDNA clone as set forth in claim 1, wherein the cDNA clone is $pBAC^{SP6}$/JVFLx/XbaI containing the JEV cDNA represented by SEQ. ID. No 45 or $pBAC^{T7}$/JVFLx/XbaI containing the JEV cDNA represented by SEQ. ID. No 48.

6. The cDNA clone as set forth in claim 5, wherein the vector is $pBAC^{T7}$/JVFLx/XbaI having T7 promoter and deposited under Accession No: KCTC 10346BP.

7. The cDNA clone as set forth in claim 5, wherein the cDNA clone is $pBAC^{SP6}$/JVFLx/XbaI having SP6 promoter and deposited under Accession No: KCTC 10347BP.

8. The cDNA clone as set forth in claim 1, wherein the JEV genomic RNA consists of a 5' nontranslated region (NTR), a single polypeptide coding region, and a 3' NTR.

9. A full-length infectious and genetically stable cDNA clone of Japanese encephalitis virus (JEV), comprising:

SEQ. ID. No 45 having SP6 promoter, wherein the cDNA clone contains a promoter at the beginning of 5' end of a DNA sequence corresponding to a JEV genomic RNA and a restriction endonuclease recognition sequence at the end of 3' end of the DNA sequence as a runoff site.

10. A vector, comprising:

a full-length infectious and genetically stable cDNA clone of Japanese encephalitis virus (JEV), wherein the vector is $pBAC^{SP6}$/JVFLx/XbaI.

11. The vector according to claim 10, wherein the vector is $pBAC^{SP6}$/JVFLx/XbaI having SP6 promoter and deposited under Accession No: KCTC 10347BP.

12. The vector according to claim 10, wherein the JEV comprises SEQ. ID. No 45.

13. A full-length infectious and genetically stable cDNA clone of Japanese encephalitis virus (JEV), comprising:

SEQ. ID. No 48 having T7 promoter, wherein the cDNA clone contains a promoter at the beginning of 5' end of a DNA sequence corresponding to a JEV genomic RNA and a restriction endonuclease recognition sequence at the end of 3' end of the DNA sequence as a runoff site.

14. A vector, comprising:

a full-length infectious and genetically stable cDNA clone of Japanese encephalitis virus (JEV), wherein the vector is $pBAC^{T7}$/JVFLx/XbaI.

15. The vector according to claim 14, wherein the vector is $pBAC^{T7}$/JVFLx/XbaI having T7 promoter and deposited under Accession No: KCTC 10346BP.

16. The vector according to claim 14, wherein the JEV comprises SEQ. ID. No 48.

* * * * *

SEQUENCE LISTING

```
<160> NUMBER OF SEQ ID NOS: 71

<210> SEQ ID NO 1
<211> LENGTH: 18
<212> TYPE: DNA
<213> ORGANISM: Artificial Sequence
<220> FEATURE:
<223> OTHER INFORMATION: primer J7, complementary to nt 3986-4004 of
      the JEV genome

<400> SEQUENCE: 1

agcgctaaga ctggcatg                                                   18


<210> SEQ ID NO 2
<211> LENGTH: 28
<212> TYPE: DNA
<213> ORGANISM: Artificial Sequence
<220> FEATURE:
<223> OTHER INFORMATION: primer J8, complementary to nt 1-18 of
      the JEV genome

<400> SEQUENCE: 2

gatcggaccg agaagtttat ctgtgtga                                        28


<210> SEQ ID NO 3
<211> LENGTH: 21
<212> TYPE: DNA
<213> ORGANISM: Artificial Sequence
<220> FEATURE:
<223> OTHER INFORMATION: primer J6, complementary to nt 3845-3865 of
      the JEV genome

<400> SEQUENCE: 3

gcccctagga ccagaaccac g                                               21


<210> SEQ ID NO 4
<211> LENGTH: 21
<212> TYPE: DNA
<213> ORGANISM: Artificial Sequence
<220> FEATURE:
<223> OTHER INFORMATION: primer J4, complementary to nt 8150-8170 of
      the JEV genome

<400> SEQUENCE: 4

aggacgcgta gtgtgcgttg t                                               21
```

-continued

<210> SEQ ID NO 5
<211> LENGTH: 18
<212> TYPE: DNA
<213> ORGANISM: Artificial Sequence
<220> FEATURE:
<223> OTHER INFORMATION: primer J20, complementary to nt 3266-3283 of the JEV genome

<400> SEQUENCE: 5
aaaccaggga ccttggga 18

<210> SEQ ID NO 6
<211> LENGTH: 21
<212> TYPE: DNA
<213> ORGANISM: Artificial Sequence
<220> FEATURE:
<223> OTHER INFORMATION: primer J1, complementary to nt 10947-10967 of the JEV genome

<400> SEQUENCE: 6
gatcctgtgt tcttcctcac c 21

<210> SEQ ID NO 7
<211> LENGTH: 27
<212> TYPE: DNA
<213> ORGANISM: Artificial Sequence
<220> FEATURE:
<223> OTHER INFORMATION: primer J12, complementary to nt 7565-7582 of the JEV genome

<400> SEQUENCE: 7
gatcggaccg aattccacca cagccac 27

<210> SEQ ID NO 8
<211> LENGTH: 24
<212> TYPE: DNA
<213> ORGANISM: Artificial Sequence
<220> FEATURE:
<223> OTHER INFORMATION: primer J2, complementary to nt 10870-10893 of the JEV genome

<400> SEQUENCE: 8
agaagatctc ccagtctatt ccca 24

<210> SEQ ID NO 9
<211> LENGTH: 10818
<212> TYPE: DNA
<213> ORGANISM: Japanese encephalitis virus

<400> SEQUENCE: 9
agagattagt gcagtttaaa cagtttttta gaacggaaga taaccatgac taaaaaacca 60
ggagggcccg gtaaaaaccg ggctatcaat atgctgaaac gcggcctacc ccgcgtattc 120
ccactagtgg gagtgaagag ggtagtaatg agcttgttgg acggcagagg accagtacgt 180
ttcgtgctgg ctcttatcac gttcttcaag tttacagcat tagccccgac caaggcgctt 240
ttaggccgat ggaaagcagt ggaaaagagt gtggcaatga aacatcttac tagtttcaaa 300
cgagaacttg gaacactcat tgacgccgtg aacaagcggg gcagaaagca aaacaaaaga 360
ggaggaaatg aaggctcaat catgtggctc gcgagtttgg cagttgtcat agcttgtgta 420
ggagccatga agttgtcaaa tttccaaggg aagcttttga tgaccattaa caacacggac 480
attgcagacg tcatcgtgat tcctacctca aaaggagaga acagatgctg ggtccgggca 540
atcgatgtcg gctacatgtg tgaggacact atcacgtacg aatgtcctaa gcttaccatg 600

-continued

```
ggcaatgatc cagaggatgt ggattgctgg tgtgacaacc aagaagtcta cgtccaatat    660
ggacggtgca cgcggaccag gcattccaag cgaagcagga ggtccgtgtc ggtccaaaca    720
catggggaga gttcactagt gaataaaaaa gaggcttggc tggattcaac gaaagccaca    780
cgatatctca tgaaaactga gaactggatc ataaggaatc ctggctatgc tttcctggcg    840
gcggtacttg gctggatgct tggcagtaac aatggtcaac gcgtggtgtt taccatcctc    900
ctgctgttgg tcgctccggc ttacagtttt aattgtctgg gaatgggcaa ccgtgacttc    960
atagaaggag ccagtggagc cacttgggtg gacttagtgc tagaaggaga tagctgcttg   1020
acaatcatgg caaacgacaa accaacattg gacgtccgca tgattaacat cgaagccagc   1080
caacttgctg aggtcagaag ctattgctat catgcttcag tcactgacat ctcgacggtg   1140
gctcggtgcc ccacgactgg agaagcccac aacgagaagc gagctgatag tagctatgtg   1200
tgcaaacaag gtttcactga tcgtgggtgg ggcaacggat gtggactttt cgggaaggga   1260
agcattgaca catgtgcaaa attctcctgc accagtaagg cgattgggag aacaatccag   1320
ccagaaaaca tcaaatacga agttggcatt tttgtgcatg gaaccaccac ctcggaaaac   1380
catgggaatt attcagcgca agtaggggcg tcccaggcgg caaagtttac agtaacaccc   1440
aatgctcctt cgataaccct caaacttggt gactacggag aagtcacact ggactgtgaa   1500
ccaaggagtg gactgaacac tgaagcgttt tacgtcatga ccgtggggtc aaagtcattt   1560
ctggtccata gggaatggtt tcatgacctc gctctcccct ggacgtcccc ttcgagcaca   1620
gcgtggagaa acagagaact cctcatggaa tttgaagagg cgcacgccac aaaacagtcc   1680
gttgttgctc ttgggtcaca ggaaggaggc ctccatcagg cgctggcagg agccatcgtg   1740
gtggagtact caagctcagt gaagttaaca tcaggccacc tgaaatgtag gctgaaaatg   1800
gacaaactgg ctctgaaagg cacaacctat ggcatgtgta cagaaaaatt ctcgttcgcg   1860
aaaaatccgg cggacactgg ccacggaaca gttgtcattg aactctccta ttctgggagt   1920
gatggcccct gcaaaattcc gattgtctcc gttgcgagcc tcaatgacat gacccccgtt   1980
gggcggctgg tgacagtgaa ccccttcgtc gcgacttcca gtgccaactc aaaggtgctg   2040
gtcgagatgg aaccccccctt cggagactcc tacatcgtag ttggaagggg agacaagcag   2100
atcaaccacc attggcataa agctggaagc acgctgggca aggctttttc aacaactttg   2160
aagggagctc aaagactggc agcgttgggc gacacagcct gggactttgg ctctattgga   2220
ggggtcttca actccatagg aaaggccgtt caccaagtgt ttggtggcgc tttcagaaca   2280
ctctttgggg gaatgtcttg gatcacacaa gggttaatgg gtgccctact actctggatg   2340
ggcatcaacg cacgagatcg atcaattgct ttggccttct tggccacagg aggtgtgctc   2400
gtgttcttag cgaccaatgt gcatgctgac actggatgtg ccattgacat cgcaagaaaa   2460
gagatgagat gcggaagtgg catcttcgtg cacaacgacg tggaagcctg ggtggatagg   2520
tataaatatt tgccagaaac gcccagatcc ctagcgaaga tcgtccacaa agcgcacaag   2580
gaaggcgtgt gcggagtcag atctgtcact agactggagc accaaatgtg ggaagccgtg   2640
cgggacgaat tgaacgtcct gctcaaagag aatgcagtgg acctcagtgt ggttgtgaac   2700
aagcccgtgg ggagatatcg ctcagcccca aaacgcctgt ccatgacgca agagaagttt   2760
gaaatgggct ggaaagcatg ggaaaaaagc attctctttg ccccggaatt ggctaactcc   2820
acatttgttg tagatggacc tgagacaaag gaatgtcctg atgagcacag agcctggaac   2880
agcatgcaaa tcgaagactt cggctttggt atcacatcaa cccgtgtgtg gctgaagatt   2940
```

-continued

```
agagaggaaa gcactgacga gtgtgatgga gcgatcatag gcacagctgt caaaggacat   3000
gtggcagttc atagtgactt gtcgtactgg attgagagtc gctacaacga cacatggaaa   3060
cttgagaggg cagtctttgg agaggtcaaa tcttgcactt ggccagagac acacactctt   3120
tggggagatg gtgttgagga aagtgaactc atcatcccgc ataccatagc cggaccaaaa   3180
agcaagcaca atcggaggga agggtacaaa acacaaaacc agggaccttg ggacgaaaac   3240
ggcatagtct tggactttga ttattgccca gggacaaaag tcaccatcac agaggattgt   3300
ggcaagagag gcccttcggt cagaaccact actgacagtg gaaagttgat tactgactgg   3360
tgctgtcgca gttgctccct tccgccccta cgattccgga cagaaaatgg ctgctggtac   3420
ggaatggaaa tcagacctgt taggcatgat gaaacaacac tcgtcagatc acaggttgat   3480
gctttcaatg gtgaaatggt tgaccctttt cagctgggcc ttctggtgat gtttctggcc   3540
acccaggagg tccttcgcaa gaggtggacg gccagattga ccattcctgc ggttttgggg   3600
gccctgcttg tgctgatgct tgggggcatc acttacactg atttggcgag gtatgtggtg   3660
ctagtcgctg ctgctttcgc agaggccaat aatggaggag acgtcctgca ccttgctttg   3720
attgccgttt ttaagatcca accagctttt ctagtgatga acatgcttag cacgagatgg   3780
acgaaccaag aaaacgtggt cctggtccta ggggctgcct tctttcaatt ggcctcagta   3840
gatctgcaaa tcggagtcca cggaatcctg aatgccgccg ctatagcatg gatgattgtt   3900
cgagcgatca ccttccccac aacctcctcc gtcaccatgc cagtcttagc gcttctaact   3960
ccgggaatga gggctctata cctagacact tacagaatca tccttctcgt catagggatt   4020
tgctccctgc tgcaagagag gaaaaagacc atggcaaaaa agaaaggagc tgtactcttg   4080
ggcttagcgc tcacatccac tggatggttc tcgcccacca ccatagctgc tggacttatg   4140
gtctgcaacc caaacaagaa gagagggtgg ccagctactg agtttctgtc ggcagtcgga   4200
ttgatgtttg ccatcgtagg tggtttggcc gagttggata ttgaatccat gtcaataccc   4260
ttcatgctgg caggtcttat ggcagtgtcc tacgtagtgt caggaaaagc aacagatatg   4320
tggctcgaac gggccgccga catcagctgg gagatggatg ctgcaatcac aggaagcagt   4380
cggaggctgg atgtgaaact ggatgatgac ggagattttc acttgattga tgatcccggc   4440
gttccatgga aagtttgggt cttgcgcatg tcttgcattg gcttagccgc cctcacgcct   4500
tgggccattg ttcccgccgc tttcggttac tggctcactt taaaaacaac aaaaagaggg   4560
ggcgtgtttt gggacacgcc atccccgaaa ccttgcttaa aaggagacac cactacagga   4620
gtctaccgaa tcatggctag agggattctt ggcacctacc aggctggcgt cggagtcatg   4680
tacgagaatg ttttccacac actatggcac acaactagag ggcagccat tatgagtgga   4740
gaaggaaaat tgacgccata ctggggtagc gtgaaagaag accgcatagc ttacggaggc   4800
ccatggagat ttgatcgaaa atggaatgga acagatgacg tgcaagtgat cgtggtagaa   4860
ccggggaagg ctgcggtaaa catccagaca aaaccaggag tgtttcggac cccccttcggg   4920
gaggttgggg ctgttagcct ggattacccg cgaggaacat ccggctcacc cattctggat   4980
tccaatggag acatcatagg cctatacggc aatggagttg agcttggcga tggctcatac   5040
gtcagcgcca tcgtgcaggg tgaccgtcag gaggaaccag tcccagaagc ttacactcca   5100
aacatgttaa gaaagagaca gatgactgtg ttagatttgc accctggttc agggaaaacc   5160
aggaaaattc tgccacaaat aattaaggat gcaatccagc agcgcctaag aacagctgtg   5220
ttggcaccga cgcgggtggt agcagcagaa atggcagaag ctttgagagg gctcccagta   5280
cgataccaaa cttcagcagt gcagagagag caccaaggga atgaaatagt ggatgtgatg   5340
```

-continued

```
tgccacgcca ctctgaccca cagattgatg tcaccgaaca gagtgcccaa ctacaatcta   5400
tttgtcatgg atgaagctca tttcaccgac ccagccagca tagccgcacg aggatacatc   5460
gctaccaagg tggaattagg agaggcagca gccatcttta tgacagcgac cccgcctgga   5520
accacggatc cttttcccga ctcaaatgcc ccaatccatg atttacaaga tgagatacca   5580
gacagggcat ggagcagtgg atacgaatgg atcacagaat atgcgggtaa aaccgtgtgg   5640
tttgtggcga gcgtaaaaat ggggaatgag attgcaatgt gcctccaaag agcgggaaaa   5700
aaggtcatcc aactcaaccg caagtcctat gacacagaat acccaaaatg taagaatgga   5760
gactgggatt ttgtcattac caccgacatc tctgaaatgg gggctaactt cggtgcgagc   5820
agggtcatcg actgcagaaa gagcgtgaaa cccaccatct tagaagaggg agaaggcaga   5880
gtcatcctcg gaaacccatc tcccataacc agtgctagcg cagctcaacg gaggggcaga   5940
gtaggcagaa accccaacca agttggagat gaataccatt atggaggggc taccagtgaa   6000
gatgacagta acctagccca ttggacagag gcaaagatca tgttagacaa catacacatg   6060
cccaatgggc tggtggccca gctctatgga ccagagaggg aaaaggcttt cacaatggat   6120
ggcgaatacc gtctcagggg tgaagaaaag aaaaacttct tagagctgct taggacggct   6180
gaccttccgg tgtggctggc ctataaggtg gcgtccaatg gcattcagta caccgacaga   6240
aagtggtgtt ttgatgggcc gcgcacgaat gccatactgg aggacaacac cgaggtagag   6300
atagtcaccc ggatgggtga gagaaagatc ctcaagccga gatggcttga tgcaagagta   6360
tacgcagatc accaagccct caagtggttc aaagactttg cagcaggaaa gagatcggcc   6420
gttagcttca tagaggtgct cggtcgcatg cctgagcatt tcatgggaaa gacgcgggaa   6480
gctttagaca ccatgtactt ggtcgcaacg gctgagaaag gtgggaaggc acaccgaatg   6540
gctctcgaag agttgccgga tgcactggaa accatcacac ttattgttgc catcactgta   6600
atgacaggag gattcttcct actaatgatg cagcgaaagg gtatagggaa gatgggtctt   6660
ggagctctag tgctcacgct agctaccttc ttcctgtggg cggcagaggt tcctggaacc   6720
aaaatagcag ggaccctgct gatcgccctg ctgctgatgg tggttctcat cccagaaccg   6780
gaaaaacaga ggtcacagac agacaaccaa ctagcggtgt ttctcatctg cgtcttgacc   6840
gtggttggag tggtggcagc aaacgagtac gggatgctag aaaaaaccaa agcagatctc   6900
aagagcatgt ttggcggaaa gacacaggca tcaggactga ctggattgcc aagcatggca   6960
ctggacctgc gtccagccac agcctgggca ctgtatgggg ggagcacagt tgtgctaacc   7020
cctcttctga agcacctgat cacgtcggaa tatgtcacca catcgctagc ctcaattaac   7080
tcacaagctg gctcattatt cgtcttgcca cgaggcgtgc ctttcaccga tctagacctg   7140
accgttggcc tcgtcttcct tggctgctgg ggtcaaatca ccctcacaac gtttttgaca   7200
gccatggttc tggcgacact tcactatggg tacatgctcc ctggatggca agcagaagca   7260
ctcagggctg cccagagaag gacggcggct ggaataatga agaatgccgt tgttgacgga   7320
atggtcgcca ctgatgtgcc tgaactggaa aggactactc ctctgatgca aaagaaagtc   7380
ggacaggtgc tcctcatagg ggtgagcgtg gcagcgtttc tcgtcaaccc taatgtcacc   7440
actgtgagag aagcaggggt gttggtgacg gcggctacgc tcaccttgtg ggataatgga   7500
gccagtgccg tttggaattc caccacagcc acgggactct gccatgtcat gcgaggtagc   7560
tacctggctg gaggctctat tgcttggact cttatcaaga acgctgacaa gccctccttg   7620
aaaaggggaa ggcctggggg caggacgcta ggggagcagt ggaaggaaaa actaaatgcc   7680
```

-continued

```
atgagcagag aagagttttt taaataccgg agagaggcca taatcgaggt ggaccgcact   7740
gaagcacgca gggctagacg tgaaaataac atagtgggag gacatccggt ttcgcgaggc   7800
tcagcaaaac tccgttggct cgtggagaaa ggattcgtct cgccaatagg aaaagtcatt   7860
gatctagggt gtgggcgtgg aggatggagc tactacgcag caaccctgaa gaaggtccag   7920
gaagtcagag gatacacgaa aggtggggcg ggacatgaag agccgatgct catgcagagc   7980
tacggctgga acctggtctc cttgaagagt ggagtggatg tgttctacaa accttcagag   8040
cctagtgaca ccctgttctg tgacataggg gaatcctccc caagtccaga agtggaagaa   8100
caacgcacac tacgcgtcct agagatgaca tccgattggt tgcatcgagg acccagagag   8160
ttctgcataa aagttctctg cccttacatg cccaaggtca tagaaaaaat ggaagttctg   8220
cagcgccgct tcggaggtgg gctagtacgt ctcccccctgt cccgaaactc caatcacgag   8280
atgtattggg ttagtggagc cgctggcaat gtggtgcacg ctgtgaacat gaccagccag   8340
gtactactgg ggcgaatgga tcgcacagtg tggagagggc caaagtatga ggaagatgtc   8400
aacctaggta gcggaacaag agccgtggga aagggagaag ttcatagcaa tcaggagaaa   8460
atcaagaaga gaatccagaa gcttaaagaa gaattcgcca caacgtggca caaagaccct   8520
gaacacccat accgcacttg gacataccac ggaagctatg aggtgaaggc tactggctca   8580
gccagctctc tcgtcaacgg agtggtgaag ctcatgagta aaccttggga cgccattgcc   8640
aacgtcacca ccatggccat gactgacacc accccttttg gacagcaaag agtttttcaag   8700
gagaaagttg acacgaaagc tcctgagcca ccagctggag tcaaggaagt gctcaacgag   8760
accaccaact ggctgtgggc ccacttgtca cgggaaaaaa gaccccgctt gtgcaccaag   8820
gaagaattta taaagaaagt caatagcaac gcggctcttg gagcagtgtt tgctgaacag   8880
aatcaatgga gcacggcgcg tgaggctgtg gacgacccgc ggttttggga gatggtcaat   8940
gaagagaggg aaaaccatct gcgaggagag tgtcacacat gtatctacaa catgatggga   9000
aaaagagaga agaagcctgg agagtttgga aaagctaaag ggagcagggc catttggttc   9060
atgtggcttg gagcacggta tctagagttt gaagctttgg ggttcctgaa tgaagaccac   9120
tggctgagcc gagagaattc aggaggtgga gtagaaggct caggcgtcca aaagttggga   9180
tacatcctcc gtgacatagc aggaaagcaa ggagggaaaa tgtacgctga tgacaccgcc   9240
gggtgggaca ctagaattac tagaactgat ttagaaaatg aagctaaggt gctggagctc   9300
ctagatggtg aacaccgcat gctcgcccgg gccataattg aactgactta caggcacaaa   9360
gtggtcaagg tcatgagacc tgcagcagaa ggaaagaccg tgatggacgt gatatcaaga   9420
gaagaccaaa gggggagtgg acaggtggtc acttatgctc tcaacacttt cacgaacatc   9480
gctgtccagc tcgttaggct gatggaggct gagggggtca ttgggccaca acacttggaa   9540
cagctgccta ggaaaaacaa gatagctgtc aggacttggc tctttgagaa tggagaggag   9600
agagtgacca ggatggcgat cagcggagac gactgtgtcg tcaagccgct ggacgacaga   9660
ttcgccacgg ccctccattt cctcaacgca atgtcaaagg ttagaaaaga catccaggaa   9720
tggaagcctt cgcacggctg gcacgattgg cagcaagttc ccttctgctc taaccacttt   9780
caggagattg tgatgaaaga cggaaggagt atagttgtcc cgtgcagagg acaggatgag   9840
ctgataggca gggctcgcat ctctccagga gctggatgga atgtgaagga cacagcttgc   9900
ctggcaaaag catatgcaca gatgtggcta ctcctatact tccatcgtag ggacctgcgt   9960
ctcatggcaa atgcgatttg ctcagcagtg ccagtggatt gggtgcccac aggcaggaca  10020
tcctggtcaa tacactcgaa aggagagtgg atgaccacgg aagacatgct gcaggtctgg  10080
```

-continued

```
aacagagtct ggattgaaga aaatgaatgg atgatggata agactcccgt cacaagctgg  10140

acagacgttc cgtatgtggg aaagcgtgag gacatctggt gtggcagcct catcggaacg  10200

cgttccagag caacctgggc tgagaacatc tatgcggcga taaaccaggt tagagctgtc  10260

attgggaaag aaaattatgt tgactacatg acctcactca ggagatacga agacgtcttg  10320

atccaggaag acagggtcat ctagtgtgac ttaaggtaga aatgtaaata atgtgaatga  10380

gaaaatgcat gtatatggag tcaggccagc aaaagctgcc accggatact gggtagacgg  10440

tgctgcctgc gtctcagtcc caggaggact gggttaacaa atctgacaac agaaagtgag  10500

aaagccctca gaaccgtctc ggaagtaggt ccctgctcac tggaagttga aagaccaacg  10560

tcaggccacg aatttgtgcc actccgctgg ggagtgcggc ctgcgcagcc ccaggaggac  10620

tgggttacca aagccgttga ggcccccacg gcccaagcct cgtctaggat gcaatagacg  10680

aggtgtaagg actagaggtt agaggagacc ccgtggaaac aacaacatgc ggcccaagcc  10740

ccctcgaagc tgtagaggag gtggaaggac tagaggttag aggagacccc gcatttgcat  10800

caaacagcat attgacac                                                10818


<210> SEQ ID NO 10
<211> LENGTH: 27
<212> TYPE: DNA
<213> ORGANISM: Artificial Sequence
<220> FEATURE:
<223> OTHER INFORMATION: synthetic oligodeoxyribonucleotide T

<400> SEQUENCE: 10

ccagtgttgt ggcctgcagg gcgaatt                                         27


<210> SEQ ID NO 11
<211> LENGTH: 27
<212> TYPE: DNA
<213> ORGANISM: Artificial Sequence
<220> FEATURE:
<223> OTHER INFORMATION: oligonucleotide TR, which is complementary
      to oligonucleotide T of the SEQ. ID. No. 10

<400> SEQUENCE: 11

gatgaattcg ccctgcaggc cacaaca                                         27


<210> SEQ ID NO 12
<211> LENGTH: 18
<212> TYPE: DNA
<213> ORGANISM: Artificial Sequence
<220> FEATURE:
<223> OTHER INFORMATION: primer J35, complementary to nt 10259-10276 of
      the JEV genome

<400> SEQUENCE: 12

agcaacctgg gctgagaa                                                   18


<210> SEQ ID NO 13
<211> LENGTH: 18
<212> TYPE: DNA
<213> ORGANISM: Artificial Sequence
<220> FEATURE:
<223> OTHER INFORMATION: primer J40, complementary to nt 215-232 of
      the JEV genome

<400> SEQUENCE: 13

aaacgtactg gtcctctg                                                   18
```

-continued

```
<210> SEQ ID NO 14
<211> LENGTH: 18
<212> TYPE: DNA
<213> ORGANISM: Artificial Sequence
<220> FEATURE:
<223> OTHER INFORMATION: primer J39, which is complementary to nt
      164-181 of the JEV genome

<400> SEQUENCE: 14

cccactagtg ggaatacg                                                   18


<210> SEQ ID NO 15
<211> LENGTH: 10968
<212> TYPE: DNA
<213> ORGANISM: Japanese encephalitis virus

<400> SEQUENCE: 15

agaagtttat ctgtgtgaac ttcttggctt agtatcgttg agaagaatcg agagattagt     60

gcagtttaaa cagtttttta gaacggaaga taaccatgac taaaaaacca ggagggcccg    120

gtaaaaaccg ggctatcaat atgctgaaac gcggcctacc ccgcgtattc ccactagtgg    180

gagtgaagag ggtagtaatg agcttgttgg acggcagagg accagtacgt ttcgtgctgg    240

ctcttatcac gttcttcaag tttacagcat tagccccgac caaggcgctt ttaggccgat    300

ggaaagcagt ggaaaagagt gtggcaatga aacatcttac tagtttcaaa cgagaacttg    360

gaacactcat tgacgccgtg aacaagcggg gcagaaagca aaacaaaaga ggaggaaatg    420

aaggctcaat catgtggctc gcgagtttgg cagttgtcat agcttgtgta ggagccatga    480

agttgtcaaa tttccaaggg aagcttttga tgaccattaa caacacggac attgcagacg    540

tcatcgtgat tcctacctca aaaggagaga acagatgctg ggtccgggca atcgatgtcg    600

gctacatgtg tgaggacact atcacgtacg aatgtcctaa gcttaccatg ggcaatgatc    660

cagaggatgt ggattgctgg tgtgacaacc aagaagtcta cgtccaatat ggacggtgca    720

cgcggaccag gcattccaag cgaagcagga ggtccgtgtc ggtccaaaca catggggaga    780

gttcactagt gaataaaaaa gaggcttggc tggattcaac gaaagccaca cgatatctca    840

tgaaaactga gaactggatc ataaggaatc ctggctatgc tttcctggcg gcggtacttg    900

gctggatgct tggcagtaac aatggtcaac gcgtggtgtt taccatcctc ctgctgttgg    960

tcgctccggc ttacagtttt aattgtctgg gaatgggcaa ccgtgacttc atagaaggag   1020

ccagtggagc cacttgggtg gacttagtgc tagaaggaga tagctgcttg acaatcatgg   1080

caaacgacaa accaacattg gacgtccgca tgattaacat cgaagccagc caacttgctg   1140

aggtcagaag ctattgctat catgcttcag tcactgacat ctcgacggtg gctcggtgcc   1200

ccacgactgg agaagcccac aacgagaagc gagctgatag tagctatgtg tgcaaacaag   1260

gtttcactga tcgtgggtgg ggcaacggat gtggactttt cgggaaggga agcattgaca   1320

catgtgcaaa attctcctgc accagtaagg cgattgggag aacaatccag ccagaaaaca   1380

tcaaatacga agttggcatt tttgtgcatg gaaccaccac ctcggaaaac catgggaatt   1440

attcagcgca agtaggggcg tcccaggcgg caaagtttac agtaacaccc aatgctcctt   1500

cgataaccct caaacttggt gactacggag aagtcacact ggactgtgaa ccaaggagtg   1560

gactgaacac tgaagcgttt tacgtcatga ccgtggggtc aaagtcattt ctggtccata   1620

gggaatggtt tcatgacctc gctctcccct ggacgtcccc ttcgagcaca gcgtggagaa   1680

acagagaact cctcatggaa tttgaagagg cgcacgccac aaaacagtcc gttgttgctc   1740

ttgggtcaca ggaaggaggc ctccatcagg cgctggcagg agccatcgtg gtggagtact   1800
```

-continued

```
caagctcagt gaagttaaca tcaggccacc tgaaatgtag gctgaaaatg gacaaactgg   1860
ctctgaaagg cacaacctat ggcatgtgta cagaaaaatt ctcgttcgcg aaaaatccgg   1920
cggacactgg ccacggaaca gttgtcattg aactctccta ttctgggagt gatggcccct   1980
gcaaaattcc gattgtctcc gttgcgagcc tcaatgacat gacccccgtt gggcggctgg   2040
tgacagtgaa ccccttcgtc gcgacttcca gtgccaactc aaaggtgctg gtcgagatgg   2100
aaccccccctt cggagactcc tacatcgtag ttggaagggg agacaagcag atcaaccacc   2160
attggcataa agctggaagc acgctgggca aggcttttc aacaactttg aagggagctc   2220
aaagactggc agcgttgggc gacacagcct gggactttgg ctctattgga ggggtcttca   2280
actccatagg aaaggccgtt caccaagtgt ttggtggcgc tttcagaaca ctctttgggg   2340
gaatgtcttg gatcacacaa gggttaatgg gtgccctact actctggatg ggcatcaacg   2400
cacgagatcg atcaattgct ttggccttct tggccacagg aggtgtgctc gtgttcttag   2460
cgaccaatgt gcatgctgac actggatgtg ccattgacat cgcaagaaaa gagatgagat   2520
gcggaagtgg catcttcgtg cacaacgacg tggaagcctg ggtggatagg tataaatatt   2580
tgccagaaac gcccagatcc ctagcgaaga tcgtccacaa agcgcacaag gaaggcgtgt   2640
gcggagtcag atctgtcact agactggagc accaaatgtg ggaagccgtg cgggacgaat   2700
tgaacgtcct gctcaaagag aatgcagtgg acctcagtgt ggttgtgaac aagcccgtgg   2760
ggagatatcg ctcagcccca aaacgcctgt ccatgacgca agagaagttt gaaatgggct   2820
ggaaagcatg ggaaaaaagc attctctttg ccccggaatt ggctaactcc acatttgttg   2880
tagatggacc tgagacaaag gaatgtcctg atgagcacag agcctggaac agcatgcaaa   2940
tcgaagactt cggctttggt atcacatcaa cccgtgtgtg gctgaagatt agagaggaaa   3000
gcactgacga gtgtgatgga gcgatcatag gcacagctgt caaaggacat gtggcagttc   3060
atagtgactt gtcgtactgg attgagagtc gctacaacga cacatggaaa cttgagaggg   3120
cagtctttgg agaggtcaaa tcttgcactt ggccagagac acacactctt tggggagatg   3180
gtgttgagga aagtgaactc atcatcccgc ataccatagc cggaccaaaa agcaagcaca   3240
atcggaggga agggtacaaa acacaaaacc agggaccttg ggacgaaaac ggcatagtct   3300
tggactttga ttattgccca gggacaaaag tcaccatcac agaggattgt ggcaagagag   3360
gcccttcggt cagaaccact actgacagtg gaaagttgat tactgactgg tgctgtcgca   3420
gttgctccct tccgccccta cgattccgga cagaaaatgg ctgctggtac ggaatggaaa   3480
tcagacctgt taggcatgat gaaacaacac tcgtcagatc acaggttgat gctttcaatg   3540
gtgaaatggt tgaccctttt cagctgggcc ttctggtgat gtttctggcc acccaggagg   3600
tccttcgcaa gaggtggacg gccagattga ccattcctgc ggttttgggg gccctgcttg   3660
tgctgatgct tgggggcatc acttacactg atttggcgag gtatgtggtg ctagtcgctg   3720
ctgctttcgc agaggccaat aatggaggag acgtcctgca ccttgctttg attgccgttt   3780
ttaagatcca accagctttt ctagtgatga acatgcttag cacgagatgg acgaaccaag   3840
aaaacgtggt cctggtccta ggggctgcct tctttcaatt ggcctcagta gatctgcaaa   3900
tcggagtcca cggaatcctg aatgccgccg ctatagcatg gatgattgtt cgagcgatca   3960
ccttccccac aacctcctcc gtcaccatgc cagtcttagc gcttctaact ccgggaatga   4020
gggctctata cctagacact tacagaatca tccttctcgt catagggatt tgctccctgc   4080
tgcaagagag gaaaaagacc atggcaaaaa agaaaggagc tgtactcttg ggcttagcgc   4140
```

-continued

```
tcacatccac tggatggttc tcgcccacca ccatagctgc tggacttatg gtctgcaacc   4200
caaacaagaa gagagggtgg ccagctactg agtttctgtc ggcagtcgga ttgatgtttg   4260
ccatcgtagg tggtttggcc gagttggata ttgaatccat gtcaataccc ttcatgctgg   4320
caggtcttat ggcagtgtcc tacgtagtgt caggaaaagc aacagatatg tggctcgaac   4380
gggccgccga catcagctgg gagatggatg ctgcaatcac aggaagcagt cggaggctgg   4440
atgtgaaact ggatgatgac ggagattttc acttgattga tgatcccggc gttccatgga   4500
aagtttgggt cttgcgcatg tcttgcattg gcttagccgc cctcacgcct tgggccattg   4560
ttcccgccgc tttcggttac tggctcactt taaaaacaac aaaaagaggg ggcgtgtttt   4620
gggacacgcc atccccgaaa ccttgcttaa aaggagacac cactacagga gtctaccgaa   4680
tcatggctag agggattctt ggcacctacc aggctggcgt cggagtcatg tacgagaatg   4740
ttttccacac actatggcac acaactagag ggcagccat tatgagtgga gaaggaaaat   4800
tgacgccata ctggggtagc gtgaaagaag accgcatagc ttacggaggc ccatggagat   4860
ttgatcgaaa atggaatgga acagatgacg tgcaagtgat cgtggtagaa ccggggaagg   4920
ctgcggtaaa catccagaca aaaccaggag tgtttcggac cccccttcggg gaggttgggg   4980
ctgttagcct ggattacccg cgaggaacat ccggctcacc cattctggat tccaatggag   5040
acatcatagg cctatacggc aatggagttg agcttggcga tggctcatac gtcagcgcca   5100
tcgtgcaggg tgaccgtcag gaggaaccag tcccagaagc ttacactcca aacatgttaa   5160
gaaagagaca gatgactgtg ttagatttgc accctggttc agggaaaacc aggaaaattc   5220
tgccacaaat aattaaggat gcaatccagc agcgcctaag aacagctgtg ttggcaccga   5280
cgcgggtggt agcagcagaa atggcagaag ctttgagagg gctcccagta cgataccaaa   5340
cttcagcagt gcagagagag caccaaggga atgaaatagt ggatgtgatg tgccacgcca   5400
ctctgaccca cagattgatg tcaccgaaca gagtgcccaa ctacaatcta tttgtcatgg   5460
atgaagctca tttcaccgac ccagccagca tagccgcacg aggatacatc gctaccaagg   5520
tggaattagg agaggcagca gccatcttta tgacagcgac cccgcctgga accacggatc   5580
cttttcccga ctcaaatgcc ccaatccatg atttacaaga tgagatacca gacagggcat   5640
ggagcagtgg atacgaatgg atcacagaat atgcgggtaa aaccgtgtgg tttgtggcga   5700
gcgtaaaaat ggggaatgag attgcaatgt gcctccaaag agcgggaaaa aaggtcatcc   5760
aactcaaccg caagtcctat gacacagaat acccaaaatg taagaatgga gactgggatt   5820
ttgtcattac caccgacatc tctgaaatgg gggctaactt cggtgcgagc agggtcatcg   5880
actgcagaaa gagcgtgaaa cccaccatct tagaagaggg agaaggcaga gtcatcctcg   5940
gaaacccatc tcccataacc agtgctagcg cagctcaacg gaggggcaga gtaggcagaa   6000
accccaacca agttggagat gaataccatt atggaggggc taccagtgaa gatgacagta   6060
acctagccca ttggacagag gcaaagatca tgttagacaa catacacatg cccaatgggc   6120
tggtggccca gctctatgga ccagagaggg aaaaggcttt cacaatggat ggcgaatacc   6180
gtctcagggg tgaagaaaag aaaaacttct tagagctgct taggacggct gaccttccgg   6240
tgtggctggc ctataaggtg gcgtccaatg gcattcagta caccgacaga aagtggtgtt   6300
ttgatgggcc gcgcacgaat gccatactgg aggacaacac cgaggtagag atagtcaccc   6360
ggatgggtga gagaaagatc ctcaagccga gatggcttga tgcaagagta tacgcagatc   6420
accaagccct caagtggttc aaagactttg cagcaggaaa gagatcggcc gttagcttca   6480
tagaggtgct cggtcgcatg cctgagcatt tcatgggaaa gacgcgggaa gctttagaca   6540
```

-continued

```
ccatgtactt ggtcgcaacg gctgagaaag gtgggaaggc acaccgaatg gctctcgaag   6600
agttgccgga tgcactggaa accatcacac ttattgttgc catcactgta atgacaggag   6660
gattcttcct actaatgatg cagcgaaagg gtatagggaa gatgggtctt ggagctctag   6720
tgctcacgct agctaccttc ttcctgtggg cggcagaggt tcctggaacc aaaatagcag   6780
ggaccctgct gatcgccctg ctgctgatgg tggttctcat cccagaaccg gaaaaacaga   6840
ggtcacagac agacaaccaa ctagcggtgt ttctcatctg cgtcttgacc gtggttggag   6900
tggtggcagc aaacgagtac gggatgctag aaaaaaccaa agcagatctc aagagcatgt   6960
ttggcggaaa gacacaggca tcaggactga ctggattgcc aagcatggca ctggacctgc   7020
gtccagccac agcctgggca ctgtatgggg ggagcacagt tgtgctaacc cctcttctga   7080
agcacctgat cacgtcggaa tatgtcacca catcgctagc ctcaattaac tcacaagctg   7140
gctcattatt cgtcttgcca cgaggcgtgc ctttcaccga tctagacctg accgttggcc   7200
tcgtcttcct tggctgctgg ggtcaaatca ccctcacaac gtttttgaca gccatggttc   7260
tggcgacact tcactatggg tacatgctcc ctggatggca agcagaagca ctcagggctg   7320
cccagagaag gacggcggct ggaataatga agaatgccgt tgttgacgga atggtcgcca   7380
ctgatgtgcc tgaactggaa aggactactc ctctgatgca aaagaaagtc ggacaggtgc   7440
tcctcatagg ggtgagcgtg gcagcgtttc tcgtcaaccc taatgtcacc actgtgagag   7500
aagcaggggt gttggtgacg gcggctacgc tcaccttgtg ggataatgga gccagtgccg   7560
tttggaattc caccacagcc acgggactct gccatgtcat gcgaggtagc tacctggctg   7620
gaggctctat tgcttggact cttatcaaga acgctgacaa gccctccttg aaaaggggaa   7680
ggcctggggg caggacgcta ggggagcagt ggaaggaaaa actaaatgcc atgagcagag   7740
aagagttttt taaataccgg agagaggcca taatcgaggt ggaccgcact gaagcacgca   7800
gggctagacg tgaaaataac atagtgggag gacatccggt ttcgcgaggc tcagcaaaac   7860
tccgttggct cgtggagaaa ggattcgtct cgccaatagg aaaagtcatt gatctagggt   7920
gtgggcgtgg aggatggagc tactacgcag caaccctgaa gaaggtccag gaagtcagag   7980
gatacacgaa aggtggggcg ggacatgaag agccgatgct catgcagagc tacggctgga   8040
acctggtctc cttgaagagt ggagtggatg tgttctacaa accttcagag cctagtgaca   8100
ccctgttctg tgacataggg gaatcctccc caagtccaga agtggaagaa caacgcacac   8160
tacgcgtcct agagatgaca tccgattggt tgcatcgagg acccagagag ttctgcataa   8220
aagttctctg cccttacatg cccaaggtca tagaaaaaat ggaagttctg cagcgccgct   8280
tcggaggtgg gctagtacgt ctccccctgt cccgaaactc caatcacgag atgtattggg   8340
ttagtggagc cgctggcaat gtggtgcacg ctgtgaacat gaccagccag gtactactgg   8400
ggcgaatgga tcgcacagtg tggagagggc caaagtatga ggaagatgtc aacctaggta   8460
gcggaacaag agccgtggga aagggagaag ttcatagcaa tcaggagaaa atcaagaaga   8520
gaatccagaa gcttaaagaa gaattcgcca caacgtggca caaagaccct gaacacccat   8580
accgcacttg gacataccac ggaagctatg aggtgaaggc tactggctca gccagctctc   8640
tcgtcaacgg agtggtgaag ctcatgagta aaccttggga cgccattgcc aacgtcacca   8700
ccatggccat gactgacacc accccttttg gacagcaaag agttttcaag gagaaagttg   8760
acacgaaagc tcctgagcca ccagctggag tcaaggaagt gctcaacgag accaccaact   8820
ggctgtgggc ccacttgtca cgggaaaaaa gaccccgctt gtgcaccaag gaagaattta   8880
```

-continued

```
taaagaaagt caatagcaac gcggctcttg gagcagtgtt tgctgaacag aatcaatgga   8940
gcacggcgcg tgaggctgtg gacgacccgc ggttttggga gatggtcaat gaagagaggg   9000
aaaaccatct gcgaggagag tgtcacacat gtatctacaa catgatggga aaaagagaga   9060
agaagcctgg agagtttgga aaagctaaag ggagcagggc catttggttc atgtggcttg   9120
gagcacggta tctagagttt gaagctttgg ggttcctgaa tgaagaccac tggctgagcc   9180
gagagaattc aggaggtgga gtagaaggct caggcgtcca aaagttggga tacatcctcc   9240
gtgacatagc aggaaagcaa ggagggaaaa tgtacgctga tgacaccgcc gggtgggaca   9300
ctagaattac tagaactgat ttagaaaatg aagctaaggt gctggagctc ctagatggtg   9360
aacaccgcat gctcgcccgg gccataattg aactgactta caggcacaaa gtggtcaagg   9420
tcatgagacc tgcagcagaa ggaaagaccg tgatggacgt gatatcaaga gaagaccaaa   9480
gggggagtgg acaggtggtc acttatgctc tcaacacttt cacgaacatc gctgtccagc   9540
tcgttaggct gatggaggct gagggggtca ttgggccaca acacttggaa cagctgccta   9600
ggaaaaacaa gatagctgtc aggacttggc tctttgagaa tggagaggag agagtgacca   9660
ggatggcgat cagcggagac gactgtgtcg tcaagccgct ggacgacaga ttcgccacgg   9720
ccctccattt cctcaacgca atgtcaaagg ttagaaaaga catccaggaa tggaagcctt   9780
cgcacggctg gcacgattgg cagcaagttc ccttctgctc taaccacttt caggagattg   9840
tgatgaaaga cggaaggagt atagttgtcc cgtgcagagg acaggatgag ctgataggca   9900
gggctcgcat ctctccagga gctggatgga atgtgaagga cacagcttgc ctggcaaaag   9960
catatgcaca gatgtggcta ctcctatact tccatcgtag ggacctgcgt ctcatggcaa  10020
atgcgatttg ctcagcagtg ccagtggatt gggtgcccac aggcaggaca tcctggtcaa  10080
tacactcgaa aggagagtgg atgaccacgg aagacatgct gcaggtctgg aacagagtct  10140
ggattgaaga aaatgaatgg atgatggata agactcccgt cacaagctgg acagacgttc  10200
cgtatgtggg aaagcgtgag gacatctggt gtggcagcct catcggaacg cgttccagag  10260
caacctgggc tgagaacatc tatgcggcga taaaccaggt tagagctgtc attgggaaag  10320
aaaattatgt tgactacatg acctcactca ggagatacga agacgtcttg atccaggaag  10380
acagggtcat ctagtgtgac ttaaggtaga aatgtaaata atgtgaatga gaaaatgcat  10440
gtatatggag tcaggccagc aaaagctgcc accggatact gggtagacgg tgctgcctgc  10500
gtctcagtcc caggaggact gggttaacaa atctgacaac agaaagtgag aaagccctca  10560
gaaccgtctc ggaagtaggt ccctgctcac tggaagttga aagaccaacg tcaggccacg  10620
aatttgtgcc actccgctgg ggagtgcggc ctgcgcagcc ccaggaggac tgggttacca  10680
aagccgttga ggcccccacg gcccaagcct cgtctaggat gcaatagacg aggtgtaagg  10740
actagaggtt agaggagacc ccgtggaaac aacaacatgc ggcccaagcc ccctcgaagc  10800
tgtagaggag gtggaaggac tagaggttag aggagacccc gcatttgcat caaacagcat  10860
attgacacct gggaatagac tgggagatct tctgctctat ctcaacatca gctactaggc  10920
acagagcgcc gaagtatgta gctggtggtg aggaagaaca caggatct               10968
```

<210> SEQ ID NO 16
<211> LENGTH: 18
<212> TYPE: DNA
<213> ORGANISM: Artificial Sequence
<220> FEATURE:
<223> OTHER INFORMATION: primer J41

<400> SEQUENCE: 16

-continued tccgtggaat gaacaatg 18

<210> SEQ ID NO 17
<211> LENGTH: 30
<212> TYPE: DNA
<213> ORGANISM: Artificial Sequence
<220> FEATURE:
<223> OTHER INFORMATION: primer J43

<400> SEQUENCE: 17
acagataaac ttctctatag tgtcccctaa 30

<210> SEQ ID NO 18
<211> LENGTH: 18
<212> TYPE: DNA
<213> ORGANISM: Artificial Sequence
<220> FEATURE:
<223> OTHER INFORMATION: primer J42

<400> SEQUENCE: 18
gagaagttta tctgtgtg 18

<210> SEQ ID NO 19
<211> LENGTH: 18
<212> TYPE: DNA
<213> ORGANISM: Artificial Sequence
<220> FEATURE:
<223> OTHER INFORMATION: primer J40

<400> SEQUENCE: 19
aaacgtactg gtcctctg 18

<210> SEQ ID NO 20
<211> LENGTH: 20
<212> TYPE: DNA
<213> ORGANISM: Artificial Sequence
<220> FEATURE:
<223> OTHER INFORMATION: primer J90

<400> SEQUENCE: 20
ttgaggcccc cacggcccaa 20

<210> SEQ ID NO 21
<211> LENGTH: 41
<212> TYPE: DNA
<213> ORGANISM: Artificial Sequence
<220> FEATURE:
<223> OTHER INFORMATION: primer J45

<400> SEQUENCE: 21
agtactagtc ggtccgcggc cgctcgagat cctgtgttct t 41

<210> SEQ ID NO 22
<211> LENGTH: 18
<212> TYPE: DNA
<213> ORGANISM: Artificial Sequence
<220> FEATURE:
<223> OTHER INFORMATION: primer J31

<400> SEQUENCE: 22
ggctgtgggc ccacttgt 18

<210> SEQ ID NO 23
<211> LENGTH: 24
<212> TYPE: DNA

-continued

<213> ORGANISM: Artificial Sequence
<220> FEATURE:
<223> OTHER INFORMATION: primer J47

<400> SEQUENCE: 23
ccaaagcttc aaactcaaga tacc 24

<210> SEQ ID NO 24
<211> LENGTH: 43
<212> TYPE: DNA
<213> ORGANISM: Artificial Sequence
<220> FEATURE:
<223> OTHER INFORMATION: primer J46

<400> SEQUENCE: 24
agtactagtc ggtccgcggc cgctctagag atcctgtgtt ctt 43

<210> SEQ ID NO 25
<211> LENGTH: 18
<212> TYPE: DNA
<213> ORGANISM: Artificial Sequence
<220> FEATURE:
<223> OTHER INFORMATION: primer J81

<400> SEQUENCE: 25
tcttgcccgc ctgatgaa 18

<210> SEQ ID NO 26
<211> LENGTH: 30
<212> TYPE: DNA
<213> ORGANISM: Artificial Sequence
<220> FEATURE:
<223> OTHER INFORMATION: primer J80

<400> SEQUENCE: 26
acagataaac ttctctatag tgagtcgtat 30

<210> SEQ ID NO 27
<211> LENGTH: 18
<212> TYPE: DNA
<213> ORGANISM: Artificial Sequence
<220> FEATURE:
<223> OTHER INFORMATION: primer J42

<400> SEQUENCE: 27
gagaagttta tctgtgtg 18

<210> SEQ ID NO 28
<211> LENGTH: 18
<212> TYPE: DNA
<213> ORGANISM: Artificial Sequence
<220> FEATURE:
<223> OTHER INFORMATION: primer J82

<400> SEQUENCE: 28
gcccatggta agcttagg 18

<210> SEQ ID NO 29
<211> LENGTH: 27
<212> TYPE: DNA
<213> ORGANISM: Artificial Sequence
<220> FEATURE:
<223> OTHER INFORMATION: primer J48

<400> SEQUENCE: 29
actgagctca cgcgtcctcg agatgac 27

-continued

<210> SEQ ID NO 30
<211> LENGTH: 30
<212> TYPE: DNA
<213> ORGANISM: Artificial Sequence
<220> FEATURE:
<223> OTHER INFORMATION: primer J3

<400> SEQUENCE: 30
gatttaatta acacctcctc tacagcttcg 30

<210> SEQ ID NO 31
<211> LENGTH: 20
<212> TYPE: DNA
<213> ORGANISM: Artificial Sequence
<220> FEATURE:
<223> OTHER INFORMATION: primer J72

<400> SEQUENCE: 31
gaaggtaccc cattgtatgg 20

<210> SEQ ID NO 32
<211> LENGTH: 30
<212> TYPE: DNA
<213> ORGANISM: Artificial Sequence
<220> FEATURE:
<223> OTHER INFORMATION: primer J73

<400> SEQUENCE: 32
ttctccttta cccatggttg tggcaagctt 30

<210> SEQ ID NO 33
<211> LENGTH: 18
<212> TYPE: DNA
<213> ORGANISM: Artificial Sequence
<220> FEATURE:
<223> OTHER INFORMATION: primer J74

<400> SEQUENCE: 33
atgggtaaag gagaagaa 18

<210> SEQ ID NO 34
<211> LENGTH: 30
<212> TYPE: DNA
<213> ORGANISM: Artificial Sequence
<220> FEATURE:
<223> OTHER INFORMATION: primer J75

<400> SEQUENCE: 34
aagatgcatt cattaaccgt cgactgcaga 30

<210> SEQ ID NO 35
<211> LENGTH: 30
<212> TYPE: DNA
<213> ORGANISM: Artificial Sequence
<220> FEATURE:
<223> OTHER INFORMATION: primer J76

<400> SEQUENCE: 35
tttggcgtct tccatggttg tggcaagctt 30

<210> SEQ ID NO 36
<211> LENGTH: 18
<212> TYPE: DNA
<213> ORGANISM: Artificial Sequence
<220> FEATURE:

-continued

<223> OTHER INFORMATION: primer J77

<400> SEQUENCE: 36
atggaagacg ccaaaaac 18

<210> SEQ ID NO 37
<211> LENGTH: 30
<212> TYPE: DNA
<213> ORGANISM: Artificial Sequence
<220> FEATURE:
<223> OTHER INFORMATION: primer J78

<400> SEQUENCE: 37
cttaagatgc attcattaca cggcgatctt 30

<210> SEQ ID NO 38
<211> LENGTH: 20
<212> TYPE: DNA
<213> ORGANISM: Artificial Sequence
<220> FEATURE:
<223> OTHER INFORMATION: primer J89

<400> SEQUENCE: 38
tgctttggcc ttcttggcca 20

<210> SEQ ID NO 39
<211> LENGTH: 30
<212> TYPE: DNA
<213> ORGANISM: Artificial Sequence
<220> FEATURE:
<223> OTHER INFORMATION: primer J91

<400> SEQUENCE: 39
acccgcatat tctgtgatcc gtggttccag 30

<210> SEQ ID NO 40
<211> LENGTH: 18
<212> TYPE: DNA
<213> ORGANISM: Artificial Sequence
<220> FEATURE:
<223> OTHER INFORMATION: primer J92

<400> SEQUENCE: 40
acagaatatg cgggtaaa 18

<210> SEQ ID NO 41
<211> LENGTH: 21
<212> TYPE: DNA
<213> ORGANISM: Artificial Sequence
<220> FEATURE:
<223> OTHER INFORMATION: primer J93

<400> SEQUENCE: 41
agctaacggc cgatctcttt c 21

<210> SEQ ID NO 42
<211> LENGTH: 16847
<212> TYPE: DNA
<213> ORGANISM: Artificial Sequence
<220> FEATURE:
<223> OTHER INFORMATION: sequence for pBAC/SV vector

<400> SEQUENCE: 42
attgacggcg tagtacacac tattgaatca aacagccgac caattgcact accatcacaa 60
tggagaagcc agtagtaaac gtagacgtag acccccagag tccgtttgtc gtgcaactgc 120

-continued aaaaaagctt cccgcaattt gaggtagtag cacagcaggt cactccaaat gaccatgcta 180
atgccagagc attttcgcat ctggccagta aactaatcga gctggaggtt cctaccacag 240
cgacgatctt ggacataggc agcgcaccgg ctcgtagaat gttttccgag caccagtatc 300
attgtgtctg ccccatgcgt agtccagaag acccggaccg catgatgaaa tacgccagta 360
aactggcgga aaaagcgtgc aagattacaa acaagaactt gcatgagaag attaaggatc 420
tccggaccgt acttgatacg ccggatgctg aaacaccatc gctctgcttt cacaacgatg 480
ttacctgcaa catgcgtgcc gaatattccg tcatgcagga cgtgtatatc aacgctcccg 540
gaactatcta tcatcaggct atgaaaggcg tgcggaccct gtactggatt ggcttcgaca 600
ccacccagtt catgttctcg gctatggcag gttcgtaccc tgcgtacaac accaactggg 660
ccgacgagaa agtccttgaa gcgcgtaaca tcggactttg cagcacaaag ctgagtgaag 720
gtaggacagg aaaattgtcg ataatgagga agaaggagtt gaagcccggg tcgcgggttt 780
atttctccgt aggatcgaca ctttatccag aacacagagc cagcttgcag agctggcatc 840
ttccatcggt gttccacttg aatggaaagc agtcgtacac ttgccgctgt gatacagtgg 900
tgagttgcga aggctacgta gtgaagaaaa tcaccatcag tcccgggatc acgggagaaa 960
ccgtgggata cgcggttaca cacaatagcg agggcttctt gctatgcaaa gttactgaca 1020
cagtaaaagg agaacgggta tcgttccctg tgtgcacgta catcccggcc accatatgcg 1080
atcagatgac tggtataatg gccacggata tatcacctga cgatgcacaa aaacttctgg 1140
ttgggctcaa ccagcgaatt gtcattaacg gtaggactaa caggaacacc aacaccatgc 1200
aaaattacct tctgccgatc atagcacaag ggttcagcaa atgggctaag gagcgcaagg 1260
atgatcttga taacgagaaa atgctgggta ctagagaacg caagcttacg tatggctgct 1320
tgtgggcgtt tcgcactaag aaagtacatt cgttttatcg cccacctgga acgcagacct 1380
gcgtaaaagt cccagcctct tttagcgctt ttcccatgtc gtccgtatgg acgacctctt 1440
tgcccatgtc gctgaggcag aaattgaaac tggcattgca accaaagaag gaggaaaaac 1500
tgctgcaggt ctcggaggaa ttagtcatgg aggccaaggc tgcttttgag gatgctcagg 1560
aggaagccag agcggagaag ctccgagaag cacttccacc attagtggca gacaaaggca 1620
tcgaggcagc cgcagaagtt gtctgcgaag tggaggggct ccaggcggac atcggagcag 1680
cattagttga aaccccgcgc ggtcacgtaa ggataatacc tcaagcaaat gaccgtatga 1740
tcggacagta tatcgttgtc tcgccaaact ctgtgctgaa gaatgccaaa ctcgcaccag 1800
cgcacccgct agcagatcag gttaagatca taacacactc cggaagatca ggaaggtacg 1860
cggtcgaacc atacgacgct aaagtactga tgccagcagg aggtgccgta ccatggccag 1920
aattcctagc actgagtgag agcgccacgt tagtgtacaa cgaaagagag tttgtgaacc 1980
gcaaactata ccacattgcc atgcatggcc ccgccaagaa tacagaagag gagcagtaca 2040
aggttacaaa ggcagagctt gcagaaacag agtacgtgtt tgacgtggac aagaagcgtt 2100
gcgttaagaa ggaagaagcc tcaggtctgg tcctctcggg agaactgacc aaccctccct 2160
atcatgagct agctctggag ggactgaaga cccgacctgc ggtcccgtac aaggtcgaaa 2220
caataggagt gataggcaca ccggggtcgg gcaagtcagc tattatcaag tcaactgtca 2280
cggcacgaga tcttgttacc agcggaaaga aagaaaattg tcgcgaaatt gaggccgacg 2340
tgctaagact gaggggtatg cagattacgt cgaagacagt agattcggtt atgctcaacg 2400
gatgccacaa agccgtagaa gtgctgtacg ttgacgaagc gttcgcgtgc cacgcaggag 2460

-continued

```
cactacttgc cttgattgct atcgtcaggc cccgcaagaa ggtagtacta tgcggagacc   2520

ccatgcaatg cggattcttc aacatgatgc aactaaaggt acatttcaat caccctgaaa   2580

aagacatatg caccaagaca ttctacaagt atatctcccg gcgttgcaca cagccagtta   2640

cagctattgt atcgacactg cattacgatg gaaagatgaa aaccacgaac ccgtgcaaga   2700

agaacattga aatcgatatt acaggggcca caaagccgaa gccaggggat atcatcctga   2760

catgtttccg cgggtgggtt aagcaattgc aaatcgacta tcccggacat gaagtaatga   2820

cagccgcggc ctcacaaggg ctaaccagaa aaggagtgta tgccgtccgg caaaaagtca   2880

atgaaaaccc actgtacgcg atcacatcag agcatgtgaa cgtgttgctc acccgcactg   2940

aggacaggct agtgtggaaa accttgcagg gcgacccatg gattaagcag cccactaaca   3000

tacctaaagg aaactttcag gctactatag aggactggga agctgaacac aagggaataa   3060

ttgctgcaat aaacagcccc actccccgtg ccaatccgtt cagctgcaag accaacgttt   3120

gctgggcgaa agcattggaa ccgatactag ccacggccgg tatcgtactt accggttgcc   3180

agtggagcga actgttccca cagtttgcgg atgacaaacc acattcggcc atttacgcct   3240

tagacgtaat ttgcattaag tttttcggca tggacttgac aagcggactg ttttctaaac   3300

agagcatccc actaacgtac catcccgccg attcagcgag gccggtagct cattgggaca   3360

acagcccagg aacccgcaag tatgggtacg atcacgccat tgccgccgaa ctctcccgta   3420

gatttccggt gttccagcta gctgggaagg gcacacaact tgatttgcag acggggagaa   3480

ccagagttat ctctgcacag cataacctgg tcccggtgaa ccgcaatctt cctcacgcct   3540

tagtccccga gtacaaggag aagcaacccg gcccggtcaa aaaattcttg aaccagttca   3600

aacaccactc agtacttgtg gtatcagagg aaaaaattga agctccccgt aagagaatcg   3660

aatggatcgc cccgattggc atagccggtg cagataagaa ctacaacctg gctttcgggt   3720

ttccgccgca ggcacggtac gacctggtgt tcatcaacat tggaactaaa tacagaaacc   3780

accactttca gcagtgcgaa gaccatgcgg cgaccttaaa aaccctttcg cgttcggccc   3840

tgaattgcct taacctagga ggcaccctcg tggtgaagtc ctatggctac gccgaccgca   3900

acagtgagga cgtagtcacc gctcttgcca gaaagtttgt cagggtgtct gcagcgagac   3960

cagattgtgt ctcaagcaat acagaaatgt acctgatttt ccgacaacta gacaacagcc   4020

gtacacggca attcaccccg caccatctga attgcgtgat ttcgtccgtg tatgagggta   4080

caagagatgg agttggagcc gcgccgtcat accgcaccaa aagggagaat attgctgact   4140

gtcaagagga agcagttgtc aacgcagcca atccgctggg tagaccaggc gaaggagtct   4200

gccgtgccat ctataaacgt tggccgacca gttttaccga ttcagccacg gagacaggca   4260

ccgcaagaat gactgtgtgc ctaggaaaga aagtgatcca cgcggtcggc cctgatttcc   4320

ggaagcaccc agaagcagaa gccttgaaat tgctacaaaa cgcctaccat gcagtggcag   4380

acttagtaaa tgaacataac atcaagtctg tcgccattcc actgctatct acaggcattt   4440

acgcagccgg aaaagaccgc cttgaagtat cacttaactg cttgacaacc gcgctagaca   4500

gaactgacgc ggacgtaacc atctattgcc tggataagaa gtggaaggaa agaatcgacg   4560

cggcactcca acttaaggag tctgtaacag agctgaagga tgaagatatg gagatcgacg   4620

atgagttagt atggattcat ccagacagtt gcttgaaggg aagaaaggga ttcagtacta   4680

caaaaggaaa attgtattcg tacttcgaag gcaccaaatt ccatcaagca gcaaaagaca   4740

tggcggagat aaaggtcctg ttccctaatg accaggaaag taatgaacaa ctgtgtgcct   4800

acatattggg tgagaccatg gaagcaatcc gcgaaaagtg cccggtcgac cataacccgt   4860
```

-continued

```
cgtctagccc gcccaaaacg ttgccgtgcc tttgcatgta tgccatgacg ccagaaaggg   4920
tccacagact tagaagcaat aacgtcaaag aagttacagt atgctcctcc accccccttc   4980
ctaagcacaa aattaagaat gttcagaagg ttcagtgcac gaaagtagtc ctgtttaatc   5040
cgcacactcc cgcattcgtt cccgcccgta agtacataga agtgccagaa cagcctaccg   5100
ctcctcctgc acaggccgag gaggccccccg aagttgtagc gacaccgtca ccatctacag   5160
ctgataacac ctcgcttgat gtcacagaca tctcactgga tatggatgac agtagcgaag   5220
gctcactttt ttcgagcttt agcggatcgg acaactctat tactagtatg gacagttggt   5280
cgtcaggacc tagttcacta gagatagtag accgaaggca ggtggtggtg gctgacgttc   5340
atgccgtcca agagcctgcc cctattccac cgccaaggct aaagaagatg gcccgcctgg   5400
cagcggcaag aaaagagccc actccaccgg caagcaatag ctctgagtcc ctccacctct   5460
cttttggtgg ggtatccatg tccctcggat caattttcga cggagagacg gcccgccagg   5520
cagcggtaca acccctggca acaggcccca cggatgtgcc tatgtctttc ggatcgtttt   5580
ccgacggaga gattgatgag ctgagccgca gagtaactga gtccgaaccc gtcctgtttg   5640
gatcatttga accgggcgaa gtgaactcaa ttatatcgtc ccgatcagcc gtatcttttc   5700
cactacgcaa gcagagacgt agacgcagga gcaggaggac tgaatactga ctaaccgggg   5760
taggtgggta catattttcg acggacacag gccctgggca cttgcaaaag aagtccgttc   5820
tgcagaacca gcttacagaa ccgaccttgg agcgcaatgt cctggaaaga attcatgccc   5880
cggtgctcga cacgtcgaaa gaggaacaac tcaaactcag gtaccagatg atgcccaccg   5940
aagccaacaa aagtaggtac cagtctcgta aagtagaaaa tcagaaagcc ataaccactg   6000
agcgactact gtcaggacta cgactgtata actctgccac agatcagcca gaatgctata   6060
agatcaccta tccgaaacca ttgtactcca gtagcgtacc ggcgaactac tccgatccac   6120
agttcgctgt agctgtctgt aacaactatc tgcatgagaa ctatccgaca gtagcatctt   6180
atcagattac tgacgagtac gatgcttact tggatatggt agacgggaca gtcgcctgcc   6240
tggatactgc aaccttctgc cccgctaagc ttagaagtta cccgaaaaaa catgagtata   6300
gagccccgaa tatccgcagt gcggttccat cagcgatgca gaacacgcta caaaatgtgc   6360
tcattgccgc aactaaaaga aattgcaacg tcacgcagat gcgtgaactg ccaacactgg   6420
actcagcgac attcaatgtc gaatgctttc gaaaatatgc atgtaatgac gagtattggg   6480
aggagttcgc tcggaagcca attaggatta ccactgagtt tgtcaccgca tatgtagcta   6540
gactgaaagg ccctaaggcc gccgcactat ttgcaaagac gtataatttg gtcccattgc   6600
aagaagtgcc tatggataga ttcgtcatgg acatgaaaag agacgtgaaa gttacaccag   6660
gcacgaaaca cacagaagaa agaccgaaag tacaagtgat acaagccgca gaacccctgg   6720
cgactgctta cttatgcggg attcaccggg aattagtgcg taggcttacg gccgtcttgc   6780
ttccaaacat tcacacgctt tttgacatgt cggcggagga ttttgatgca atcatagcag   6840
aacacttcaa gcaaggcgac ccggtactgg agacggatat cgcatcattc gacaaaagcc   6900
aagacgacgc tatggcgtta accggtctga tgatcttgga ggacctgggt gtggatcaac   6960
cactactcga cttgatcgag tgcgcctttg gagaaatatc atccacccat ctacctacgg   7020
gtactcgttt taaattcggg gcgatgatga aatccggaat gttcctcaca ctttttgtca   7080
acacagtttt gaatgtcgtt atcgccagca gagtactaga agagcggctt aaaacgtcca   7140
gatgtgcagc gttcattggc gacgacaaca tcatacatgg agtagtatct gacaaagaaa   7200
```

-continued

```
tggctgagag gtgcgccacc tggctcaaca tggaggttaa gatcatcgac gcagtcatcg   7260
gtgagagacc accttacttc tgcggcggat ttatcttgca agattcggtt acttccacag   7320
cgtgccgcgt ggcggatccc ctgaaaaggc tgtttaagtt gggtaaaccg ctcccagccg   7380
acgacgagca agacgaagac agaagacgcg ctctgctaga tgaaacaaag gcgtggttta   7440
gagtaggtat aacaggcact ttagcagtgg ccgtgacgac ccggtatgag gtagacaata   7500
ttacacctgt cctactggca ttgagaactt ttgcccagag caaaagagca ttccaagcca   7560
tcagagggga aataaagcat ctctacggtg gtcctaaata gtcagcatag tacatttcat   7620
ctgactaata ccacaacacc accacctcta gacgcgtaga tctcacgtga gcatgcagga   7680
ttacacctgt cctactggca ttgagaactt ttgcccagag caaaagagca ttccaagcca   7740
tcagagggga aataaagcat ctctacggtg gtcctaaata gtcagcatag tacatttcat   7800
ctgactaata ctacaacacc accacctcta gctagagctt accatgaccg agtacaagcc   7860
cacggtgcgc ctcgccaccc gcgacgacgt cccccgggcc gtacgcaccc tcgccgccgc   7920
gttcgccgac taccccgcca cgcgccacac cgtcgacccg gaccgccaca tcgagcgggt   7980
caccgagctg caagaactct tcctcacgcg cgtcgggctc gacatcggca aggtgtgggt   8040
cgcggacgac ggcgccgcgg tggcggtctg gaccacgccg gagagcgtcg aagcgggggc   8100
ggtgttcgcc gagatcggcc cgcgcatggc cgagttgagc ggttcccggc tggccgcgca   8160
gcaacagatg gaaggcctcc tggcgccgca ccggcccaag gagcccgcgt ggttcctggc   8220
caccgtcggc gtctcgcccg accaccaggg caagggtctg ggcagcgccg tcgtgctccc   8280
cggagtggag gcggccgagc gcgccggggt gcccgccttc ctggagacct ccgcgccccg   8340
caacctcccc ttctacgagc ggctcggctt caccgtcacc gccgacgtcg agtgcccgaa   8400
ggaccgcgcg acctggtgca tgacccgcaa gcccggtgcc tgacgcccgc cccacgaccc   8460
gcagcgcccg accgaaagga gcgcacgacc ccatgatcgc tagaccatgg ggtaccgagc   8520
tcgaattcgc ctcgtcgcta ttaattatag gacttatgat tttgcttgc agcatgatgc   8580
tgactagcac acgaagatga cgggcccaat gatccgacca gcaaaactcg atgtacttcc   8640
gaggaactga tgtgcataat gcatcaggct ggtacattag atccccgctt accgcgggca   8700
atatagcaac actaaaaact cgatgtactt ccgaggaagc gcagtgcata atgctgcgca   8760
gtgttgccac ataaccacta tattaaccat ttatctagcg gacgccaaaa actcaatgta   8820
tttctgagga agcgtggtgc ataatgccac gcagcgtctg cataactttt attatttctt   8880
ttattaatca acaaaatttt gtttttaaca tttcaaaaaa aaaaaaaaaa aaaaaaaaaa   8940
aaaaaaaaaa agggaattcc tcgattaatt aagcggccgc tcgaggggaa ttaattcttg   9000
aagacgaaag ggccaggtgg cacttttcgg ggaaatgtgc gcggaacccc tatttgttta   9060
tttttctaaa tacattcaaa tatgtatccg ctcatgagac aataaccctg ataaatgctt   9120
caataatccc tcgtccacgt ggcatctcga gacctttatt ccaaggcgtc gaaccactga   9180
cgactaccct gtactcaggg cttaagccat ccaacgaact caccactgtt gctacccccc   9240
tcattatgct agtcctacta agggcatggc tagcctcttt tcggccttcg ctgagaggga   9300
tttgttccct aggcctaatt attattttta attgcccaat acgtatacga gtgccttttc   9360
taattctcgt atactatagt gagtcgtatt atctagccgc ccgggccgtc gaccaattct   9420
catgtttgac agcttatcat cgaatttctg ccattcatcc gcttattatc acttattcag   9480
gcgtagcaac caggcgttta agggcaccaa taactgcctt aaaaaaatta cgccccgccc   9540
tgccactcat cgcagtactg ttgtaattca ttaagcattc tgccgacatg gaagccatca   9600
```

-continued

```
caaacggcat gatgaacctg aatcgccagc ggcatcagca ccttgtcgcc ttgcgtataa   9660
tatttgccca tggtgaaaac gggggcgaag aagttgtcca tattggccac gtttaaatca   9720
aaactggtga aactcaccca gggattggct gagacgaaaa acatattctc aataaaccct   9780
ttagggaaat aggccaggtt ttcaccgtaa cacgccacat cttgcgaata tatgtgtaga   9840
aactgccgga aatcgtcgtg gtattcactc cagagcgatg aaaacgtttc agtttgctca   9900
tggaaaacgg tgtaacaagg gtgaacacta tcccatatca ccagctcacc gtctttcatt   9960
gccatacgga attccggatg agcattcatc aggcgggcaa gaatgtgaat aaaggccgga  10020
taaaacttgt gcttattttt ctttacggtc tttaaaaagg ccgtaatatc cagctgaacg  10080
gtctggttat aggtacattg agcaactgac tgaaatgcct caaaatgttc tttacgatgc  10140
cattgggata tatcaacggt ggtatatcca gtgatttttt tctccatttt agcttcctta  10200
gctcctgaaa atctcgataa ctcaaaaaat acgcccggta gtgatcttat ttcattatgg  10260
tgaaagttgg aacctcttac gtgccgatca acgtctcatt ttcgccaaaa gttggcccag  10320
ggcttcccgg tatcaacagg gacaccagga tttatttatt ctgcgaagtg atcttccgtc  10380
acaggtattt attcgcgata agctcatgga gcggcgtaac cgtcgcacag gaaggacaga  10440
gaaagcgcgg atctgggaag tgacggacag aacggtcagg acctggattg gggaggcggt  10500
tgccgccgct gctgctgacg gtgtgacgtt ctctgttccg gtcacaccac atacgttccg  10560
ccattcctat gcgatgcaca tgctgtatgc cggtataccg ctgaaagttc tgcaaagcct  10620
gatgggacat aagtccatca gttcaacgga agtctacacg aaggtttttg cgctggatgt  10680
ggctgcccgg caccgggtgc agtttgcgat gccggagtct gatgcggttg cgatgctgaa  10740
acaattatcc tgagaataaa tgccttggcc tttatatgga aatgtggaac tgagtggata  10800
tgctgttttt gtctgttaaa cagagaagct ggctgttatc cactgagaag cgaacgaaac  10860
agtcgggaaa atctcccatt atcgtagaga tccgcattat taatctcagg agcctgtgta  10920
gcgtttatag gaagtagtgt tctgtcatga tgcctgcaag cggtaacgaa aacgatttga  10980
atatgccttc aggaacaata gaaatcttcg tgcggtgtta cgttgaagtg gagcggatta  11040
tgtcagcaat ggacagaaca acctaatgaa cacagaacca tgatgtggtc tgtcctttta  11100
cagccagtag tgctcgccgc agtcgagcga cagggcgaag ccctcgagtg agcgaggaag  11160
caccagggaa cagcacttat atattctgct tacacacgat gcctgaaaaa acttcccttg  11220
gggttatcca cttatccacg gggatatttt tataattatt tttttatag tttttagatc  11280
ttcttttta gagcgccttg taggccttta tccatgctgg ttctagagaa ggtgttgtga  11340
caaattgccc tttcagtgtg acaaatcacc ctcaaatgac agtcctgtct gtgacaaatt  11400
gcccttaacc ctgtgacaaa ttgccctcag aagaagctgt tttttcacaa agttatccct  11460
gcttattgac tcttttttat ttagtgtgac aatctaaaaa cttgtcacac ttcacatgga  11520
tctgtcatgg cggaaacagc ggttatcaat cacaagaaac gtaaaaatag cccgcgaatc  11580
gtccagtcaa acgacctcac tgaggcggca tatagtctct cccgggatca aaaacgtatg  11640
ctgtatctgt tcgttgacca gatcagaaaa tctgatggca ccctacagga acatgacggt  11700
atctgcgaga tccatgttgc taaatatgct gaaatattcg gattgacctc tgcggaagcc  11760
agtaaggata tacggcaggc attgaagagt ttcgcgggga aggaagtggt tttttatcgc  11820
cctgaagagg atgccggcga tgaaaaaggc tatgaatctt ttccttggtt tatcaaacgt  11880
gcgcacagtc catccagagg gctttacagt gtacatatca acccatatct cattcccttc  11940
```

-continued

```
tttatcgggt tacagaaccg gtttacgcag tttcggctta gtgaaacaaa agaaatcacc  12000
aatccgtatg ccatgcgttt atacgaatcc ctgtgtcagt atcgtaagcc ggatggctca  12060
ggcatcgtct ctctgaaaat cgactggatc atagagcgtt accagctgcc tcaaagttac  12120
cagcgtatgc ctgacttccg ccgccgcttc ctgcaggtct gtgttaatga gatcaacagc  12180
agaactccaa tgcgcctctc atacattgag aaaaagaaag gccgccagac gactcatatc  12240
gtattttcct tccgcgatat cacttccatg acgacaggat agtctgaggg ttatctgtca  12300
cagatttgag ggtggttcgt cacatttgtt ctgacctact gagggtaatt tgtcacagtt  12360
ttgctgtttc cttcagcctg catggatttt ctcatacttt ttgaactgta atttttaagg  12420
aagccaaatt tgagggcagt ttgtcacagt tgatttcctt ctctttccct tcgtcatgtg  12480
acctgatatc gggggttagt tcgtcatcat tgatgagggt tgattatcac agtttattac  12540
tctgaattgg ctatccgcgt gtgtacctct acctggagtt tttcccacgg tggatatttc  12600
ttcttgcgct gagcgtaaga gctatctgac agaacagttc ttctttgctt cctcgccagt  12660
tcgctcgcta tgctcggtta cacggctgcg gcgagcgcta gtgataataa gtgactgagg  12720
tatgtgctct tcttatctcc ttttgtagtg ttgctcttat tttaaacaac tttgcggttt  12780
tttgatgact ttgcgatttt gttgttgctt tgcagtaaat tgcaagattt aataaaaaaa  12840
cgcaaagcaa tgattaaagg atgttcagaa tgaaactcat ggaaacactt aaccagtgca  12900
taaacgctgg tcatgaaatg acgaaggcta tcgccattgc acagtttaat gatgacagcc  12960
cggaagcgag gaaaataacc cggcgctgga gaataggtga agcagcggat ttagttgggg  13020
tttcttctca ggctatcaga gatgccgaga aagcagggcg actaccgcac ccggatatgg  13080
aaattcgagg acgggttgag caacgtgttg gttatacaat tgaacaaatt aatcatatgc  13140
gtgatgtgtt tggtacgcga ttgcgacgtg ctgaagacgt atttccaccg gtgatcgggg  13200
ttgctgccca taaaggtggc gtttacaaaa cctcagtttc tgttcatctt gctcaggatc  13260
tggctctgaa ggggctacgt gttttgctcg tggaaggtaa cgacccccag ggaacagcct  13320
caatgtatca cggatgggta ccagatcttc atattcatgc agaagacact ctcctgcctt  13380
tctatcttgg ggaaaaggac gatgtcactt atgcaataaa gcccacttgc tggccggggc  13440
ttgacattat tccttcctgt ctggctctgc accgtattga aactgagtta atgggcaaat  13500
ttgatgaagg taaactgccc accgatccac acctgatgct ccgactggcc attgaaactg  13560
ttgctcatga ctatgatgtc atagttattg acagcgcgcc taacctgggt atcggcacga  13620
ttaatgtcgt atgtgctgct gatgtgctga ttgttcccac gcctgctgag ttgtttgact  13680
acacctccgc actgcagttt ttcgatatgc ttcgtgatct gctcaagaac gttgatctta  13740
aagggttcga gcctgatgta cgtattttgc ttaccaaata cagcaatagt aatggctctc  13800
agtccccgtg gatggaggag caaattcggg atgcctgggg aagcatggtt ctaaaaaatg  13860
ttgtacgtga aacggatgaa gttggtaaag gtcagatccg gatgagaact gtttttgaac  13920
aggccattga tcaacgctct tcaactggtg cctggagaaa tgctctttct atttgggaac  13980
ctgtctgcaa tgaaattttc gatcgtctga ttaaaccacg ctgggagatt agataatgaa  14040
gcgtgcgcct gttattccaa aacatacgct caatactcaa ccggttgaag atacttcgtt  14100
atcgacacca gctgccccga tggtggattc gttaattgcg cgcgtaggag taatggctcg  14160
cggtaatgcc attactttgc ctgtatgtgg tcgggatgtg aagtttactc ttgaagtgct  14220
ccggggtgat agtgttgaga agacctctcg ggtatggtca ggtaatgaac gtgaccagga  14280
gctgcttact gaggacgcac tggatgatct catcccttct tttctactga ctggtcaaca  14340
```

-continued

```
gacaccggcg ttcggtcgaa gagtatctgg tgtcatagaa attgccgatg ggagtcgccg  14400
tcgtaaagct gctgcactta ccgaaagtga ttatcgtgtt ctggttggcg agctggatga  14460
tgagcagatg gctgcattat ccagattggg taacgattat cgcccaacaa gtgcttatga  14520
acgtggtcag cgttatgcaa gccgattgca gaatgaattt gctggaaata tttctgcgct  14580
ggctgatgcg gaaaatattt cacgtaagat tattacccgc tgtatcaaca ccgccaaatt  14640
gcctaaatca gttgttgctc ttttttctca ccccggtgaa ctatctgccc ggtcaggtga  14700
tgcacttcaa aaagccttta cagataaaga ggaattactt aagcagcagg catctaacct  14760
tcatgagcag aaaaaagctg ggtgatattt tgaagctgaa gaagttatca ctcttttaac  14820
ttctgtgctt aaaacgtcat ctgcatcaag aactagttta agctcacgac atcagtttgc  14880
tcctggagcg acagtattgt ataagggcga taaaatggtg cttaacctgg acaggtctcg  14940
tgttccaact gagtgtatag agaaaattga ggccattctt aaggaacttg aaaagccagc  15000
accctgatgc gaccacgttt tagtctacgt ttatctgtct ttacttaatg tcctttgtta  15060
caggccagaa agcataactg gcctgaatat tctctctggg cccactgttc cacttgtatc  15120
gtcggtctga taatcagact gggaccacgg tcccactcgt atcgtcggtc tgattattag  15180
tctgggacca cggtcccact cgtatcgtcg gtctgattat tagtctggga ccacggtccc  15240
actcgtatcg tcggtctgat aatcagactg ggaccacggt cccactcgta tcgtcggtct  15300
gattattagt ctgggaccat ggtcccactc gtatcgtcgg tctgattatt agtctgggac  15360
cacggtccca ctcgtatcgt cggtctgatt attagtctgg aaccacggtc ccactcgtat  15420
cgtcggtctg attattagtc tgggaccacg gtcccactcg tatcgtcggt ctgattatta  15480
gtctgggacc acgatcccac tcgtgttgtc ggtctgatta tcggtctggg accacggtcc  15540
cacttgtatt gtcgatcaga ctatcagcgt gagactacga ttccatcaat gcctgtcaag  15600
ggcaagtatt gacatgtcgt cgtaacctgt agaacggagt aacctcggtg tgcggttgta  15660
tgcctgctgt ggattgctgc tgtgtcctgc ttatccacaa cattttgcgc acggttatgt  15720
ggacaaaata cctggttacc caggccgtgc cggcacgtta accgggctgc atccgatgca  15780
agtgtgtcgc tgtcgacgag ctcgcgagct cggacatgag gttgccccgt attcagtgtc  15840
gctgatttgt attgtctgaa gttgttttta cgttaagttg atgcagatca attaatacga  15900
tacctgcgtc ataattgatt atttgacgtg gtttgatggc ctccacgcac gttgtgatat  15960
gtagatgata atcattatca ctttacgggt cctttccggt gatccgacag gttacggggc  16020
ggcgacctcg cgggttttcg ctatttatga aaattttccg gtttaaggcg tttccgttct  16080
tcttcgtcat aacttaatgt ttttatttaa aataccctct gaaaagaaag gaaacgacag  16140
gtgctgaaag cgagcttttt ggcctctgtc gtttcctttc tctgtttttg tccgtggaat  16200
gaacaatgga agtccgagct catcgctaat aacttcgtat agcatacatt atacgaagtt  16260
atattcgatg cggccgctga ggtctgcctc gtgaagaagg tgttgctgac tcataccagg  16320
gctgaatcgc cccatcatcc agccagaaag tgagggagcc acggttgatg agagctttgt  16380
tgtaggtgga ccagttggtg attttgaact tttgctttgc cacggaacgg tctgcgttgt  16440
cgggaagatg cgtgatctga tccttcaact cagcaaaagt tcgatttatt caacaaagcc  16500
acgtgtctca aaatctctga tgttacattg cacaagataa aaatatatca tcatgaacaa  16560
taaaactgtc tgcttacata aacagtaata caaggggtgt tatgagccat attcaacggg  16620
aaacgtcttg ctcgacgatg ataagctgtc aaacatgaga attgggtcgt caatatgcta  16680
```

-continued

```
aaacgcggca taccccgcgt attcccacta gttaattaac ctgcaggggg ctgttagagg  16740

tcttccctag tccaactata gcgtatggac atattgtcgt tagaacgcgg ctacaattaa  16800

tacataacct tatgtatcat acacatacga tttaggggac actatag               16847
```

<210> SEQ ID NO 43
<211> LENGTH: 18563
<212> TYPE: DNA
<213> ORGANISM: Artificial Sequence
<220> FEATURE:
<223> OTHER INFORMATION: sequence for pBACsp6/JVFL/XhoI

<400> SEQUENCE: 43

```
agaagtttat ctgtgtgaac ttcttggctt agtatcgttg agaagaatcg agagattagt     60

gcagtttaaa cagtttttta gaacggaaga taaccatgac taaaaaacca ggagggcccg    120

gtaaaaaccg ggctatcaat atgctgaaac gcggcctacc ccgcgtattc ccactagtgg    180

gagtgaagag ggtagtaatg agcttgttgg acggcagagg accagtacgt ttcgtgctgg    240

ctcttatcac gttcttcaag tttacagcat tagccccgac caaggcgctt ttaggccgat    300

ggaaagcagt ggaaaagagt gtggcaatga aacatcttac tagtttcaaa cgagaacttg    360

gaacactcat tgacgccgtg aacaagcggg gcagaaagca aaacaaaaga ggaggaaatg    420

aaggctcaat catgtggctc gcgagtttgg cagttgtcat agcttgtgta ggagccatga    480

agttgtcaaa tttccaaggg aagcttttga tgaccattaa caacacggac attgcagacg    540

tcatcgtgat tcctacctca aaaggagaga acagatgctg ggtccgggca atcgatgtcg    600

gctacatgtg tgaggacact atcacgtacg aatgtcctaa gcttaccatg ggcaatgatc    660

cagaggatgt ggattgctgg tgtgacaacc aagaagtcta cgtccaatat ggacggtgca    720

cgcggaccag gcattccaag cgaagcagga ggtccgtgtc ggtccaaaca catggggaga    780

gttcactagt gaataaaaaa gaggcttggc tggattcaac gaaagccaca cgatatctca    840

tgaaaactga gaactggatc ataaggaatc ctggctatgc tttcctggcg gcggtacttg    900

gctggatgct tggcagtaac aatggtcaac gcgtggtgtt taccatcctc ctgctgttgg    960

tcgctccggc ttacagtttt aattgtctgg gaatgggcaa ccgtgacttc atagaaggag   1020

ccagtggagc cacttgggtg gacttagtgc tagaaggaga tagctgcttg acaatcatgg   1080

caaacgacaa accaacattg gacgtccgca tgattaacat cgaagccagc caacttgctg   1140

aggtcagaag ctactgctat catgcttcag tcactgacat ctcgacggtg gctcggtgcc   1200

ccacgactgg agaagcccac aacgagaagc gagctgatag tagctatgtg tgcaaacaag   1260

gtttcactga tcgtgggtgg ggcaacggat gtggactttt cgggaaggga agcattgaca   1320

catgtgcaaa attctcctgc accagtaagg cgattgggag aacaatccag ccagaaaaca   1380

tcaaatacga agttggcatt tttgtgcatg gaaccaccac ctcggaaaac catgggaatt   1440

attcagcgca agtagggggcg tcccaggcgg caaagtttac agtaacaccc aatgctcctt   1500

cgataaccct caaacttggt gactacggag aagtcacact ggactgtgaa ccaaggagtg   1560

gactgaacac tgaagcgttt tacgtcatga ccgtggggtc aaagtcattt ctggtccata   1620

gggaatggtt tcatgacctc gctctcccct ggacgtcccc ttcgagcaca gcgtggagaa   1680

acagagaact cctcatggaa tttgaagagg cgcacgccac aaaacagtcc gttgttgctc   1740

ttgggtcaca ggaaggaggc ctccatcagg cgctggcagg agccatcgtg gtggagtact   1800

caagctcagt gaagttaaca tcaggccacc tgaaatgtag gctgaaaatg gacaaactgg   1860

ctctgaaagg cacaacctat ggcatgtgta cagaaaaatt ctcgttcgcg aaaaatccgg   1920
```

-continued

```
cggacactgg ccacggaaca gttgtcattg aactctccta ttctgggagt gatggcccct   1980
gcaaaattcc gattgtctcc gttgcgagcc tcaatgacat gacccccgtt gggcggctgg   2040
tgacagtgaa ccccttcgtc gcgacttcca gtgccaactc aaaggtgctg gtcgagatgg   2100
aaccccccctt cggagactcc tacatcgtag ttggaagggg agacaagcag atcaaccacc   2160
attggcataa agctggaagc acgctgggca aggcttttc aacaactttg aagggagctc   2220
aaagactggc agcgttgggc gacacagcct gggactttgg ctctattgga ggggtcttca   2280
actccatagg aaaggccgtt caccaagtgt ttggtggcgc tttcagaaca ctctttgggg   2340
gaatgtcttg gatcacacaa gggttaatgg gtgccctact actctggatg ggcatcaacg   2400
cacgagatcg atcaattgct ttggccttct tggccacagg aggtgtgctc gtgttcttag   2460
cgaccaatgt gcatgctgac actggatgtg ccattgacat cgcaagaaaa gagatgagat   2520
gcggaagtgg catcttcgtg cacaacgacg tggaagcctg ggtggatagg tataaatatt   2580
tgccagaaac gcccagatcc ctagcgaaga tcgtccacaa agcgcacaag gaaggcgtgt   2640
gcggagtcag atctgtcact agactggagc accaaatgtg ggaagccgtg cgggacgaat   2700
tgaacgtcct gctcaaagag aatgcagtgg acctcagtgt ggttgtgaac aagcccgtgg   2760
ggagatatcg ctcagcccca aaacgcctgt ccatgacgca agagaagttt gaaatgggct   2820
ggaaagcatg ggaaaaaagc attctctttg ccccggaatt ggctaactcc acatttgttg   2880
tagatggacc tgagacaaag gaatgtcctg atgagcacag agcctggaac agcatgcaaa   2940
tcgaagactt cggctttggt atcacatcaa cccgtgtgtg gctgaagatt agagaggaaa   3000
gcactgacga gtgtgatgga gcgatcatag gcacagctgt caaaggacat gtggcagttc   3060
atagtgactt gtcgtactgg attgagagtc gctacaacga cacatggaaa cttgagaggg   3120
cagtctttgg agaggtcaaa tcttgcactt ggccagagac acacactctt tggggagatg   3180
gtgttgagga aagtgaactc atcatcccgc ataccatagc cggaccaaaa agcaagcaca   3240
atcggaggga agggtacaaa acacaaaacc agggaccttg ggacgaaaac ggcatagtct   3300
tggactttga ttattgccca gggacaaaag tcaccatcac agaggattgt ggcaagagag   3360
gcccttcggt cagaaccact actgacagtg gaaagttgat tactgactgg tgctgtcgca   3420
gttgctccct tccgccccta cgattccgga cagaaaatgg ctgctggtac ggaatggaaa   3480
tcagacctgt taggcatgat gaaacaacac tcgtcagatc acaggttgat gctttcaatg   3540
gtgaaatggt tgaccctttt cagctgggcc ttctggtgat gtttctggcc acccaggagg   3600
tccttcgcaa gaggtggacg gccagattga ccattcctgc ggttttgggg gccctgcttg   3660
tgctgatgct tgggggcatc acttacactg atttggcgag gtatgtggtg ctagtcgctg   3720
ctgctttcgc agaggccaat aatggaggag acgtcctgca ccttgctttg attgccgttt   3780
ttaagatcca accagctttt ctagtgatga acatgcttag cacgagatgg acgaaccaag   3840
aaaacgtggt cctggtccta ggggctgcct tctttcaatt ggcctcagta gatctgcaaa   3900
tcggagtcca cggaatcctg aatgccgccg ctatagcatg gatgattgtt cgagcgatca   3960
ccttccccac aacctcctcc gtcaccatgc cagtcttagc gcttctaact ccgggaatga   4020
gggctctata cctagacact tacagaatca tccttctcgt catagggatt tgctccctgc   4080
tgcaagagag gaaaaagacc atggcaaaaa agaaaggagc tgtactcttg ggcttagcgc   4140
tcacatccac tggatggttc tcgcccacca ccatagctgc tggactaatg gtctgcaacc   4200
caaacaagaa gagagggtgg ccagctactg agtttctgtc ggcagtcgga ttgatgtttg   4260
```

-continued

```
ccatcgtagg tggtttggcc gagttggata ttgaatccat gtcaataccc ttcatgctgg   4320
caggtcttat ggcagtgtcc tacgtagtgt caggaaaagc aacagatatg tggctcgaac   4380
gggccgccga catcagctgg gagatggatg ctgcaatcac aggaagcagt cggaggctgg   4440
atgtgaaact ggatgatgac ggagattttc acttgattga tgatcccggc gttccatgga   4500
aagtttgggt cttgcgcatg tcttgcattg gcttagccgc cctcacgcct tgggccattg   4560
ttcccgccgc tttcggttac tggctcactt taaaaacaac aaaaagaggg ggcgtgtttt   4620
gggacacgcc atccccgaaa ccttgcttaa aaggagacac cactacagga gtctaccgaa   4680
tcatggctag agggattctt ggcacctacc aggctggcgt cggagtcatg tacgagaatg   4740
ttttccacac actatggcac acaactagag gggcagccat tatgagtgga gaaggaaaat   4800
tgacgccata ctggggtagc gtgaaagaag accgcatagc ttacggaggc ccatggagat   4860
ttgatcgaaa atggaatgga acagatgacg tgcaagtgat cgtggtagaa ccggggaagg   4920
ctgcggtaaa catccagaca aaaccaggag tgtttcggac cccccttcggg gaggttgggg   4980
ctgttagcct ggattacccg cgaggaacat ccggctcacc cattctggat tccaatggag   5040
acatcatagg cctatacggc aatggagttg agcttggcga tggctcatac gtcagcgcca   5100
tcgtgcaggg tgaccgtcag gaggaaccag tcccagaagc ttacactcca aacatgttaa   5160
gaaagagaca gatgactgtg ttagatttgc accctggttc agggaaaacc aggaaaattc   5220
tgccacaaat aattaaggat gcaatccagc agcgcctaag aacagctgtg ttggcaccga   5280
cgcgggtggt agcagcagaa atggcagaag ctttgagagg gctcccagta cgataccaaa   5340
cttcagcagt gcagagagag caccaaggga atgaaatagt ggatgtgatg tgccacgcca   5400
ctctgaccca cagattgatg tcaccgaaca gagtgcccaa ctacaatctg tttgtcatgg   5460
atgaagctca tttcaccgac ccagccagca tagccgcacg aggatacatc gctaccaagg   5520
tggaattagg agaggcagca gccatcttta tgacagcgac cccgcctgga accacggatc   5580
cttttcccga ctcaaatgcc ccaatccatg atttacaaga tgagatacca gacagggcat   5640
ggagcagtgg atacgaatgg atcacagaat atgcgggtaa aaccgtgtgg tttgtggcga   5700
gcgtaaaaat ggggaatgag attgcaatgt gcctccaaag agcgggaaaa aaggtcatcc   5760
aactcaaccg caagtcctat gacacagaat acccaaaatg taagaatgga gactgggatt   5820
ttgtcattac caccgacatc tctgaaatgg gggctaactt cggtgcgagc agggtcatcg   5880
actgcagaaa gagcgtgaaa cccaccatct tagaagaggg agaaggcaga gtcatcctcg   5940
gaaacccatc tcccataacc agtgctagcg cagctcaacg gaggggcaga gtaggcagaa   6000
accccaacca agttggagat gaataccatt atggaggggc taccagtgaa gatgacagta   6060
acctagccca ttggacagag gcaaagatca tgttagacaa catacacatg cccaatgggc   6120
tggtggccca gctctatgga ccagagaggg aaaaggcttt cacaatggat ggcgaatacc   6180
gtctcagggg tgaagaaaag aaaaacttct tagagctgct taggacggct gaccttccgg   6240
tgtggctggc ctataaggtg gcgtccaatg gcattcagta caccgacaga aagtggtgtt   6300
ttgatgggcc gcgcacgaat gccatactgg aggacaacac cgaggtagag atagtcaccc   6360
ggatgggtga gagaaagatc ctcaagccga gatggcttga tgcaagagta tacgcagatc   6420
accaagccct caagtggttc aaagactttg cagcaggaaa gagatcggcc gttagcttca   6480
tagaggtgct cggtcgcatg cctgagcatt tcatgggaaa gacgcgggaa gctttagaca   6540
ccatgtactt ggtcgcaacg gctgagaaag gtgggaaggc acaccgaatg gctctcgaag   6600
agttgccgga tgcactggaa accatcacac ttattgttgc catcactgta atgacaggag   6660
```

-continued

```
gattcttcct actaatgatg cagcgaaagg gtatagggaa gatgggtctt ggagctctag   6720
tgctcacgct agctaccttc ttcctgtggg cggcagaggt tcctggaacc aaaatagcag   6780
ggaccctgct gatcgccctg ctgctgatgg tggttctcat cccagaaccg gaaaaacaga   6840
ggtcacagac agacaaccaa ctagcggtgt ttctcatctg cgtcttgacc gtggttggag   6900
tggtggcagc aaacgagtac gggatgctag aaaaaaccaa agcagatctc aagagcatgt   6960
ttggcggaaa gacacaggca tcaggactga ctggattgcc aagcatggca ctggacctgc   7020
gtccagccac agcctgggca ctgtatgggg ggagcacagt tgtgctaacc cctcttctga   7080
agcacctgat cacgtcggaa tatgtcacca catcgctagc ctcaattaac tcacaagctg   7140
gctcattatt cgtcttgcca cgaggcgtgc ctttcaccga tctagacctg accgttggcc   7200
tcgtcttcct tggctgctgg ggtcaaatca ccctcacaac gtttttgaca gccatggttc   7260
tggcgacact tcactatggg tacatgctcc ctggatggca agcagaagca ctcagggctg   7320
cccagagaag gacggcggct ggaataatga agaatgccgt tgttgacgga atggtcgcca   7380
ctgatgtgcc tgaactggaa aggactactc ctctgatgca aaagaaagtc ggacaggtgc   7440
tcctcatagg ggtgagcgtg gcagcgtttc tcgtcaaccc taatgtcacc actgtgagag   7500
aagcaggggt gttggtgacg gcggctacgc tcaccttgtg ggataatgga gccagtgccg   7560
tttggaattc caccacagcc acgggactct gccatgtcat gcgaggtagc tacctggctg   7620
gaggctctat tgcttggact cttatcaaga acgctgacaa gccctccttg aaaaggggaa   7680
ggcctggggg caggacgcta ggggagcagt ggaaggaaaa actaaatgcc atgagcagag   7740
aagagttttt taaataccgg agagaggcca taatcgaggt ggaccgcact gaagcacgca   7800
gggctagacg tgaaaataac atagtgggag gacatccggt ttcgcgaggc tcagcaaaac   7860
tccgttggct cgtggagaaa ggattcgtct cgccaatagg aaaagtcatt gatctagggt   7920
gtgggcgtgg aggatggagc tactacgcag caaccctgaa gaaggtccag gaagtcagag   7980
gatacacgaa aggtggggcg ggacatgaag agccgatgct catgcagagc tacggctgga   8040
acctggtctc cttgaagagt ggagtggatg tgttctacaa accttcagag cctagtgaca   8100
ccctgttctg tgacataggg gaatcctccc caagtccaga agtggaagaa caacgcacac   8160
tacgcgtcct agagatgaca tccgattggt tgcatcgagg acccagagag ttctgcataa   8220
aagttctctg cccttacatg cccaaggtca tagaaaaaat ggaagttctg cagcgccgct   8280
tcggaggtgg gctagtacgt ctcccccctgt cccgaaactc caatcacgag atgtattggg   8340
ttagtggagc cgctggcaat gtggtgcacg ctgtgaacat gaccagccag gtactactgg   8400
ggcgaatgga tcgcacagtg tggagagggc caaagtatga ggaagatgtc aacctaggta   8460
gcggaacaag agccgtggga aagggagaag ttcatagcaa tcaggagaaa atcaagaaga   8520
gaatccagaa gcttaaagaa gaattcgcca caacgtggca caaagaccct gaacacccat   8580
accgcacttg gacataccac ggaagctatg aggtgaaggc tactggctca gccagctctc   8640
tcgtcaacgg agtggtgaag ctcatgagta aaccttggga cgccattgcc aacgtcacca   8700
ccatggccat gactgacacc accccttttg gacagcaaag agttttcaag gagaaagttg   8760
acacgaaagc tcctgagcca ccagctggag tcaaggaagt gctcaacgag accaccaact   8820
ggctgtgggc ccacttgtca cgggaaaaaa gacccccgctt gtgcaccaag gaagaattta   8880
taaagaaagt caatagcaac gcggctcttg gagcagtgtt tgctgaacag aatcaatgga   8940
gcacggcgcg tgaggctgtg gacgacccgc ggttttggga gatggtcaat gaagagaggg   9000
```

-continued

```
aaaaccatct gcgaggagag tgtcacacat gtatctacaa catgatggga aaaagagaga   9060
agaagcctgg agagtttgga aaagctaaag ggagcagggc catttggttc atgtggcttg   9120
gagcacggta tctagagttt gaagctttgg ggttcctgaa tgaagaccac tggctgagcc   9180
gagagaattc aggaggtgga gtagaaggct caggcgtcca aaagttggga tacatcctcc   9240
gtgacatagc aggaaagcaa ggagggaaaa tgtacgctga tgacaccgcc gggtgggaca   9300
ctagaattac tagaactgat ttagaaaatg aagctaaggt gctggagctc ctagatggtg   9360
aacaccgcat gctcgcccgg gccataattg aactgactta caggcacaaa gtggtcaagg   9420
tcatgagacc tgcagcagaa ggaaagaccg tgatggacgt gatatcaaga gaagaccaaa   9480
gggggagtgg acaggtggtc acttatgctc tcaacacttt cacgaacatc gctgtccagc   9540
tcgttaggct gatggaggct gagggggtca ttgggccaca acacttggaa cagctgccta   9600
ggaaaaacaa gatagctgtc aggacttggc tctttgagaa tggagaggag agagtgacca   9660
ggatggcgat cagcggagac gactgtgtcg tcaagccgct ggacgacaga ttcgccacgg   9720
ccctccattt cctcaacgca atgtcaaagg ttagaaaaga catccaggaa tggaagcctt   9780
cgcacggctg gcacgattgg cagcaagttc ccttctgctc taaccacttt caggagattg   9840
tgatgaaaga cggaaggagt atagttgtcc cgtgcagagg acaggatgag ctgataggca   9900
gggctcgcat ctctccagga gctggatgga atgtgaagga cacagcttgc ctggcaaaag   9960
catatgcaca gatgtggcta ctcctatact tccatcgtag ggacctgcgt ctcatggcaa  10020
atgcgatttg ctcagcagtg ccagtggatt gggtgcccac aggcaggaca tcctggtcaa  10080
tacactcgaa aggagagtgg atgaccacgg aagacatgct gcaggtctgg aacagagtct  10140
ggattgaaga aaatgaatgg atgatggata agactcccgt cacaagctgg acagacgttc  10200
cgtatgtggg aaagcgtgag gacatctggt gtggcagcct catcggaacg cgttccagag  10260
caacctgggc tgagaacatc tatgcggcga taaaccaggt tagagctgtc attgggaaag  10320
aaaattatgt tgactacatg acctcactca ggagatacga agacgtcttg atccaggaag  10380
acagggtcat ctagtgtgac ttaaggtaga aatgtaaata atgtgaatga gaaaatgcat  10440
gtatatggag tcaggccagc aaaagctgcc accggatact gggtagacgg tgctgcctgc  10500
gtctcagtcc caggaggact gggttaacaa atctgacaac agaaagtgag aaagccctca  10560
gaaccgtctc ggaagtaggt ccctgctcac tggaagttga aagaccaacg tcaggccacg  10620
aatttgtgcc actccgctgg ggagtgcggc ctgcgcagcc ccaggaggac tgggttacca  10680
aagccgttga ggcccccacg gcccaagcct cgtctaggat gcaatagacg aggtgtaagg  10740
actagaggtt agaggagacc ccgtggaaac aacaacatgc ggcccaagcc ccctcgaagc  10800
tgtagaggag gtggaaggac tagaggttag aggagacccc gcatttgcat caaacagcat  10860
attgacacct gggaatagac tgggagatct tctgctctat ctcaacatca gctactaggc  10920
acagagcgcc gaagtatgta gctggtggtg aggaagaaca caggatctcg agcggccgcg  10980
gaccgactag cctcttttcg gccttcgctg agagggattt gttccctagg cctaattatt  11040
atttttaatt gcccaatacg tatacgagtg ccttttctaa ttctcgtata ctatagtgag  11100
tcgtattatc tagccgcccg ggccgtcgac caattctcat gtttgacagc ttatcatcga  11160
atttctgcca ttcatccgct tattatcact tattcaggcg tagcaaccag gcgtttaagg  11220
gcaccaataa ctgccttaaa aaaattacgc cccgccctgc cactcatcgc agtactgttg  11280
taattcatta agcattctgc cgacatggaa gccatcacaa acggcatgat gaacctgaat  11340
cgccagcggc atcagcacct tgtcgccttg cgtataatat ttgcccatgg tgaaaacggg  11400
```

-continued

```
ggcgaagaag ttgtccatat tggccacgtt taaatcaaaa ctggtgaaac tcacccaggg  11460
attggctgag acgaaaaaca tattctcaat aaacccttta gggaaatagg ccaggttttc  11520
accgtaacac gccacatctt gcgaatatat gtgtagaaac tgccggaaat cgtcgtggta  11580
ttcactccag agcgatgaaa acgtttcagt ttgctcatgg aaaacggtgt aacaagggtg  11640
aacactatcc catatcacca gctcaccgtc tttcattgcc atacggaatt ccggatgagc  11700
attcatcagg cgggcaagaa tgtgaataaa ggccggataa aacttgtgct tatttttctt  11760
tacggtcttt aaaaaggccg taatatccag ctgaacggtc tggttatagg tacattgagc  11820
aactgactga aatgcctcaa aatgttcttt acgatgccat tgggatatat caacggtggt  11880
atatccagtg atttttttct ccattttagc ttccttagct cctgaaaatc tcgataactc  11940
aaaaaatacg cccggtagtg atcttatttc attatggtga aagttggaac ctcttacgtg  12000
ccgatcaacg tctcattttc gccaaaagtt ggcccagggc ttcccggtat caacagggac  12060
accaggattt atttattctg cgaagtgatc ttccgtcaca ggtatttatt cgcgataagc  12120
tcatggagcg gcgtaaccgt cgcacaggaa ggacagagaa agcgcggatc tgggaagtga  12180
cggacagaac ggtcaggacc tggattgggg aggcggttgc cgccgctgct gctgacggtg  12240
tgacgttctc tgttccggtc acaccacata cgttccgcca ttcctatgcg atgcacatgc  12300
tgtatgccgg tataccgctg aaagttctgc aaagcctgat gggacataag tccatcagtt  12360
caacggaagt ctacacgaag gtttttgcgc tggatgtggc tgcccggcac cgggtgcagt  12420
ttgcgatgcc ggagtctgat gcggttgcga tgctgaaaca attatcctga gaataaatgc  12480
cttggccttt atatggaaat gtggaactga gtggatatgc tgtttttgtc tgttaaacag  12540
agaagctggc tgttatccac tgagaagcga acgaaacagt cgggaaaatc tcccattatc  12600
gtagagatcc gcattattaa tctcaggagc ctgtgtagcg tttataggaa gtagtgttct  12660
gtcatgatgc ctgcaagcgg taacgaaaac gatttgaata tgccttcagg aacaatagaa  12720
atcttcgtgc ggtgttacgt tgaagtggag cggattatgt cagcaatgga cagaacaacc  12780
taatgaacac agaaccatga tgtggtctgt ccttttacag ccagtagtgc tcgccgcagt  12840
cgagcgacag ggcgaagccc tcgagtgagc gaggaagcac cagggaacag cacttatata  12900
ttctgcttac acacgatgcc tgaaaaaact tcccttgggg ttatccactt atccacgggg  12960
atatttttat aattattttt tttatagttt ttagatcttc ttttttagag cgccttgtag  13020
gcctttatcc atgctggttc tagagaaggt gttgtgacaa attgcccttt cagtgtgaca  13080
aatcaccctc aaatgacagt cctgtctgtg acaaattgcc cttaaccctg tgacaaattg  13140
ccctcagaag aagctgtttt ttcacaaagt tatccctgct tattgactct tttttattta  13200
gtgtgacaat ctaaaaactt gtcacacttc acatggatct gtcatggcgg aaacagcggt  13260
tatcaatcac aagaaacgta aaaatagccc gcgaatcgtc cagtcaaacg acctcactga  13320
ggcggcatat agtctctccc gggatcaaaa acgtatgctg tatctgttcg ttgaccagat  13380
cagaaaatct gatggcaccc tacaggaaca tgacggtatc tgcgagatcc atgttgctaa  13440
atatgctgaa atattcggat tgacctctgc ggaagccagt aaggatatac ggcaggcatt  13500
gaagagtttc gcggggaagg aagtggtttt ttatcgccct gaagaggatg ccggcgatga  13560
aaaaggctat gaatcttttc cttggtttat caaacgtgcg cacagtccat ccagagggct  13620
ttacagtgta catatcaacc catatctcat tcccttcttt atcgggttac agaaccggtt  13680
tacgcagttt cggcttagtg aaacaaaaga aatcaccaat ccgtatgcca tgcgtttata  13740
```

-continued

```
cgaatccctg tgtcagtatc gtaagccgga tggctcaggc atcgtctctc tgaaaatcga  13800
ctggatcata gagcgttacc agctgcctca aagttaccag cgtatgcctg acttccgccg  13860
ccgcttcctg caggtctgtg ttaatgagat caacagcaga actccaatgc gcctctcata  13920
cattgagaaa aagaaaggcc gccagacgac tcatatcgta ttttccttcc gcgatatcac  13980
ttccatgacg acaggatagt ctgagggtta tctgtcacag atttgagggt ggttcgtcac  14040
atttgttctg acctactgag ggtaatttgt cacagttttg ctgtttcctt cagcctgcat  14100
ggattttctc atactttttg aactgtaatt tttaaggaag ccaaatttga gggcagtttg  14160
tcacagttga tttccttctc tttcccttcg tcatgtgacc tgatatcggg ggttagttcg  14220
tcatcattga tgagggttga ttatcacagt ttattactct gaattggcta tccgcgtgtg  14280
tacctctacc tggagttttt cccacggtgg atatttcttc ttgcgctgag cgtaagagct  14340
atctgacaga acagttcttc tttgcttcct cgccagttcg ctcgctatgc tcggttacac  14400
ggctgcggcg agcgctagtg ataataagtg actgaggtat gtgctcttct tatctccttt  14460
tgtagtgttg ctcttatttt aaacaacttt gcggtttttt gatgactttg cgattttgtt  14520
gttgctttgc agtaaattgc aagatttaat aaaaaaacgc aaagcaatga ttaaaggatg  14580
ttcagaatga aactcatgga aacacttaac cagtgcataa acgctggtca tgaaatgacg  14640
aaggctatcg ccattgcaca gtttaatgat gacagcccgg aagcgaggaa aataacccgg  14700
cgctggagaa taggtgaagc agcggattta gttggggttt cttctcaggc tatcagagat  14760
gccgagaaag cagggcgact accgcacccg gatatggaaa ttcgaggacg ggttgagcaa  14820
cgtgttggtt atacaattga acaaattaat catatgcgtg atgtgtttgg tacgcgattg  14880
cgacgtgctg aagacgtatt tccaccggtg atcggggttg ctgcccataa aggtggcgtt  14940
tacaaaacct cagtttctgt tcatcttgct caggatctgg ctctgaaggg gctacgtgtt  15000
ttgctcgtgg aaggtaacga cccccaggga acagcctcaa tgtatcacgg atgggtacca  15060
gatcttcata ttcatgcaga agacactctc ctgcctttct atcttgggga aaaggacgat  15120
gtcacttatg caataaagcc cacttgctgg ccggggcttg acattattcc ttcctgtctg  15180
gctctgcacc gtattgaaac tgagttaatg ggcaaatttg atgaaggtaa actgcccacc  15240
gatccacacc tgatgctccg actggccatt gaaactgttg ctcatgacta tgatgtcata  15300
gttattgaca gcgcgcctaa cctgggtatc ggcacgatta atgtcgtatg tgctgctgat  15360
gtgctgattg ttcccacgcc tgctgagttg tttgactaca cctccgcact gcagtttttc  15420
gatatgcttc gtgatctgct caagaacgtt gatcttaaag ggttcgagcc tgatgtacgt  15480
attttgctta ccaaatacag caatagtaat ggctctcagt ccccgtggat ggaggagcaa  15540
attcgggatg cctggggaag catggttcta aaaaatgttg tacgtgaaac ggatgaagtt  15600
ggtaaaggtc agatccggat gagaactgtt tttgaacagg ccattgatca acgctcttca  15660
actggtgcct ggagaaatgc tctttctatt tgggaacctg tctgcaatga aattttcgat  15720
cgtctgatta aaccacgctg ggagattaga taatgaagcg tgcgcctgtt attccaaaac  15780
atacgctcaa tactcaaccg gttgaagata cttcgttatc gacaccagct gccccgatgg  15840
tggattcgtt aattgcgcgc gtaggagtaa tggctcgcgg taatgccatt actttgcctg  15900
tatgtggtcg ggatgtgaag tttactcttg aagtgctccg ggtgatagt gttgagaaga  15960
cctctcgggt atggtcaggt aatgaacgtg accaggagct gcttactgag gacgcactgg  16020
atgatctcat cccttctttt ctactgactg gtcaacagac accggcgttc ggtcgaagag  16080
tatctggtgt catagaaatt gccgatggga gtcgccgtcg taaagctgct gcacttaccg  16140
```

-continued

```
aaagtgatta tcgtgttctg gttggcgagc tggatgatga gcagatggct gcattatcca  16200
gattgggtaa cgattatcgc ccaacaagtg cttatgaacg tggtcagcgt tatgcaagcc  16260
gattgcagaa tgaatttgct ggaaatattt ctgcgctggc tgatgcggaa aatatttcac  16320
gtaagattat tacccgctgt atcaacaccg ccaaattgcc taaatcagtt gttgctcttt  16380
tttctcaccc cggtgaacta tctgcccggt caggtgatgc acttcaaaaa gcctttacag  16440
ataaagagga attacttaag cagcaggcat ctaaccttca tgagcagaaa aaagctgggg  16500
tgatatttga agctgaagaa gttatcactc ttttaacttc tgtgcttaaa acgtcatctg  16560
catcaagaac tagtttaagc tcacgacatc agtttgctcc tggagcgaca gtattgtata  16620
agggcgataa aatggtgctt aacctggaca ggtctcgtgt tccaactgag tgtatagaga  16680
aaattgaggc cattcttaag gaacttgaaa agccagcacc ctgatgcgac cacgttttag  16740
tctacgttta tctgtcttta cttaatgtcc tttgttacag gccagaaagc ataactggcc  16800
tgaatattct ctctgggccc actgttccac ttgtatcgtc ggtctgataa tcagactggg  16860
accacggtcc cactcgtatc gtcggtctga ttattagtct gggaccacgg tcccactcgt  16920
atcgtcggtc tgattattag tctgggacca cggtcccact cgtatcgtcg gtctgataat  16980
cagactggga ccacggtccc actcgtatcg tcggtctgat tattagtctg ggaccatggt  17040
cccactcgta tcgtcggtct gattattagt ctgggaccac ggtcccactc gtatcgtcgg  17100
tctgattatt agtctggaac cacggtccca ctcgtatcgt cggtctgatt attagtctgg  17160
gaccacggtc ccactcgtat cgtcggtctg attattagtc tgggaccacg atcccactcg  17220
tgttgtcggt ctgattatcg gtctgggacc acggtcccac ttgtattgtc gatcagacta  17280
tcagcgtgag actacgattc catcaatgcc tgtcaagggc aagtattgac atgtcgtcgt  17340
aacctgtaga acggagtaac ctcggtgtgc ggttgtatgc ctgctgtgga ttgctgctgt  17400
gtcctgctta tccacaacat tttgcgcacg gttatgtgga caaaatacct ggttacccag  17460
gccgtgccgg cacgttaacc gggctgcatc cgatgcaagt gtgtcgctgt cgacgagctc  17520
gcgagctcgg acatgaggtt gccccgtatt cagtgtcgct gatttgtatt gtctgaagtt  17580
gtttttacgt taagttgatg cagatcaatt aatacgatac ctgcgtcata attgattatt  17640
tgacgtggtt tgatggcctc cacgcacgtt gtgatatgta gatgataatc attatcactt  17700
tacgggtcct ttccggtgat ccgacaggtt acggggcggc gacctcgcgg gttttcgcta  17760
tttatgaaaa ttttccggtt taaggcgttt ccgttcttct tcgtcataac ttaatgtttt  17820
tatttaaaat accctctgaa aagaaaggaa acgacaggtg ctgaaagcga gctttttggc  17880
ctctgtcgtt tcctttctct gtttttgtcc gtggaatgaa caatggaagt ccgagctcat  17940
cgctaataac ttcgtatagc atacattata cgaagttata ttcgatgcgg cgctgaggtc  18000
tgcctcgtga agaaggtgtt gctgactcat accaggcctg aatcgcccca tcatccagcc  18060
agaaagtgag ggagccacgg ttgatgagag ctttgttgta ggtggaccag ttggtgattt  18120
tgaacttttg ctttgccacg gaacggtctg cgttgtcggg aagatgcgtg atctgatcct  18180
tcaactcagc aaaagttcga tttattcaac aaagccacgt gtctcaaaat ctctgatgtt  18240
acattgcaca agataaaaat atatcatcat gaacaataaa actgtctgct tacataaaca  18300
gtaatacaag gggtgttatg agccatattc aacgggaaac gtcttgctcg acgatgataa  18360
gctgtcaaac atgagaattg ggtcgtcaat atgctaaaac gcggcatacc ccgcgtattc  18420
ccactagtta attaacctgc agggggctgt tagaggtctt ccctagtcca actatagcgt  18480
```

-continued atggacatat tgtcgttaga acgcggctac aattaataca taaccttatg tatcatacac 18540
atacgattta ggggacacta tag 18563

<210> SEQ ID NO 44
<211> LENGTH: 18563
<212> TYPE: DNA
<213> ORGANISM: Artificial Sequence
<220> FEATURE:
<223> OTHER INFORMATION: sequence for pBACsp6/JVFLx/XhoI

<400> SEQUENCE: 44
agaagtttat ctgtgtgaac ttcttggctt agtatcgttg agaagaatcg agagattagt 60
gcagtttaaa cagtttttta gaacggaaga taaccatgac taaaaaacca ggagggcccg 120
gtaaaaaccg ggctatcaat atgctgaaac gcggcctacc ccgcgtattc ccactagtgg 180
gagtgaagag ggtagtaatg agcttgttgg acggcagagg accagtacgt ttcgtgctgg 240
ctcttatcac gttcttcaag tttacagcat tagccccgac caaggcgctt ttaggccgat 300
ggaaagcagt ggaaaagagt gtggcaatga aacatcttac tagtttcaaa cgagaacttg 360
gaacactcat tgacgccgtg aacaagcggg gcagaaagca aaacaaaaga ggaggaaatg 420
aaggctcaat catgtggctc gcgagtttgg cagttgtcat agcttgtgta ggagccatga 480
agttgtcaaa tttccaaggg aagcttttga tgaccattaa caacacggac attgcagacg 540
tcatcgtgat tcctacctca aaaggagaga acagatgctg ggtccgggca atcgatgtcg 600
gctacatgtg tgaggacact atcacgtacg aatgtcctaa gcttaccatg ggcaatgatc 660
cagaggatgt ggattgctgg tgtgacaacc aagaagtcta cgtccaatat ggacggtgca 720
cgcggaccag gcattccaag cgaagcagga ggtccgtgtc ggtccaaaca catggggaga 780
gttcactagt gaataaaaaa gaggcttggc tggattcaac gaaagccaca cgatatctca 840
tgaaaactga gaactggatc ataaggaatc ctggctatgc tttcctggcg gcggtacttg 900
gctggatgct tggcagtaac aatggtcaac gcgtggtgtt taccatcctc ctgctgttgg 960
tcgctccggc ttacagtttt aattgtctgg gaatgggcaa ccgtgacttc atagaaggag 1020
ccagtggagc cacttgggtg gacttagtgc tagaaggaga tagctgcttg acaatcatgg 1080
caaacgacaa accaacattg gacgtccgca tgattaacat cgaagccagc caacttgctg 1140
aggtcagaag ctactgctat catgcttcag tcactgacat ctcgacggtg gctcggtgcc 1200
ccacgactgg agaagcccac aacgagaagc gagctgatag tagctatgtg tgcaaacaag 1260
gtttcactga tcgtgggtgg ggcaacggat gtggactttt cgggaaggga agcattgaca 1320
catgtgcaaa attctcctgc accagtaagg cgattgggag aacaatccag ccagaaaaca 1380
tcaaatacga agttggcatt tttgtgcatg gaaccaccac ctcggaaaac catgggaatt 1440
attcagcgca agtaggggcg tcccaggcgg caaagtttac agtaacaccc aatgctcctt 1500
cgataaccct caaacttggt gactacggag aagtcacact ggactgtgaa ccaaggagtg 1560
gactgaacac tgaagcgttt tacgtcatga ccgtggggtc aaagtcattt ctggtccata 1620
gggaatggtt tcatgacctc gctctcccct ggacgtcccc ttcgagcaca gcgtggagaa 1680
acagagaact cctcatggaa tttgaagagg cgcacgccac aaaacagtcc gttgttgctc 1740
ttgggtcaca ggaaggaggc ctccatcagg cgctggcagg agccatcgtg gtggagtact 1800
caagctcagt gaagttaaca tcaggccacc tgaaatgtag gctgaaaatg gacaaactgg 1860
ctctgaaagg cacaacctat ggcatgtgta cagaaaaatt ctcgttcgcg aaaaatccgg 1920
cggacactgg ccacggaaca gttgtcattg aactctccta ttctgggagt gatggcccct 1980

-continued

```
gcaaaattcc gattgtctcc gttgcgagcc tcaatgacat gacccccgtt gggcggctgg   2040
tgacagtgaa ccccttcgtc gcgacttcca gtgccaactc aaaggtgctg gtcgagatgg   2100
aacccccctt cggagactcc tacatcgtag ttggaagggg agacaagcag atcaaccacc   2160
attggcataa agctggaagc acgctgggca aggctttttc aacaactttg aagggagctc   2220
aaagactggc agcgttgggc gacacagcct gggactttgg ctctattgga ggggtcttca   2280
actccatagg aaaggccgtt caccaagtgt ttggtggcgc tttcagaaca ctctttgggg   2340
gaatgtcttg gatcacacaa gggttaatgg gtgccctact actctggatg ggcatcaacg   2400
cacgagatcg atcaattgct ttggccttct tggccacagg aggtgtgctc gtgttcttag   2460
cgaccaatgt gcatgctgac actggatgtg ccattgacat cgcaagaaaa gagatgagat   2520
gcggaagtgg catcttcgtg cacaacgacg tggaagcctg ggtggatagg tataaatatt   2580
tgccagaaac gcccagatcc ctagcgaaga tcgtccacaa agcgcacaag gaaggcgtgt   2640
gcggagtcag atctgtcact agactggagc accaaatgtg ggaagccgtg cgggacgaat   2700
tgaacgtcct gctcaaagag aatgcagtgg acctcagtgt ggttgtgaac aagcccgtgg   2760
ggagatatcg ctcagcccca aaacgcctgt ccatgacgca agagaagttt gaaatgggct   2820
ggaaagcatg ggaaaaaagc attctctttg ccccggaatt ggctaactcc acatttgttg   2880
tagatggacc tgagacaaag gaatgtcctg atgagcacag agcctggaac agcatgcaaa   2940
tcgaagactt cggctttggt atcacatcaa cccgtgtgtg gctgaagatt agagaggaaa   3000
gcactgacga gtgtgatgga gcgatcatag gcacagctgt caaaggacat gtggcagttc   3060
atagtgactt gtcgtactgg attgagagtc gctacaacga cacatggaaa cttgagaggg   3120
cagtctttgg agaggtcaaa tcttgcactt ggccagagac acacactctt tggggagatg   3180
gtgttgagga aagtgaactc atcatcccgc ataccatagc cggaccaaaa agcaagcaca   3240
atcggaggga agggtacaaa acacaaaacc agggaccttg ggacgaaaac ggcatagtct   3300
tggactttga ttattgccca gggacaaaag tcaccatcac agaggattgt ggcaagagag   3360
gcccttcggt cagaaccact actgacagtg gaaagttgat tactgactgg tgctgtcgca   3420
gttgctccct tccgccccta cgattccgga cagaaaatgg ctgctggtac ggaatggaaa   3480
tcagacctgt taggcatgat gaaacaacac tcgtcagatc acaggttgat gctttcaatg   3540
gtgaaatggt tgaccctttt cagctgggcc ttctggtgat gtttctggcc acccaggagg   3600
tccttcgcaa gaggtggacg gccagattga ccattcctgc ggttttgggg gccctgcttg   3660
tgctgatgct tgggggcatc acttacactg atttggcgag gtatgtggtg ctagtcgctg   3720
ctgctttcgc agaggccaat aatggaggag acgtcctgca ccttgctttg attgccgttt   3780
ttaagatcca accagctttt ctagtgatga acatgcttag cacgagatgg acgaaccaag   3840
aaaacgtggt cctggtccta ggggctgcct tctttcaatt ggcctcagta gatctgcaaa   3900
tcggagtcca cggaatcctg aatgccgccg ctatagcatg gatgattgtt cgagcgatca   3960
ccttccccac aacctcctcc gtcaccatgc cagtcttagc gcttctaact ccgggaatga   4020
gggctctata cctagacact tacagaatca tccttctcgt catagggatt tgctccctgc   4080
tgcaagagag gaaaaagacc atggcaaaaa agaaaggagc tgtactcttg ggcttagcgc   4140
tcacatccac tggatggttc tcgcccacca ccatagctgc tggactaatg gtctgcaacc   4200
caaacaagaa gagagggtgg ccagctactg agtttctgtc ggcagtcgga ttgatgtttg   4260
ccatcgtagg tggtttggcc gagttggata ttgaatccat gtcaataccc ttcatgctgg   4320
```

-continued

```
caggtcttat ggcagtgtcc tacgtagtgt caggaaaagc aacagatatg tggctcgaac   4380
gggccgccga catcagctgg gagatggatg ctgcaatcac aggaagcagt cggaggctgg   4440
atgtgaaact ggatgatgac ggagattttc acttgattga tgatcccggc gttccatgga   4500
aagtttgggt cttgcgcatg tcttgcattg gcttagccgc cctcacgcct tgggccattg   4560
ttcccgccgc tttcggttac tggctcactt taaaaacaac aaaaagaggg ggcgtgtttt   4620
gggacacgcc atccccgaaa ccttgcttaa aaggagacac cactacagga gtctaccgaa   4680
tcatggctag agggattctt ggcacctacc aggctggcgt cggagtcatg tacgagaatg   4740
ttttccacac actatggcac acaactagag ggcagccat tatgagtgga gaaggaaaat   4800
tgacgccata ctggggtagc gtgaaagaag accgcatagc ttacggaggc ccatggagat   4860
ttgatcgaaa atggaatgga acagatgacg tgcaagtgat cgtggtagaa ccggggaagg   4920
ctgcggtaaa catccagaca aaaccaggag tgtttcggac cccccttcggg gaggttgggg   4980
ctgttagcct ggattacccg cgaggaacat ccggctcacc cattctggat tccaatggag   5040
acatcatagg cctatacggc aatggagttg agcttggcga tggctcatac gtcagcgcca   5100
tcgtgcaggg tgaccgtcag gaggaaccag tcccagaagc ttacactcca aacatgttaa   5160
gaaagagaca gatgactgtg ttagatttgc accctggttc agggaaaacc aggaaaattc   5220
tgccacaaat aattaaggat gcaatccagc agcgcctaag aacagctgtg ttggcaccga   5280
cgcgggtggt agcagcagaa atggcagaag ctttgagagg gctcccagta cgataccaaa   5340
cttcagcagt gcagagagag caccaaggga atgaaatagt ggatgtgatg tgccacgcca   5400
ctctgaccca cagattgatg tcaccgaaca gagtgcccaa ctacaatctg tttgtcatgg   5460
atgaagctca tttcaccgac ccagccagca tagccgcacg aggatacatc gctaccaagg   5520
tggaattagg agaggcagca gccatcttta tgacagcgac cccgcctgga accacggatc   5580
cttttcccga ctcaaatgcc ccaatccatg atttacaaga tgagatacca gacagggcat   5640
ggagcagtgg atacgaatgg atcacagaat atgcgggtaa aaccgtgtgg tttgtggcga   5700
gcgtaaaaat ggggaatgag attgcaatgt gcctccaaag agcgggaaaa aaggtcatcc   5760
aactcaaccg caagtcctat gacacagaat acccaaaatg taagaatgga gactgggatt   5820
ttgtcattac caccgacatc tctgaaatgg gggctaactt cggtgcgagc agggtcatcg   5880
actgcagaaa gagcgtgaaa cccaccatct tagaagaggg agaaggcaga gtcatcctcg   5940
gaaacccatc tcccataacc agtgctagcg cagctcaacg gaggggcaga gtaggcagaa   6000
accccaacca agttggagat gaataccatt atggaggggc taccagtgaa gatgacagta   6060
acctagccca ttggacagag gcaaagatca tgttagacaa catacacatg cccaatgggc   6120
tggtggccca gctctatgga ccagagaggg aaaaggcttt cacaatggat ggcgaatacc   6180
gtctcagggg tgaagaaaag aaaaacttct tagagctgct taggacggct gaccttccgg   6240
tgtggctggc ctataaggtg gcgtccaatg gcattcagta caccgacaga aagtggtgtt   6300
ttgatgggcc gcgcacgaat gccatactgg aggacaacac cgaggtagag atagtcaccc   6360
ggatgggtga gagaaagatc ctcaagccga gatggcttga tgcaagagta tacgcagatc   6420
accaagccct caagtggttc aaagactttg cagcaggaaa gagatcggcc gttagcttca   6480
tagaggtgct cggtcgcatg cctgagcatt tcatgggaaa gacgcgggaa gctttagaca   6540
ccatgtactt ggtcgcaacg gctgagaaag gtgggaaggc acaccgaatg gctctcgaag   6600
agttgccgga tgcactggaa accatcacac ttattgttgc catcactgta atgacaggag   6660
gattcttcct actaatgatg cagcgaaagg gtatagggaa gatgggtctt ggagctctag   6720
```

-continued

```
tgctcacgct agctaccttc ttcctgtggg cggcagaggt tcctggaacc aaaatagcag   6780
ggaccctgct gatcgccctg ctgctgatgg tggttctcat cccagaaccg gaaaaacaga   6840
ggtcacagac agacaaccaa ctagcggtgt ttctcatctg cgtcttgacc gtggttggag   6900
tggtggcagc aaacgagtac gggatgctag aaaaaaccaa agcagatctc aagagcatgt   6960
ttggcggaaa gacacaggca tcaggactga ctggattgcc aagcatggca ctggacctgc   7020
gtccagccac agcctgggca ctgtatgggg ggagcacagt tgtgctaacc cctcttctga   7080
agcacctgat cacgtcggaa tatgtcacca catcgctagc ctcaattaac tcacaagctg   7140
gctcattatt cgtcttgcca cgaggcgtgc ctttcaccga tctagacctg accgttggcc   7200
tcgtcttcct tggctgctgg ggtcaaatca ccctcacaac gtttttgaca gccatggttc   7260
tggcgacact tcactatggg tacatgctcc ctggatggca agcagaagca ctcagggctg   7320
cccagagaag gacggcggct ggaataatga agaatgccgt tgttgacgga atggtcgcca   7380
ctgatgtgcc tgaactggaa aggactactc ctctgatgca aaagaaagtc ggacaggtgc   7440
tcctcatagg ggtgagcgtg gcagcgtttc tcgtcaaccc taatgtcacc actgtgagag   7500
aagcaggggt gttggtgacg gcggctacgc tcaccttgtg ggataatgga gccagtgccg   7560
tttggaattc caccacagcc acgggactct gccatgtcat gcgaggtagc tacctggctg   7620
gaggctctat tgcttggact cttatcaaga acgctgacaa gccctccttg aaaaggggaa   7680
ggcctggggg caggacgcta ggggagcagt ggaaggaaaa actaaatgcc atgagcagag   7740
aagagttttt taaataccgg agagaggcca taatcgaggt ggaccgcact gaagcacgca   7800
gggctagacg tgaaaataac atagtgggag gacatccggt ttcgcgaggc tcagcaaaac   7860
tccgttggct cgtggagaaa ggattcgtct cgccaatagg aaaagtcatt gatctagggt   7920
gtgggcgtgg aggatggagc tactacgcag caaccctgaa gaaggtccag gaagtcagag   7980
gatacacgaa aggtggggcg ggacatgaag agccgatgct catgcagagc tacggctgga   8040
acctggtctc cttgaagagt ggagtggatg tgttctacaa accttcagag cctagtgaca   8100
ccctgttctg tgacataggg gaatcctccc caagtccaga agtggaagaa caacgcacac   8160
tacgcgtcct agagatgaca tccgattggt tgcatcgagg acccagagag ttctgcataa   8220
aagttctctg cccttacatg cccaaggtca tagaaaaaat ggaagttctg cagcgccgct   8280
tcggaggtgg gctagtacgt ctccccctgt cccgaaactc caatcacgag atgtattggg   8340
ttagtggagc cgctggcaat gtggtgcacg ctgtgaacat gaccagccag gtactactgg   8400
ggcgaatgga tcgcacagtg tggagagggc caaagtatga ggaagatgtc aacctaggta   8460
gcggaacaag agccgtggga aagggagaag ttcatagcaa tcaggagaaa atcaagaaga   8520
gaatccagaa gcttaaagaa gaattcgcca caacgtggca caaagaccct gaacacccat   8580
accgcacttg gacataccac ggaagctatg aggtgaaggc tactggctca gccagctctc   8640
tcgtcaacgg agtggtgaag ctcatgagta aaccttggga cgccattgcc aacgtcacca   8700
ccatggccat gactgacacc accccttttg gacagcaaag agttttcaag gagaaagttg   8760
acacgaaagc tcctgagcca ccagctggag tcaaggaagt gctcaacgag accaccaact   8820
ggctgtgggc ccacttgtca cgggaaaaaa gacccgctt gtgcaccaag gaagaattta   8880
taaagaaagt caatagcaac gcggctcttg gagcagtgtt tgctgaacag aatcaatgga   8940
gcacggcgcg tgaggctgtg gacgacccgc ggttttggga gatggtcaat gaagagaggg   9000
aaaaccatct gcgaggagag tgtcacacat gtatctacaa catgatggga aaaagagaga   9060
```

-continued agaagcctgg agagtttgga aaagctaaag ggagcagggc catttggttc atgtggcttg 9120
gagcacggta tcttgagttt gaagctttgg ggttcctgaa tgaagaccac tggctgagcc 9180
gagagaattc aggaggtgga gtagaaggct caggcgtcca aaagttggga tacatcctcc 9240
gtgacatagc aggaaagcaa ggagggaaaa tgtacgctga tgacaccgcc gggtgggaca 9300
ctagaattac tagaactgat ttagaaaatg aagctaaggt gctggagctc ctagatggtg 9360
aacaccgcat gctcgcccgg gccataattg aactgactta caggcacaaa gtggtcaagg 9420
tcatgagacc tgcagcagaa ggaaagaccg tgatggacgt gatatcaaga gaagaccaaa 9480
gggggagtgg acaggtggtc acttatgctc tcaacacttt cacgaacatc gctgtccagc 9540
tcgttaggct gatggaggct gagggggtca ttgggccaca acacttggaa cagctgccta 9600
ggaaaaacaa gatagctgtc aggacttggc tctttgagaa tggagaggag agagtgacca 9660
ggatggcgat cagcggagac gactgtgtcg tcaagccgct ggacgacaga ttcgccacgg 9720
ccctccattt cctcaacgca atgtcaaagg ttagaaaaga catccaggaa tggaagcctt 9780
cgcacggctg gcacgattgg cagcaagttc ccttctgctc taaccacttt caggagattg 9840
tgatgaaaga cggaaggagt atagttgtcc cgtgcagagg acaggatgag ctgataggca 9900
gggctcgcat ctctccagga gctggatgga atgtgaagga cacagcttgc ctggcaaaag 9960
catatgcaca gatgtggcta ctcctatact tccatcgtag ggacctgcgt ctcatggcaa 10020
atgcgatttg ctcagcagtg ccagtggatt gggtgcccac aggcaggaca tcctggtcaa 10080
tacactcgaa aggagagtgg atgaccacgg aagacatgct gcaggtctgg aacagagtct 10140
ggattgaaga aaatgaatgg atgatggata agactcccgt cacaagctgg acagacgttc 10200
cgtatgtggg aaagcgtgag gacatctggt gtggcagcct catcggaacg cgttccagag 10260
caacctgggc tgagaacatc tatgcggcga taaaccaggt tagagctgtc attgggaaag 10320
aaaattatgt tgactacatg acctcactca ggagatacga agacgtcttg atccaggaag 10380
acagggtcat ctagtgtgac ttaaggtaga aatgtaaata atgtgaatga gaaaatgcat 10440
gtatatggag tcaggccagc aaaagctgcc accggatact gggtagacgg tgctgcctgc 10500
gtctcagtcc caggaggact gggttaacaa atctgacaac agaaagtgag aaagccctca 10560
gaaccgtctc ggaagtaggt ccctgctcac tggaagttga aagaccaacg tcaggccacg 10620
aatttgtgcc actccgctgg ggagtgcggc ctgcgcagcc ccaggaggac tgggttacca 10680
aagccgttga ggcccccacg gcccaagcct cgtctaggat gcaatagacg aggtgtaagg 10740
actagaggtt agaggagacc ccgtggaaac aacaacatgc ggcccaagcc ccctcgaagc 10800
tgtagaggag gtggaaggac tagaggttag aggagacccc gcatttgcat caaacagcat 10860
attgacacct gggaatagac tgggagatct tctgctctat ctcaacatca gctactaggc 10920
acagagcgcc gaagtatgta gctggtggtg aggaagaaca caggatctcg agcggccgcg 10980
gaccgactag cctcttttcg gccttcgctg agagggattt gttccctagg cctaattatt 11040
atttttaatt gcccaatacg tatacgagtg ccttttctaa ttctcgtata ctatagtgag 11100
tcgtattatc tagccgcccg ggccgtcgac caattctcat gtttgacagc ttatcatcga 11160
atttctgcca ttcatccgct tattatcact tattcaggcg tagcaaccag gcgtttaagg 11220
gcaccaataa ctgccttaaa aaaattacgc cccgccctgc cactcatcgc agtactgttg 11280
taattcatta agcattctgc cgacatggaa gccatcacaa acggcatgat gaacctgaat 11340
cgccagcggc atcagcacct tgtcgccttg cgtataatat ttgcccatgg tgaaaacggg 11400
ggcgaagaag ttgtccatat tggccacgtt taaatcaaaa ctggtgaaac tcacccaggg 11460

-continued attggctgag acgaaaaaca tattctcaat aaacccttta gggaaatagg ccaggttttc 11520
accgtaacac gccacatctt gcgaatatat gtgtagaaac tgccggaaat cgtcgtggta 11580
ttcactccag agcgatgaaa acgtttcagt ttgctcatgg aaaacggtgt aacaagggtg 11640
aacactatcc catatcacca gctcaccgtc tttcattgcc atacggaatt ccggatgagc 11700
attcatcagg cgggcaagaa tgtgaataaa ggccggataa aacttgtgct tatttttctt 11760
tacggtcttt aaaaaggccg taatatccag ctgaacggtc tggttatagg tacattgagc 11820
aactgactga aatgcctcaa aatgttcttt acgatgccat tgggatatat caacggtggt 11880
atatccagtg attttttct ccattttagc ttccttagct cctgaaaatc tcgataactc 11940
aaaaaatacg cccggtagtg atcttatttc attatggtga aagttggaac ctcttacgtg 12000
ccgatcaacg tctcattttc gccaaaagtt ggcccagggc ttcccggtat caacagggac 12060
accaggattt atttattctg cgaagtgatc ttccgtcaca ggtatttatt cgcgataagc 12120
tcatggagcg gcgtaaccgt cgcacaggaa ggacagagaa agcgcggatc tgggaagtga 12180
cggacagaac ggtcaggacc tggattgggg aggcggttgc cgccgctgct gctgacggtg 12240
tgacgttctc tgttccggtc acaccacata cgttccgcca ttcctatgcg atgcacatgc 12300
tgtatgccgg tataccgctg aaagttctgc aaagcctgat gggacataag tccatcagtt 12360
caacggaagt ctacacgaag gtttttgcgc tggatgtggc tgcccggcac cgggtgcagt 12420
ttgcgatgcc ggagtctgat gcggttgcga tgctgaaaca attatcctga gaataaatgc 12480
cttggccttt atatggaaat gtggaactga gtggatatgc tgtttttgtc tgttaaacag 12540
agaagctggc tgttatccac tgagaagcga acgaaacagt cgggaaaatc tcccattatc 12600
gtagagatcc gcattattaa tctcaggagc ctgtgtagcg tttataggaa gtagtgttct 12660
gtcatgatgc ctgcaagcgg taacgaaaac gatttgaata tgccttcagg aacaatagaa 12720
atcttcgtgc ggtgttacgt tgaagtggag cggattatgt cagcaatgga cagaacaacc 12780
taatgaacac agaaccatga tgtggtctgt ccttttacag ccagtagtgc tcgccgcagt 12840
cgagcgacag ggcgaagccc tcgagtgagc gaggaagcac cagggaacag cacttatata 12900
ttctgcttac acacgatgcc tgaaaaaact tcccttgggg ttatccactt atccacgggg 12960
atatttttat aattattttt tttatagttt ttagatcttc ttttttagag cgccttgtag 13020
gcctttatcc atgctggttc tagagaaggt gttgtgacaa attgcccttt cagtgtgaca 13080
aatcaccctc aaatgacagt cctgtctgtg acaaattgcc cttaaccctg tgacaaattg 13140
ccctcagaag aagctgtttt ttcacaaagt tatccctgct tattgactct tttttattta 13200
gtgtgacaat ctaaaaactt gtcacacttc acatggatct gtcatggcgg aaacagcggt 13260
tatcaatcac aagaaacgta aaaatagccc gcgaatcgtc cagtcaaacg acctcactga 13320
ggcggcatat agtctctccc gggatcaaaa acgtatgctg tatctgttcg ttgaccagat 13380
cagaaaatct gatggcaccc tacaggaaca tgacggtatc tgcgagatcc atgttgctaa 13440
atatgctgaa atattcggat tgacctctgc ggaagccagt aaggatatac ggcaggcatt 13500
gaagagtttc gcggggaagg aagtggtttt ttatcgccct gaagaggatg ccggcgatga 13560
aaaaggctat gaatcttttc cttggtttat caaacgtgcg cacagtccat ccagagggct 13620
ttacagtgta catatcaacc catatctcat tcccttcttt atcgggttac agaaccggtt 13680
tacgcagttt cggcttagtg aaacaaaaga aatcaccaat ccgtatgcca tgcgtttata 13740
cgaatccctg tgtcagtatc gtaagccgga tggctcaggc atcgtctctc tgaaaatcga 13800

-continued

```
ctggatcata gagcgttacc agctgcctca aagttaccag cgtatgcctg acttccgccg  13860
ccgcttcctg caggtctgtg ttaatgagat caacagcaga actccaatgc gcctctcata  13920
cattgagaaa aagaaaggcc gccagacgac tcatatcgta ttttccttcc gcgatatcac  13980
ttccatgacg acaggatagt ctgagggtta tctgtcacag atttgagggt ggttcgtcac  14040
atttgttctg acctactgag ggtaatttgt cacagttttg ctgtttcctt cagcctgcat  14100
ggattttctc atacttttg aactgtaatt tttaaggaag ccaaatttga gggcagtttg  14160
tcacagttga tttccttctc tttcccttcg tcatgtgacc tgatatcggg ggttagttcg  14220
tcatcattga tgagggttga ttatcacagt ttattactct gaattggcta tccgcgtgtg  14280
tacctctacc tggagttttt cccacggtgg atatttcttc ttgcgctgag cgtaagagct  14340
atctgacaga acagttcttc tttgcttcct cgccagttcg ctcgctatgc tcggttacac  14400
ggctgcggcg agcgctagtg ataataagtg actgaggtat gtgctcttct tatctccttt  14460
tgtagtgttg ctcttatttt aaacaacttt gcggtttttt gatgactttg cgattttgtt  14520
gttgctttgc agtaaattgc aagatttaat aaaaaaacgc aaagcaatga ttaaaggatg  14580
ttcagaatga aactcatgga aacacttaac cagtgcataa acgctggtca tgaaatgacg  14640
aaggctatcg ccattgcaca gtttaatgat gacagcccgg aagcgaggaa aataacccgg  14700
cgctggagaa taggtgaagc agcggattta gttggggttt cttctcaggc tatcagagat  14760
gccgagaaag cagggcgact accgcacccg gatatggaaa ttcgaggacg ggttgagcaa  14820
cgtgttggtt atacaattga acaaattaat catatgcgtg atgtgtttgg tacgcgattg  14880
cgacgtgctg aagacgtatt tccaccggtg atcggggttg ctgcccataa aggtggcgtt  14940
tacaaaacct cagtttctgt tcatcttgct caggatctgg ctctgaaggg gctacgtgtt  15000
ttgctcgtgg aaggtaacga cccccaggga acagcctcaa tgtatcacgg atgggtacca  15060
gatcttcata ttcatgcaga agacactctc ctgcctttct atcttgggga aaaggacgat  15120
gtcacttatg caataaagcc cacttgctgg ccggggcttg acattattcc ttcctgtctg  15180
gctctgcacc gtattgaaac tgagttaatg ggcaaatttg atgaaggtaa actgcccacc  15240
gatccacacc tgatgctccg actggccatt gaaactgttg ctcatgacta tgatgtcata  15300
gttattgaca gcgcgcctaa cctgggtatc ggcacgatta atgtcgtatg tgctgctgat  15360
gtgctgattg ttcccacgcc tgctgagttg tttgactaca cctccgcact gcagtttttc  15420
gatatgcttc gtgatctgct caagaacgtt gatcttaaag ggttcgagcc tgatgtacgt  15480
attttgctta ccaaatacag caatagtaat ggctctcagt ccccgtggat ggaggagcaa  15540
attcgggatg cctggggaag catggttcta aaaaatgttg tacgtgaaac ggatgaagtt  15600
ggtaaaggtc agatccggat gagaactgtt tttgaacagg ccattgatca acgctcttca  15660
actggtgcct ggagaaatgc tctttctatt tgggaacctg tctgcaatga aattttcgat  15720
cgtctgatta aaccacgctg ggagattaga taatgaagcg tgcgcctgtt attccaaaac  15780
atacgctcaa tactcaaccg gttgaagata cttcgttatc gacaccagct gccccgatgg  15840
tggattcgtt aattgcgcgc gtaggagtaa tggctcgcgg taatgccatt actttgcctg  15900
tatgtggtcg ggatgtgaag tttactcttg aagtgctccg gggtgatagt gttgagaaga  15960
cctctcgggt atggtcaggt aatgaacgtg accaggagct gcttactgag gacgcactgg  16020
atgatctcat cccttctttt ctactgactg gtcaacagac accggcgttc ggtcgaagag  16080
tatctggtgt catagaaatt gccgatggga gtcgccgtcg taaagctgct gcacttaccg  16140
aaagtgatta tcgtgttctg gttggcgagc tggatgatga gcagatggct gcattatcca  16200
```

-continued

```
gattgggtaa cgattatcgc ccaacaagtg cttatgaacg tggtcagcgt tatgcaagcc  16260
gattgcagaa tgaatttgct ggaaatattt ctgcgctggc tgatgcggaa aatatttcac  16320
gtaagattat tacccgctgt atcaacaccg ccaaattgcc taaatcagtt gttgctcttt  16380
tttctcaccc cggtgaacta tctgcccggt caggtgatgc acttcaaaaa gcctttacag  16440
ataaagagga attacttaag cagcaggcat ctaaccttca tgagcagaaa aaagctgggg  16500
tgatatttga agctgaagaa gttatcactc ttttaacttc tgtgcttaaa acgtcatctg  16560
catcaagaac tagtttaagc tcacgacatc agtttgctcc tggagcgaca gtattgtata  16620
agggcgataa aatggtgctt aacctggaca ggtctcgtgt tccaactgag tgtatagaga  16680
aaattgaggc cattcttaag gaacttgaaa agccagcacc ctgatgcgac cacgttttag  16740
tctacgttta tctgtcttta cttaatgtcc tttgttacag gccagaaagc ataactggcc  16800
tgaatattct ctctgggccc actgttccac ttgtatcgtc ggtctgataa tcagactggg  16860
accacggtcc cactcgtatc gtcggtctga ttattagtct gggaccacgg tcccactcgt  16920
atcgtcggtc tgattattag tctgggacca cggtcccact cgtatcgtcg gtctgataat  16980
cagactggga ccacggtccc actcgtatcg tcggtctgat tattagtctg ggaccatggt  17040
cccactcgta tcgtcggtct gattattagt ctgggaccac ggtcccactc gtatcgtcgg  17100
tctgattatt agtctggaac cacggtccca ctcgtatcgt cggtctgatt attagtctgg  17160
gaccacggtc ccactcgtat cgtcggtctg attattagtc tgggaccacg atcccactcg  17220
tgttgtcggt ctgattatcg gtctgggacc acggtcccac ttgtattgtc gatcagacta  17280
tcagcgtgag actacgattc catcaatgcc tgtcaagggc aagtattgac atgtcgtcgt  17340
aacctgtaga acggagtaac ctcggtgtgc ggttgtatgc ctgctgtgga ttgctgctgt  17400
gtcctgctta tccacaacat tttgcgcacg gttatgtgga caaaatacct ggttacccag  17460
gccgtgccgg cacgttaacc gggctgcatc cgatgcaagt gtgtcgctgt cgacgagctc  17520
gcgagctcgg acatgaggtt gccccgtatt cagtgtcgct gatttgtatt gtctgaagtt  17580
gtttttacgt taagttgatg cagatcaatt aatacgatac ctgcgtcata attgattatt  17640
tgacgtggtt tgatggcctc cacgcacgtt gtgatatgta gatgataatc attatcactt  17700
tacgggtcct ttccggtgat ccgacaggtt acggggcggc gacctcgcgg gttttcgcta  17760
tttatgaaaa ttttccggtt taaggcgttt ccgttcttct tcgtcataac ttaatgtttt  17820
tatttaaaat accctctgaa aagaaaggaa acgacaggtg ctgaaagcga gctttttggc  17880
ctctgtcgtt tcctttctct gtttttgtcc gtggaatgaa caatggaagt ccgagctcat  17940
cgctaataac ttcgtatagc atacattata cgaagttata ttcgatgcgg cgctgaggtc  18000
tgcctcgtga agaaggtgtt gctgactcat accaggcctg aatcgcccca tcatccagcc  18060
agaaagtgag ggagccacgg ttgatgagag ctttgttgta ggtggaccag ttggtgattt  18120
tgaacttttg ctttgccacg gaacggtctg cgttgtcggg aagatgcgtg atctgatcct  18180
tcaactcagc aaaagttcga tttattcaac aaagccacgt gtctcaaaat ctctgatgtt  18240
acattgcaca agataaaaat atatcatcat gaacaataaa actgtctgct tacataaaca  18300
gtaatacaag gggtgttatg agccatattc aacgggaaac gtcttgctcg acgatgataa  18360
gctgtcaaac atgagaattg ggtcgtcaat atgctaaaac gcggcatacc ccgcgtattc  18420
ccactagtta attaacctgc agggggctgt tagaggtctt ccctagtcca actatagcgt  18480
atggacatat tgtcgttaga acgcggctac aattaataca taaccttatg tatcatacac  18540
```

-continued

```
atacgattta ggggacacta tag                                        18563

<210> SEQ ID NO 45
<211> LENGTH: 18565
<212> TYPE: DNA
<213> ORGANISM: Artificial Sequence
<220> FEATURE:
<223> OTHER INFORMATION: sequence for pBACsp6/JVFLx/XbaI

<400> SEQUENCE: 45

agaagtttat ctgtgtgaac ttcttggctt agtatcgttg agaagaatcg agagattagt      60

gcagtttaaa cagtttttta gaacggaaga taaccatgac taaaaaacca ggagggcccg     120

gtaaaaaccg ggctatcaat atgctgaaac gcggcctacc ccgcgtattc ccactagtgg     180

gagtgaagag ggtagtaatg agcttgttgg acggcagagg accagtacgt ttcgtgctgg     240

ctcttatcac gttcttcaag tttacagcat tagccccgac caaggcgctt ttaggccgat     300

ggaaagcagt ggaaaagagt gtggcaatga aacatcttac tagtttcaaa cgagaacttg     360

gaacactcat tgacgccgtg aacaagcggg gcagaaagca aaacaaaaga ggaggaaatg     420

aaggctcaat catgtggctc gcgagtttgg cagttgtcat agcttgtgta ggagccatga     480

agttgtcaaa tttccaaggg aagcttttga tgaccattaa caacacggac attgcagacg     540

tcatcgtgat tcctacctca aaaggagaga acagatgctg ggtccgggca atcgatgtcg     600

gctacatgtg tgaggacact atcacgtacg aatgtcctaa gcttaccatg ggcaatgatc     660

cagaggatgt ggattgctgg tgtgacaacc aagaagtcta cgtccaatat ggacggtgca     720

cgcggaccag gcattccaag cgaagcagga ggtccgtgtc ggtccaaaca catggggaga     780

gttcactagt gaataaaaaa gaggcttggc tggattcaac gaaagccaca cgatatctca     840

tgaaaactga gaactggatc ataaggaatc ctggctatgc tttcctggcg gcggtacttg     900

gctggatgct tggcagtaac aatggtcaac gcgtggtgtt taccatcctc ctgctgttgg     960

tcgctccggc ttacagtttt aattgtctgg gaatgggcaa ccgtgacttc atagaaggag    1020

ccagtggagc cacttgggtg gacttagtgc tagaaggaga tagctgcttg acaatcatgg    1080

caaacgacaa accaacattg gacgtccgca tgattaacat cgaagccagc caacttgctg    1140

aggtcagaag ctactgctat catgcttcag tcactgacat ctcgacggtg gctcggtgcc    1200

ccacgactgg agaagcccac aacgagaagc gagctgatag tagctatgtg tgcaaacaag    1260

gtttcactga tcgtgggtgg ggcaacggat gtggactttt cgggaaggga agcattgaca    1320

catgtgcaaa attctcctgc accagtaagg cgattgggag aacaatccag ccagaaaaca    1380

tcaaatacga agttggcatt tttgtgcatg gaaccaccac ctcggaaaac catgggaatt    1440

attcagcgca agtagggggcg tcccaggcgg caaagtttac agtaacaccc aatgctcctt    1500

cgataaccct caaacttggt gactacggag aagtcacact ggactgtgaa ccaaggagtg    1560

gactgaacac tgaagcgttt tacgtcatga ccgtggggtc aaagtcattt ctggtccata    1620

gggaatggtt tcatgacctc gctctcccct ggacgtcccc ttcgagcaca gcgtggagaa    1680

acagagaact cctcatggaa tttgaagagg cgcacgccac aaaacagtcc gttgttgctc    1740

ttgggtcaca ggaaggaggc ctccatcagg cgctggcagg agccatcgtg gtggagtact    1800

caagctcagt gaagttaaca tcaggccacc tgaaatgtag gctgaaaatg gacaaactgg    1860

ctctgaaagg cacaacctat ggcatgtgta cagaaaaatt ctcgttcgcg aaaaatccgg    1920

cggacactgg ccacggaaca gttgtcattg aactctccta ttctgggagt gatggcccct    1980

gcaaaattcc gattgtctcc gttgcgagcc tcaatgacat gacccccgtt gggcggctgg    2040
```

-continued tgacagtgaa ccccttcgtc gcgacttcca gtgccaactc aaaggtgctg gtcgagatgg 2100
aacccccctt cggagactcc tacatcgtag ttggaagggg agacaagcag atcaaccacc 2160
attggcataa agctggaagc acgctgggca aggctttttc aacaactttg aagggagctc 2220
aaagactggc agcgttgggc gacacagcct gggactttgg ctctattgga ggggtcttca 2280
actccatagg aaaggccgtt caccaagtgt ttggtggcgc tttcagaaca ctctttgggg 2340
gaatgtcttg gatcacacaa gggttaatgg gtgccctact actctggatg ggcatcaacg 2400
cacgagatcg atcaattgct ttggccttct tggccacagg aggtgtgctc gtgttcttag 2460
cgaccaatgt gcatgctgac actggatgtg ccattgacat cgcaagaaaa gagatgagat 2520
gcggaagtgg catcttcgtg cacaacgacg tggaagcctg ggtggatagg tataaatatt 2580
tgccagaaac gcccagatcc ctagcgaaga tcgtccacaa agcgcacaag gaaggcgtgt 2640
gcggagtcag atctgtcact agactggagc accaaatgtg ggaagccgtg cgggacgaat 2700
tgaacgtcct gctcaaagag aatgcagtgg acctcagtgt ggttgtgaac aagcccgtgg 2760
ggagatatcg ctcagcccca aaacgcctgt ccatgacgca agagaagttt gaaatgggct 2820
ggaaagcatg ggaaaaaagc attctctttg ccccggaatt ggctaactcc acatttgttg 2880
tagatggacc tgagacaaag gaatgtcctg atgagcacag agcctggaac agcatgcaaa 2940
tcgaagactt cggctttggt atcacatcaa cccgtgtgtg gctgaagatt agagaggaaa 3000
gcactgacga gtgtgatgga gcgatcatag gcacagctgt caaaggacat gtggcagttc 3060
atagtgactt gtcgtactgg attgagagtc gctacaacga cacatggaaa cttgagaggg 3120
cagtctttgg agaggtcaaa tcttgcactt ggccagagac acacactctt tggggagatg 3180
gtgttgagga aagtgaactc atcatcccgc ataccatagc cggaccaaaa agcaagcaca 3240
atcggaggga agggtacaaa acacaaaacc agggaccttg ggacgaaaac ggcatagtct 3300
tggactttga ttattgccca gggacaaaag tcaccatcac agaggattgt ggcaagagag 3360
gcccttcggt cagaaccact actgacagtg gaaagttgat tactgactgg tgctgtcgca 3420
gttgctccct tccgccccta cgattccgga cagaaaatgg ctgctggtac ggaatggaaa 3480
tcagacctgt taggcatgat gaaacaacac tcgtcagatc acaggttgat gctttcaatg 3540
gtgaaatggt tgaccctttt cagctgggcc ttctggtgat gtttctggcc acccaggagg 3600
tccttcgcaa gaggtggacg gccagattga ccattcctgc ggttttgggg gccctgcttg 3660
tgctgatgct tgggggcatc acttacactg atttggcgag gtatgtggtg ctagtcgctg 3720
ctgctttcgc agaggccaat aatggaggag acgtcctgca ccttgctttg attgccgttt 3780
ttaagatcca accagctttt ctagtgatga acatgcttag cacgagatgg acgaaccaag 3840
aaaacgtggt cctggtccta ggggctgcct tctttcaatt ggcctcagta gatctgcaaa 3900
tcggagtcca cggaatcctg aatgccgccg ctatagcatg gatgattgtt cgagcgatca 3960
ccttccccac aacctcctcc gtcaccatgc cagtcttagc gcttctaact ccgggaatga 4020
gggctctata cctagacact tacagaatca tccttctcgt catagggatt tgctccctgc 4080
tgcaagagag gaaaaagacc atggcaaaaa agaaaggagc tgtactcttg ggcttagcgc 4140
tcacatccac tggatggttc tcgcccacca ccatagctgc tggactaatg gtctgcaacc 4200
caaacaagaa gagagggtgg ccagctactg agtttctgtc ggcagtcgga ttgatgtttg 4260
ccatcgtagg tggtttggcc gagttggata ttgaatccat gtcaataccc ttcatgctgg 4320
caggtcttat ggcagtgtcc tacgtagtgt caggaaaagc aacagatatg tggctcgaac 4380

-continued

```
gggccgccga catcagctgg gagatggatg ctgcaatcac aggaagcagt cggaggctgg   4440

atgtgaaact ggatgatgac ggagattttc acttgattga tgatcccggc gttccatgga   4500

aagtttgggt cttgcgcatg tcttgcattg gcttagccgc cctcacgcct tgggccattg   4560

ttcccgccgc tttcggttac tggctcactt taaaaacaac aaaaagaggg ggcgtgtttt   4620

gggacacgcc atccccgaaa ccttgcttaa aaggagacac cactacagga gtctaccgaa   4680

tcatggctag agggattctt ggcacctacc aggctggcgt cggagtcatg tacgagaatg   4740

ttttccacac actatggcac acaactagag ggcagccat tatgagtgga gaaggaaaat   4800

tgacgccata ctggggtagc gtgaaagaag accgcatagc ttacggaggc ccatggagat   4860

ttgatcgaaa atggaatgga acagatgacg tgcaagtgat cgtggtagaa ccggggaagg   4920

ctgcggtaaa catccagaca aaaccaggag tgtttcggac cccccttcggg gaggttgggg   4980

ctgttagcct ggattacccg cgaggaacat ccggctcacc cattctggat tccaatggag   5040

acatcatagg cctatacggc aatggagttg agcttggcga tggctcatac gtcagcgcca   5100

tcgtgcaggg tgaccgtcag gaggaaccag tcccagaagc ttacactcca aacatgttaa   5160

gaaagagaca gatgactgtg ttagatttgc accctggttc agggaaaacc aggaaaattc   5220

tgccacaaat aattaaggat gcaatccagc agcgcctaag aacagctgtg ttggcaccga   5280

cgcgggtggt agcagcagaa atggcagaag ctttgagagg gctcccagta cgataccaaa   5340

cttcagcagt gcagagagag caccaaggga atgaaatagt ggatgtgatg tgccacgcca   5400

ctctgaccca cagattgatg tcaccgaaca gagtgcccaa ctacaatctg tttgtcatgg   5460

atgaagctca tttcaccgac ccagccagca tagccgcacg aggatacatc gctaccaagg   5520

tggaattagg agaggcagca gccatcttta tgacagcgac cccgcctgga accacggatc   5580

cttttcccga ctcaaatgcc ccaatccatg atttacaaga tgagatacca gacagggcat   5640

ggagcagtgg atacgaatgg atcacagaat atgcgggtaa aaccgtgtgg tttgtggcga   5700

gcgtaaaaat ggggaatgag attgcaatgt gcctccaaag agcgggaaaa aaggtcatcc   5760

aactcaaccg caagtcctat gacacagaat acccaaaatg taagaatgga gactgggatt   5820

ttgtcattac caccgacatc tctgaaatgg gggctaactt cggtgcgagc agggtcatcg   5880

actgcagaaa gagcgtgaaa cccaccatct tagaagaggg agaaggcaga gtcatcctcg   5940

gaaacccatc tcccataacc agtgctagcg cagctcaacg gaggggcaga gtaggcagaa   6000

accccaacca agttggagat gaataccatt atggaggggc taccagtgaa gatgacagta   6060

acctagccca ttggacagag gcaaagatca tgttagacaa catacacatg cccaatgggc   6120

tggtggccca gctctatgga ccagagaggg aaaaggcttt cacaatggat ggcgaatacc   6180

gtctcagggg tgaagaaaag aaaaacttct tagagctgct taggacggct gaccttccgg   6240

tgtggctggc ctataaggtg gcgtccaatg gcattcagta caccgacaga aagtggtgtt   6300

ttgatgggcc gcgcacgaat gccatactgg aggacaacac cgaggtagag atagtcaccc   6360

ggatgggtga gagaaagatc ctcaagccga gatggcttga tgcaagagta tacgcagatc   6420

accaagccct caagtggttc aaagactttg cagcaggaaa gagatcggcc gttagcttca   6480

tagaggtgct cggtcgcatg cctgagcatt tcatgggaaa gacgcgggaa gctttagaca   6540

ccatgtactt ggtcgcaacg gctgagaaag gtgggaaggc acaccgaatg gctctcgaag   6600

agttgccgga tgcactggaa accatcacac ttattgttgc catcactgta atgacaggag   6660

gattcttcct actaatgatg cagcgaaagg gtatagggaa gatgggtctt ggagctctag   6720

tgctcacgct agctaccttc ttcctgtggg cggcagaggt tcctggaacc aaaatagcag   6780
```

-continued ggaccctgct gatcgccctg ctgctgatgg tggttctcat cccagaaccg gaaaaacaga 6840
ggtcacagac agacaaccaa ctagcggtgt ttctcatctg cgtcttgacc gtggttggag 6900
tggtggcagc aaacgagtac gggatgctag aaaaaaccaa agcagatctc aagagcatgt 6960
ttggcggaaa gacacaggca tcaggactga ctggattgcc aagcatggca ctggacctgc 7020
gtccagccac agcctgggca ctgtatgggg ggagcacagt tgtgctaacc cctcttctga 7080
agcacctgat cacgtcggaa tatgtcacca catcgctagc ctcaattaac tcacaagctg 7140
gctcattatt cgtcttgcca cgaggcgtgc ctttcaccga tctagacctg accgttggcc 7200
tcgtcttcct tggctgctgg ggtcaaatca ccctcacaac gtttttgaca gccatggttc 7260
tggcgacact tcactatggg tacatgctcc ctggatggca agcagaagca ctcagggctg 7320
cccagagaag gacggcggct ggaataatga agaatgccgt tgttgacgga atggtcgcca 7380
ctgatgtgcc tgaactggaa aggactactc ctctgatgca aaagaaagtc ggacaggtgc 7440
tcctcatagg ggtgagcgtg gcagcgtttc tcgtcaaccc taatgtcacc actgtgagag 7500
aagcaggggt gttggtgacg gcggctacgc tcaccttgtg ggataatgga gccagtgccg 7560
tttggaattc caccacagcc acgggactct gccatgtcat gcgaggtagc tacctggctg 7620
gaggctctat tgcttggact cttatcaaga acgctgacaa gccctccttg aaaaggggaa 7680
ggcctggggg caggacgcta ggggagcagt ggaaggaaaa actaaatgcc atgagcagag 7740
aagagttttt taaataccgg agagaggcca taatcgaggt ggaccgcact gaagcacgca 7800
gggctagacg tgaaaataac atagtgggag gacatccggt ttcgcgaggc tcagcaaaac 7860
tccgttggct cgtggagaaa ggattcgtct cgccaatagg aaaagtcatt gatctagggt 7920
gtgggcgtgg aggatggagc tactacgcag caaccctgaa gaaggtccag gaagtcagag 7980
gatacacgaa aggtggggcg ggacatgaag agccgatgct catgcagagc tacggctgga 8040
acctggtctc cttgaagagt ggagtggatg tgttctacaa accttcagag cctagtgaca 8100
ccctgttctg tgacataggg gaatcctccc caagtccaga agtggaagaa caacgcacac 8160
tacgcgtcct agagatgaca tccgattggt tgcatcgagg acccagagag ttctgcataa 8220
aagttctctg cccttacatg cccaaggtca tagaaaaaat ggaagttctg cagcgccgct 8280
tcggaggtgg gctagtacgt ctcccccctgt cccgaaactc caatcacgag atgtattggg 8340
ttagtggagc cgctggcaat gtggtgcacg ctgtgaacat gaccagccag gtactactgg 8400
ggcgaatgga tcgcacagtg tggagagggc caaagtatga ggaagatgtc aacctaggta 8460
gcggaacaag agccgtggga aagggagaag ttcatagcaa tcaggagaaa atcaagaaga 8520
gaatccagaa gcttaaagaa gaattcgcca caacgtggca caaagaccct gaacacccat 8580
accgcacttg gacataccac ggaagctatg aggtgaaggc tactggctca gccagctctc 8640
tcgtcaacgg agtggtgaag ctcatgagta aaccttggga cgccattgcc aacgtcacca 8700
ccatggccat gactgacacc accccttttg gacagcaaag agttttcaag gagaaagttg 8760
acacgaaagc tcctgagcca ccagctggag tcaaggaagt gctcaacgag accaccaact 8820
ggctgtgggc ccacttgtca cgggaaaaaa gacccccgctt gtgcaccaag gaagaattta 8880
taaagaaagt caatagcaac gcggctcttg gagcagtgtt tgctgaacag aatcaatgga 8940
gcacggcgcg tgaggctgtg gacgacccgc ggttttggga gatggtcaat gaagagaggg 9000
aaaaccatct gcgaggagag tgtcacacat gtatctacaa catgatggga aaaagagaga 9060
agaagcctgg agagtttgga aaagctaaag ggagcagggc catttggttc atgtggcttg 9120

-continued

```
gagcacggta tcttgagttt gaagctttgg ggttcctgaa tgaagaccac tggctgagcc   9180
gagagaattc aggaggtgga gtagaaggct caggcgtcca aaagttggga tacatcctcc   9240
gtgacatagc aggaaagcaa ggagggaaaa tgtacgctga tgacaccgcc gggtgggaca   9300
ctagaattac tagaactgat ttagaaaatg aagctaaggt gctggagctc ctagatggtg   9360
aacaccgcat gctcgcccgg gccataattg aactgactta caggcacaaa gtggtcaagg   9420
tcatgagacc tgcagcagaa ggaaagaccg tgatggacgt gatatcaaga gaagaccaaa   9480
gggggagtgg acaggtggtc acttatgctc tcaacacttt cacgaacatc gctgtccagc   9540
tcgttaggct gatggaggct gagggggtca ttgggccaca acacttggaa cagctgccta   9600
ggaaaaacaa gatagctgtc aggacttggc tctttgagaa tggagaggag agagtgacca   9660
ggatggcgat cagcggagac gactgtgtcg tcaagccgct ggacgacaga ttcgccacgg   9720
ccctccattt cctcaacgca atgtcaaagg ttagaaaaga catccaggaa tggaagcctt   9780
cgcacggctg gcacgattgg cagcaagttc ccttctgctc taaccacttt caggagattg   9840
tgatgaaaga cggaaggagt atagttgtcc cgtgcagagg acaggatgag ctgataggca   9900
gggctcgcat ctctccagga gctggatgga atgtgaagga cacagcttgc ctggcaaaag   9960
catatgcaca gatgtggcta ctcctatact tccatcgtag ggacctgcgt ctcatggcaa  10020
atgcgatttg ctcagcagtg ccagtggatt gggtgcccac aggcaggaca tcctggtcaa  10080
tacactcgaa aggagagtgg atgaccacgg aagacatgct gcaggtctgg aacagagtct  10140
ggattgaaga aaatgaatgg atgatggata agactcccgt cacaagctgg acagacgttc  10200
cgtatgtggg aaagcgtgag gacatctggt gtggcagcct catcggaacg cgttccagag  10260
caacctgggc tgagaacatc tatgcggcga taaaccaggt tagagctgtc attgggaaag  10320
aaaattatgt tgactacatg acctcactca ggagatacga agacgtcttg atccaggaag  10380
acagggtcat ctagtgtgac ttaaggtaga aatgtaaata atgtgaatga gaaaatgcat  10440
gtatatggag tcaggccagc aaaagctgcc accggatact gggtagacgg tgctgcctgc  10500
gtctcagtcc caggaggact gggttaacaa atctgacaac agaaagtgag aaagccctca  10560
gaaccgtctc ggaagtaggt ccctgctcac tggaagttga aagaccaacg tcaggccacg  10620
aatttgtgcc actccgctgg ggagtgcggc ctgcgcagcc ccaggaggac tgggttacca  10680
aagccgttga ggcccccacg gcccaagcct cgtctaggat gcaatagacg aggtgtaagg  10740
actagaggtt agaggagacc ccgtggaaac aacaacatgc ggcccaagcc ccctcgaagc  10800
tgtagaggag gtggaaggac tagaggttag aggagacccc gcatttgcat caaacagcat  10860
attgacacct gggaatagac tgggagatct tctgctctat ctcaacatca gctactaggc  10920
acagagcgcc gaagtatgta gctggtggtg aggaagaaca caggatctct agagcggccg  10980
cggaccgact agcctctttt cggccttcgc tgagagggat ttgttcccta ggcctaatta  11040
ttatttttaa ttgcccaata cgtatacgag tgccttttct aattctcgta tactatagtg  11100
agtcgtatta tctagccgcc cgggccgtcg accaattctc atgtttgaca gcttatcatc  11160
gaatttctgc cattcatccg cttattatca cttattcagg cgtagcaacc aggcgtttaa  11220
gggcaccaat aactgcctta aaaaaattac gccccgccct gccactcatc gcagtactgt  11280
tgtaattcat taagcattct gccgacatgg aagccatcac aaacggcatg atgaacctga  11340
atcgccagcg gcatcagcac cttgtcgcct tgcgtataat atttgcccat ggtgaaaacg  11400
ggggcgaaga agttgtccat attggccacg tttaaatcaa aactggtgaa actcacccag  11460
ggattggctg agacgaaaaa catattctca ataaaccctt tagggaaata ggccaggttt  11520
```

-continued

```
tcaccgtaac acgccacatc ttgcgaatat atgtgtagaa actgccggaa atcgtcgtgg  11580
tattcactcc agagcgatga aaacgtttca gtttgctcat ggaaaacggt gtaacaaggg  11640
tgaacactat cccatatcac cagctcaccg tctttcattg ccatacggaa ttccggatga  11700
gcattcatca ggcgggcaag aatgtgaata aaggccggat aaaacttgtg cttatttttc  11760
tttacggtct ttaaaaaggc cgtaatatcc agctgaacgg tctggttata ggtacattga  11820
gcaactgact gaaatgcctc aaaatgttct ttacgatgcc attgggatat atcaacggtg  11880
gtatatccag tgattttttt ctccatttta gcttccttag ctcctgaaaa tctcgataac  11940
tcaaaaaata cgcccggtag tgatcttatt tcattatggt gaaagttgga acctcttacg  12000
tgccgatcaa cgtctcattt tcgccaaaag ttggcccagg gcttcccggt atcaacaggg  12060
acaccaggat ttatttattc tgcgaagtga tcttccgtca caggtattta ttcgcgataa  12120
gctcatggag cggcgtaacc gtcgcacagg aaggacagag aaagcgcgga tctgggaagt  12180
gacggacaga acggtcagga cctggattgg ggaggcggtt gccgccgctg ctgctgacgg  12240
tgtgacgttc tctgttccgg tcacaccaca tacgttccgc cattcctatg cgatgcacat  12300
gctgtatgcc ggtataccgc tgaaagttct gcaaagcctg atgggacata agtccatcag  12360
ttcaacggaa gtctacacga aggtttttgc gctggatgtg gctgcccggc accgggtgca  12420
gtttgcgatg ccggagtctg atgcggttgc gatgctgaaa caattatcct gagaataaat  12480
gccttggcct ttatatggaa atgtggaact gagtggatat gctgtttttg tctgttaaac  12540
agagaagctg gctgttatcc actgagaagc gaacgaaaca gtcgggaaaa tctcccatta  12600
tcgtagagat ccgcattatt aatctcagga gcctgtgtag cgtttatagg aagtagtgtt  12660
ctgtcatgat gcctgcaagc ggtaacgaaa acgatttgaa tatgccttca ggaacaatag  12720
aaatcttcgt gcggtgttac gttgaagtgg agcggattat gtcagcaatg gacagaacaa  12780
cctaatgaac acagaaccat gatgtggtct gtccttttac agccagtagt gctcgccgca  12840
gtcgagcgac agggcgaagc cctcgagtga gcgaggaagc accagggaac agcacttata  12900
tattctgctt acacacgatg cctgaaaaaa cttcccttgg ggttatccac ttatccacgg  12960
ggatattttt ataattattt tttttatagt ttttagatct tctttttttag agcgccttgt  13020
aggcctttat ccatgctggt tctagagaag gtgttgtgac aaattgccct ttcagtgtga  13080
caaatcaccc tcaaatgaca gtcctgtctg tgacaaattg cccttaaccc tgtgacaaat  13140
tgccctcaga agaagctgtt ttttcacaaa gttatccctg cttattgact cttttttatt  13200
tagtgtgaca atctaaaaac ttgtcacact tcacatggat ctgtcatggc ggaaacagcg  13260
gttatcaatc acaagaaacg taaaaatagc ccgcgaatcg tccagtcaaa cgacctcact  13320
gaggcggcat atagtctctc ccgggatcaa aaacgtatgc tgtatctgtt cgttgaccag  13380
atcagaaaat ctgatggcac cctacaggaa catgacggta tctgcgagat ccatgttgct  13440
aaatatgctg aaatattcgg attgacctct gcggaagcca gtaaggatat acggcaggca  13500
ttgaagagtt tcgcggggaa ggaagtggtt ttttatcgcc ctgaagagga tgccggcgat  13560
gaaaaaggct atgaatcttt tccttggttt atcaaacgtg cgcacagtcc atccagaggg  13620
ctttacagtg tacatatcaa cccatatctc attcccttct ttatcgggtt acagaaccgg  13680
tttacgcagt ttcggcttag tgaaacaaaa gaaatcacca atccgtatgc catgcgttta  13740
tacgaatccc tgtgtcagta tcgtaagccg gatggctcag gcatcgtctc tctgaaaatc  13800
gactggatca tagagcgtta ccagctgcct caaagttacc agcgtatgcc tgacttccgc  13860
```

-continued cgccgcttcc tgcaggtctg tgttaatgag atcaacagca gaactccaat gcgcctctca 13920
tacattgaga aaaagaaagg ccgccagacg actcatatcg tattttcctt ccgcgatatc 13980
acttccatga cgacaggata gtctgagggt tatctgtcac agatttgagg gtggttcgtc 14040
acatttgttc tgacctactg agggtaattt gtcacagttt tgctgtttcc ttcagcctgc 14100
atggattttc tcatactttt tgaactgtaa tttttaagga agccaaattt gagggcagtt 14160
tgtcacagtt gatttccttc tctttccctt cgtcatgtga cctgatatcg gggttagtt 14220
cgtcatcatt gatgagggtt gattatcaca gtttattact ctgaattggc tatccgcgtg 14280
tgtacctcta cctggagttt ttcccacggt ggatatttct tcttgcgctg agcgtaagag 14340
ctatctgaca gaacagttct tctttgcttc ctcgccagtt cgctcgctat gctcggttac 14400
acggctgcgg cgagcgctag tgataataag tgactgaggt atgtgctctt cttatctcct 14460
tttgtagtgt tgctcttatt ttaaacaact ttgcggtttt ttgatgactt tgcgattttg 14520
ttgttgcttt gcagtaaatt gcaagattta ataaaaaaac gcaaagcaat gattaaagga 14580
tgttcagaat gaaactcatg gaaacactta accagtgcat aaacgctggt catgaaatga 14640
cgaaggctat cgccattgca cagtttaatg atgacagccc ggaagcgagg aaaataaccc 14700
ggcgctggag aataggtgaa gcagcggatt tagttggggt ttcttctcag gctatcagag 14760
atgccgagaa agcagggcga ctaccgcacc cggatatgga aattcgagga cgggttgagc 14820
aacgtgttgg ttatacaatt gaacaaatta atcatatgcg tgatgtgttt ggtacgcgat 14880
tgcgacgtgc tgaagacgta tttccaccgg tgatcggggt tgctgcccat aaaggtggcg 14940
tttacaaaac ctcagtttct gttcatcttg ctcaggatct ggctctgaag ggctacgtg 15000
ttttgctcgt ggaaggtaac gacccccagg gaacagcctc aatgtatcac ggatgggtac 15060
cagatcttca tattcatgca gaagacactc tcctgccttt ctatcttggg gaaaaggacg 15120
atgtcactta tgcaataaag cccacttgct ggccggggct tgacattatt ccttcctgtc 15180
tggctctgca ccgtattgaa actgagttaa tgggcaaatt tgatgaaggt aaactgccca 15240
ccgatccaca cctgatgctc cgactggcca ttgaaactgt tgctcatgac tatgatgtca 15300
tagttattga cagcgcgcct aacctgggta tcggcacgat taatgtcgta tgtgctgctg 15360
atgtgctgat tgttcccacg cctgctgagt tgtttgacta cacctccgca ctgcagtttt 15420
tcgatatgct tcgtgatctg ctcaagaacg ttgatcttaa agggttcgag cctgatgtac 15480
gtattttgct taccaaatac agcaatagta atggctctca gtccccgtgg atggaggagc 15540
aaattcggga tgcctgggga agcatggttc taaaaaatgt tgtacgtgaa acggatgaag 15600
ttggtaaagg tcagatccgg atgagaactg tttttgaaca ggccattgat caacgctctt 15660
caactggtgc ctggagaaat gctctttcta tttgggaacc tgtctgcaat gaaattttcg 15720
atcgtctgat taaaccacgc tgggagatta gataatgaag cgtgcgcctg ttattccaaa 15780
acatacgctc aatactcaac cggttgaaga tacttcgtta tcgacaccag ctgccccgat 15840
ggtggattcg ttaattgcgc gcgtaggagt aatggctcgc ggtaatgcca ttactttgcc 15900
tgtatgtggt cgggatgtga agtttactct tgaagtgctc cggggtgata gtgttgagaa 15960
gacctctcgg gtatggtcag gtaatgaacg tgaccaggag ctgcttactg aggacgcact 16020
ggatgatctc atcccttctt ttctactgac tggtcaacag acaccggcgt tcggtcgaag 16080
agtatctggt gtcatagaaa ttgccgatgg gagtcgccgt cgtaaagctg ctgcacttac 16140
cgaaagtgat tatcgtgttc tggttggcga gctggatgat gagcagatgg ctgcattatc 16200
cagattgggt aacgattatc gcccaacaag tgcttatgaa cgtggtcagc gttatgcaag 16260

-continued

```
ccgattgcag aatgaatttg ctggaaatat ttctgcgctg gctgatgcgg aaaatatttc  16320
acgtaagatt attacccgct gtatcaacac cgccaaattg cctaaatcag ttgttgctct  16380
tttttctcac cccggtgaac tatctgcccg gtcaggtgat gcacttcaaa aagcctttac  16440
agataaagag gaattactta agcagcaggc atctaacctt catgagcaga aaaaagctgg  16500
ggtgatattt gaagctgaag aagttatcac tcttttaact tctgtgctta aaacgtcatc  16560
tgcatcaaga actagtttaa gctcacgaca tcagtttgct cctggagcga cagtattgta  16620
taagggcgat aaaatggtgc ttaacctgga caggtctcgt gttccaactg agtgtataga  16680
gaaaattgag gccattctta aggaacttga aaagccagca ccctgatgcg accacgtttt  16740
agtctacgtt tatctgtctt tacttaatgt cctttgttac aggccagaaa gcataactgg  16800
cctgaatatt ctctctgggc ccactgttcc acttgtatcg tcggtctgat aatcagactg  16860
ggaccacggt cccactcgta tcgtcggtct gattattagt ctgggaccac ggtcccactc  16920
gtatcgtcgg tctgattatt agtctgggac cacggtccca ctcgtatcgt cggtctgata  16980
atcagactgg gaccacggtc ccactcgtat cgtcggtctg attattagtc tgggaccatg  17040
gtcccactcg tatcgtcggt ctgattatta gtctgggacc acggtcccac tcgtatcgtc  17100
ggtctgatta ttagtctgga accacggtcc cactcgtatc gtcggtctga ttattagtct  17160
gggaccacgg tcccactcgt atcgtcggtc tgattattag tctgggacca cgatcccact  17220
cgtgttgtcg gtctgattat cggtctggga ccacggtccc acttgtattg tcgatcagac  17280
tatcagcgtg agactacgat tccatcaatg cctgtcaagg gcaagtattg acatgtcgtc  17340
gtaacctgta gaacggagta acctcggtgt gcggttgtat gcctgctgtg gattgctgct  17400
gtgtcctgct tatccacaac attttgcgca cggttatgtg gacaaaatac ctggttaccc  17460
aggccgtgcc ggcacgttaa ccgggctgca tccgatgcaa gtgtgtcgct gtcgacgagc  17520
tcgcgagctc ggacatgagg ttgccccgta ttcagtgtcg ctgatttgta ttgtctgaag  17580
ttgtttttac gttaagttga tgcagatcaa ttaatacgat acctgcgtca taattgatta  17640
tttgacgtgg tttgatggcc tccacgcacg ttgtgatatg tagatgataa tcattatcac  17700
tttacgggtc ctttccggtg atccgacagg ttacggggcg gcgacctcgc gggttttcgc  17760
tatttatgaa aattttccgg tttaaggcgt ttccgttctt cttcgtcata acttaatgtt  17820
tttatttaaa ataccctctg aaaagaaagg aaacgacagg tgctgaaagc gagctttttg  17880
gcctctgtcg tttcctttct ctgtttttgt ccgtggaatg aacaatggaa gtccgagctc  17940
atcgctaata acttcgtata gcatacatta tacgaagtta tattcgatgc ggcgctgagg  18000
tctgcctcgt gaagaaggtg ttgctgactc ataccaggcc tgaatcgccc catcatccag  18060
ccagaaagtg agggagccac ggttgatgag agctttgttg taggtggacc agttggtgat  18120
tttgaacttt tgctttgcca cggaacggtc tgcgttgtcg ggaagatgcg tgatctgatc  18180
cttcaactca gcaaaagttc gatttattca acaaagccac gtgtctcaaa atctctgatg  18240
ttacattgca caagataaaa atatatcatc atgaacaata aaactgtctg cttacataaa  18300
cagtaataca aggggtgtta tgagccatat tcaacgggaa acgtcttgct cgacgatgat  18360
aagctgtcaa acatgagaat tgggtcgtca atatgctaaa acgcggcata ccccgcgtat  18420
tcccactagt taattaacct gcagggggct gttagaggtc ttccctagtc caactatagc  18480
gtatggacat attgtcgtta gaacgcggct acaattaata cataacctta tgtatcatac  18540
acatacgatt taggggacac tatag                                        18565
```

-continued

<210> SEQ ID NO 46
<211> LENGTH: 19038
<212> TYPE: DNA
<213> ORGANISM: Artificial Sequence
<220> FEATURE:
<223> OTHER INFORMATION: sequence for pBACt7/JVFL/XhoI

<400> SEQUENCE: 46
agaagtttat ctgtgtgaac ttcttggctt agtatcgttg agaagaatcg agagattagt 60
gcagtttaaa cagtttttta gaacggaaga taaccatgac taaaaaacca ggagggcccg 120
gtaaaaaccg ggctatcaat atgctgaaac gcggcctacc ccgcgtattc ccactagtgg 180
gagtgaagag ggtagtaatg agcttgttgg acggcagagg accagtacgt ttcgtgctgg 240
ctcttatcac gttcttcaag tttacagcat tagccccgac caaggcgctt ttaggccgat 300
ggaaagcagt ggaaaagagt gtggcaatga aacatcttac tagtttcaaa cgagaacttg 360
gaacactcat tgacgccgtg aacaagcggg gcagaaagca aaacaaaaga ggaggaaatg 420
aaggctcaat catgtggctc gcgagtttgg cagttgtcat agcttgtgta ggagccatga 480
agttgtcaaa tttccaaggg aagcttttga tgaccattaa caacacggac attgcagacg 540
tcatcgtgat tcctacctca aaaggagaga acagatgctg ggtccgggca atcgatgtcg 600
gctacatgtg tgaggacact atcacgtacg aatgtcctaa gcttaccatg ggcaatgatc 660
cagaggatgt ggattgctgg tgtgacaacc aagaagtcta cgtccaatat ggacggtgca 720
cgcggaccag gcattccaag cgaagcagga ggtccgtgtc ggtccaaaca catggggaga 780
gttcactagt gaataaaaaa gaggcttggc tggattcaac gaaagccaca cgatatctca 840
tgaaaactga gaactggatc ataaggaatc ctggctatgc tttcctggcg gcggtacttg 900
gctggatgct tggcagtaac aatggtcaac gcgtggtgtt taccatcctc ctgctgttgg 960
tcgctccggc ttacagtttt aattgtctgg gaatgggcaa ccgtgacttc atagaaggag 1020
ccagtggagc cacttgggtg gacttagtgc tagaaggaga tagctgcttg acaatcatgg 1080
caaacgacaa accaacattg gacgtccgca tgattaacat cgaagccagc caacttgctg 1140
aggtcagaag ctactgctat catgcttcag tcactgacat ctcgacggtg gctcggtgcc 1200
ccacgactgg agaagcccac aacgagaagc gagctgatag tagctatgtg tgcaaacaag 1260
gtttcactga tcgtgggtgg ggcaacggat gtggactttt cgggaaggga agcattgaca 1320
catgtgcaaa attctcctgc accagtaagg cgattgggag aacaatccag ccagaaaaca 1380
tcaaatacga agttggcatt tttgtgcatg gaaccaccac ctcggaaaac catgggaatt 1440
attcagcgca agtaggggcg tcccaggcgg caaagtttac agtaacaccc aatgctcctt 1500
cgataaccct caaacttggt gactacggag aagtcacact ggactgtgaa ccaaggagtg 1560
gactgaacac tgaagcgttt tacgtcatga ccgtggggtc aaagtcattt ctggtccata 1620
gggaatggtt tcatgacctc gctctcccct ggacgtcccc ttcgagcaca gcgtggagaa 1680
acagagaact cctcatggaa tttgaagagg cgcacgccac aaaacagtcc gttgttgctc 1740
ttgggtcaca ggaaggaggc ctccatcagg cgctggcagg agccatcgtg gtggagtact 1800
caagctcagt gaagttaaca tcaggccacc tgaaatgtag gctgaaaatg gacaaactgg 1860
ctctgaaagg cacaacctat ggcatgtgta cagaaaaatt ctcgttcgcg aaaaatccgg 1920
cggacactgg ccacggaaca gttgtcattg aactctccta ttctgggagt gatggcccct 1980
gcaaaattcc gattgtctcc gttgcgagcc tcaatgacat gacccccgtt gggcggctgg 2040
tgacagtgaa ccccttcgtc gcgacttcca gtgccaactc aaaggtgctg gtcgagatgg 2100

-continued

```
aaccccccctt cggagactcc tacatcgtag ttggaagggg agacaagcag atcaaccacc   2160
attggcataa agctggaagc acgctgggca aggctttttc aacaactttg aagggagctc   2220
aaagactggc agcgttgggc gacacagcct gggactttgg ctctattgga ggggtcttca   2280
actccatagg aaaggccgtt caccaagtgt ttggtggcgc tttcagaaca ctctttgggg   2340
gaatgtcttg gatcacacaa gggttaatgg gtgccctact actctggatg ggcatcaacg   2400
cacgagatcg atcaattgct ttggccttct tggccacagg aggtgtgctc gtgttcttag   2460
cgaccaatgt gcatgctgac actggatgtg ccattgacat cgcaagaaaa gagatgagat   2520
gcggaagtgg catcttcgtg cacaacgacg tggaagcctg ggtggatagg tataaatatt   2580
tgccagaaac gcccagatcc ctagcgaaga tcgtccacaa agcgcacaag gaaggcgtgt   2640
gcggagtcag atctgtcact agactggagc accaaatgtg ggaagccgtg cgggacgaat   2700
tgaacgtcct gctcaaagag aatgcagtgg acctcagtgt ggttgtgaac aagcccgtgg   2760
ggagatatcg ctcagcccca aaacgcctgt ccatgacgca agagaagttt gaaatgggct   2820
ggaaagcatg ggaaaaaagc attctctttg ccccggaatt ggctaactcc acatttgttg   2880
tagatggacc tgagacaaag gaatgtcctg atgagcacag agcctggaac agcatgcaaa   2940
tcgaagactt cggctttggt atcacatcaa cccgtgtgtg gctgaagatt agagaggaaa   3000
gcactgacga gtgtgatgga gcgatcatag gcacagctgt caaaggacat gtggcagttc   3060
atagtgactt gtcgtactgg attgagagtc gctacaacga cacatggaaa cttgagaggg   3120
cagtctttgg agaggtcaaa tcttgcactt ggccagagac acacactctt tggggagatg   3180
gtgttgagga aagtgaactc atcatcccgc ataccatagc cggaccaaaa agcaagcaca   3240
atcggaggga agggtacaaa acacaaaacc agggaccttg ggacgaaaac ggcatagtct   3300
tggactttga ttattgccca gggacaaaag tcaccatcac agaggattgt ggcaagagag   3360
gcccttcggt cagaaccact actgacagtg gaaagttgat tactgactgg tgctgtcgca   3420
gttgctccct tccgccccta cgattccgga cagaaaatgg ctgctggtac ggaatggaaa   3480
tcagacctgt taggcatgat gaaacaacac tcgtcagatc acaggttgat gctttcaatg   3540
gtgaaatggt tgaccctttt cagctgggcc ttctggtgat gtttctggcc acccaggagg   3600
tccttcgcaa gaggtggacg gccagattga ccattcctgc ggttttgggg gccctgcttg   3660
tgctgatgct tgggggcatc acttacactg atttggcgag gtatgtggtg ctagtcgctg   3720
ctgctttcgc agaggccaat aatggaggag acgtcctgca ccttgctttg attgccgttt   3780
ttaagatcca accagctttt ctagtgatga acatgcttag cacgagatgg acgaaccaag   3840
aaaacgtggt cctggtccta ggggctgcct tctttcaatt ggcctcagta gatctgcaaa   3900
tcggagtcca cggaatcctg aatgccgccg ctatagcatg gatgattgtt cgagcgatca   3960
ccttccccac aacctcctcc gtcaccatgc cagtcttagc gcttctaact ccgggaatga   4020
gggctctata cctagacact tacagaatca tccttctcgt catagggatt tgctccctgc   4080
tgcaagagag gaaaaagacc atggcaaaaa agaaaggagc tgtactcttg ggcttagcgc   4140
tcacatccac tggatggttc tcgcccacca ccatagctgc tggactaatg gtctgcaacc   4200
caaacaagaa gagagggtgg ccagctactg agtttctgtc ggcagtcgga ttgatgtttg   4260
ccatcgtagg tggtttggcc gagttggata ttgaatccat gtcaataccc ttcatgctgg   4320
caggtcttat ggcagtgtcc tacgtagtgt caggaaaagc aacagatatg tggctcgaac   4380
gggccgccga catcagctgg gagatggatg ctgcaatcac aggaagcagt cggaggctgg   4440
```

-continued

```
atgtgaaact ggatgatgac ggagattttc acttgattga tgatcccggc gttccatgga   4500
aagtttgggt cttgcgcatg tcttgcattg gcttagccgc cctcacgcct tgggccattg   4560
ttcccgccgc tttcggttac tggctcactt taaaaacaac aaaaagaggg ggcgtgtttt   4620
gggacacgcc atccccgaaa ccttgcttaa aaggagacac cactacagga gtctaccgaa   4680
tcatggctag agggattctt ggcacctacc aggctggcgt cggagtcatg tacgagaatg   4740
ttttccacac actatggcac acaactagag gggcagccat tatgagtgga gaaggaaaat   4800
tgacgccata ctggggtagc gtgaaagaag accgcatagc ttacggaggc ccatggagat   4860
ttgatcgaaa atggaatgga acagatgacg tgcaagtgat cgtggtagaa ccggggaagg   4920
ctgcggtaaa catccagaca aaaccaggag tgtttcggac cccccttcggg gaggttgggg   4980
ctgttagcct ggattacccg cgaggaacat ccggctcacc cattctggat tccaatggag   5040
acatcatagg cctatacggc aatggagttg agcttggcga tggctcatac gtcagcgcca   5100
tcgtgcaggg tgaccgtcag gaggaaccag tcccagaagc ttacactcca aacatgttaa   5160
gaaagagaca gatgactgtg ttagatttgc accctggttc agggaaaacc aggaaaattc   5220
tgccacaaat aattaaggat gcaatccagc agcgcctaag aacagctgtg ttggcaccga   5280
cgcgggtggt agcagcagaa atggcagaag ctttgagagg gctcccagta cgataccaaa   5340
cttcagcagt gcagagagag caccaaggga atgaaatagt ggatgtgatg tgccacgcca   5400
ctctgaccca cagattgatg tcaccgaaca gagtgcccaa ctacaatctg tttgtcatgg   5460
atgaagctca tttcaccgac ccagccagca tagccgcacg aggatacatc gctaccaagg   5520
tggaattagg agaggcagca gccatcttta tgacagcgac cccgcctgga accacggatc   5580
cttttcccga ctcaaatgcc ccaatccatg atttacaaga tgagatacca gacagggcat   5640
ggagcagtgg atacgaatgg atcacagaat atgcgggtaa aaccgtgtgg tttgtggcga   5700
gcgtaaaaat ggggaatgag attgcaatgt gcctccaaag agcgggaaaa aaggtcatcc   5760
aactcaaccg caagtcctat gacacagaat acccaaaatg taagaatgga gactgggatt   5820
ttgtcattac caccgacatc tctgaaatgg gggctaactt cggtgcgagc agggtcatcg   5880
actgcagaaa gagcgtgaaa cccaccatct tagaagaggg agaaggcaga gtcatcctcg   5940
gaaacccatc tcccataacc agtgctagcg cagctcaacg gaggggcaga gtaggcagaa   6000
accccaacca agttggagat gaataccatt atggaggggc taccagtgaa gatgacagta   6060
acctagccca ttggacagag gcaaagatca tgttagacaa catacacatg cccaatgggc   6120
tggtggccca gctctatgga ccagagaggg aaaaggcttt cacaatggat ggcgaatacc   6180
gtctcagggg tgaagaaaag aaaaacttct tagagctgct taggacggct gaccttccgg   6240
tgtggctggc ctataaggtg gcgtccaatg gcattcagta caccgacaga aagtggtgtt   6300
ttgatgggcc gcgcacgaat gccatactgg aggacaacac cgaggtagag atagtcaccc   6360
ggatgggtga gagaaagatc ctcaagccga gatggcttga tgcaagagta tacgcagatc   6420
accaagccct caagtggttc aaagactttg cagcaggaaa gagatcggcc gttagcttca   6480
tagaggtgct cggtcgcatg cctgagcatt tcatgggaaa gacgcgggaa gctttagaca   6540
ccatgtactt ggtcgcaacg gctgagaaag gtgggaaggc acaccgaatg gctctcgaag   6600
agttgccgga tgcactggaa accatcacac ttattgttgc catcactgta atgacaggag   6660
gattcttcct actaatgatg cagcgaaagg gtatagggaa gatgggtctt ggagctctag   6720
tgctcacgct agctaccttc ttcctgtggg cggcagaggt tcctggaacc aaaatagcag   6780
ggaccctgct gatcgccctg ctgctgatgg tggttctcat cccagaaccg gaaaaacaga   6840
```

-continued

```
ggtcacagac agacaaccaa ctagcggtgt ttctcatctg cgtcttgacc gtggttggag   6900
tggtggcagc aaacgagtac gggatgctag aaaaaaccaa agcagatctc aagagcatgt   6960
ttggcggaaa gacacaggca tcaggactga ctggattgcc aagcatggca ctggacctgc   7020
gtccagccac agcctgggca ctgtatgggg ggagcacagt tgtgctaacc cctcttctga   7080
agcacctgat cacgtcggaa tatgtcacca catcgctagc ctcaattaac tcacaagctg   7140
gctcattatt cgtcttgcca cgaggcgtgc ctttcaccga tctagacctg accgttggcc   7200
tcgtcttcct tggctgctgg ggtcaaatca ccctcacaac gtttttgaca gccatggttc   7260
tggcgacact tcactatggg tacatgctcc ctggatggca agcagaagca ctcagggctg   7320
cccagagaag gacggcggct ggaataatga agaatgccgt tgttgacgga atggtcgcca   7380
ctgatgtgcc tgaactggaa aggactactc ctctgatgca aaagaaagtc ggacaggtgc   7440
tcctcatagg ggtgagcgtg gcagcgtttc tcgtcaaccc taatgtcacc actgtgagag   7500
aagcaggggt gttggtgacg gcggctacgc tcaccttgtg ggataatgga gccagtgccg   7560
tttggaattc caccacagcc acgggactct gccatgtcat gcgaggtagc tacctggctg   7620
gaggctctat tgcttggact cttatcaaga acgctgacaa gccctccttg aaaaggggaa   7680
ggcctggggg caggacgcta ggggagcagt ggaaggaaaa actaaatgcc atgagcagag   7740
aagagttttt taaataccgg agagaggcca taatcgaggt ggaccgcact gaagcacgca   7800
gggctagacg tgaaaataac atagtgggag gacatccggt ttcgcgaggc tcagcaaaac   7860
tccgttggct cgtggagaaa ggattcgtct cgccaatagg aaaagtcatt gatctagggt   7920
gtgggcgtgg aggatggagc tactacgcag caaccctgaa gaaggtccag gaagtcagag   7980
gatacacgaa aggtggggcg ggacatgaag agccgatgct catgcagagc tacggctgga   8040
acctggtctc cttgaagagt ggagtggatg tgttctacaa accttcagag cctagtgaca   8100
ccctgttctg tgacataggg gaatcctccc caagtccaga agtggaagaa caacgcacac   8160
tacgcgtcct agagatgaca tccgattggt tgcatcgagg acccagagag ttctgcataa   8220
aagttctctg cccttacatg cccaaggtca tagaaaaaat ggaagttctg cagcgccgct   8280
tcggaggtgg gctagtacgt ctccccctgt cccgaaactc caatcacgag atgtattggg   8340
ttagtggagc cgctggcaat gtggtgcacg ctgtgaacat gaccagccag gtactactgg   8400
ggcgaatgga tcgcacagtg tggagagggc caaagtatga ggaagatgtc aacctaggta   8460
gcggaacaag agccgtggga aagggagaag ttcatagcaa tcaggagaaa atcaagaaga   8520
gaatccagaa gcttaaagaa gaattcgcca caacgtggca caaagaccct gaacacccat   8580
accgcacttg gacataccac ggaagctatg aggtgaaggc tactggctca gccagctctc   8640
tcgtcaacgg agtggtgaag ctcatgagta aaccttggga cgccattgcc aacgtcacca   8700
ccatggccat gactgacacc accccttttg gacagcaaag agttttcaag gagaaagttg   8760
acacgaaagc tcctgagcca ccagctggag tcaaggaagt gctcaacgag accaccaact   8820
ggctgtgggc ccacttgtca cgggaaaaaa gaccccgctt gtgcaccaag gaagaattta   8880
taaagaaagt caatagcaac gcggctcttg gagcagtgtt tgctgaacag aatcaatgga   8940
gcacggcgcg tgaggctgtg gacgacccgc ggttttggga gatggtcaat gaagagaggg   9000
aaaaccatct gcgaggagag tgtcacacat gtatctacaa catgatggga aaaagagaga   9060
agaagcctgg agagtttgga aaagctaaag ggagcagggc catttggttc atgtggcttg   9120
gagcacggta tctagagttt gaagctttgg ggttcctgaa tgaagaccac tggctgagcc   9180
```

-continued

```
gagagaattc aggaggtgga gtagaaggct caggcgtcca aaagttggga tacatcctcc   9240
gtgacatagc aggaaagcaa ggagggaaaa tgtacgctga tgacaccgcc gggtgggaca   9300
ctagaattac tagaactgat ttagaaaatg aagctaaggt gctggagctc ctagatggtg   9360
aacaccgcat gctcgcccgg gccataattg aactgactta caggcacaaa gtggtcaagg   9420
tcatgagacc tgcagcagaa ggaaagaccg tgatggacgt gatatcaaga gaagaccaaa   9480
gggggagtgg acaggtggtc acttatgctc tcaacacttt cacgaacatc gctgtccagc   9540
tcgttaggct gatggaggct gagggggtca ttgggccaca acacttggaa cagctgccta   9600
ggaaaaacaa gatagctgtc aggacttggc tctttgagaa tggagaggag agagtgacca   9660
ggatggcgat cagcggagac gactgtgtcg tcaagccgct ggacgacaga ttcgccacgg   9720
ccctccattt cctcaacgca atgtcaaagg ttagaaaaga catccaggaa tggaagcctt   9780
cgcacggctg gcacgattgg cagcaagttc ccttctgctc taaccacttt caggagattg   9840
tgatgaaaga cggaaggagt atagttgtcc cgtgcagagg acaggatgag ctgataggca   9900
gggctcgcat ctctccagga gctggatgga atgtgaagga cacagcttgc ctggcaaaag   9960
catatgcaca gatgtggcta ctcctatact tccatcgtag ggacctgcgt ctcatggcaa  10020
atgcgatttg ctcagcagtg ccagtggatt gggtgcccac aggcaggaca tcctggtcaa  10080
tacactcgaa aggagagtgg atgaccacgg aagacatgct gcaggtctgg aacagagtct  10140
ggattgaaga aaatgaatgg atgatggata agactcccgt cacaagctgg acagacgttc  10200
cgtatgtggg aaagcgtgag gacatctggt gtggcagcct catcggaacg cgttccagag  10260
caacctgggc tgagaacatc tatgcggcga taaaccaggt tagagctgtc attgggaaag  10320
aaaattatgt tgactacatg acctcactca ggagatacga agacgtcttg atccaggaag  10380
acagggtcat ctagtgtgac ttaaggtaga aatgtaaata atgtgaatga gaaaatgcat  10440
gtatatggag tcaggccagc aaaagctgcc accggatact gggtagacgg tgctgcctgc  10500
gtctcagtcc caggaggact gggttaacaa atctgacaac agaaagtgag aaagccctca  10560
gaaccgtctc ggaagtaggt ccctgctcac tggaagttga aagaccaacg tcaggccacg  10620
aatttgtgcc actccgctgg ggagtgcggc ctgcgcagcc ccaggaggac tgggttacca  10680
aagccgttga ggcccccacg gcccaagcct cgtctaggat gcaatagacg aggtgtaagg  10740
actagaggtt agaggagacc ccgtggaaac aacaacatgc ggcccaagcc ccctcgaagc  10800
tgtagaggag gtggaaggac tagaggttag aggagacccc gcatttgcat caaacagcat  10860
attgacacct gggaatagac tgggagatct tctgctctat ctcaacatca gctactaggc  10920
acagagcgcc gaagtatgta gctggtggtg aggaagaaca caggatctcg agcggccgcg  10980
gaccgactag cctcttttcg gccttcgctg agagggattt gttccctagg cctaattatt  11040
atttttaatt gcccaatacg tatacgagtg ccttttctaa ttctcgtata ctatagtgag  11100
tcgtattatc tagccgcccg ggccgtcgac caattctcat gtttgacagc ttatcatcga  11160
atttctgcca ttcatccgct tattatcact tattcaggcg tagcaaccag gcgtttaagg  11220
gcaccaataa ctgccttaaa aaaattacgc cccgccctgc cactcatcgc agtactgttg  11280
taattcatta agcattctgc cgacatggaa gccatcacaa acggcatgat gaacctgaat  11340
cgccagcggc atcagcacct tgtcgccttg cgtataatat ttgcccatgg tgaaaacggg  11400
ggcgaagaag ttgtccatat tggccacgtt taaatcaaaa ctggtgaaac tcacccaggg  11460
attggctgag acgaaaaaca tattctcaat aaacccttta gggaaatagg ccaggttttc  11520
accgtaacac gccacatctt gcgaatatat gtgtagaaac tgccggaaat cgtcgtggta  11580
```

-continued

```
ttcactccag agcgatgaaa acgtttcagt ttgctcatgg aaaacggtgt aacaagggtg  11640
aacactatcc catatcacca gctcaccgtc tttcattgcc atacggaatt ccggatgagc  11700
attcatcagg cgggcaagaa tgtgaataaa ggccggataa aacttgtgct tatttttctt  11760
tacggtcttt aaaaaggccg taatatccag ctgaacggtc tggttatagg tacattgagc  11820
aactgactga aatgcctcaa aatgttcttt acgatgccat tgggatatat caacggtggt  11880
atatccagtg atttttttct ccattttagc ttccttagct cctgaaaatc tcgataactc  11940
aaaaaatacg cccggtagtg atcttatttc attatggtga aagttggaac ctcttacgtg  12000
ccgatcaacg tctcattttc gccaaaagtt ggcccagggc ttcccggtat caacagggac  12060
accaggattt atttattctg cgaagtgatc ttccgtcaca ggtatttatt cgcgataagc  12120
tcatggagcg gcgtaaccgt cgcacaggaa ggacagagaa agcgcggatc tgggaagtga  12180
cggacagaac ggtcaggacc tggattgggg aggcggttgc cgccgctgct gctgacggtg  12240
tgacgttctc tgttccggtc acaccacata cgttccgcca ttcctatgcg atgcacatgc  12300
tgtatgccgg tataccgctg aaagttctgc aaagcctgat gggacataag tccatcagtt  12360
caacggaagt ctacacgaag gtttttgcgc tggatgtggc tgcccggcac cgggtgcagt  12420
ttgcgatgcc ggagtctgat gcggttgcga tgctgaaaca attatcctga gaataaatgc  12480
cttggccttt atatggaaat gtggaactga gtggatatgc tgtttttgtc tgttaaacag  12540
agaagctggc tgttatccac tgagaagcga acgaaacagt cgggaaaatc tcccattatc  12600
gtagagatcc gcattattaa tctcaggagc ctgtgtagcg tttataggaa gtagtgttct  12660
gtcatgatgc ctgcaagcgg taacgaaaac gatttgaata tgccttcagg aacaatagaa  12720
atcttcgtgc ggtgttacgt tgaagtggag cggattatgt cagcaatgga cagaacaacc  12780
taatgaacac agaaccatga tgtggtctgt ccttttacag ccagtagtgc tcgccgcagt  12840
cgagcgacag ggcgaagccc tcgagtgagc gaggaagcac cagggaacag cacttatata  12900
ttctgcttac acacgatgcc tgaaaaaact tcccttgggg ttatccactt atccacgggg  12960
atatttttat aattattttt tttatagttt ttagatcttc tttttagag cgccttgtag  13020
gcctttatcc atgctggttc tagagaaggt gttgtgacaa attgcccttt cagtgtgaca  13080
aatcaccctc aaatgacagt cctgtctgtg acaaattgcc cttaaccctg tgacaaattg  13140
ccctcagaag aagctgtttt ttcacaaagt tatccctgct tattgactct tttttattta  13200
gtgtgacaat ctaaaaactt gtcacacttc acatggatct gtcatggcgg aaacagcggt  13260
tatcaatcac aagaaacgta aaaatagccc gcgaatcgtc cagtcaaacg acctcactga  13320
ggcggcatat agtctctccc gggatcaaaa acgtatgctg tatctgttcg ttgaccagat  13380
cagaaaatct gatggcaccc tacaggaaca tgacggtatc tgcgagatcc atgttgctaa  13440
atatgctgaa atattcggat tgacctctgc ggaagccagt aaggatatac ggcaggcatt  13500
gaagagtttc gcggggaagg aagtggtttt ttatcgccct gaagaggatg ccggcgatga  13560
aaaaggctat gaatcttttc cttggtttat caaacgtgcg cacagtccat ccagagggct  13620
ttacagtgta catatcaacc catatctcat tcccttcttt atcgggttac agaaccggtt  13680
tacgcagttt cggcttagtg aaacaaaaga aatcaccaat ccgtatgcca tgcgtttata  13740
cgaatccctg tgtcagtatc gtaagccgga tggctcaggc atcgtctctc tgaaaatcga  13800
ctggatcata gagcgttacc agctgcctca aagttaccag cgtatgcctg acttccgccg  13860
ccgcttcctg caggtctgtg ttaatgagat caacagcaga actccaatgc gcctctcata  13920
```

-continued

```
cattgagaaa aagaaaggcc gccagacgac tcatatcgta ttttccttcc gcgatatcac  13980
ttccatgacg acaggatagt ctgagggtta tctgtcacag atttgagggt ggttcgtcac  14040
atttgttctg acctactgag ggtaatttgt cacagttttg ctgtttcctt cagcctgcat  14100
ggattttctc atactttttg aactgtaatt tttaaggaag ccaaatttga gggcagtttg  14160
tcacagttga tttccttctc tttcccttcg tcatgtgacc tgatatcggg ggttagttcg  14220
tcatcattga tgagggttga ttatcacagt ttattactct gaattggcta tccgcgtgtg  14280
tacctctacc tggagttttt cccacggtgg atatttcttc ttgcgctgag cgtaagagct  14340
atctgacaga acagttcttc tttgcttcct cgccagttcg ctcgctatgc tcggttacac  14400
ggctgcggcg agcgctagtg ataataagtg actgaggtat gtgctcttct tatctccttt  14460
tgtagtgttg ctcttatttt aaacaacttt gcggtttttt gatgactttg cgattttgtt  14520
gttgctttgc agtaaattgc aagatttaat aaaaaaacgc aaagcaatga ttaaaggatg  14580
ttcagaatga aactcatgga aacacttaac cagtgcataa acgctggtca tgaaatgacg  14640
aaggctatcg ccattgcaca gtttaatgat gacagcccgg aagcgaggaa aataacccgg  14700
cgctggagaa taggtgaagc agcggattta gttggggttt cttctcaggc tatcagagat  14760
gccgagaaag cagggcgact accgcacccg gatatggaaa ttcgaggacg ggttgagcaa  14820
cgtgttggtt atacaattga acaaattaat catatgcgtg atgtgtttgg tacgcgattg  14880
cgacgtgctg aagacgtatt tccaccggtg atcggggttg ctgcccataa aggtggcgtt  14940
tacaaaacct cagtttctgt tcatcttgct caggatctgg ctctgaaggg gctacgtgtt  15000
ttgctcgtgg aaggtaacga cccccaggga acagcctcaa tgtatcacgg atgggtacca  15060
gatcttcata ttcatgcaga agacactctc ctgcctttct atcttgggga aaaggacgat  15120
gtcacttatg caataaagcc cacttgctgg ccggggcttg acattattcc ttcctgtctg  15180
gctctgcacc gtattgaaac tgagttaatg ggcaaatttg atgaaggtaa actgcccacc  15240
gatccacacc tgatgctccg actggccatt gaaactgttg ctcatgacta tgatgtcata  15300
gttattgaca gcgcgcctaa cctgggtatc ggcacgatta atgtcgtatg tgctgctgat  15360
gtgctgattg ttcccacgcc tgctgagttg tttgactaca cctccgcact gcagtttttc  15420
gatatgcttc gtgatctgct caagaacgtt gatcttaaag ggttcgagcc tgatgtacgt  15480
attttgctta ccaaatacag caatagtaat ggctctcagt ccccgtggat ggaggagcaa  15540
attcgggatg cctggggaag catggttcta aaaaatgttg tacgtgaaac ggatgaagtt  15600
ggtaaaggtc agatccggat gagaactgtt tttgaacagg ccattgatca acgctcttca  15660
actggtgcct ggagaaatgc tctttctatt tgggaacctg tctgcaatga aattttcgat  15720
cgtctgatta aaccacgctg ggagattaga taatgaagcg tgcgcctgtt attccaaaac  15780
atacgctcaa tactcaaccg gttgaagata cttcgttatc gacaccagct gccccgatgg  15840
tggattcgtt aattgcgcgc gtaggagtaa tggctcgcgg taatgccatt actttgcctg  15900
tatgtggtcg ggatgtgaag tttactcttg aagtgctccg ggggtgatagt gttgagaaga  15960
cctctcgggt atggtcaggt aatgaacgtg accaggagct gcttactgag gacgcactgg  16020
atgatctcat cccttctttt ctactgactg gtcaacagac accggcgttc ggtcgaagag  16080
tatctggtgt catagaaatt gccgatggga gtcgccgtcg taaagctgct gcacttaccg  16140
aaagtgatta tcgtgttctg gttggcgagc tggatgatga gcagatggct gcattatcca  16200
gattgggtaa cgattatcgc ccaacaagtg cttatgaacg tggtcagcgt tatgcaagcc  16260
gattgcagaa tgaatttgct ggaaatattt ctgcgctggc tgatgcggaa aatatttcac  16320
```

-continued

```
gtaagattat tacccgctgt atcaacaccg ccaaattgcc taaatcagtt gttgctcttt  16380
tttctcaccc cggtgaacta tctgcccggt caggtgatgc acttcaaaaa gcctttacag  16440
ataaagagga attacttaag cagcaggcat ctaaccttca tgagcagaaa aaagctgggg  16500
tgatatttga agctgaagaa gttatcactc ttttaacttc tgtgcttaaa acgtcatctg  16560
catcaagaac tagtttaagc tcacgacatc agtttgctcc tggagcgaca gtattgtata  16620
agggcgataa aatggtgctt aacctggaca ggtctcgtgt tccaactgag tgtatagaga  16680
aaattgaggc cattcttaag gaacttgaaa agccagcacc ctgatgcgac cacgttttag  16740
tctacgttta tctgtcttta cttaatgtcc tttgttacag gccagaaagc ataactggcc  16800
tgaatattct ctctgggccc actgttccac ttgtatcgtc ggtctgataa tcagactggg  16860
accacggtcc cactcgtatc gtcggtctga ttattagtct gggaccacgg tcccactcgt  16920
atcgtcggtc tgattattag tctgggacca cggtcccact cgtatcgtcg gtctgataat  16980
cagactggga ccacggtccc actcgtatcg tcggtctgat tattagtctg ggaccatggt  17040
cccactcgta tcgtcggtct gattattagt ctgggaccac ggtcccactc gtatcgtcgg  17100
tctgattatt agtctggaac cacggtccca ctcgtatcgt cggtctgatt attagtctgg  17160
gaccacggtc ccactcgtat cgtcggtctg attattagtc tgggaccacg atcccactcg  17220
tgttgtcggt ctgattatcg gtctgggacc acggtcccac ttgtattgtc gatcagacta  17280
tcagcgtgag actacgattc catcaatgcc tgtcaagggc aagtattgac atgtcgtcgt  17340
aacctgtaga acggagtaac ctcggtgtgc ggttgtatgc ctgctgtgga ttgctgctgt  17400
gtcctgctta tccacaacat tttgcgcacg gttatgtgga caaaatacct ggttacccag  17460
gccgtgccgg cacgttaacc gggctgcatc cgatgcaagt gtgtcgctgt cgacgagctc  17520
gcgagctcgg acatgaggtt gccccgtatt cagtgtcgct gatttgtatt gtctgaagtt  17580
gtttttacgt taagttgatg cagatcaatt aatacgatac ctgcgtcata attgattatt  17640
tgacgtggtt tgatggcctc cacgcacgtt gtgatatgta gatgataatc attatcactt  17700
tacgggtcct ttccggtgat ccgacaggtt acggggcggc gacctcgcgg gttttcgcta  17760
tttatgaaaa ttttccggtt taaggcgttt ccgttcttct tcgtcataac ttaatgtttt  17820
tatttaaaat accctctgaa aagaaaggaa acgacaggtg ctgaaagcga gctttttggc  17880
ctctgtcgtt tcctttctct gtttttgtcc gtggaatgaa caatggaagt ccgagctcat  17940
cgctaataac ttcgtatagc atacattata cgaagttata ttcgatgcgg cgctgaggtc  18000
tgcctcgtga agaaggtgtt gctgactcat accaggcctg aatcgcccca tcatccagcc  18060
agaaagtgag ggagccacgg ttgatgagag ctttgttgta ggtggaccag ttggtgattt  18120
tgaacttttg ctttgccacg gaacggtctg cgttgtcggg aagatgcgtg atctgatcct  18180
tcaactcagc aaaagttcga tttattcaac aaagccacgt gtctcaaaat ctctgatgtt  18240
acattgcaca agataaaaat atatcatcat gaacaataaa actgtctgct tacataaaca  18300
gtaatacaag gggtgttatg agccatattc aacgggaaac gtcttgctcg acgatgataa  18360
gctgtcaaac atgagaattg ggtcgtcaat atgctaaaac gcggcatacc ccgcgtattc  18420
ccactagtta atcgtacgaa ttccgtatgg caatgaaaga cggtgagctg gtgatatggg  18480
atagtgttca cccttgttac accgttttcc atgagcaaac tgaaacgttt tcatcgctct  18540
ggagtgaata ccacgacgat ttccggcagt ttctacacat atattcgcaa gatgtggcgt  18600
gttacggtga aaacctggcc tatttcccta aagggtttat tgagaatatg tttttcgtct  18660
```

-continued

```
cagccaatcc ctgggtgagt ttcaccagtt ttgatttaaa cgtggccaat atggacaact  18720

tcttcgcccc cgttttcacc atgggcaaat attatacgca aggcgacaag gtgctgatgc  18780

cgctggcgat tcaggttcat catgccgttt gtgatggctt ccatgtcggc agaatgctta  18840

atgaattaca acagtactgc gatgagtggc agggcggggc gtaatttttt taaggcagtt  18900

attggtgccc ttaaacgcct ggttgctacg cctgaataag tgataataag cggatgaatg  18960

gcagaaattc gatgataagc tgtcaaacat gagaattggt cgacggcccg ggcggctaga  19020

taatacgact cactatag                                                19038
```

<210> SEQ ID NO 47
<211> LENGTH: 19038
<212> TYPE: DNA
<213> ORGANISM: Artificial Sequence
<220> FEATURE:
<223> OTHER INFORMATION: sequence for pBACt7/JVFLx/XhoI

<400> SEQUENCE: 47

```
agaagtttat ctgtgtgaac ttcttggctt agtatcgttg agaagaatcg agagattagt     60

gcagtttaaa cagtttttta gaacggaaga taaccatgac taaaaaacca ggagggcccg    120

gtaaaaaccg ggctatcaat atgctgaaac gcggcctacc ccgcgtattc ccactagtgg    180

gagtgaagag ggtagtaatg agcttgttgg acggcagagg accagtacgt ttcgtgctgg    240

ctcttatcac gttcttcaag tttacagcat tagccccgac caaggcgctt ttaggccgat    300

ggaaagcagt ggaaaagagt gtggcaatga aacatcttac tagtttcaaa cgagaacttg    360

gaacactcat tgacgccgtg aacaagcggg gcagaaagca aaacaaaaga ggaggaaatg    420

aaggctcaat catgtggctc gcgagtttgg cagttgtcat agcttgtgta ggagccatga    480

agttgtcaaa tttccaaggg aagcttttga tgaccattaa caacacggac attgcagacg    540

tcatcgtgat tcctacctca aaaggagaga acagatgctg ggtccgggca atcgatgtcg    600

gctacatgtg tgaggacact atcacgtacg aatgtcctaa gcttaccatg ggcaatgatc    660

cagaggatgt ggattgctgg tgtgacaacc aagaagtcta cgtccaatat ggacggtgca    720

cgcggaccag gcattccaag cgaagcagga ggtccgtgtc ggtccaaaca catggggaga    780

gttcactagt gaataaaaaa gaggcttggc tggattcaac gaaagccaca cgatatctca    840

tgaaaactga gaactggatc ataaggaatc ctggctatgc tttcctggcg gcggtacttg    900

gctggatgct tggcagtaac aatggtcaac gcgtggtgtt taccatcctc ctgctgttgg    960

tcgctccggc ttacagtttt aattgtctgg gaatgggcaa ccgtgacttc atagaaggag   1020

ccagtggagc cacttgggtg gacttagtgc tagaaggaga tagctgcttg acaatcatgg   1080

caaacgacaa accaacattg gacgtccgca tgattaacat cgaagccagc caacttgctg   1140

aggtcagaag ctactgctat catgcttcag tcactgacat ctcgacggtg gctcggtgcc   1200

ccacgactgg agaagcccac aacgagaagc gagctgatag tagctatgtg tgcaaacaag   1260

gtttcactga tcgtgggtgg ggcaacggat gtggactttt cgggaaggga agcattgaca   1320

catgtgcaaa attctcctgc accagtaagg cgattgggag aacaatccag ccagaaaaca   1380

tcaaatacga agttggcatt tttgtgcatg gaaccaccac ctcggaaaac catgggaatt   1440

attcagcgca agtaggggcg tcccaggcgg caaagtttac agtaacaccc aatgctcctt   1500

cgataaccct caaacttggt gactacggag aagtcacact ggactgtgaa ccaaggagtg   1560

gactgaacac tgaagcgttt tacgtcatga ccgtggggtc aaagtcattt ctggtccata   1620

gggaatggtt tcatgacctc gctctcccct ggacgtcccc ttcgagcaca gcgtggagaa   1680
```

-continued

```
acagagaact cctcatggaa tttgaagagg cgcacgccac aaaacagtcc gttgttgctc   1740
ttgggtcaca ggaaggaggc ctccatcagg cgctggcagg agccatcgtg gtggagtact   1800
caagctcagt gaagttaaca tcaggccacc tgaaatgtag gctgaaaatg gacaaactgg   1860
ctctgaaagg cacaacctat ggcatgtgta cagaaaaatt ctcgttcgcg aaaaatccgg   1920
cggacactgg ccacggaaca gttgtcattg aactctccta ttctgggagt gatggcccct   1980
gcaaaattcc gattgtctcc gttgcgagcc tcaatgacat gacccccgtt gggcggctgg   2040
tgacagtgaa ccccttcgtc gcgacttcca gtgccaactc aaaggtgctg gtcgagatgg   2100
aacccccctt cggagactcc tacatcgtag ttggaagggg agacaagcag atcaaccacc   2160
attggcataa agctggaagc acgctgggca aggctttttc aacaactttg aagggagctc   2220
aaagactggc agcgttgggc gacacagcct gggactttgg ctctattgga ggggtcttca   2280
actccatagg aaaggccgtt caccaagtgt ttggtggcgc tttcagaaca ctctttgggg   2340
gaatgtcttg gatcacacaa gggttaatgg gtgccctact actctggatg ggcatcaacg   2400
cacgagatcg atcaattgct ttggccttct tggccacagg aggtgtgctc gtgttcttag   2460
cgaccaatgt gcatgctgac actggatgtg ccattgacat cgcaagaaaa gagatgagat   2520
gcggaagtgg catcttcgtg cacaacgacg tggaagcctg ggtggatagg tataaatatt   2580
tgccagaaac gcccagatcc ctagcgaaga tcgtccacaa agcgcacaag gaaggcgtgt   2640
gcggagtcag atctgtcact agactggagc accaaatgtg ggaagccgtg cgggacgaat   2700
tgaacgtcct gctcaaagag aatgcagtgg acctcagtgt ggttgtgaac aagcccgtgg   2760
ggagatatcg ctcagcccca aaacgcctgt ccatgacgca agagaagttt gaaatgggct   2820
ggaaagcatg ggaaaaaagc attctctttg ccccggaatt ggctaactcc acatttgttg   2880
tagatggacc tgagacaaag gaatgtcctg atgagcacag agcctggaac agcatgcaaa   2940
tcgaagactt cggctttggt atcacatcaa cccgtgtgtg gctgaagatt agagaggaaa   3000
gcactgacga gtgtgatgga gcgatcatag gcacagctgt caaaggacat gtggcagttc   3060
atagtgactt gtcgtactgg attgagagtc gctacaacga cacatggaaa cttgagaggg   3120
cagtctttgg agaggtcaaa tcttgcactt ggccagagac acacactctt tggggagatg   3180
gtgttgagga aagtgaactc atcatcccgc ataccatagc cggaccaaaa agcaagcaca   3240
atcggaggga agggtacaaa acacaaaacc agggaccttg ggacgaaaac ggcatagtct   3300
tggactttga ttattgccca gggacaaaag tcaccatcac agaggattgt ggcaagagag   3360
gcccttcggt cagaaccact actgacagtg gaaagttgat tactgactgg tgctgtcgca   3420
gttgctccct tccgccccta cgattccgga cagaaaatgg ctgctggtac ggaatggaaa   3480
tcagacctgt taggcatgat gaaacaacac tcgtcagatc acaggttgat gctttcaatg   3540
gtgaaatggt tgaccctttt cagctgggcc ttctggtgat gtttctggcc acccaggagg   3600
tccttcgcaa gaggtggacg gccagattga ccattcctgc ggttttgggg gccctgcttg   3660
tgctgatgct tgggggcatc acttacactg atttggcgag gtatgtggtg ctagtcgctg   3720
ctgctttcgc agaggccaat aatggaggag acgtcctgca ccttgctttg attgccgttt   3780
ttaagatcca accagctttt ctagtgatga acatgcttag cacgagatgg acgaaccaag   3840
aaaacgtggt cctggtccta ggggctgcct tctttcaatt ggcctcagta gatctgcaaa   3900
tcggagtcca cggaatcctg aatgccgccg ctatagcatg gatgattgtt cgagcgatca   3960
ccttccccac aacctcctcc gtcaccatgc cagtcttagc gcttctaact ccgggaatga   4020
```

-continued

```
gggctctata cctagacact tacagaatca tccttctcgt catagggatt tgctccctgc   4080
tgcaagagag gaaaaagacc atggcaaaaa agaaaggagc tgtactcttg ggcttagcgc   4140
tcacatccac tggatggttc tcgcccacca ccatagctgc tggactaatg gtctgcaacc   4200
caaacaagaa gagagggtgg ccagctactg agtttctgtc ggcagtcgga ttgatgtttg   4260
ccatcgtagg tggtttggcc gagttggata ttgaatccat gtcaataccc ttcatgctgg   4320
caggtcttat ggcagtgtcc tacgtagtgt caggaaaagc aacagatatg tggctcgaac   4380
gggccgccga catcagctgg gagatggatg ctgcaatcac aggaagcagt cggaggctgg   4440
atgtgaaact ggatgatgac ggagattttc acttgattga tgatcccggc gttccatgga   4500
aagtttgggt cttgcgcatg tcttgcattg gcttagccgc cctcacgcct tgggccattg   4560
ttcccgccgc tttcggttac tggctcactt taaaaacaac aaaaagaggg ggcgtgtttt   4620
gggacacgcc atccccgaaa ccttgcttaa aaggagacac cactacagga gtctaccgaa   4680
tcatggctag agggattctt ggcacctacc aggctggcgt cggagtcatg tacgagaatg   4740
ttttccacac actatggcac acaactagag ggcagccat tatgagtgga gaaggaaaat   4800
tgacgccata ctggggtagc gtgaaagaag accgcatagc ttacggaggc ccatggagat   4860
ttgatcgaaa atggaatgga acagatgacg tgcaagtgat cgtggtagaa ccggggaagg   4920
ctgcggtaaa catccagaca aaaccaggag tgtttcggac cccttcggg gaggttgggg   4980
ctgttagcct ggattacccg cgaggaacat ccggctcacc cattctggat tccaatggag   5040
acatcatagg cctatacggc aatggagttg agcttggcga tggctcatac gtcagcgcca   5100
tcgtgcaggg tgaccgtcag gaggaaccag tcccagaagc ttacactcca aacatgttaa   5160
gaaagagaca gatgactgtg ttagatttgc accctggttc agggaaaacc aggaaaattc   5220
tgccacaaat aattaaggat gcaatccagc agcgcctaag aacagctgtg ttggcaccga   5280
cgcgggtggt agcagcagaa atggcagaag ctttgagagg gctcccagta cgataccaaa   5340
cttcagcagt gcagagagag caccaaggga atgaaatagt ggatgtgatg tgccacgcca   5400
ctctgaccca cagattgatg tcaccgaaca gagtgcccaa ctacaatctg tttgtcatgg   5460
atgaagctca tttcaccgac ccagccagca tagccgcacg aggatacatc gctaccaagg   5520
tggaattagg agaggcagca gccatcttta tgacagcgac cccgcctgga accacggatc   5580
cttttcccga ctcaaatgcc ccaatccatg atttacaaga tgagatacca gacagggcat   5640
ggagcagtgg atacgaatgg atcacagaat atgcgggtaa aaccgtgtgg tttgtggcga   5700
gcgtaaaaat ggggaatgag attgcaatgt gcctccaaag agcgggaaaa aaggtcatcc   5760
aactcaaccg caagtcctat gacacagaat acccaaaatg taagaatgga gactgggatt   5820
ttgtcattac caccgacatc tctgaaatgg gggctaactt cggtgcgagc agggtcatcg   5880
actgcagaaa gagcgtgaaa cccaccatct tagaagaggg agaaggcaga gtcatcctcg   5940
gaaacccatc tcccataacc agtgctagcg cagctcaacg gaggggcaga gtaggcagaa   6000
accccaacca agttggagat gaataccatt atggaggggc taccagtgaa gatgacagta   6060
acctagccca ttggacagag gcaaagatca tgttagacaa catacacatg cccaatgggc   6120
tggtggccca gctctatgga ccagagaggg aaaaggcttt cacaatggat ggcgaatacc   6180
gtctcagggg tgaagaaaag aaaaacttct tagagctgct taggacggct gaccttccgg   6240
tgtggctggc ctataaggtg gcgtccaatg gcattcagta caccgacaga aagtggtgtt   6300
ttgatgggcc gcgcacgaat gccatactgg aggacaacac cgaggtagag atagtcaccc   6360
ggatgggtga gagaaagatc ctcaagccga gatggcttga tgcaagagta tacgcagatc   6420
```

-continued

```
accaagccct caagtggttc aaagactttg cagcaggaaa gagatcggcc gttagcttca   6480
tagaggtgct cggtcgcatg cctgagcatt tcatgggaaa gacgcgggaa gctttagaca   6540
ccatgtactt ggtcgcaacg gctgagaaag gtgggaaggc acaccgaatg gctctcgaag   6600
agttgccgga tgcactggaa accatcacac ttattgttgc catcactgta atgacaggag   6660
gattcttcct actaatgatg cagcgaaagg gtatagggaa gatgggtctt ggagctctag   6720
tgctcacgct agctaccttc ttcctgtggg cggcagaggt tcctggaacc aaaatagcag   6780
ggaccctgct gatcgccctg ctgctgatgg tggttctcat cccagaaccg gaaaaacaga   6840
ggtcacagac agacaaccaa ctagcggtgt ttctcatctg cgtcttgacc gtggttggag   6900
tggtggcagc aaacgagtac gggatgctag aaaaaaccaa agcagatctc aagagcatgt   6960
ttggcggaaa gacacaggca tcaggactga ctggattgcc aagcatggca ctggacctgc   7020
gtccagccac agcctgggca ctgtatgggg ggagcacagt tgtgctaacc cctcttctga   7080
agcacctgat cacgtcggaa tatgtcacca catcgctagc ctcaattaac tcacaagctg   7140
gctcattatt cgtcttgcca cgaggcgtgc ctttcaccga tctagacctg accgttggcc   7200
tcgtcttcct tggctgctgg ggtcaaatca ccctcacaac gtttttgaca gccatggttc   7260
tggcgacact tcactatggg tacatgctcc ctggatggca agcagaagca ctcagggctg   7320
cccagagaag gacggcggct ggaataatga agaatgccgt tgttgacgga atggtcgcca   7380
ctgatgtgcc tgaactggaa aggactactc ctctgatgca aaagaaagtc ggacaggtgc   7440
tcctcatagg ggtgagcgtg gcagcgtttc tcgtcaaccc taatgtcacc actgtgagag   7500
aagcaggggt gttggtgacg gcggctacgc tcaccttgtg ggataatgga gccagtgccg   7560
tttggaattc caccacagcc acgggactct gccatgtcat gcgaggtagc tacctggctg   7620
gaggctctat tgcttggact cttatcaaga acgctgacaa gccctccttg aaaaggggaa   7680
ggcctggggg caggacgcta ggggagcagt ggaaggaaaa actaaatgcc atgagcagag   7740
aagagttttt taaataccgg agagaggcca taatcgaggt ggaccgcact gaagcacgca   7800
gggctagacg tgaaaataac atagtgggag gacatccggt ttcgcgaggc tcagcaaaac   7860
tccgttggct cgtggagaaa ggattcgtct cgccaatagg aaaagtcatt gatctagggt   7920
gtgggcgtgg aggatggagc tactacgcag caaccctgaa gaaggtccag gaagtcagag   7980
gatacacgaa aggtggggcg ggacatgaag agccgatgct catgcagagc tacggctgga   8040
acctggtctc cttgaagagt ggagtggatg tgttctacaa accttcagag cctagtgaca   8100
ccctgttctg tgacataggg gaatcctccc caagtccaga agtggaagaa caacgcacac   8160
tacgcgtcct agagatgaca tccgattggt tgcatcgagg acccagagag ttctgcataa   8220
aagttctctg cccttacatg cccaaggtca tagaaaaaat ggaagttctg cagcgccgct   8280
tcggaggtgg gctagtacgt ctccccctgt cccgaaactc caatcacgag atgtattggg   8340
ttagtggagc cgctggcaat gtggtgcacg ctgtgaacat gaccagccag gtactactgg   8400
ggcgaatgga tcgcacagtg tggagagggc caaagtatga ggaagatgtc aacctaggta   8460
gcggaacaag agccgtggga aagggagaag ttcatagcaa tcaggagaaa atcaagaaga   8520
gaatccagaa gcttaaagaa gaattcgcca caacgtggca caaagaccct gaacacccat   8580
accgcacttg gacataccac ggaagctatg aggtgaaggc tactggctca gccagctctc   8640
tcgtcaacgg agtggtgaag ctcatgagta aaccttggga cgccattgcc aacgtcacca   8700
ccatggccat gactgacacc accccttttg gacagcaaag agttttcaag gagaaagttg   8760
```

-continued

```
acacgaaagc tcctgagcca ccagctggag tcaaggaagt gctcaacgag accaccaact   8820
ggctgtgggc ccacttgtca cgggaaaaaa gacccccgctt gtgcaccaag gaagaattta   8880
taaagaaagt caatagcaac gcggctcttg gagcagtgtt tgctgaacag aatcaatgga   8940
gcacggcgcg tgaggctgtg gacgacccgc ggttttggga gatggtcaat gaagagaggg   9000
aaaaccatct gcgaggagag tgtcacacat gtatctacaa catgatggga aaaagagaga   9060
agaagcctgg agagtttgga aaagctaaag ggagcagggc catttggttc atgtggcttg   9120
gagcacggta tcttgagttt gaagctttgg ggttcctgaa tgaagaccac tggctgagcc   9180
gagagaattc aggaggtgga gtagaaggct caggcgtcca aaagttggga tacatcctcc   9240
gtgacatagc aggaaagcaa ggagggaaaa tgtacgctga tgacaccgcc gggtgggaca   9300
ctagaattac tagaactgat ttagaaaatg aagctaaggt gctggagctc ctagatggtg   9360
aacaccgcat gctcgcccgg gccataattg aactgactta caggcacaaa gtggtcaagg   9420
tcatgagacc tgcagcagaa ggaaagaccg tgatggacgt gatatcaaga gaagaccaaa   9480
gggggagtgg acaggtggtc acttatgctc tcaacacttt cacgaacatc gctgtccagc   9540
tcgttaggct gatggaggct gagggggtca ttgggccaca acacttggaa cagctgccta   9600
ggaaaaacaa gatagctgtc aggacttggc tctttgagaa tggagaggag agagtgacca   9660
ggatggcgat cagcggagac gactgtgtcg tcaagccgct ggacgacaga ttcgccacgg   9720
ccctccattt cctcaacgca atgtcaaagg ttagaaaaga catccaggaa tggaagcctt   9780
cgcacggctg gcacgattgg cagcaagttc ccttctgctc taaccacttt caggagattg   9840
tgatgaaaga cggaaggagt atagttgtcc cgtgcagagg acaggatgag ctgataggca   9900
gggctcgcat ctctccagga gctggatgga atgtgaagga cacagcttgc ctggcaaaag   9960
catatgcaca gatgtggcta ctcctatact tccatcgtag ggacctgcgt ctcatggcaa  10020
atgcgatttg ctcagcagtg ccagtggatt gggtgcccac aggcaggaca tcctggtcaa  10080
tacactcgaa aggagagtgg atgaccacgg aagacatgct gcaggtctgg aacagagtct  10140
ggattgaaga aaatgaatgg atgatggata agactcccgt cacaagctgg acagacgttc  10200
cgtatgtggg aaagcgtgag gacatctggt gtggcagcct catcggaacg cgttccagag  10260
caacctgggc tgagaacatc tatgcggcga taaaccaggt tagagctgtc attgggaaag  10320
aaaattatgt tgactacatg acctcactca ggagatacga agacgtcttg atccaggaag  10380
acagggtcat ctagtgtgac ttaaggtaga aatgtaaata atgtgaatga gaaaatgcat  10440
gtatatggag tcaggccagc aaaagctgcc accggatact gggtagacgg tgctgcctgc  10500
gtctcagtcc caggaggact gggttaacaa atctgacaac agaaagtgag aaagccctca  10560
gaaccgtctc ggaagtaggt ccctgctcac tggaagttga aagaccaacg tcaggccacg  10620
aatttgtgcc actccgctgg ggagtgcggc ctgcgcagcc ccaggaggac tgggttacca  10680
aagccgttga ggcccccacg gcccaagcct cgtctaggat gcaatagacg aggtgtaagg  10740
actagaggtt agaggagacc ccgtggaaac aacaacatgc ggcccaagcc ccctcgaagc  10800
tgtagaggag gtggaaggac tagaggttag aggagacccc gcatttgcat caaacagcat  10860
attgacacct gggaatagac tgggagatct tctgctctat ctcaacatca gctactaggc  10920
acagagcgcc gaagtatgta gctggtggtg aggaagaaca caggatctcg agcggccgcg  10980
gaccgactag cctcttttcg gccttcgctg agagggattt gttccctagg cctaattatt  11040
atttttaatt gcccaatacg tatacgagtg ccttttctaa ttctcgtata ctatagtgag  11100
tcgtattatc tagccgcccg ggccgtcgac caattctcat gtttgacagc ttatcatcga  11160
```

-continued

```
atttctgcca ttcatccgct tattatcact tattcaggcg tagcaaccag gcgtttaagg  11220
gcaccaataa ctgccttaaa aaaattacgc cccgccctgc cactcatcgc agtactgttg  11280
taattcatta agcattctgc cgacatggaa gccatcacaa acggcatgat gaacctgaat  11340
cgccagcggc atcagcacct tgtcgccttg cgtataatat ttgcccatgg tgaaaacggg  11400
ggcgaagaag ttgtccatat tggccacgtt taaatcaaaa ctggtgaaac tcacccaggg  11460
attggctgag acgaaaaaca tattctcaat aaacccttta gggaaatagg ccaggttttc  11520
accgtaacac gccacatctt gcgaatatat gtgtagaaac tgccggaaat cgtcgtggta  11580
ttcactccag agcgatgaaa acgtttcagt ttgctcatgg aaaacggtgt aacaagggtg  11640
aacactatcc catatcacca gctcaccgtc tttcattgcc atacggaatt ccggatgagc  11700
attcatcagg cgggcaagaa tgtgaataaa ggccggataa aacttgtgct tatttttctt  11760
tacggtcttt aaaaaggccg taatatccag ctgaacggtc tggttatagg tacattgagc  11820
aactgactga aatgcctcaa aatgttcttt acgatgccat tgggatatat caacggtggt  11880
atatccagtg attttttct ccattttagc ttccttagct cctgaaaatc tcgataactc  11940
aaaaaatacg cccggtagtg atcttatttc attatggtga aagttggaac ctcttacgtg  12000
ccgatcaacg tctcattttc gccaaaagtt ggcccagggc ttcccggtat caacagggac  12060
accaggattt atttattctg cgaagtgatc ttccgtcaca ggtatttatt cgcgataagc  12120
tcatggagcg gcgtaaccgt cgcacaggaa ggacagagaa agcgcggatc tgggaagtga  12180
cggacagaac ggtcaggacc tggattgggg aggcggttgc cgccgctgct gctgacggtg  12240
tgacgttctc tgttccggtc acaccacata cgttccgcca ttcctatgcg atgcacatgc  12300
tgtatgccgg tataccgctg aaagttctgc aaagcctgat gggacataag tccatcagtt  12360
caacggaagt ctacacgaag gtttttgcgc tggatgtggc tgcccggcac cgggtgcagt  12420
ttgcgatgcc ggagtctgat gcggttgcga tgctgaaaca attatcctga gaataaatgc  12480
cttggccttt atatggaaat gtggaactga gtggatatgc tgtttttgtc tgttaaacag  12540
agaagctggc tgttatccac tgagaagcga acgaaacagt cgggaaaatc tcccattatc  12600
gtagagatcc gcattattaa tctcaggagc ctgtgtagcg tttataggaa gtagtgttct  12660
gtcatgatgc ctgcaagcgg taacgaaaac gatttgaata tgccttcagg aacaatagaa  12720
atcttcgtgc ggtgttacgt tgaagtggag cggattatgt cagcaatgga cagaacaacc  12780
taatgaacac agaaccatga tgtggtctgt ccttttacag ccagtagtgc tcgccgcagt  12840
cgagcgacag ggcgaagccc tcgagtgagc gaggaagcac cagggaacag cacttatata  12900
ttctgcttac acacgatgcc tgaaaaaact tcccttgggg ttatccactt atccacgggg  12960
atatttttat aattattttt tttatagttt ttagatcttc tttttagag cgccttgtag  13020
gcctttatcc atgctggttc tagagaaggt gttgtgacaa attgcccttt cagtgtgaca  13080
aatcaccctc aaatgacagt cctgtctgtg acaaattgcc cttaaccctg tgacaaattg  13140
ccctcagaag aagctgtttt ttcacaaagt tatccctgct tattgactct tttttattta  13200
gtgtgacaat ctaaaaactt gtcacacttc acatggatct gtcatggcgg aaacagcggt  13260
tatcaatcac aagaaacgta aaaatagccc gcgaatcgtc cagtcaaacg acctcactga  13320
ggcggcatat agtctctccc gggatcaaaa acgtatgctg tatctgttcg ttgaccagat  13380
cagaaaatct gatggcaccc tacaggaaca tgacggtatc tgcgagatcc atgttgctaa  13440
atatgctgaa atattcggat tgacctctgc ggaagccagt aaggatatac ggcaggcatt  13500
```

-continued

```
gaagagtttc gcggggaagg aagtggtttt ttatcgccct gaagaggatg ccggcgatga  13560
aaaaggctat gaatcttttc cttggtttat caaacgtgcg cacagtccat ccagagggct  13620
ttacagtgta catatcaacc catatctcat tcccttcttt atcgggttac agaaccggtt  13680
tacgcagttt cggcttagtg aaacaaaaga aatcaccaat ccgtatgcca tgcgtttata  13740
cgaatccctg tgtcagtatc gtaagccgga tggctcaggc atcgtctctc tgaaaatcga  13800
ctggatcata gagcgttacc agctgcctca aagttaccag cgtatgcctg acttccgccg  13860
ccgcttcctg caggtctgtg ttaatgagat caacagcaga actccaatgc gcctctcata  13920
cattgagaaa aagaaaggcc gccagacgac tcatatcgta ttttccttcc gcgatatcac  13980
ttccatgacg acaggatagt ctgagggtta tctgtcacag atttgagggt ggttcgtcac  14040
atttgttctg acctactgag ggtaatttgt cacagttttg ctgtttcctt cagcctgcat  14100
ggattttctc atactttttg aactgtaatt tttaaggaag ccaaatttga gggcagtttg  14160
tcacagttga tttccttctc tttcccttcg tcatgtgacc tgatatcggg ggttagttcg  14220
tcatcattga tgagggttga ttatcacagt ttattactct gaattggcta tccgcgtgtg  14280
tacctctacc tggagttttt cccacggtgg atatttcttc ttgcgctgag cgtaagagct  14340
atctgacaga acagttcttc tttgcttcct cgccagttcg ctcgctatgc tcggttacac  14400
ggctgcggcg agcgctagtg ataataagtg actgaggtat gtgctcttct tatctccttt  14460
tgtagtgttg ctcttatttt aaacaacttt gcggtttttt gatgactttg cgattttgtt  14520
gttgctttgc agtaaattgc aagatttaat aaaaaaacgc aaagcaatga ttaaaggatg  14580
ttcagaatga aactcatgga aacacttaac cagtgcataa acgctggtca tgaaatgacg  14640
aaggctatcg ccattgcaca gtttaatgat gacagcccgg aagcgaggaa aataacccgg  14700
cgctggagaa taggtgaagc agcggattta gttggggttt cttctcaggc tatcagagat  14760
gccgagaaag cagggcgact accgcacccg gatatggaaa ttcgaggacg ggttgagcaa  14820
cgtgttggtt atacaattga acaaattaat catatgcgtg atgtgtttgg tacgcgattg  14880
cgacgtgctg aagacgtatt tccaccggtg atcggggttg ctgcccataa aggtggcgtt  14940
tacaaaacct cagtttctgt tcatcttgct caggatctgg ctctgaaggg gctacgtgtt  15000
ttgctcgtgg aaggtaacga cccccaggga acagcctcaa tgtatcacgg atgggtacca  15060
gatcttcata ttcatgcaga agacactctc ctgccttttct atcttgggga aaaggacgat  15120
gtcacttatg caataaagcc cacttgctgg ccggggcttg acattattcc ttcctgtctg  15180
gctctgcacc gtattgaaac tgagttaatg ggcaaatttg atgaaggtaa actgcccacc  15240
gatccacacc tgatgctccg actggccatt gaaactgttg ctcatgacta tgatgtcata  15300
gttattgaca gcgcgcctaa cctgggtatc ggcacgatta atgtcgtatg tgctgctgat  15360
gtgctgattg ttcccacgcc tgctgagttg tttgactaca cctccgcact gcagtttttc  15420
gatatgcttc gtgatctgct caagaacgtt gatcttaaag ggttcgagcc tgatgtacgt  15480
attttgctta ccaaatacag caatagtaat ggctctcagt ccccgtggat ggaggagcaa  15540
attcgggatg cctggggaag catggttcta aaaaatgttg tacgtgaaac ggatgaagtt  15600
ggtaaaggtc agatccggat gagaactgtt tttgaacagg ccattgatca acgctcttca  15660
actggtgcct ggagaaatgc tctttctatt tgggaacctg tctgcaatga aattttcgat  15720
cgtctgatta aaccacgctg ggagattaga taatgaagcg tgcgcctgtt attccaaaac  15780
atacgctcaa tactcaaccg gttgaagata cttcgttatc gacaccagct gccccgatgg  15840
tggattcgtt aattgcgcgc gtaggagtaa tggctcgcgg taatgccatt actttgcctg  15900
```

-continued

```
tatgtggtcg ggatgtgaag tttactcttg aagtgctccg ggtgatagt gttgagaaga  15960
cctctcgggt atggtcaggt aatgaacgtg accaggagct gcttactgag gacgcactgg  16020
atgatctcat cccttctttt ctactgactg gtcaacagac accggcgttc ggtcgaagag  16080
tatctggtgt catagaaatt gccgatggga gtcgccgtcg taaagctgct gcacttaccg  16140
aaagtgatta tcgtgttctg gttggcgagc tggatgatga gcagatggct gcattatcca  16200
gattgggtaa cgattatcgc ccaacaagtg cttatgaacg tggtcagcgt tatgcaagcc  16260
gattgcagaa tgaatttgct ggaaatattt ctgcgctggc tgatgcggaa aatatttcac  16320
gtaagattat tacccgctgt atcaacaccg ccaaattgcc taaatcagtt gttgctcttt  16380
tttctcaccc cggtgaacta tctgcccggt caggtgatgc acttcaaaaa gcctttacag  16440
ataaagagga attacttaag cagcaggcat ctaaccttca tgagcagaaa aaagctgggg  16500
tgatatttga agctgaagaa gttatcactc ttttaacttc tgtgcttaaa acgtcatctg  16560
catcaagaac tagtttaagc tcacgacatc agtttgctcc tggagcgaca gtattgtata  16620
agggcgataa aatggtgctt aacctggaca ggtctcgtgt tccaactgag tgtatagaga  16680
aaattgaggc cattcttaag gaacttgaaa agccagcacc ctgatgcgac cacgttttag  16740
tctacgttta tctgtcttta cttaatgtcc tttgttacag gccagaaagc ataactggcc  16800
tgaatattct ctctgggccc actgttccac ttgtatcgtc ggtctgataa tcagactggg  16860
accacggtcc cactcgtatc gtcggtctga ttattagtct gggaccacgg tcccactcgt  16920
atcgtcggtc tgattattag tctgggacca cggtcccact cgtatcgtcg gtctgataat  16980
cagactggga ccacggtccc actcgtatcg tcggtctgat tattagtctg ggaccatggt  17040
cccactcgta tcgtcggtct gattattagt ctgggaccac ggtcccactc gtatcgtcgg  17100
tctgattatt agtctggaac cacggtccca ctcgtatcgt cggtctgatt attagtctgg  17160
gaccacggtc ccactcgtat cgtcggtctg attattagtc tgggaccacg atcccactcg  17220
tgttgtcggt ctgattatcg gtctgggacc acggtcccac ttgtattgtc gatcagacta  17280
tcagcgtgag actacgattc catcaatgcc tgtcaagggc aagtattgac atgtcgtcgt  17340
aacctgtaga acggagtaac ctcggtgtgc ggttgtatgc ctgctgtgga ttgctgctgt  17400
gtcctgctta tccacaacat tttgcgcacg gttatgtgga caaaatacct ggttacccag  17460
gccgtgccgg cacgttaacc gggctgcatc cgatgcaagt gtgtcgctgt cgacgagctc  17520
gcgagctcgg acatgaggtt gccccgtatt cagtgtcgct gatttgtatt gtctgaagtt  17580
gtttttacgt taagttgatg cagatcaatt aatacgatac ctgcgtcata attgattatt  17640
tgacgtggtt tgatggcctc cacgcacgtt gtgatatgta gatgataatc attatcactt  17700
tacgggtcct ttccggtgat ccgacaggtt acggggcggc gacctcgcgg gttttcgcta  17760
tttatgaaaa ttttccggtt taaggcgttt ccgttcttct tcgtcataac ttaatgtttt  17820
tatttaaaat accctctgaa aagaaaggaa acgacaggtg ctgaaagcga gctttttggc  17880
ctctgtcgtt tcctttctct gtttttgtcc gtggaatgaa caatggaagt ccgagctcat  17940
cgctaataac ttcgtatagc atacattata cgaagttata ttcgatgcgg cgctgaggtc  18000
tgcctcgtga agaaggtgtt gctgactcat accaggcctg aatcgcccca tcatccagcc  18060
agaaagtgag ggagccacgg ttgatgagag ctttgttgta ggtggaccag ttggtgattt  18120
tgaacttttg ctttgccacg gaacggtctg cgttgtcggg aagatgcgtg atctgatcct  18180
tcaactcagc aaaagttcga tttattcaac aaagccacgt gtctcaaaat ctctgatgtt  18240
```

-continued

```
acattgcaca agataaaaat atatcatcat gaacaataaa actgtctgct tacataaaca  18300

gtaatacaag gggtgttatg agccatattc aacgggaaac gtcttgctcg acgatgataa  18360

gctgtcaaac atgagaattg ggtcgtcaat atgctaaaac gcggcatacc ccgcgtattc  18420

ccactagtta atcgtacgaa ttccgtatgg caatgaaaga cggtgagctg gtgatatggg  18480

atagtgttca cccttgttac accgttttcc atgagcaaac tgaaacgttt tcatcgctct  18540

ggagtgaata ccacgacgat ttccggcagt ttctacacat atattcgcaa gatgtggcgt  18600

gttacggtga aaacctggcc tatttcccta aagggtttat tgagaatatg tttttcgtct  18660

cagccaatcc ctgggtgagt ttcaccagtt ttgatttaaa cgtggccaat atggacaact  18720

tcttcgcccc cgttttcacc atgggcaaat attatacgca aggcgacaag gtgctgatgc  18780

cgctggcgat tcaggttcat catgccgttt gtgatggctt ccatgtcggc agaatgctta  18840

atgaattaca acagtactgc gatgagtggc agggcggggc gtaatttttt taaggcagtt  18900

attggtgccc ttaaacgcct ggttgctacg cctgaataag tgataataag cggatgaatg  18960

gcagaaattc gatgataagc tgtcaaacat gagaattggt cgacggcccg ggcggctaga  19020

taatacgact cactatag                                                19038
```

<210> SEQ ID NO 48
<211> LENGTH: 19040
<212> TYPE: DNA
<213> ORGANISM: Artificial Sequence
<220> FEATURE:
<223> OTHER INFORMATION: sequence for pBACt7/JVFLx/XbaI

<400> SEQUENCE: 48

```
agaagtttat ctgtgtgaac ttcttggctt agtatcgttg agaagaatcg agagattagt     60

gcagtttaaa cagtttttta gaacggaaga taaccatgac taaaaaacca ggagggcccg    120

gtaaaaaccg ggctatcaat atgctgaaac gcggcctacc ccgcgtattc ccactagtgg    180

gagtgaagag ggtagtaatg agcttgttgg acggcagagg accagtacgt ttcgtgctgg    240

ctcttatcac gttcttcaag tttacagcat tagccccgac caaggcgctt ttaggccgat    300

ggaaagcagt ggaaaagagt gtggcaatga aacatcttac tagtttcaaa cgagaacttg    360

gaacactcat tgacgccgtg aacaagcggg gcagaaagca aaacaaaaga ggaggaaatg    420

aaggctcaat catgtggctc gcgagtttgg cagttgtcat agcttgtgta ggagccatga    480

agttgtcaaa tttccaaggg aagcttttga tgaccattaa caacacggac attgcagacg    540

tcatcgtgat tcctacctca aaaggagaga acagatgctg ggtccgggca atcgatgtcg    600

gctacatgtg tgaggacact atcacgtacg aatgtcctaa gcttaccatg ggcaatgatc    660

cagaggatgt ggattgctgg tgtgacaacc aagaagtcta cgtccaatat ggacggtgca    720

cgcggaccag gcattccaag cgaagcagga ggtccgtgtc ggtccaaaca catggggaga    780

gttcactagt gaataaaaaa gaggcttggc tggattcaac gaaagccaca cgatatctca    840

tgaaaactga gaactggatc ataaggaatc ctggctatgc tttcctggcg gcggtacttg    900

gctggatgct tggcagtaac aatggtcaac gcgtggtgtt taccatcctc ctgctgttgg    960

tcgctccggc ttacagtttt aattgtctgg gaatgggcaa ccgtgacttc atagaaggag   1020

ccagtggagc cacttgggtg gacttagtgc tagaaggaga tagctgcttg acaatcatgg   1080

caaacgacaa accaacattg gacgtccgca tgattaacat cgaagccagc caacttgctg   1140

aggtcagaag ctactgctat catgcttcag tcactgacat ctcgacggtg gctcggtgcc   1200

ccacgactgg agaagcccac aacgagaagc gagctgatag tagctatgtg tgcaaacaag   1260
```

-continued

```
gtttcactga tcgtgggtgg ggcaacggat gtggactttt cgggaaggga agcattgaca   1320
catgtgcaaa attctcctgc accagtaagg cgattgggag aacaatccag ccagaaaaca   1380
tcaaatacga agttggcatt tttgtgcatg gaaccaccac ctcggaaaac catgggaatt   1440
attcagcgca agtaggggcg tcccaggcgg caaagtttac agtaacaccc aatgctcctt   1500
cgataaccct caaacttggt gactacggag aagtcacact ggactgtgaa ccaaggagtg   1560
gactgaacac tgaagcgttt tacgtcatga ccgtggggtc aaagtcattt ctggtccata   1620
gggaatggtt tcatgacctc gctctcccct ggacgtcccc ttcgagcaca gcgtggagaa   1680
acagagaact cctcatggaa tttgaagagg cgcacgccac aaaacagtcc gttgttgctc   1740
ttgggtcaca ggaaggaggc ctccatcagg cgctggcagg agccatcgtg gtggagtact   1800
caagctcagt gaagttaaca tcaggccacc tgaaatgtag gctgaaaatg gacaaactgg   1860
ctctgaaagg cacaacctat ggcatgtgta cagaaaaatt ctcgttcgcg aaaaatccgg   1920
cggacactgg ccacggaaca gttgtcattg aactctccta ttctgggagt gatggcccct   1980
gcaaaattcc gattgtctcc gttgcgagcc tcaatgacat gacccccgtt gggcggctgg   2040
tgacagtgaa ccccttcgtc gcgacttcca gtgccaactc aaaggtgctg gtcgagatgg   2100
aacccccctt cggagactcc tacatcgtag ttggaagggg agacaagcag atcaaccacc   2160
attggcataa agctggaagc acgctgggca aggctttttc aacaactttg aagggagctc   2220
aaagactggc agcgttgggc gacacagcct gggactttgg ctctattgga ggggtcttca   2280
actccatagg aaaggccgtt caccaagtgt ttggtggcgc tttcagaaca ctctttgggg   2340
gaatgtcttg gatcacacaa gggttaatgg gtgccctact actctggatg ggcatcaacg   2400
cacgagatcg atcaattgct ttggccttct tggccacagg aggtgtgctc gtgttcttag   2460
cgaccaatgt gcatgctgac actggatgtg ccattgacat cgcaagaaaa gagatgagat   2520
gcggaagtgg catcttcgtg cacaacgacg tggaagcctg ggtggatagg tataaatatt   2580
tgccagaaac gcccagatcc ctagcgaaga tcgtccacaa agcgcacaag gaaggcgtgt   2640
gcggagtcag atctgtcact agactggagc accaaatgtg ggaagccgtg cgggacgaat   2700
tgaacgtcct gctcaaagag aatgcagtgg acctcagtgt ggttgtgaac aagcccgtgg   2760
ggagatatcg ctcagcccca aaacgcctgt ccatgacgca agagaagttt gaaatgggct   2820
ggaaagcatg ggaaaaaagc attctctttg ccccggaatt ggctaactcc acatttgttg   2880
tagatggacc tgagacaaag gaatgtcctg atgagcacag agcctggaac agcatgcaaa   2940
tcgaagactt cggctttggt atcacatcaa cccgtgtgtg gctgaagatt agagaggaaa   3000
gcactgacga gtgtgatgga gcgatcatag gcacagctgt caaaggacat gtggcagttc   3060
atagtgactt gtcgtactgg attgagagtc gctacaacga cacatggaaa cttgagaggg   3120
cagtctttgg agaggtcaaa tcttgcactt ggccagagac acacactctt tggggagatg   3180
gtgttgagga aagtgaactc atcatcccgc ataccatagc cggaccaaaa agcaagcaca   3240
atcggaggga agggtacaaa acacaaaacc agggaccttg ggacgaaaac ggcatagtct   3300
tggactttga ttattgccca gggacaaaag tcaccatcac agaggattgt ggcaagagag   3360
gcccttcggt cagaaccact actgacagtg gaaagttgat tactgactgg tgctgtcgca   3420
gttgctccct tccgccccta cgattccgga cagaaaatgg ctgctggtac ggaatggaaa   3480
tcagacctgt taggcatgat gaaacaacac tcgtcagatc acaggttgat gctttcaatg   3540
gtgaaatggt tgaccctttt cagctgggcc ttctggtgat gtttctggcc acccaggagg   3600
```

-continued

```
tccttcgcaa gaggtggacg gccagattga ccattcctgc ggttttgggg gccctgcttg   3660
tgctgatgct tgggggcatc acttacactg atttggcgag gtatgtggtg ctagtcgctg   3720
ctgctttcgc agaggccaat aatggaggag acgtcctgca ccttgctttg attgccgttt   3780
ttaagatcca accagctttt ctagtgatga acatgcttag cacgagatgg acgaaccaag   3840
aaaacgtggt cctggtccta ggggctgcct tctttcaatt ggcctcagta gatctgcaaa   3900
tcggagtcca cggaatcctg aatgccgccg ctatagcatg gatgattgtt cgagcgatca   3960
ccttccccac aacctcctcc gtcaccatgc cagtcttagc gcttctaact ccgggaatga   4020
gggctctata cctagacact tacagaatca tccttctcgt catagggatt tgctccctgc   4080
tgcaagagag gaaaaagacc atggcaaaaa agaaaggagc tgtactcttg ggcttagcgc   4140
tcacatccac tggatggttc tcgcccacca ccatagctgc tggactaatg gtctgcaacc   4200
caaacaagaa gagagggtgg ccagctactg agtttctgtc ggcagtcgga ttgatgtttg   4260
ccatcgtagg tggtttggcc gagttggata ttgaatccat gtcaataccc ttcatgctgg   4320
caggtcttat ggcagtgtcc tacgtagtgt caggaaaagc aacagatatg tggctcgaac   4380
gggccgccga catcagctgg gagatggatg ctgcaatcac aggaagcagt cggaggctgg   4440
atgtgaaact ggatgatgac ggagattttc acttgattga tgatcccggc gttccatgga   4500
aagtttgggt cttgcgcatg tcttgcattg gcttagccgc cctcacgcct tgggccattg   4560
ttcccgccgc tttcggttac tggctcactt taaaaacaac aaaaagaggg ggcgtgtttt   4620
gggacacgcc atccccgaaa ccttgcttaa aaggagacac cactacagga gtctaccgaa   4680
tcatggctag agggattctt ggcacctacc aggctggcgt cggagtcatg tacgagaatg   4740
ttttccacac actatggcac acaactagag ggcagccat tatgagtgga gaaggaaaat    4800
tgacgccata ctggggtagc gtgaaagaag accgcatagc ttacggaggc ccatggagat   4860
ttgatcgaaa atggaatgga acagatgacg tgcaagtgat cgtggtagaa ccggggaagg   4920
ctgcggtaaa catccagaca aaaccaggag tgtttcggac cccccttcggg gaggttgggg   4980
ctgttagcct ggattacccg cgaggaacat ccggctcacc cattctggat tccaatggag   5040
acatcatagg cctatacggc aatggagttg agcttggcga tggctcatac gtcagcgcca   5100
tcgtgcaggg tgaccgtcag gaggaaccag tcccagaagc ttacactcca aacatgttaa   5160
gaaagagaca gatgactgtg ttagatttgc accctggttc agggaaaacc aggaaaattc   5220
tgccacaaat aattaaggat gcaatccagc agcgcctaag aacagctgtg ttggcaccga   5280
cgcgggtggt agcagcagaa atggcagaag ctttgagagg gctcccagta cgataccaaa   5340
cttcagcagt gcagagagag caccaaggga atgaaatagt ggatgtgatg tgccacgcca   5400
ctctgaccca cagattgatg tcaccgaaca gagtgcccaa ctacaatctg tttgtcatgg   5460
atgaagctca tttcaccgac ccagccagca tagccgcacg aggatacatc gctaccaagg   5520
tggaattagg agaggcagca gccatcttta tgacagcgac cccgcctgga accacggatc   5580
cttttcccga ctcaaatgcc ccaatccatg atttacaaga tgagatacca gacagggcat   5640
ggagcagtgg atacgaatgg atcacagaat atgcgggtaa aaccgtgtgg tttgtggcga   5700
gcgtaaaaat ggggaatgag attgcaatgt gcctccaaag agcgggaaaa aaggtcatcc   5760
aactcaaccg caagtcctat gacacagaat acccaaaatg taagaatgga gactgggatt   5820
ttgtcattac caccgacatc tctgaaatgg gggctaactt cggtgcgagc agggtcatcg   5880
actgcagaaa gagcgtgaaa cccaccatct tagaagaggg agaaggcaga gtcatcctcg   5940
gaaacccatc tcccataacc agtgctagcg cagctcaacg gaggggcaga gtaggcagaa   6000
```

-continued

```
accccaacca agttggagat gaataccatt atggaggggc taccagtgaa gatgacagta   6060
acctagccca ttggacagag gcaaagatca tgttagacaa catacacatg cccaatgggc   6120
tggtggccca gctctatgga ccagagaggg aaaaggcttt cacaatggat ggcgaatacc   6180
gtctcagggg tgaagaaaag aaaaacttct tagagctgct taggacggct gaccttccgg   6240
tgtggctggc ctataaggtg gcgtccaatg gcattcagta caccgacaga aagtggtgtt   6300
ttgatgggcc gcgcacgaat gccatactgg aggacaacac cgaggtagag atagtcaccc   6360
ggatgggtga gagaaagatc ctcaagccga gatggcttga tgcaagagta tacgcagatc   6420
accaagccct caagtggttc aaagactttg cagcaggaaa gagatcggcc gttagcttca   6480
tagaggtgct cggtcgcatg cctgagcatt tcatgggaaa gacgcgggaa gctttagaca   6540
ccatgtactt ggtcgcaacg gctgagaaag gtgggaaggc acaccgaatg gctctcgaag   6600
agttgccgga tgcactggaa accatcacac ttattgttgc catcactgta atgacaggag   6660
gattcttcct actaatgatg cagcgaaagg gtatagggaa gatgggtctt ggagctctag   6720
tgctcacgct agctaccttc ttcctgtggg cggcagaggt tcctggaacc aaaatagcag   6780
ggaccctgct gatcgccctg ctgctgatgg tggttctcat cccagaaccg gaaaaacaga   6840
ggtcacagac agacaaccaa ctagcggtgt ttctcatctg cgtcttgacc gtggttggag   6900
tggtggcagc aaacgagtac gggatgctag aaaaaaccaa agcagatctc aagagcatgt   6960
ttggcggaaa gacacaggca tcaggactga ctggattgcc aagcatggca ctggacctgc   7020
gtccagccac agcctgggca ctgtatgggg ggagcacagt tgtgctaacc cctcttctga   7080
agcacctgat cacgtcggaa tatgtcacca catcgctagc ctcaattaac tcacaagctg   7140
gctcattatt cgtcttgcca cgaggcgtgc ctttcaccga tctagacctg accgttggcc   7200
tcgtcttcct tggctgctgg ggtcaaatca ccctcacaac gtttttgaca gccatggttc   7260
tggcgacact tcactatggg tacatgctcc ctggatggca agcagaagca ctcagggctg   7320
cccagagaag gacggcggct ggaataatga agaatgccgt tgttgacgga atggtcgcca   7380
ctgatgtgcc tgaactggaa aggactactc ctctgatgca aaagaaagtc ggacaggtgc   7440
tcctcatagg ggtgagcgtg gcagcgtttc tcgtcaaccc taatgtcacc actgtgagag   7500
aagcaggggt gttggtgacg gcggctacgc tcaccttgtg ggataatgga gccagtgccg   7560
tttggaattc caccacagcc acgggactct gccatgtcat gcgaggtagc tacctggctg   7620
gaggctctat tgcttggact cttatcaaga acgctgacaa gccctccttg aaaaggggaa   7680
ggcctggggg caggacgcta ggggagcagt ggaaggaaaa actaaatgcc atgagcagag   7740
aagagttttt taaataccgg agagaggcca taatcgaggt ggaccgcact gaagcacgca   7800
gggctagacg tgaaaataac atagtgggag gacatccggt ttcgcgaggc tcagcaaaac   7860
tccgttggct cgtggagaaa ggattcgtct cgccaatagg aaaagtcatt gatctagggt   7920
gtgggcgtgg aggatggagc tactacgcag caaccctgaa gaaggtccag gaagtcagag   7980
gatacacgaa aggtggggcg ggacatgaag agccgatgct catgcagagc tacggctgga   8040
acctggtctc cttgaagagt ggagtggatg tgttctacaa accttcagag cctagtgaca   8100
ccctgttctg tgacataggg gaatcctccc caagtccaga agtggaagaa caacgcacac   8160
tacgcgtcct agagatgaca tccgattggt tgcatcgagg acccagagag ttctgcataa   8220
aagttctctg cccttacatg cccaaggtca tagaaaaaat ggaagttctg cagcgccgct   8280
tcggaggtgg gctagtacgt ctccccctgt cccgaaactc caatcacgag atgtattggg   8340
```

-continued

```
ttagtggagc cgctggcaat gtggtgcacg ctgtgaacat gaccagccag gtactactgg   8400
ggcgaatgga tcgcacagtg tggagagggc caaagtatga ggaagatgtc aacctaggta   8460
gcggaacaag agccgtggga aagggagaag ttcatagcaa tcaggagaaa atcaagaaga   8520
gaatccagaa gcttaaagaa gaattcgcca caacgtggca caaagaccct gaacacccat   8580
accgcacttg gacataccac ggaagctatg aggtgaaggc tactggctca gccagctctc   8640
tcgtcaacgg agtggtgaag ctcatgagta aaccttggga cgccattgcc aacgtcacca   8700
ccatggccat gactgacacc accccttttg gacagcaaag agttttcaag gagaaagttg   8760
acacgaaagc tcctgagcca ccagctggag tcaaggaagt gctcaacgag accaccaact   8820
ggctgtgggc ccacttgtca cgggaaaaaa gaccccgctt gtgcaccaag gaagaattta   8880
taaagaaagt caatagcaac gcggctcttg gagcagtgtt tgctgaacag aatcaatgga   8940
gcacggcgcg tgaggctgtg gacgacccgc ggttttggga gatggtcaat gaagagaggg   9000
aaaaccatct gcgaggagag tgtcacacat gtatctacaa catgatggga aaaagagaga   9060
agaagcctgg agagtttgga aaagctaaag ggagcagggc catttggttc atgtggcttg   9120
gagcacggta tcttgagttt gaagctttgg ggttcctgaa tgaagaccac tggctgagcc   9180
gagagaattc aggaggtgga gtagaaggct caggcgtcca aaagttggga tacatcctcc   9240
gtgacatagc aggaaagcaa ggagggaaaa tgtacgctga tgacaccgcc gggtgggaca   9300
ctagaattac tagaactgat ttagaaaatg aagctaaggt gctggagctc ctagatggtg   9360
aacaccgcat gctcgcccgg gccataattg aactgactta caggcacaaa gtggtcaagg   9420
tcatgagacc tgcagcagaa ggaaagaccg tgatggacgt gatatcaaga gaagaccaaa   9480
gggggagtgg acaggtggtc acttatgctc tcaacacttt cacgaacatc gctgtccagc   9540
tcgttaggct gatggaggct gagggggtca ttgggccaca acacttggaa cagctgccta   9600
ggaaaaacaa gatagctgtc aggacttggc tctttgagaa tggagaggag agagtgacca   9660
ggatggcgat cagcggagac gactgtgtcg tcaagccgct ggacgacaga ttcgccacgg   9720
ccctccattt cctcaacgca atgtcaaagg ttagaaaaga catccaggaa tggaagcctt   9780
cgcacggctg gcacgattgg cagcaagttc ccttctgctc taaccacttt caggagattg   9840
tgatgaaaga cggaaggagt atagttgtcc cgtgcagagg acaggatgag ctgataggca   9900
gggctcgcat ctctccagga gctggatgga atgtgaagga cacagcttgc ctggcaaaag   9960
catatgcaca gatgtggcta ctcctatact tccatcgtag ggacctgcgt ctcatggcaa   10020
atgcgatttg ctcagcagtg ccagtggatt gggtgcccac aggcaggaca tcctggtcaa   10080
tacactcgaa aggagagtgg atgaccacgg aagacatgct gcaggtctgg aacagagtct   10140
ggattgaaga aaatgaatgg atgatggata agactcccgt cacaagctgg acagacgttc   10200
cgtatgtggg aaagcgtgag gacatctggt gtggcagcct catcggaacg cgttccagag   10260
caacctgggc tgagaacatc tatgcggcga taaaccaggt tagagctgtc attgggaaag   10320
aaaattatgt tgactacatg acctcactca ggagatacga agacgtcttg atccaggaag   10380
acagggtcat ctagtgtgac ttaaggtaga aatgtaaata atgtgaatga gaaaatgcat   10440
gtatatggag tcaggccagc aaaagctgcc accggatact gggtagacgg tgctgcctgc   10500
gtctcagtcc caggaggact gggttaacaa atctgacaac agaaagtgag aaagccctca   10560
gaaccgtctc ggaagtaggt ccctgctcac tggaagttga aagaccaacg tcaggccacg   10620
aatttgtgcc actccgctgg ggagtgcggc ctgcgcagcc ccaggaggac tgggttacca   10680
aagccgttga ggcccccacg gcccaagcct cgtctaggat gcaatagacg aggtgtaagg   10740
```

-continued actagaggtt agaggagacc ccgtggaaac aacaacatgc ggcccaagcc ccctcgaagc 10800
tgtagaggag gtggaaggac tagaggttag aggagacccc gcatttgcat caaacagcat 10860
attgacacct gggaatagac tgggagatct tctgctctat ctcaacatca gctactaggc 10920
acagagcgcc gaagtatgta gctggtggtg aggaagaaca caggatctct agagcggccg 10980
cggaccgact agcctctttt cggccttcgc tgagagggat ttgttcccta ggcctaatta 11040
ttatttttaa ttgcccaata cgtatacgag tgccttttct aattctcgta tactatagtg 11100
agtcgtatta tctagccgcc cgggccgtcg accaattctc atgtttgaca gcttatcatc 11160
gaatttctgc cattcatccg cttattatca cttattcagg cgtagcaacc aggcgtttaa 11220
gggcaccaat aactgcctta aaaaaattac gccccgccct gccactcatc gcagtactgt 11280
tgtaattcat taagcattct gccgacatgg aagccatcac aaacggcatg atgaacctga 11340
atcgccagcg gcatcagcac cttgtcgcct tgcgtataat atttgcccat ggtgaaaacg 11400
ggggcgaaga agttgtccat attggccacg tttaaatcaa aactggtgaa actcacccag 11460
ggattggctg agacgaaaaa catattctca ataaaccctt tagggaaata ggccaggttt 11520
tcaccgtaac acgccacatc ttgcgaatat atgtgtagaa actgccggaa atcgtcgtgg 11580
tattcactcc agagcgatga aaacgtttca gtttgctcat ggaaaacggt gtaacaaggg 11640
tgaacactat cccatatcac cagctcaccg tctttcattg ccatacggaa ttccggatga 11700
gcattcatca ggcgggcaag aatgtgaata aaggccggat aaaacttgtg cttatttttc 11760
tttacggtct ttaaaaaggc cgtaatatcc agctgaacgg tctggttata ggtacattga 11820
gcaactgact gaaatgcctc aaaatgttct ttacgatgcc attgggatat atcaacggtg 11880
gtatatccag tgattttttt ctccatttta gcttccttag ctcctgaaaa tctcgataac 11940
tcaaaaaata cgcccggtag tgatcttatt tcattatggt gaaagttgga acctcttacg 12000
tgccgatcaa cgtctcattt tcgccaaaag ttggcccagg gcttcccggt atcaacaggg 12060
acaccaggat ttatttattc tgcgaagtga tcttccgtca caggtattta ttcgcgataa 12120
gctcatggag cggcgtaacc gtcgcacagg aaggacagag aaagcgcgga tctgggaagt 12180
gacggacaga acggtcagga cctggattgg ggaggcggtt gccgccgctg ctgctgacgg 12240
tgtgacgttc tctgttccgg tcacaccaca tacgttccgc cattcctatg cgatgcacat 12300
gctgtatgcc ggtataccgc tgaaagttct gcaaagcctg atgggacata agtccatcag 12360
ttcaacggaa gtctacacga aggtttttgc gctggatgtg gctgcccggc accgggtgca 12420
gtttgcgatg ccggagtctg atgcggttgc gatgctgaaa caattatcct gagaataaat 12480
gccttggcct ttatatggaa atgtggaact gagtggatat gctgtttttg tctgttaaac 12540
agagaagctg gctgttatcc actgagaagc gaacgaaaca gtcgggaaaa tctcccatta 12600
tcgtagagat ccgcattatt aatctcagga gcctgtgtag cgtttatagg aagtagtgtt 12660
ctgtcatgat gcctgcaagc ggtaacgaaa acgatttgaa tatgccttca ggaacaatag 12720
aaatcttcgt gcggtgttac gttgaagtgg agcggattat gtcagcaatg gacagaacaa 12780
cctaatgaac acagaaccat gatgtggtct gtccttttac agccagtagt gctcgccgca 12840
gtcgagcgac agggcgaagc cctcgagtga gcgaggaagc accagggaac agcacttata 12900
tattctgctt acacacgatg cctgaaaaaa cttcccttgg ggttatccac ttatccacgg 12960
ggatattttt ataattattt tttttatagt ttttagatct tcttttttag agcgccttgt 13020
aggcctttat ccatgctggt tctagagaag gtgttgtgac aaattgccct ttcagtgtga 13080

-continued caaatcaccc tcaaatgaca gtcctgtctg tgacaaattg cccttaaccc tgtgacaaat 13140
tgccctcaga agaagctgtt ttttcacaaa gttatccctg cttattgact ctttttttatt 13200
tagtgtgaca atctaaaaac ttgtcacact tcacatggat ctgtcatggc ggaaacagcg 13260
gttatcaatc acaagaaacg taaaaatagc ccgcgaatcg tccagtcaaa cgacctcact 13320
gaggcggcat atagtctctc ccgggatcaa aaacgtatgc tgtatctgtt cgttgaccag 13380
atcagaaaat ctgatggcac cctacaggaa catgacggta tctgcgagat ccatgttgct 13440
aaatatgctg aaatattcgg attgacctct gcggaagcca gtaaggatat acggcaggca 13500
ttgaagagtt tcgcggggaa ggaagtggtt ttttatcgcc ctgaagagga tgccggcgat 13560
gaaaaaggct atgaatcttt tccttggttt atcaaacgtg cgcacagtcc atccagaggg 13620
ctttacagtg tacatatcaa cccatatctc attcccttct ttatcgggtt acagaaccgg 13680
tttacgcagt ttcggcttag tgaaacaaaa gaaatcacca atccgtatgc catgcgttta 13740
tacgaatccc tgtgtcagta tcgtaagccg gatggctcag gcatcgtctc tctgaaaatc 13800
gactggatca tagagcgtta ccagctgcct caaagttacc agcgtatgcc tgacttccgc 13860
cgccgcttcc tgcaggtctg tgttaatgag atcaacagca gaactccaat gcgcctctca 13920
tacattgaga aaaagaaagg ccgccagacg actcatatcg tattttcctt ccgcgatatc 13980
acttccatga cgacaggata gtctgagggt tatctgtcac agatttgagg gtggttcgtc 14040
acatttgttc tgacctactg agggtaattt gtcacagttt tgctgtttcc ttcagcctgc 14100
atggattttc tcatactttt tgaactgtaa tttttaagga agccaaattt gagggcagtt 14160
tgtcacagtt gatttccttc tctttccctt cgtcatgtga cctgatatcg gggttagtt 14220
cgtcatcatt gatgagggtt gattatcaca gtttattact ctgaattggc tatccgcgtg 14280
tgtacctcta cctggagttt ttcccacggt ggatatttct tcttgcgctg agcgtaagag 14340
ctatctgaca gaacagttct tctttgcttc ctcgccagtt cgctcgctat gctcggttac 14400
acggctgcgg cgagcgctag tgataataag tgactgaggt atgtgctctt cttatctcct 14460
tttgtagtgt tgctcttatt ttaaacaact ttgcggtttt ttgatgactt tgcgattttg 14520
ttgttgcttt gcagtaaatt gcaagattta ataaaaaaac gcaaagcaat gattaaagga 14580
tgttcagaat gaaactcatg gaaacactta accagtgcat aaacgctggt catgaaatga 14640
cgaaggctat cgccattgca cagtttaatg atgacagccc ggaagcgagg aaaataaccc 14700
ggcgctggag aataggtgaa gcagcggatt tagttggggt ttcttctcag gctatcagag 14760
atgccgagaa agcagggcga ctaccgcacc cggatatgga aattcgagga cgggttgagc 14820
aacgtgttgg ttatacaatt gaacaaatta atcatatgcg tgatgtgttt ggtacgcgat 14880
tgcgacgtgc tgaagacgta tttccaccgg tgatcggggt tgctgcccat aaaggtggcg 14940
tttacaaaac ctcagtttct gttcatcttg ctcaggatct ggctctgaag gggctacgtg 15000
ttttgctcgt ggaaggtaac gacccccagg gaacagcctc aatgtatcac ggatgggtac 15060
cagatcttca tattcatgca gaagacactc tcctgccttt ctatcttggg gaaaaggacg 15120
atgtcactta tgcaataaag cccacttgct ggccggggct tgacattatt ccttcctgtc 15180
tggctctgca ccgtattgaa actgagttaa tgggcaaatt tgatgaaggt aaactgccca 15240
ccgatccaca cctgatgctc cgactggcca ttgaaactgt tgctcatgac tatgatgtca 15300
tagttattga cagcgcgcct aacctgggta tcggcacgat taatgtcgta tgtgctgctg 15360
atgtgctgat tgttcccacg cctgctgagt tgtttgacta cacctccgca ctgcagtttt 15420
tcgatatgct tcgtgatctg ctcaagaacg ttgatcttaa agggttcgag cctgatgtac 15480

-continued

```
gtattttgct taccaaatac agcaatagta atggctctca gtccccgtgg atggaggagc  15540
aaattcggga tgcctgggga agcatggttc taaaaaatgt tgtacgtgaa acggatgaag  15600
ttggtaaagg tcagatccgg atgagaactg tttttgaaca ggccattgat caacgctctt  15660
caactggtgc ctggagaaat gctctttcta tttgggaacc tgtctgcaat gaaattttcg  15720
atcgtctgat taaaccacgc tgggagatta gataatgaag cgtgcgcctg ttattccaaa  15780
acatacgctc aatactcaac cggttgaaga tacttcgtta tcgacaccag ctgccccgat  15840
ggtggattcg ttaattgcgc gcgtaggagt aatggctcgc ggtaatgcca ttactttgcc  15900
tgtatgtggt cgggatgtga agtttactct tgaagtgctc cggggtgata gtgttgagaa  15960
gacctctcgg gtatggtcag gtaatgaacg tgaccaggag ctgcttactg aggacgcact  16020
ggatgatctc atcccttctt ttctactgac tggtcaacag acaccggcgt tcggtcgaag  16080
agtatctggt gtcatagaaa ttgccgatgg gagtcgccgt cgtaaagctg ctgcacttac  16140
cgaaagtgat tatcgtgttc tggttggcga gctggatgat gagcagatgg ctgcattatc  16200
cagattgggt aacgattatc gcccaacaag tgcttatgaa cgtggtcagc gttatgcaag  16260
ccgattgcag aatgaatttg ctggaaatat ttctgcgctg gctgatgcgg aaaatatttc  16320
acgtaagatt attacccgct gtatcaacac cgccaaattg cctaaatcag ttgttgctct  16380
tttttctcac cccggtgaac tatctgcccg gtcaggtgat gcacttcaaa aagcctttac  16440
agataaagag gaattactta agcagcaggc atctaacctt catgagcaga aaaaagctgg  16500
ggtgatattt gaagctgaag aagttatcac tcttttaact tctgtgctta aaacgtcatc  16560
tgcatcaaga actagtttaa gctcacgaca tcagtttgct cctggagcga cagtattgta  16620
taagggcgat aaaatggtgc ttaacctgga caggtctcgt gttccaactg agtgtataga  16680
gaaaattgag gccattctta aggaacttga aaagccagca ccctgatgcg accacgtttt  16740
agtctacgtt tatctgtctt tacttaatgt cctttgttac aggccagaaa gcataactgg  16800
cctgaatatt ctctctgggc ccactgttcc acttgtatcg tcggtctgat aatcagactg  16860
ggaccacggt cccactcgta tcgtcggtct gattattagt ctgggaccac ggtcccactc  16920
gtatcgtcgg tctgattatt agtctgggac cacggtccca ctcgtatcgt cggtctgata  16980
atcagactgg gaccacggtc ccactcgtat cgtcggtctg attattagtc tgggaccatg  17040
gtcccactcg tatcgtcggt ctgattatta gtctgggacc acggtcccac tcgtatcgtc  17100
ggtctgatta ttagtctgga accacggtcc cactcgtatc gtcggtctga ttattagtct  17160
gggaccacgg tcccactcgt atcgtcggtc tgattattag tctgggacca cgatcccact  17220
cgtgttgtcg gtctgattat cggtctggga ccacggtccc acttgtattg tcgatcagac  17280
tatcagcgtg agactacgat tccatcaatg cctgtcaagg gcaagtattg acatgtcgtc  17340
gtaacctgta gaacggagta acctcggtgt gcggttgtat gcctgctgtg gattgctgct  17400
gtgtcctgct tatccacaac attttgcgca cggttatgtg gacaaaatac ctggttaccc  17460
aggccgtgcc ggcacgttaa ccgggctgca tccgatgcaa gtgtgtcgct gtcgacgagc  17520
tcgcgagctc ggacatgagg ttgccccgta ttcagtgtcg ctgatttgta ttgtctgaag  17580
ttgtttttac gttaagttga tgcagatcaa ttaatacgat acctgcgtca taattgatta  17640
tttgacgtgg tttgatggcc tccacgcacg ttgtgatatg tagatgataa tcattatcac  17700
tttacgggtc ctttccggtg atccgacagg ttacggggcg gcgacctcgc gggttttcgc  17760
tatttatgaa aattttccgg tttaaggcgt ttccgttctt cttcgtcata acttaatgtt  17820
```

-continued

```
tttatttaaa ataccctctg aaaagaaagg aaacgacagg tgctgaaagc gagctttttg  17880

gcctctgtcg tttcctttct ctgtttttgt ccgtggaatg aacaatggaa gtccgagctc  17940

atcgctaata acttcgtata gcatacatta tacgaagtta tattcgatgc ggcgctgagg  18000

tctgcctcgt gaagaaggtg ttgctgactc ataccaggcc tgaatcgccc catcatccag  18060

ccagaaagtg agggagccac ggttgatgag agctttgttg taggtggacc agttggtgat  18120

tttgaacttt tgctttgcca cggaacggtc tgcgttgtcg ggaagatgcg tgatctgatc  18180

cttcaactca gcaaaagttc gatttattca acaaagccac gtgtctcaaa atctctgatg  18240

ttacattgca caagataaaa atatatcatc atgaacaata aaactgtctg cttacataaa  18300

cagtaataca aggggtgtta tgagccatat tcaacgggaa acgtcttgct cgacgatgat  18360

aagctgtcaa acatgagaat tgggtcgtca atatgctaaa acgcggcata ccccgcgtat  18420

tcccactagt taatcgtacg aattccgtat ggcaatgaaa gacggtgagc tggtgatatg  18480

ggatagtgtt cacccttgtt acaccgtttt ccatgagcaa actgaaacgt tttcatcgct  18540

ctggagtgaa taccacgacg atttccggca gtttctacac atatattcgc aagatgtggc  18600

gtgttacggt gaaaacctgg cctatttccc taaagggttt attgagaata tgtttttcgt  18660

ctcagccaat ccctgggtga gtttcaccag ttttgattta aacgtggcca atatggacaa  18720

cttcttcgcc cccgttttca ccatgggcaa atattatacg caaggcgaca aggtgctgat  18780

gccgctggcg attcaggttc atcatgccgt ttgtgatggc ttccatgtcg gcagaatgct  18840

taatgaatta caacagtact gcgatgagtg gcagggcggg gcgtaatttt tttaaggcag  18900

ttattggtgc ccttaaacgc ctggttgcta cgcctgaata agtgataata agcggatgaa  18960

tggcagaaat tcgatgataa gctgtcaaac atgagaattg gtcgacggcc cgggcggcta  19020

gataatacga ctcactatag                                              19040
```

```
<210> SEQ ID NO 49
<211> LENGTH: 18
<212> TYPE: DNA
<213> ORGANISM: Artificial Sequence
<220> FEATURE:
<223> OTHER INFORMATION: primer EGFPF

<400> SEQUENCE: 49

tcgccaccat ggtgagca                                                   18


<210> SEQ ID NO 50
<211> LENGTH: 30
<212> TYPE: DNA
<213> ORGANISM: Artificial Sequence
<220> FEATURE:
<223> OTHER INFORMATION: primer EGFPR

<400> SEQUENCE: 50

cataggcctc tattaaccgt cgactgcaga                                      30


<210> SEQ ID NO 51
<211> LENGTH: 27
<212> TYPE: DNA
<213> ORGANISM: Artificial Sequence
<220> FEATURE:
<223> OTHER INFORMATION: primer PACF

<400> SEQUENCE: 51

gatcacgttg tgagttggat agttgtg                                         27
```

-continued

<210> SEQ ID NO 52
<211> LENGTH: 27
<212> TYPE: DNA
<213> ORGANISM: Artificial Sequence
<220> FEATURE:
<223> OTHER INFORMATION: primer PACR

<400> SEQUENCE: 52
atcatgcatt catggggtcg tgcgctc 27

<210> SEQ ID NO 53
<211> LENGTH: 27
<212> TYPE: DNA
<213> ORGANISM: Artificial Sequence
<220> FEATURE:
<223> OTHER INFORMATION: primer DelF

<400> SEQUENCE: 53
gatttaatta acctgcaggg ggctgtt 27

<210> SEQ ID NO 54
<211> LENGTH: 27
<212> TYPE: DNA
<213> ORGANISM: Artificial Sequence
<220> FEATURE:
<223> OTHER INFORMATION: primer C1R

<400> SEQUENCE: 54
gatctcgagc cggtttttac cgggccc 27

<210> SEQ ID NO 55
<211> LENGTH: 27
<212> TYPE: DNA
<213> ORGANISM: Artificial Sequence
<220> FEATURE:
<223> OTHER INFORMATION: primer C2F

<400> SEQUENCE: 55
gatctcgaga aaagaggagg aaatgaa 27

<210> SEQ ID NO 56
<211> LENGTH: 27
<212> TYPE: DNA
<213> ORGANISM: Artificial Sequence
<220> FEATURE:
<223> OTHER INFORMATION: primer DelR

<400> SEQUENCE: 56
tgtggccaag aaggccaaag caattga 27

<210> SEQ ID NO 57
<211> LENGTH: 27
<212> TYPE: DNA
<213> ORGANISM: Artificial Sequence
<220> FEATURE:
<223> OTHER INFORMATION: primer C3R

<400> SEQUENCE: 57
gatctcgagc attactaccc tcttcac 27

<210> SEQ ID NO 58
<211> LENGTH: 27
<212> TYPE: DNA
<213> ORGANISM: Artificial Sequence
<220> FEATURE:
<223> OTHER INFORMATION: primer prM1R -continued

<400> SEQUENCE: 58
gatctcgagg tccgtgttgt taatggt 27

<210> SEQ ID NO 59
<211> LENGTH: 27
<212> TYPE: DNA
<213> ORGANISM: Artificial Sequence
<220> FEATURE:
<223> OTHER INFORMATION: primer prM2F

<400> SEQUENCE: 59
gatctcgagg attcaacgaa agccaca 27

<210> SEQ ID NO 60
<211> LENGTH: 27
<212> TYPE: DNA
<213> ORGANISM: Artificial Sequence
<220> FEATURE:
<223> OTHER INFORMATION: primer E1R

<400> SEQUENCE: 60
gatctcgagg gctccactgg ctccttc 27

<210> SEQ ID NO 61
<211> LENGTH: 27
<212> TYPE: DNA
<213> ORGANISM: Artificial Sequence
<220> FEATURE:
<223> OTHER INFORMATION: primer E2F

<400> SEQUENCE: 61
gatctcgaga caactttgaa gggagct 27

<210> SEQ ID NO 62
<211> LENGTH: 30
<212> TYPE: DNA
<213> ORGANISM: Artificial Sequence
<220> FEATURE:
<223> OTHER INFORMATION: primer NS1R

<400> SEQUENCE: 62
ggcacatcca gtgtcggctc ctacacaagc 30

<210> SEQ ID NO 63
<211> LENGTH: 18
<212> TYPE: DNA
<213> ORGANISM: Artificial Sequence
<220> FEATURE:
<223> OTHER INFORMATION: primer NS1F

<400> SEQUENCE: 63
gacactggat gtgccatt 18

<210> SEQ ID NO 64
<211> LENGTH: 21
<212> TYPE: DNA
<213> ORGANISM: Artificial Sequence
<220> FEATURE:
<223> OTHER INFORMATION: primer RR

<400> SEQUENCE: 64
tcgtcccgca cggcttccca c 21

<210> SEQ ID NO 65
<211> LENGTH: 24

-continued

<212> TYPE: DNA
<213> ORGANISM: Artificial Sequence
<220> FEATURE:
<223> OTHER INFORMATION: primer JEVCF

<400> SEQUENCE: 65
gattctagaa tgactaaaaa acca 24

<210> SEQ ID NO 66
<211> LENGTH: 31
<212> TYPE: DNA
<213> ORGANISM: Artificial Sequence
<220> FEATURE:
<223> OTHER INFORMATION: primer JEVER

<400> SEQUENCE: 66
gatgtttaaa ctattaagca tgcacattgg t 31

<210> SEQ ID NO 67
<211> LENGTH: 31
<212> TYPE: DNA
<213> ORGANISM: Artificial Sequence
<220> FEATURE:
<223> OTHER INFORMATION: primer JEVNS1R

<400> SEQUENCE: 67
gatgtttaaa ctattaagca tcaacctgtg a 31

<210> SEQ ID NO 68
<211> LENGTH: 10
<212> TYPE: DNA
<213> ORGANISM: Artificial Sequence
<220> FEATURE:
<223> OTHER INFORMATION: 5' termini of full-length JEV cDNA clone

<400> SEQUENCE: 68
tatagagaag 10

<210> SEQ ID NO 69
<211> LENGTH: 10
<212> TYPE: DNA
<213> ORGANISM: Artificial Sequence
<220> FEATURE:
<223> OTHER INFORMATION: 3' termini of SP6- or T7-driven JEV cDNA
template digested with XhoI

<400> SEQUENCE: 69
aggatccgag 10

<210> SEQ ID NO 70
<211> LENGTH: 12
<212> TYPE: DNA
<213> ORGANISM: Artificial Sequence
<220> FEATURE:
<223> OTHER INFORMATION: 3' termini of SP6- or T7-driven JEV cDNA
templated digested with XbaI

<400> SEQUENCE: 70
aggatctcta ga 12

<210> SEQ ID NO 71
<211> LENGTH: 7
<212> TYPE: DNA
<213> ORGANISM: Artificial Sequence
<220> FEATURE:
<223> OTHER INFORMATION: 3' termini of JEV cDNA template treated with
mung bean nuclease -continued

<400> SEQUENCE: 71 aggatct 7